(12) United States Patent
Ricke et al.

(10) Patent No.: US 11,655,498 B2
(45) Date of Patent: May 23, 2023

(54) SYSTEMS AND METHODS FOR GENETIC IDENTIFICATION AND ANALYSIS

(71) Applicant: Massachusetts Institute of Technology, Cambridge, MA (US)

(72) Inventors: Darrell Orlyn Ricke, Winchester, MA (US); James Harper, Jamaica Plain, MA (US); Brian S. Helfer, Brookline, MA (US); Joseph Isaacson, Latham, NY (US); Adam M. Michaleas, Hudson, NH (US); Martha S. Petrovick, Barre, MA (US); Eric Schwoebel, Woburn, MA (US); Anna Shcherbina, East Palo Alto, CA (US); Philip Fremont-Smith, Medford, MA (US); James G. Watkins, Sutton, MA (US); Edward C. Wack, Waltham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 488 days.

(21) Appl. No.: 16/629,081

(22) PCT Filed: Jul. 6, 2018

(86) PCT No.: PCT/US2018/041081
§ 371 (c)(1),
(2) Date: Jan. 7, 2020

(87) PCT Pub. No.: WO2019/010410
PCT Pub. Date: Jan. 10, 2019

(65) Prior Publication Data
US 2021/0017592 A1    Jan. 21, 2021

Related U.S. Application Data

(60) Provisional application No. 62/529,939, filed on Jul. 7, 2017, provisional application No. 62/534,590, filed on Jul. 19, 2017.

(51) Int. Cl.
*C12Q 1/68* (2018.01)
*C12Q 1/6858* (2018.01)
(Continued)

(52) U.S. Cl.
CPC ......... *C12Q 1/6858* (2013.01); *C12Q 1/6869* (2013.01); *C12Q 1/6886* (2013.01);
(Continued)

(58) Field of Classification Search
CPC ....... G16B 40/10; G16B 20/00; C12Q 1/6858
See application file for complete search history.

(56) References Cited

U.S. PATENT DOCUMENTS 6,025,136 A * 2/2000 Drmanac ............ B01J 19/0046
                                                        435/6.12
7,840,519 B2 * 11/2010 Birdwell ................. G06F 40/18
                                                           706/47
(Continued)

FOREIGN PATENT DOCUMENTS

WO    WO 2011/067765 A1    6/2011

OTHER PUBLICATIONS

Invitation to Pay Additional Fees dated Sep. 10, 2018, for Application No. PCT/US2018/041081.
(Continued)

*Primary Examiner* — Eliyah S. Harper
(74) *Attorney, Agent, or Firm* — Wolf, Greenfield & Sacks, P.C.

(57) ABSTRACT

The disclosure provides various systems and methods for identifying individuals from one or more samples. In particular, improved systems and methods of analysis are provided for handling multiple contributors, as well as systems and methods that model not only individual error rates per locus but factor in amplification of errors induced through PCR cycles. In some embodiments, modeling of
(Continued)

error rates can be applied in multi-contributor settings to more accurately establish real alleles from artifacts. Other aspects involve application of sequencing in error modeling. Further, methods are provided for determining the presence of common individual DNA profiles in one or more complex DNA mixtures and for deconvolution of multiple complex DNA mixtures into shared individual components.

20 Claims, 94 Drawing Sheets

(51) Int. Cl.
    *G16B 40/10*         (2019.01)
    *C12Q 1/6869*       (2018.01)
    *C12Q 1/6886*       (2018.01)
    *G16B 20/00*         (2019.01)

(52) U.S. Cl.
    CPC ............. *G16B 20/00* (2019.02); *G16B 40/10* (2019.02); *C12Q 2600/156* (2013.01)

(56) References Cited

U.S. PATENT DOCUMENTS

| | | | |
|---|---|---|---|
| 9,447,474 B2 | 9/2016 | Darvasi et al. | |
| 9,708,642 B2 | 7/2017 | Perlin | |
| 2003/0186280 A1* | 10/2003 | Kennedy | C12Q 1/6837 506/10 |
| 2003/0190644 A1* | 10/2003 | Braun | C12Q 1/6827 702/20 |
| 2005/0243398 A1* | 11/2005 | Latypov | G03F 7/705 359/237 |
| 2007/0184467 A1* | 8/2007 | Rabinowitz | G16B 20/00 435/6.12 |
| 2008/0243398 A1 | 10/2008 | Rabinowitz et al. | |
| 2010/0075308 A1* | 3/2010 | Sadee | C12Q 1/6883 435/6.14 |
| 2013/0115595 A1* | 5/2013 | Hantash | C12Q 1/6858 702/19 |
| 2013/0323731 A1* | 12/2013 | Lo | G16B 30/00 435/6.11 |
| 2015/0078552 A1* | 3/2015 | Perlin | G16B 20/20 380/255 |
| 2017/0342477 A1* | 11/2017 | Jensen | C12Q 1/6858 |
| 2019/0345560 A1* | 11/2019 | Zhang | C12Q 1/6858 |

OTHER PUBLICATIONS

International Search Report and Written Opinion dated Nov. 8, 2018, for Application No. PCT/US2018/041081.
International Preliminary Report on Patentability dated Jan. 16, 2020, for Application No. PCT/US2018/041081.
Adey et al., Rapid, low-input, low-bias construction of shotgun fragment libraries by high-density in vitro transposition. Genome Biol. 2010;11(12):R119. doi: 10.1186/gb-2010-11-12-r119. Epub Dec. 8, 2010.
Ballantyne et al., A new future of forensic Y-chromosome analysis: rapidly mutating Y-STRs for differentiating male relatives and paternal lineages. Forensic Sci Int Genet. Mar. 2012;6(2):208-18. doi: 10.1016/j.fsigen.2011.04.017. Epub May 25, 2011.
Cheung et al., ALFRED: an allele frequency database for diverse populations and DNA polymorphisms. Nucleic Acids Res. Jan. 1, 2000;28(1):361-3.
Cowen et al., A likelihood ratio approach to familial searching of large DNA databases. Forensic Sci Int: Genet Suppl. 2008; 1: 643-5.
Eriksson et al., Web-based, participant-driven studies yield novel genetic associations for common traits. PLoS Genet. Jun. 24, 2010;6(6):e1000993.
Ge et al., Comparisons of familial DNA database searching strategies. J Forensic Sci. Nov. 2011;56(6):1448-56. doi: 10.1111/j.1556-4029.2011.01867.x. Epub Aug. 9, 2011. Erratum in: J Forensic Sci. Jan. 2012;57(1):283.

Heinrich et al., A likelihood ratio-based method to predict exact pedigrees for complex families from next-generation sequencing data. Bioinformatics. Jan. 1, 2017;33(1):72-78. doi: 10.1093/bioinformatics/btw550. Epub Aug. 26, 2016.
Hong, On computing the distribution function for the Poisson binomial distribution. Computational Statistics & Data Analysis, Mar. 2013;59:41-51.
Huff et al., Maximum-likelihood estimation of recent shared ancestry (ERSA). Genome Res. May 2011;21(5):768-74. doi: 10.1101/gr.115972.110. Epub Feb. 8, 2011.
Huisman, Pedigree reconstruction from SNP data: parentage assignment, sibship clustering and beyond. Mol Ecol Resour. Sep. 2017;17(5):1009-1024. doi: 10.1111/1755-0998.12665. Epub Apr. 6, 2017.
Hwa et al., A 1204-single nucleotide polymorphism and insertion-deletion polymorphism panel for massively parallel sequencing analysis of DNA mixtures. Forensic Sci Int Genet. Jan. 2018;32:94-101. doi: 10.1016/j.fsigen.2017.11.002. Epub Nov. 6, 2017.
Isaacson et al., Robust detection of individual forensic profiles in DNA mixtures. Forensic Sci Int Genet. Jan. 2015;14:31-7. doi: 10.1016/j.fsigen.2014.09.003. Epub Sep. 16, 2014.
Kidd et al., Expanding data and resources for forensic use of SNPs in individual identification. Forensic Sci Int Genet. Sep. 2012;6(5):646-52. doi: 10.1016/j.fsigen.2012.02.012. Epub Mar. 22, 2012.
Kling et al., Evaluating the statistical power of DNA-based identification, exemplified by 'The missing grandchildren of Argentina'. Forensic Sci Int Genet. Nov. 2017;31:57-66. doi: 10.1016/j.fsigen.2017.08.006. Epub Aug. 12, 2017.
Liu et al., A genome-wide association study identifies five loci influencing facial morphology in Europeans. PLoS Genet. Sep. 2012;8(9):e1002932. doi: 10.1371/journal.pgen.1002932. Epub Sep. 13, 2012.
Liu et al., A convenient guideline to determine if two Y-STR profiles are from the same lineage. Electrophoresis. Jul. 2016;37(12):1659-68. doi: 10.1002/elps.201500566. Epub May 3, 2016.
Manichaikul et al., Robust relationship inference in genome-wide association studies. Bioinformatics. Nov. 15, 2010;26(22):2867-73. doi: 10.1093/bioinformatics/btq559. Epub Oct. 5, 2010.
Mo et al., A 472-SNP panel for pairwise kinship testing of second-degree relatives. Forensic Sci Int Genet. May 2018;34:178-185. doi: 10.1016/j.fsigen.2018.02.019. Epub Mar. 2, 2018.
Morimoto et al., Discrimination of relationships with the same degree of kinship using chromosomal sharing patterns estimated from high-density SNPs. Forensic Sci Int Genet. Mar. 2018;33:10-16. doi: 10.1016/j.fsigen.2017.11.010. Epub Nov. 22, 2017.
Nassir et al., An ancestry informative marker set for determining continental origin: validation and extension using human genome diversity panels. BMC Genet. Jul. 24, 2009;10:39.
Niedzwiecki et al., Understanding Familial DNA Searching: Coming to a Consensus on Terminology, ICF International, 2016. 16 pages.
Pakstis et al., Candidate SNPs for a universal individual identification panel. Hum Genet. May 2007;121(3-4):305-17. doi: 10.1007/s00439-007-0342-2. Epub Feb. 27, 2007.
Pakstis et al., SNPs for a universal individual identification panel. Hum Genet. Mar. 2010;127(3):315-24.
Quail et al., A tale of three next generation sequencing platforms: comparison of Ion Torrent, Pacific Biosciences and Illumina MiSeq sequencers. BMC Genomics. Jul. 24, 2012;13:341.
Ricke et al., GrigoraSNPs: Optimized Analysis of SNPs for DNA Forensics. J Forensic Sci. Nov. 2018;63(6):1841-1845. doi: 10.1111/1556-4029.13794. Epub Apr. 16, 2018.
Shcherbina et al., KinLinks: Software toolkit for kinship analysis and pedigree generation from HTS datasets. 2016 IEEE International Symposium on Technologies for Homeland Security (HST), IEEE, 2016; 6 pages.
Shifman et al., Linkage disequilibrium patterns of the human genome across populations. Hum Mol Genet. Apr. 1, 2003;12(7):771-6.
Sobrino et al., SNPs in forensic genetics: a review on SNP typing methodologies. Forensic Sci Int. Nov. 25, 2005;154(2-3):181-94. doi: 10.1016/j.forsciint.2004.10.020. Epub Jan. 11, 2005.

(56) References Cited

OTHER PUBLICATIONS

Tian et al., Analysis and application of European genetic substructure using 300 K SNP information. PLoS Genet. Jan. 2008;4(1):e4.

Voskoboinik et al., Forensic identification of an individual in complex DNA mixtures. Forensic Sci Int Genet. Nov. 2011;5(5):428-35. doi: 10.1016/j.fsigen.2010.09.002. Epub Oct. 2, 2010.

Walsh et al., IrisPlex: a sensitive DNA tool for accurate prediction of blue and brown eye colour in the absence of ancestry information. Forensic Sci Int Genet. Jun. 2011;5(3):170-80. doi: 10.1016/j.fsigen.2010.02.004. Epub Mar. 27, 2010.

Wolinsky, CSI on steroids: DNA-based phenotyping is helping police derive visual information from crime scene samples to aid in the hunt for suspects. EMBO Rep. Jul. 2015;16(7):782-6. doi: 10.15252/embr.201540714. Epub Jun. 15, 2015.

Zettler et al., 23andMe, the Food and Drug Administration, and the future of genetic testing. JAMA Intern Med. Apr. 2014;174(4):493-4.

PCT/US2018/041081, Sep. 10, 2018, Invitation to Pay Additional Fees.

PCT/US2018/041081, Nov. 8, 2018, International Search Report and Written Opinion.

PCT/US2018/041081, Jan. 16, 2020, International Preliminary Report on Patentability.

\* cited by examiner

| Sample Name | Mismatches | % of MAs |
|---|---|---|
| ZR5HE:IX - 23 | 0 | 0.0% |

Relatives

| Person | Relationship | Related | Degree | Confidence | Mismatches |
|---|---|---|---|---|---|
| OELSG:IX - 21 | | | 3 | | 1319 |
| ZR5HE:IX - 22 | | | 2 | | 1085 |

*FIG. 15*

Results from Mixture Analysis Using 468 SNPs with Minor Allele Frequency of ≈ 0.05

| Number of Contributors | Number of Minor Alleles (Truth) | False Negatives (Minor Alleles Missed) | False Positives | P(RMNE) | Pd |
|---|---|---|---|---|---|
| 3 | 139 | 0 | 7 | 8.85E-14 | 1 |
| 3 | 182 | 0 | 28 | 3.533E-12 | 1 |
| 5 | 232 | 1 | 25 | 2.182E-10 | 0.8 |
| 5 | 237 | 0 | 14 | 3.454E-10 | 1 |
| 5 | 229 | 1 | 10 | 2.74E-10 | 0.8 |
| 8 | 300 | 0 | 8 | 1.192E-07 | 1 |
| 8 | 310 | 1 | 18 | 2.725E-07 | 0.875 |
| 10 | 349 | 0 | 11 | 7.859E-06 | 1 |
| 15 | 391 | 20 | 0 | 0.0003445 | 0.42857145 |

Mixtures containing equal amounts of DNA from 8, 5, 3, 10 and 15 individuals were amplified using Fluidigm multiplexed PCR technology and sequenced on Ion Torrent PGM.

FIG. 27

Results from a Mixture Analysis Using 975 SNPs with a Minor Allele Frequency of ~ 0.05

| Number of Contributors | Number of Minor Alleles (Truth) | False Negatives (Minor Alleles Missed) | False Positives | P(RMNE) | Pd |
|---|---|---|---|---|---|
| 8 | 597 | 0 | 12 | 1.445E-15 | 1 |
| 10 | 683 | 0 | 8 | 2.565E-12 | 1 |
| 15 | 793 | 2 | 4 | 6.69E-08 | 0.8666667 |
| 20 | 851 | 1 | 2 | 1.711E-05 | 0.95 |

Mixtures containing equal amounts of DNA from 8, 10, 15 and 20 individuals were amplified using Ampliseq multiplexed PCR technology and sequenced on Ion Torrent PGM.

FIG. 29

| | Mix03p | Mix04p | Mix05p | Mix12p |
|---|---|---|---|---|
| Ind00 | 28 | 24 | 22 | 0 |
| Ind01 | 15 | 11 | 11 | 7 |
| Ind02 | 15 | 0 | 0 | 0 |
| Ind03 | 24 | 0 | 0 | 0 |
| Ind04 | 0 | 17 | 0 | 0 |
| Ind05 | 17 | 10 | 9 | 4 |
| Ind06 | 26 | 22 | 16 | 0 |
| Ind07 | 14 | 14 | 0 | 0 |
| Ind08 | 17 | 10 | 10 | 8 |
| Ind09 | 14 | 10 | 8 | 1 |
| Ind10 | 0 | 15 | 10 | 0 |
| Ind11 | 17 | 10 | 11 | 3 |
| Ind12 | 16 | 11 | 7 | 0 |
| Ind13 | 23 | 19 | 17 | 9 |
| Ind14 | 15 | 13 | 8 | 6 |
| Ind15 | 20 | 0 | 8 | 0 |
| Ind16 | 15 | 9 | 8 | 4 |
| Ind17 | 0 | 14 | 0 | 0 |
| Ind18 | 20 12 | 17 6 | 10 6 | 7 2 |
| Ind19 | 9 | 4 | 3 | 1 |
| Ind20 | 16 | 0 | 11 | 0 |
| Ind21 | 18 | 11 | 9 | 5 |
| Ind22 | 19 | 11 | 12 | 9 |
| Ind23 | 24 23 24 | 18 17 17 | 10 13 13 | 4 3 9 |
| Ind26 | 12 | 9 | 7 | 4 |
| Ind27 | 16 | 10 | 10 | 6 |
| Ind28 | 21 | 12 | 13 | 5 |

FastID Results show 10 entries

| Sample | People | Minor Alleles | Mismatches | %MAs |
|---|---|---|---|---|
| C7SC3-IX-12 | 83 | 569 | 3 | 0.5% |
| S77TX-IX-06 | mix18 | 932 | 76 | 8.2% |
| KH1E:IX-02 | mix186 | 932 | 72 | 7.7% |
| 5JJ0M:IX-08 | mix52 | 932 | 62 | 6.7% |
| X8RKV:IX-30 | mix88 | 932 | 64 | 6.9% |
| X8RKV:IX-29 | mix9 | 932 | 135 | 14.5% |

| Barcode | Primer | Flanking | SNP | Flanking | Primer | Barcode |

FIG. 71

| Sample | Locus | Allele Name | Reads |
|---|---|---|---|
| I6 | D20S482 | 14 | 2632 |
| I6 | D20S482 | 15 | 379 |
| I6 | D20S482 | 16 | 2453 |
| I6 | D6S1043 | 18 | 2150 |
| I6 | D6S1043 | 19 | 236 |
| I6 | D6S1043 | 20 | 1550 |
| I9 | D22S1045 | 14 | 41 |
| I9 | D22S1045 | 15 | 168 |
| I10 | CSF1PO | 10 | 619 |
| I10 | CSF1PO | 14 | 63 |
| I10 | CSF1PO | 15 | 614 |

*FIG. 77*

SYSTEMS AND METHODS FOR GENETIC IDENTIFICATION AND ANALYSIS

RELATED APPLICATIONS

This application is a national stage filing under 35 U.S.C. § 371 of international PCT application, PCT/US2018/041081, filed Jul. 6, 2018, entitled "SYSTEMS AND METHODS FOR GENETIC IDENTIFICATION AND ANALYSIS," which claims the benefit of the filing date of U.S. Provisional Application No. 62/529,939, filed on Jul. 7, 2017, entitled "SYSTEMS AND METHODS FOR ALLELE IDENTIFICATION AND ANALYSIS," and U.S. Provisional Application No. 62/534,590, filed on Jul. 19, 2017, entitled "DNA MIXTURES FROM ONE OR MORE SOURCES AND METHODS OF BUILDING INDIVIDUAL PROFILES THEREFROM." The contents of these applications are incorporated herein by reference in their entirety.

GOVERNMENT SUPPORT

This invention was made with Government support under Contract No. FA8721-05-C-0002 awarded by the U.S. Air Force. The Government has certain rights in the invention.

BACKGROUND

Sequence differences in the human genome are a cornerstone in human identification and forensic applications. Genetic fingerprinting is a forensic technique used to identify individuals by characteristics of their genetic information (e.g., RNA, DNA). A genetic fingerprint is a small set of one or more nucleic acid variations that is likely to be different in all unrelated individuals, thereby being as unique to individuals as are fingerprints.

Current forensic standards have been developed using unlinked short tandem repeat (STR) polymorphisms. The FBI has defined core STR loci for the Combined DNA Index System (CODIS) database as the current forensic standard in the United States. Current forensic protocols identify STR alleles by length of polymerase chain reaction (PCR) amplicons sized on capillary electrophoresis (CE) instruments.

Criminal justice DNA forensics provides for identification based on characterization of sets of short tandem repeats (STRs) found in DNA samples. For example, a sample taken from a suspect can be compared to an independent sample (e.g., from a crime scene) to determine a match. Conventional methodologies rely upon identifying the length of repeat patterns, (sizing of number of repeat units and any partial repeat units) of STR loci (specific known positions and sequences of DNA) in DNA amplified by the polymerase chain reaction (PCR). The amplified DNA is used to measure PCR product sizes with capillary electrophoresis (CE). The obtained sizes are compared to known standards to determine specific alleles (e.g., STR loci).

SUMMARY

Advances in DNA sequencing technologies now enable the sequencing of both STRs and single nucleotide polymorphisms (SNPs) for better identification. Sequencing STR loci enables distinguishing between STR with the same length but different allele sequences. Additionally, sequencing SNPs enables prediction of externally visible traits (EVTs), biogeographic ancestry, improved analysis of complex forensic samples originating from multiple individuals, characterization of trace DNA samples, etc.

It is appreciated that there are issues of PCR relating to the DNA polymerases used in preparing samples. Specifically, the DNA polymerases for PCR have an increased error rate specific to short tandemly repeated DNA sequences (STRs) and their respective length. The longer the length of the repeat sequence, the higher the probability that the polymerase will delete an entire repeat unit or create an extra copy of a repeat unit (i.e., stutter alleles). A deletion of a repeat unit is referred to as a −1 allele and an addition of a repeat unit as a +1 allele. Deletions are more likely to occur than additions. For each cycle of PCR, errors can impact errors yielding higher errors rates of −2, −3, and +2 stutter alleles over multiple cycles. The appearance of −2, −3, and +2 stutter alleles are typically proportional to the −1/+1 stutter error rate applied to stutter sequences generated in earlier cycles of PCR amplification (e.g., the ratio of −2 to −1 counts of sequences is typically slightly less than the ratio of −1 to real allele counts of sequences). DNA polymerases also have an error rate (typically less than 1%) of introducing random DNA base errors. This creates sequence variants of all of the PCR products being amplified at a lower rate than the stutter error rate.

Although the sources of PCR artifacts or errors can usually be ignored for samples from a single individual, it is realized that distinguishing real alleles from artifacts in mixtures of multiple individuals presents a new challenge area for DNA forensics. Accordingly, there is a need for improved systems and methods of analysis for handling multiple contributors, as well as systems and methods that model not only individual error rates per locus but factor in amplification of errors induced through PCR cycles. In some embodiments, modeling of error rates can be applied in multi-contributor settings to more accurately establish real alleles from artifacts. Other aspects involve application of sequencing in error modeling. For example, sequencing of the dominant stutter in the −1 allele for each locus (and/or amplification agent) enables increased identification accuracy (e.g., allele calling accuracy), and further enhances accuracy in analysis of multiple contributor samples. Other embodiments can also estimate a number of contributors within a sample based on differences in PCR amplification strength for different STR loci. Improvements based on resolving amplification strength result in greater increases in identification accuracy. For example, estimates of a number of contributors to a given sample enables greater precision in the application of error profiles—not to mention the implication for criminal investigation and knowing a specific number of contributors.

Still other aspects relate to implementing STR sequencing to improve matching of individuals to sample mixtures over conventional approaches. For example, conventional implementations match individuals to sample mixtures based on STR names and allele length matching. Various embodiments extend multi-contributor analysis further, via integration of machine learning approaches to predict the numbers of contributors in a sample based on one or both of STR and SNP profiles.

According to one aspect, a DNA analysis system is provided. The system comprising at least one processor operatively connected to a memory, a receiver component configured to receive DNA analysis information including locus and allele read information generated from PCR amplification of DNA in a DNA sample, an analysis component, executed by the at least one processor, configured to: identify a first error profile associated with a first DNA locus and evaluate the locus and allele read information against the first error profile to determine an adjusted read threshold, confirm presence of the first locus and allele in the DNA sample, responsive to the confirmed presence of the first locus and allele information adjust error analysis of at least a second allele or at least a second locus to account for amplification error reads of the confirmed first locus and allele in the DNA sample, and determine for each respective locus and allele associated with read data obtained from the DNA sample whether a total number of reads from the DNA sample exceeds an error profile adjusted threshold, and for each confirmation or exclusion of read data adjust the threshold based on the confirmation or exclusion.

According to one embodiment, the analysis component is further configured to generate, by the least one processor, an identification profile for at least one individual within the DNA sample comprising each confirmed locus and alleles for the at least one individual.

According to one embodiment, the receiver component further comprises a physical DNA sample receiver and PCR analysis element for generating read information for respective loci and alleles. According to one embodiment, the error profile for the first locus and allele includes calculations of different threshold adjustments according to PCR amplification cycles executed on the sample. According to one embodiment, the error profile includes calculations for a number of reads associated with at least −1 stutter allele, a +1 stutter allele, and a −2 stutter allele, wherein the calculations are adjusted by the analysis component to a number of PCR amplification cycles.

According to one embodiment, the analysis component is further configured to determine whether the total number of reads from the sample exceeds the error profile adjusted threshold based on a combined error read count derived from stutter alleles from at least a first and second allele. According to one embodiment, the analysis component is further configured to determine the total number of reads from the sample exceeds the error profile adjusted threshold based on a combined error read count derived from stutter alleles from at least a first, second, and third allele. According to one embodiment, the analysis component is further configured to identify PCR products from the sample for sequencing. According to one embodiment, the analysis component is further configured to evaluate confirmed alleles to determine information on a respective dominant −1 stutter allele and identify PCR products from the sample from sequencing based on the properties of the respective dominant −1 stutter allele. According to one embodiment, the analysis component is further configured to update confirmed allele information responsive to reducing reads counts for each dominant −1 stutter allele identified based on sequencing.

According to one aspect, a computer implemented method for DNA analysis is provided. The method comprises receiving, by at least one processor, DNA analysis information including locus and allele read information generated from PCR amplification of DNA in a DNA sample, identifying, by the at least one processor, a first error profile associated with a first DNA locus and evaluating, by the at least one processor, the locus and allele read information against the first error profile to determine an adjusted read threshold, confirming, by the at least one processor, a presence of the first locus and allele in the DNA sample, responsive to the confirmed presence of the first locus and allele information adjusting, by the at least one processor, error analysis of at least a second allele or at least a second locus to account for amplification error reads of the confirmed first locus and allele in the DNA sample, and determining, by the at least one processor, for each respective locus and allele associated with read data obtained from the DNA sample whether a total number of reads from the DNA sample exceeds an error profile adjusted threshold, and for each confirmation or exclusion of read data adjusting, by the at least processor, the threshold based on the confirmation or exclusion.

According to one embodiment, the method further comprises generating, by the least one processor, an identification profile for at least one individual within the DNA sample comprising each confirmed locus and allele for the at least one individual. According to one embodiment, receiving includes receiving information from a physical DNA sample receiver and PCR analysis element for generating read information for respective loci and alleles. According to one embodiment, wherein the error profile for the first locus and allele includes calculations of different threshold adjustments according to PCR amplification cycles executed on the sample.

According to one embodiment, wherein the error profile includes calculations for a number of reads associated with at least −1 stutter allele, a +1 stutter allele, and a −2 stutter allele, wherein the calculations are adjusted by the analysis component to a number of PCR amplification cycles.

According to one embodiment, the method further comprises determining whether the total number of reads from the sample exceeds the error profile adjusted threshold based on a combined error read count derived from stutter alleles from at least a first and second allele. According to one embodiment, the method further comprises determining the total number of reads from the sample exceeds the error profile adjusted threshold based on a combined error read count derived from stutter alleles from at least a first, second, and third allele. According to one embodiment, the method further comprises identifying PCR products from the sample for sequencing. According to one embodiment, the method further comprises evaluating confirmed alleles to determine information on a respective dominant −1 stutter allele and identify PCR products from the sample from sequencing based on the properties of the respective dominant −1 stutter allele.

According to one embodiment, the method further comprises updating confirmed allele information responsive to reducing reads counts for each dominant −1 stutter allele identified based on sequencing.

According to one aspect, a DNA analysis system is provided. The system comprises at least one processor operatively connected to a memory, a receiver component configured to receive DNA analysis information including locus and allele read information generated from PCR amplification analysis of DNA in a DNA sample, an analysis component, executed by the at least one processor, configured to evaluate a dominant stutter allele associated with at least a first DNA locus and allele of the first DNA locus based on DNA sequencing of at a least a portion of the DNA sample, confirm the read information matches the dominant −1 stutter allele for a first contributor based on matching the dominant −1 stutter allele sequence to sequence information obtained from the DNA sample, eliminate the read information associated with the dominant−1 stutter allele, confirm presence of the first locus and allele in the DNA sample based on the read information with the dominant stutter allele removed, determine for each respective locus and allele associated with read data from the sample whether a total number of reads from the sample exceeds a threshold, and generate, by the least one processor, an identification profile for at least one individual within the DNA sample comprising each confirmed locus and allele for the at least one individual.

According to one embodiment, the analysis component is further configured to identify a first error profile associated with a first DNA locus and evaluate the locus and allele read information against the first error profile to determine an adjusted read threshold; and confirm presence of the first locus and allele in the sample based on the adjusted threshold and any dominant stutter allele reads removed. According to one embodiment, the analysis component is further configured to: adjust error analysis of at least a second allele or at least a second locus to account for amplification error reads of the confirmed first locus and allele in the sample responsive to the confirmed presence of the first locus and allele information, determine for each respective locus and allele associated with read data from the sample whether a total number of reads from the sample exceeds an error profile adjusted threshold, and for each confirmation or exclusion of read data adjust the threshold based on the confirmation or exclusion; and generate, by the least one processor, an identification profile for at least one individual within the DNA sample comprising each confirmed locus and allele for the at least one individual.

According to one embodiment, the analysis component is further configured to adjust error analysis of at least a second allele or at least a second locus to account for amplification error reads of the confirmed first locus and allele in the sample responsive to the confirmed presence of the first locus and allele information.

According to one aspect, a computer implemented method for DNA analysis is provided. The method comprises receiving, by at least one processor, DNA analysis information including locus and allele read information generated from PCR amplification analysis of DNA in a DNA sample, evaluating, by the at least one processor, a dominant stutter allele associated with at least a first DNA locus and allele of the first DNA locus based on DNA sequencing of at a least a portion of the DNA sample, confirming, by the at least one processor, the read information matches the dominant −1 stutter allele for a first contributor based on matching the dominant −1 stutter allele sequence to sequence information obtained from the DNA sample, eliminating, by the at least one processor, the read information associated with the dominant −1 stutter allele, confirming, by the at least processor, presence of the first locus and allele in the DNA sample based on the read information with the dominant stutter allele removed, determining, by the at least one processor, for each respective locus and allele associated with read data from the sample whether a total number of reads from the sample exceeds a threshold, and generating, by the least one processor, an identification profile for at least one individual within the DNA sample comprising each confirmed locus and allele for the at least one individual.

According to one embodiment, the method further comprises identifying a first error profile associated with a first DNA locus and evaluate the locus and allele read information against the first error profile to determine an adjusted read threshold; and confirming presence of the first locus and allele in the sample based on the adjusted threshold and any dominant stutter allele reads removed. According to one embodiment, the method further comprises adjusting error analysis of at least a second allele or at least a second locus to account for amplification error reads of the confirmed first locus and allele in the sample responsive to the confirmed presence of the first locus and allele information, determining for each respective locus and allele associated with read data from the sample whether a total number of reads from the sample exceeds an error profile adjusted threshold, and for each confirmation or exclusion of read data adjust the threshold based on the confirmation or exclusion; and generating, by the least one processor, an identification profile for at least one individual within the DNA sample comprising each confirmed locus and allele for the at least one individual.

According to one embodiment, the method further comprises adjusting error analysis of at least a second allele or at least a second locus to account for amplification error reads of the confirmed first locus and allele in the sample responsive to the confirmed presence of the first locus and allele information.

According to one aspect, a DNA analysis system is provided. The system comprising at least one processor operatively connected to a memory, a receiver component configured to receive DNA analysis information including locus and allele read information generated from PCR amplification of DNA in a multiple DNA contributor sample, an analysis component, executed by the at least one processor, configured to: compare a first contributor DNA sample to the multiple DNA contributor sample, determine absence or presence of the first contributor DNA sample in the multiple DNA contributor sample, and apply an amplification strength model to improve determination accuracy for the absence or presence of the first contributor DNA sample within the multiple contributor sample.

According to one embodiment, the analysis component is further configured match a plurality of strongest amplification strength alleles to determine possible presence of the first contributor. According to one embodiment, the analysis component is further configured exclude a plurality of weakest amplification strength alleles to determine possible presence of the first contributor. According to one embodiment, the analysis component is further configured to determine an absence of a plurality of strongest amplification strength alleles to determine the absence of the first contributor in the multiple DNA contributor sample.

According to one aspect, a computer implemented DNA analysis method is provided. The method comprises receiving, by at least one processor, DNA analysis information including locus and allele read information generated from PCR amplification of DNA in a multiple DNA contributor sample, comparing, by the at least one processor, a first contributor DNA sample to the multiple DNA contributor sample, determining, by the at least one processor, absence or presence of the first contributor DNA sample in the multiple DNA contributor sample, and applying, by the at least one processor, an amplification strength model to improve determination accuracy for the absence or presence of the first contributor DNA sample within the multiple contributor sample.

According to one embodiment, the method further comprises matching, by the at least one processor, a plurality of strongest amplification strength alleles to determine possible presence of the first contributor. According to one embodiment, the method further comprises excluding a plurality of weakest amplification strength alleles to determine possible presence of the first contributor. According to one embodiment, the method further comprises determining an absence of a plurality of strongest amplification strength alleles to determine the absence of the first contributor in the multiple DNA contributor sample.

Some aspects provide for methods comprising using at least one computer hardware processor to perform: receiving sequence information obtained from a nucleic acid sample, wherein the sequence information comprises a plurality of genetic loci, the plurality of genetic loci including a first genetic locus; generating, based on the received sequence information, an encoding for the nucleic acid sample at least in part by encoding the first genetic locus using a first value when the first genetic locus is homozygous for a major allele and using a second value different from the first value when the first genetic locus is not homozygous for the major allele; comparing the generated encoding of the nucleic acid sample with a plurality of previously-generated encodings for a respective plurality of nucleic acid samples; and when it is determined that, as a result of the comparing, the generated encoding of the nucleic acid sample matches at least one encoding in the plurality of previously-generated encodings, the at least one encoding being associated with at least one person, providing an indication that the nucleic acid sample is consistent with the at least one person.

In some embodiments, generating the encoding comprises generating a lossy encoding. In some embodiments, generating the encoding comprises generating a binary encoding. In some embodiments, the first value is a binary value. In some embodiments, the first value consists of a first bit and the second value consists of a second bit different from the first bit. In some embodiments, the first bit is zero.

In some embodiments, the received sequence information obtained from the nucleic acid sample consists of sequence information for only one person. In some embodiments, the received sequence information obtained from the nucleic acid sample consists of sequence information for more than one person.

In some embodiments, when the generated encoding of the nucleic acid sample matches two different encodings in the plurality of previously-generated encodings, the two different encodings being associated with two different people, the method further comprises providing an indication that the nucleic acid sample is consistent with the two different people.

In some embodiments, generating the encoding comprises using the second value when the first genetic locus is homozygous for a minor allele or the first genetic locus is heterozygous. In some embodiments, the presence of the second value in the generated encoding indicates a presence of a single nucleotide polymorphism (SNP) at the first genetic locus. In some embodiments, the generating further comprises encoding each of the plurality of genetic loci using the first value or the second value. In some embodiments, the comparing is performed using bitwise instructions native to the at least one computer hardware processor executing the method.

Some aspects provide for a system comprising: at least one database storing a plurality of encodings for a respective plurality of nucleic acid samples; at least one computer hardware processor; at least one non-transitory computer-readable storage medium storing processor-executable instructions that, when executed by the at least one computer hardware processor, cause the at least one computer hardware processor to perform: receiving sequence information obtained from a nucleic acid sample, wherein the sequence information comprises a plurality of genetic loci, the plurality of genetic loci including a first genetic locus; generating, based on the received sequence information, an encoding for the nucleic acid sample at least in part by encoding the first genetic locus using a first value when the first genetic locus is homozygous for a major allele and using a second value different from the first value when the first genetic locus is not homozygous for the major allele; comparing the generated encoding of the nucleic acid sample with the plurality of encodings stored in the at least one database; and when it is determined that, as a result of the comparing, the generated encoding of the nucleic acid sample matches at least one encoding in the plurality of encodings stored in the at least one database, the at least one encoding being associated with at least one person, providing an indication that the nucleic acid sample is consistent with the at least one person.

In some embodiments, the at least one computer hardware processor is configured to perform a plurality of native bitwise instructions. In some embodiments, native bitwise instructions include a population count bitwise instruction, an "XOR" bitwise instruction, and an "AND" bitwise instruction. Additionally or alternatively, native bitwise instructions include a bitwise OR instruction, a bitwise NAND instruction, a bitwise NOT instruction, an arithmetic shift instruction, a logical shift instruction, a circular shift instruction, and/or any other suitable bitwise instructions that the at least one computer hardware processor is configured to execute, as aspects of the technology described herein are not limited in this respect.

Some aspects provide for methods comprising using at least one computer hardware processor to perform: receiving sequence information obtained from a nucleic acid sample, wherein the sequence information comprises at least one short tandem repeat (STR) locus, the at least one STR locus comprising a unit of nucleotides repeated a number of times; generating, based on the received sequence information, an encoding for the nucleic acid sample at least in part by encoding the at least one STR locus using a value that corresponds to the number of times the unit of nucleotides is repeated; comparing the generated encoding of the nucleic acid sample with a plurality of previously-generated encodings for a respective plurality of nucleic acid samples; and when it is determined that, as a result of the comparing, the generated encoding of the nucleic acid sample matches at least one encoding in the plurality of previously-generated encodings, the at least one encoding being associated with at least one person, providing an indication that the nucleic acid sample is consistent with the at least one person.

In some embodiments, the encoding comprises generating a lossy encoding. In some embodiments, the encoding comprises generating a binary encoding. In some embodiments, the value is a binary value. In some embodiments, the value consists of 1 bit, between 1-3 bits, between 2-4 bits, between 3-5 bits, between 4-6 bits, between 5-7 bits, between 6-8 bits, between 7-9 bits, between 8-10 bits, 10 bits, or more than 10 bits. In some embodiments, the value consists of 5 bits. In some embodiments, the value directly corresponds to the absolute number of times the unit of nucleotides is repeated. In some embodiments, the value is one of between 2-30 possible values. In some embodiments, the value is one of between 5-25 possible values. In some embodiments, the value is one of around 20 possible values.

In some embodiments, the received sequence information obtained from the nucleic acid sample consists of sequence information for only one person. In some embodiments, the received sequence information obtained from the nucleic acid sample consists of sequence information for more than one person. In some embodiments, when the generated encoding of the nucleic acid sample matches two different encodings in the plurality of previously-generated encodings, the two different encodings being associated with two different people, the method further comprises providing an indication that the nucleic acid sample is consistent with the two different people.

In some embodiments, the generating comprises encoding at least two STR loci. In some embodiments, the at least one STR locus is selected from D3S1358, vWA, FGA, D8S1179, D21S11, D18S51, D5S818, D13S317, D7S820, D16S539, THO1, TPDX, CSF1PO, AMEL, D1S1656, D2S441, D2S1338, D 10S1248, D125391, D19S433. D22S1045, or any other STR loci In some embodiments, the comparing is performed using bitwise instructions native to the at least one computer hardware processor executing the method.

Some aspects provide for a system comprising: at least one database storing a plurality of encodings for a respective plurality of nucleic acid samples; at least one computer hardware processor; at least one non-transitory computer-readable storage medium storing processor-executable instructions that, when executed by the at least one computer hardware processor, cause the at least one computer hardware processor to perform: receiving sequence information obtained from a nucleic acid sample, wherein the sequence information comprises at least one short tandem repeat (STR) locus, the at least one STR locus comprising a unit of nucleotides repeated a number of times; generating, based on the received sequence information, an encoding for the nucleic acid sample at least in part by encoding the at least one STR locus using a value that corresponds to the number of times the unit of nucleotides is repeated; comparing the generated encoding of the nucleic acid sample with a plurality of previously-generated encodings for a respective plurality of nucleic acid samples; and when it is determined that, as a result of the comparing, the generated encoding of the nucleic acid sample matches at least one encoding in the plurality of previously-generated encodings, the at least one encoding being associated with at least one person, providing an indication that the nucleic acid sample is consistent with the at least one person.

In some embodiments, the at least one computer hardware processor is configured to perform a plurality of native bitwise instructions. In some embodiments, native bitwise instructions include a population count bitwise instruction, an "XOR" bitwise instruction, and an "AND" bitwise instruction. Additionally or alternatively, native bitwise instructions include a bitwise OR instruction, a bitwise NAND instruction, a bitwise NOT instruction, an arithmetic shift instruction, a logical shift instruction, a circular shift instruction, and/or any other suitable bitwise instructions that the at least one computer hardware processor is configured to execute, as aspects of the technology described herein are not limited in this respect.

In some aspects, techniques described herein can be used to determine kinship of one or more samples.

Further, other aspects relate to determining individuals from complex mixtures. As discussed, DNA forensics is a common tool used within law enforcement and US intelligence agencies to identify unknown suspects and to accurately link crime scene evidence to criminal perpetrators. Crime scene evidence often contains DNA from multiple people however, confounding current DNA analysis techniques.

At present, the forensics community uniquely identifies individual DNA samples through extraction of short tandem repeats (STRs) and determination of mitochondrial DNA (mtDNA) sequences. Capillary electrophoresis is often used to quantify SIR lengths and mtDNA sequences. This methodology has been proven accurate for individual profile identification. However, if a given reference DNA profile is contained within a complex DNA mixture, identifying an individual profile is difficult and sometimes impossible using this methodology.

Thus, the ability to build individual profiles from a complex mixture and the direct deconvolution of a mixture into candidate and/or individual component DNA signatures are unmet needs.

To address these unmet needs, the methods of the disclosure provide a system to confirm the co-occurrence of individual DNA profiles from unknown individuals in one or more complex mixtures of DNA signatures and to build individual DNA profiles for unknown individuals from analysis of one or more complex DNA mixtures. By using a panel of between several hundred to tens of thousands of genetic markers, e.g. Single Nucleotide Polymorphism (SNPs), the methods of the disclosure may be used to build an individual profile. Moreover, by finding the intersection, or overlapping population, of genetic markers across multiple DNA mixtures, the methods of the disclosure produce a DNA SNP profile unique to the common contributors to the mixtures. The preferred genetic markers used in the methods of the disclosure include SNPs.

Methods of the disclosure provide superior properties over the existing methods of building and deconvoluting DNA profiles in a forensic setting, however, applications for the methods described herein are not confined to the context of a forensic or crime scene investigation. For example, the methods of the disclosure may be used for medical diagnosis and/or prognosis. In the field of cancer, biopsy samples often contain many cell types, of which a small proportion may form any part of a tumor. Consequently, DNA obtained from tumor biopsies is another form of complex DNA mixture. Moreover, within a tumor, the multitude of cells may be molecularly distinct with respect to the expression of factors indicating or facilitating, for example, vascularization and/or metastasis. A DNA mixture obtained from a tumor sample may also form a complex DNA mixture of the disclosure. In both of these non-limiting examples, the methods of the disclosure may be used to build individual profiles for each cell or cell type that contributes to the complex DNA mixture. Moreover, the methods of the disclosure may be used to deconvolute contributors to a complex DNA mixture. For instance, a complex DNA mixture obtained from a breast cancer tumor biopsy may be used to build an individual profile of the malignant cells. In the same patient, a brain cancer tumor biopsy, this individual profile may be used to deconvolute the contributors to the complex DNA mixture obtained from the brain cancer tumor biopsy to determine, for instance, if a malignant breast cancer cell from that subject metastasized to the brain to form a secondary tumor. This method would resolve a question as to whether the tumors arose independently, or, on the other hand, if these tumors are related.

Of significance to the methods to the disclosure, the ability of these methods to either build an individual DNA profile or to deconvolute complex DNA mixtures into component profiles does not require any prior knowledge of the components. For example, the methods described herein are effective to either build an individual DNA profile or to deconvolute complex DNA mixtures into component profiles without any knowledge of genetic markers or DNA sequences belonging to any individual or component that contributes to any one of the complex DNA mixtures. Thus, one of the superior properties of the methods of the disclosure is that the methods do not require any prior knowledge or data regarding individual profiles, contributors, or components of a complex DNA mixture.

The disclosure provides a SNP panel comprising one, two, or more loci of a single-nucleotide polymorphism (SNP) having at least one of: (a) a low fixation index (FST); (b) a low minor allele frequency (mAF) value or a low average heterozygosity value; and (c) a minimal distance between loci (e.g., a minimum recommended distance of at least 100,000 nucleic acid bases) when present within a single chromosome. In certain embodiments of the SNP panels of the disclosure, a low FST may indicate that the minor allele of the SNP has no statistically significant correlation with ancestry. In certain embodiments, a low FST is less than 0.06. In certain embodiments of the SNP panels of the disclosure, a low mAF and/or a low average heterozygosity value may indicate that the minor allele is rare in a population. In certain embodiments, a low mAF is a value between 0.01 and 0.3 or between 0.03 and 0.07 or between 0.01 and 0.06, inclusive of the endpoints for each range. A value of average heterozygosity may be calculated or derived from information provided by the Short Genetic Variations database (dbSNP)(also referred to herein as dbSNP), a publicly-available, free resource overseen by the National Center for Biotechnology Information (NCBI), a division of the National Institutes of Health (NIH). dbSNP may be accessed at www.ncbi.mnlm.nih.gov. Other sources may be used, such as the 1,000 genomes project. Links to heterozygosity from the dbSNP page provide detailed methods for the computation of average heterozygosity from variation data submitted for SNPs by members (sec, for example, www.ncbi.nlm.nih.gov/SNP/Hetfreq.html). In certain embodiments of the SNP panels and methods of the disclosure, a value of average heterozygosity may either be obtained from public databases (e.g. dbSNP) or independently calculated from the raw data provided by this database or other sources of SNP information. In certain embodiments of the SNP panels of the disclosure, the value of average heterozygosity may be between 0.058 and 0.13, inclusive of the endpoints. In certain embodiments of the SNP panels of the disclosure, the minimal distance between loci is, in one example implementation, at least 500,000 nucleic acid bases when present within a single chromosome.

In certain embodiments, the disclosure provides a SNP panel comprising one, two, or more loci of a single-nucleotide polymorphism (SNP) having at least two of: (a) a low fixation index (FST); (b) a low minor allele frequency (mAF) value or a low average heterozygosity value; and (c) a minimal distance between loci of at least 100,000 nucleic acid bases (or as close as 50,000 nucleic acid bases) when present within a single chromosome.

In certain embodiments, the disclosure provides a SNP panel comprising one, two, or more loci of a single-nucleotide polymorphisms (SNPs) having: (a) a low fixation index (FST); (b) a low minor allele frequency (mAF) value or a low average heterozygosity value; and (c) a minimal distance between loci of at least 100,000 nucleic acid bases when present within a single chromosome.

The disclosure also provides a SNP panel comprising one, two, or more loci of a single-nucleotide polymorphisms (SNPs) selected according to any method of the disclosure.

The disclosure provides methods for selecting one, two, or more loci of a single-nucleotide polymorphisms (SNPs) for inclusion in a SNP panel comprising selecting one, two, or more loci having at least one of: (a) no statistically significant correlation of a minor allele of the SNP with ancestry; (b) a low minor allele frequency (mAF) value or a low average heterozygosity value; and (c) a minimal distance between loci of at least 100,000 nucleic acid bases when present within a single chromosome; and eliminating one or more loci that: (d) generate data from only one strand of DNA; (e) produce a result that contradicts a relationship from a known family tree; and/or (f) have a minor allele ratio outside of expected values from a known reference sample. In certain embodiments, the method may further comprise eliminating one or more loci that produce results that could not be verified when compared to a known family tree. In certain embodiments of this method, loci are chosen that produce data that are strongly indicative of an individual's genotype, with minor allele ratios from an individual reference samples of approximately 0, 0.5, or 1.0. For example, for the OptMix panel used herein, ambiguous was defined as mAF>0.0025 and <0.4 (or 0.6->0.9975). In addition, a locus preferably is not selected for (or is eliminated from) a panel if the locus gives few reads (<10% of average total number of calls); gives impossible calls (conflicting with homozygous parents); produces biased data from one DNA strand (>9:1 ratio); or is a locus for which the major allele is never observed. Other analytical thresholds can be used to classify major, major:minor, and minor:minor alleles in reference samples and DNA mixtures.

As used in the context of the expected value of a minor allele ratio from a known reference sample, the term approximately includes the expected value of 0, 0.5, or 1.0 with a range below or above these expected values to account for variability (e.g. statistical noise) within the data and/or statistical analysis.

In certain embodiments, this method may further comprise calculating a fixation index (FST) for each locus, wherein a low FST indicates that the minor allele of the SNP correlates poorly with ancestry. In certain embodiments, a low FST is less than 0.06. The FST may be determined by any number of methods, including, for example. utilizing the ALlele FREquency Database (ALFRED). In certain embodiments, this method may further comprise calculating a minor allele frequency (mAF) for each locus, wherein a low mAF indicates that the minor allele is rare in a population. In certain embodiments, a low mAF is a value between 0.01 and 0.3 or between 0.03 and 0.07 or between 0.01 and 0.06, inclusive of the endpoints for each range. In certain embodiments, this method may further comprise calculating a value of average heterozygosity for each locus, wherein a low average heterozygosity value indicates that the minor allele of the SNP is rare in a population. In certain embodiments, the value of average heterozygosity may be calculated or derived from information provided by dbSNP. In certain embodiments, the value of average heterozygosity may be between 0.058 and 0.13, inclusive of the endpoints. In certain embodiments of this method, the minimal distance between loci is at least 500,000 nucleic acid bases when present within a single chromosome. In certain embodiments, a locus may contain more than one SNP.

The disclosure provides methods for selecting one, two, or more loci having at least two of: (a) a poor correlation of the SNP allele with ancestry; (b) a low minor allele frequency (mAF) value or a low average heterozygosity value; and (c) a minimal distance between loci of at least 100,000 nucleic acid bases when present within a single chromosome.

The disclosure provides methods for selecting one, two, or more loci having: (a) a poor correlation of a minor allele of the SNP with ancestry; (b) a low minor allele frequency (mAF) value or a low average heterozygosity value; and (c) a minimal distance between loci of at least 100,000 nucleic acid bases when present within a single chromosome.

The disclosure provides methods for building an individual DNA profile from one, two, or more complex DNA mixtures comprising the steps of: (a) determining the presence of at least one minor SNP allele from a SNP panel in a first complex DNA mixture; (b) determining the presence of at least one minor SNP allele in a second complex DNA mixture; (c) identifying a common set of minor alleles present in the first and second complex mixtures, wherein the occurrence of a common set of minor alleles indicates the presence of a common individual contributor or subset of contributors to each of the first and the second complex mixtures; and (d) assembling all common minor alleles identified in (c) to generate an individual DNA profile, thereby building an individual DNA profile of a shared contributor or contributors to one, two, or more complex DNA mixtures. In certain embodiments of this method, the method involves building an individual genetic profile from one, two, or more samples containing complex DNA mixtures comprising the steps of: (a) determining the presence of at least one minor SNP allele from the SNP panel of the disclosure in a first complex DNA mixture, represented by the numeric value 1 at the position for that SNP in a vector over all loci; (b) determining the presence of at least one minor SNP allele in a second complex DNA mixture, represented by the numeric value 1 at the position for that SNP in a vector over all loci and 0 for major alleles; (c) identifying any common minor alleles present in the first and second complex mixtures represented by the numeric value 1 in a vector for each mixture, wherein the occurrence of a common minor allele indicates the presence of a common individual contributor to each of the first and the second complex mixtures and; (d) assembling all common minor alleles identified in (c) to generate an individual DNA profile via a multiplication of the two vectors in (a) and (b); thereby building an individual DNA profile from one, two, or more complex DNA mixtures, represented by the vector of 1 over all loci. Optionally, this embodiment may further comprise (e) isolating the summed DNA profiles from non-common contributors from the original samples by subtracting the derived profile generated in (d) from the samples in (a) and (b). In certain embodiments, the one, two, or more complex DNA mixtures are at least 3, 4, 5, 6, 7, 8, 9, 10, 11, 12. 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165,1 66, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, or more complex DNA mixtures, up to and including millions of complex DNA mixtures. In theory and in practice, there is no maximum or limit on the number of complex DNA mixtures that this method can use to build an individual DNA profile or the DNA profile of a group of individuals. Importantly, the accuracy and/or specificity of the individual DNA profile or the DNA profile of a group of individuals increases as the number of complex mixtures increases. In certain embodiments of this method, one, two, or more complex DNA mixtures are obtained from a crime and/or forensic kit and/or laboratory. In certain embodiments of this method, one, two, or more complex DNA mixtures are obtained from a medical or biological sample or a genetically heterogeneous medical or biological sample. The SNP panel used for this method, as well as any method of the disclosure, may be any SNP panel described by the disclosure. For example, the SNP panel comprises one, two, or more loci of a single-nucleotide polymorphism (SNP) having at least one of: (a) a low fixation index (FST); (b) a low minor allele frequency (mAF) value or a low average heterozygosity value; and (c) a minimal distance between loci of at least 100,000 nucleic acid bases when present within a single chromosome, wherein the one, two, or more loci of a SNP are selected for those loci that predict or correlate with the occurrence and/or development of a biological condition or disease. Alternatively, or in addition, SNP panels of the disclosure, including those used for this method, may include SNPs from established panels and those SNPs that predict a biological disease or condition. Moreover, the SNP panels of the disclosure, including those used for this method, may include SNPs that are particularly enriched in a particular population due to any number of factors including shared geographic and/or cultural proximity and/or isolation.

The disclosure provides a method for resolving a DNA profile for a major and/or a minor contributor from a complex DNA mixture comprising the steps of: (a) amplifying a sequence containing at least one minor SNP allele from a SNP panel of the disclosure in the complex DNA mixture using a quantitative amplification method; (b) optionally, contacting the resultant amplification product with a detectable label, wherein each sequence containing a distinct minor SNP allele contacts a distinct detectable label; (c) detecting a signal from each of the resultant amplification products; (d) comparing the signal amplitude between amplification products, wherein the signal amplitude of a minor-allele-containing sequence provided by a major contributor is greater than the signal amplitude of a minor-allele-containing sequence provided by a minor contributor, and (e) assembling the minor allele sequences having a low signal amplitude into a DNA profile to identify a minor contributor to the complex DNA mixture, and/or (f) assembling the sequences having a high signal amplitude into a second DNA profile to identify a major contributor to the complex DNA mixture, thereby resolving separate DNA profiles for a major and/or a minor contributor from a single analysis of a non-equimolar DNA mixture. As an alternative, resolving a DNA profile for a major and/or a minor contributor from a complex DNA mixture comprises the steps of: sequencing the DNA, and counting the number of sequence reads for each allele.

In certain embodiments of the methods of the disclosure, the single multi-contributor DNA mixture may be obtained from a laboratory or forensic laboratory. In certain embodiments, the major or minor contributor is a victim of a crime. Alternatively, or in addition, the major or minor contributor is a perpetrator of a crime.

In certain embodiments of the methods of the disclosure, the complex DNA mixture may be obtained from a biopsy, a medical examination or a medical laboratory. In certain embodiments of the methods of the disclosure, the complex DNA mixture may analyzed to resolve the major and/or minor contributors to the mixture in the context of any biological condition or disease. For example, when used to resolve contributors to a biopsy sample obtained from a cancer patient, the major or minor contributor may a benign cell or tissue. Alternatively, or in addition, the major or minor contributor is a cancerous cell or tissue.

In certain embodiments of the methods of the disclosure, the percentage of DNA in the complex DNA mixture provided by a minor contributor may be between 0.001 (and lower) and 49.9 percent of total DNA. Importantly, this method can resolve a DNA profile of a minor contributor to a complex DNA mixture when the percentage of DNA attributable to that minor contributor is as minimal as between >0 and 1 percent of total DNA. As the number of contributors to a complex DNA mixture increases, the resolution of the method of deconvoluting the individual contributors decreases. Thus, this method may be use to resolve a DNA profile of an individual contributor to a complex DNA mixture when the percentage of DNA attributable to that individual contributor is less than 0.001 percent of the total DNA. In certain aspects of this method, the accuracy or efficacy of the method increases as (a) an amount of total DNA contained in the complex DNA mixture increases; and/or (b) a greater number of loci from a SNP panel of the disclosure are analyzed and/or (c) the accuracy of the ability to measure DNA improves.

In certain embodiments of the SNP panels and methods of the disclosure, contemplated populations may comprise or consist of a plurality of individuals and/or data obtained from a database. The individuals of these populations may share common features, including, but not limited to, age, gender, race, ethnicity, geography, medical condition or predisposition, inherited or novel genetic traits, and/or circumstance. For example, the individuals of these populations may share the common feature of having been diagnosed or having survived cancer. In other embodiments, the individuals of these populations may have been involved in the same event (e.g. crime and/or present at a crime scene) or be associated with that event through physical proximity and/or social/familial relationship.

Various embodiments relate, either alone or in combination with other embodiments which include:

Resolving Individual Contributions to Complex DNA Mixtures

A Venn method is provided which can be used to determine individual contributors' DNP profiles from direct comparison of complex DNA mixtures without a known reference sample. There are no known methods for directly deconvolving a DNA SNP mixture into individual profiles or sub-profiles without reference profiles. The Venn method identifies individual sub-profiles my identifying common major and minor alleles across two or more DNA mixtures. The Venn method can resolve the identity of individual contributors to DNA mixtures when the DNA profile is not known by intersecting the observed SNP profiles of two or more DNA mixtures using Venn logic on SNP alleles.

Plateau Method

A plateau method is provided to build individual sub-profiles directly from complex mixtures without known reference profiles. In some embodiments, a Plateau method is provided for directly deconvolving a single mixture into individual sub-profiles by leveraging differences in DNA concentrations of contributors to DNA mixtures. The Plateau method identifies individual sub-profiles directly from complex mixtures without known reference profiles by leveraging differences in DNA concentrations of individuals (e.g., direct mixture deconvolution) using SNP allele minor allele ratios (mAR) or minor allele counts (mAC) to assign minor alleles to different DNA contributors to the mixture.

Forensic DNA Sample and Mixture Comparison Methods

In some embodiments, Fast Identification and Mixture Analysis for SNP or STR profiles is provided using bit encode alleles combined with hardware XOR, AND, and population count instructions—FastID & FastSTR. In some implementations, high performance parallelization is possible on graphics processing units (GPUs). As the number of STR and SNP loci increases, the time complexity of searching large databases of reference profiles and mixtures also increases. Scaling up from 20 loci to 20,000 loci is 1,000 times more comparisons. The FastID and TachysSTR methods enable high performance comparison of SNP or STR profiles for reference profiles or mixture profiles against a very large set of millions of reference profiles using bit encoding of alleles and hardware XOR, AND, and population count instructions. Millions of profile comparisons can be done in seconds using a single computational thread on modern computers. Parallelization of comparisons is possible for large volume comparisons using graphical processing units (GPUs).

STRs Analysis Methods

In some embodiments, new STR analysis methods are provided including:
  Novel STR allele identification versus stutter artifacts leveraging comparison on STR sequences to identify STR alleles that are not stutter artifacts of nearby alleles
  Learning STR stutter sequences to classify HTS STR data—create database of observed (−1) and (+1) stutter sequences from reference profiles
  STR mixture analysis leveraging loci amplification levels—higher precision of results if exclude weakly amplifying STR loci
  Estimating relative contributions of DNA in STR mixtures—proportion of DNA contributed to mixture for each individual
  STR allele matching versus matching on size or name—mixture analysis results are improved if STR allele sequences are used rather than STR allele sizes or names
  Estimating number of contributors to STR mixtures with machine learning methods
  Estimating number of contributors to SNP mixtures with machine learning methods A method of analyzing sequence data from a biological sample that contains DNA comprised of the steps:
  Sample identification by optional DNA barcode enabling demultiplexing of multiple samples within a sequence dataset;
  Identification of source genome source locus by using flanking sequences of short tandem repeats (STRs);
    Determining the correct flanking sequences of STR alleles with DNA sequence reads is essential for correct allele identification;
  Identification of SNP and STR variants in flanking sequences can differentiate between individuals and enables higher precision matching of allele contributions to DNA mixtures with two or more individual contributors;
  Tallying observed variants for multiple STR loci for multiplexed samples with variants in flanking sequences for individual reference samples and DNA mixtures with contributions from two or more individuals;
  Identification of imbalances in DNA sequence reads for each DNA strand, known as strand bias, can be optionally used in data filtering of results;
  Identification of DNA polymerase stutter alleles from reference samples to identify dominant −1 and +1 stutter alleles to create a library or database of likely stutter allele sequences;
    Prediction of −2, −3, and +2 stutter alleles by recursively applying the −1 and +1 stutter losses or gain of STR unit to the observed STR stutter sequence;
    Prediction of −1, −2, −3, +1, and +2 stutter alleles by incrementally decreasing of increasing the largest subscript in a STR sequence—e.g., a $(ATAT)_2$ $(ATAG)_{10}$ STR allele would have a predicted −1 stutter allele of $(ATAT)_2(ATAG)_9$, etc.

Identification of contributed STR alleles to DNA mixtures as observed STR allele sequences that are inconsistent with being likely stutter alleles of other contributed STR alleles with unit differences in STR unit lengths that can obscure contributed STR alleles with possible stutter alleles;

Example, if a STR allele is observed with high number of read counts with two or more candidate STR alleles consistent with being −1 stutter alleles, then only one of the −1 alleles is likely, the stutter allele (and not two or more) with the remaining STR alleles having a high probability of deriving from individual contributors;

STR alleles with read counts larger than expected proportional STR stutter allele rate have a high probability of being STR alleles contributed by an individual and not stutter artifacts (e.g., if the −2 allele count is higher than the −1 allele count at a locus, then the −2 allele has a high probability of being an allele from an individual;

Poorly amplifying STR amplicons are a primary source of dropped alleles for contributors to DNA mixtures; a priori elimination of poorly amplifying STR loci prior to mixture analysis reduces dropped alleles for DNA contributors to DNA mixtures and reduces the probability of incorrect exclusion of DNA contributors;

Higher fidelity of STR mixture analysis is achieved by matching STR allele sequences rather than STR allele names or STR allele sizes due to the increased precision of STR alleles with different allele sequences but identical allele lengths;

Higher fidelity of STR mixture analysis is achieved by matching STR allele sequences and adjacent polymorphisms in flanking sequences between reference profiles and DNA mixtures; two contributed identical STR allele sequences can be differentiated by variant differences in flanking sequences;

The read counts of contributed STR alleles for an individual are proportional to the amount of DNA contributed to DNA mixtures; the percentage of contributed DNA for each known contributor to a mixture and unknown contributors can be used to estimate proportion of DNA contributed to DNA mixtures;

Machine learning methods can predict the number of individual contributors to STR mixtures;

Machine learning methods can predict the number of individual contributors to STR mixtures;

GrigoraSNPs

Fast SNP and STR sequence analysis with read lookup table to identify locus for HTS reads Higher accuracy SNP allele calling leveraging SNP flanking sequences A method of analyzing sequence data from a biological sample that contains DNA comprised of one or more of the following steps:

Sample identification by optional DNA barcode enabling demultiplexing of multiple samples within a sequence dataset;

Identification of source genome source locus by using subset(s) of the sequence (e.g., DNA tag sequence lookup table(s) mapping tag sequences to candidate loci);

Locus lookup tables enables high performance analysis of DNA sequence datasets

Identification of target SNP base by verification of matching flanking sequences on one or two sides of the target SNP base;

Higher accuracy of SNP allele calling is achieved by leveraging SNP flanking sequences to ensure correct identification of SNP with DNA sequence read Identification of one or more SNP and variant polymorphisms in a single sequence read; multiple sequence variants in a single DNA sequence read represent the variants from one source chromosome (from an individual) representing a phased microhaplotype;

Optional quality filtering of SNP bases by associated quality scores (Q20 is a frequently selected quality filter cutoff for bases in DNA sequence reads);

Tallying observed variants for multiple SNP loci for multiplexed samples with optional quality filtering;

Identification of imbalances in DNA sequence reads for each DNA strand, known as strand bias, can be optionally used in data filtering of results;

Multiple tools exist for SNP allele calling. A novel tool. named GrigoraSNPs, is described that is roughly 20 times faster than the closest tool (SAMtools) and avoids assignment of 50% of sequence reads for Y chromosome pseudoautosomal region incorrectly to the X chromosome (as seen from SAMtools results). GrigoraSNPs leverages a novel sequence tag lookup approach to rapidly identify SNP loci to match against for each HTS sequence read. High precision SNP allele calling is achieved by matching flanking sequences immediately adjacent to target SNP bases. GrigoraSNPs can automatically identify multiplexed barcodes and demultiplex reads for multiple samples to tally results. GrigoraSNPs includes an optional SNP quality base filter (frequently used Q20) for filtering identified SNP Venn Matrix Method A Venn Matrix method is provided to identify known and unknown mixture contributors. The method includes first identifying knowns, remove known profiles from mixtures, apply the Venn Method, and then analyze residues profiles to identify unknown individuals and smaller mixtures with multiple contributors (fewer than the original mixtures).

DNA Mixture-to-Mixture Analysis

In some embodiments, a visualization of overlap is provided between contributors to multiple complex mixtures. This provides overview in a glance across multiple complex mixtures/crime scenes for identification in a more expeditious manner. Further, it is appreciated that untangling overlaps between different mixtures or crime scenes can require a considerable amount of analyst time. Mixture-to-mixture visualization provides an immediate view of overlapping contributors common across multiple mixtures.

Detecting Unknowns in DNA Forensic Samples

There are no available methods to identify unknown individuals in SNP mixture samples. Four approaches are described to identify profiles for unknown individuals. First, identify contributors to mixtures can be subtracted leaving profiles for one or more unknowns (Subtraction method). Second, individual profiles common to two or more mixtures can be isolated with Venn logic by intersecting the mixtures together (Venn method). Third, some profiles can be directly derived from individual mixtures be leveraging differences in contributed DNA concentrations to that mixture (Plateau method). Fourth, the FastID method can be used to identify contributors to mixtures and sub-mixtures derived from the Subtraction method can be overlapped with the Venn method to identify common contributors (Venn Matrix method).

Identification of unknowns in DNA forensic samples
Subtraction of knowns
Venn method
Plateau method
Venn matrix method Advanced DNA Forensics Software Platform According to various embodiments, an integrated Forensics platform for SNPs and STR forensic analysis is provided. In some implementations, a unified forensic analysis system is provided with all data processing and analysis modules integrated.

A method of combining multiple SNP and STR sequence analysis tools to provide an integrated DNA forensic system with capabilities for one or more of:
Identification
Mixture analysis
Mixture deconvolution
Saturated mixture analysis
Identification of contributors of trace profiles
Detection of unknown contributors
Estimating number of contributors to SNP or STR mixtures
Prediction of externally visible traits (EVTs) or phenotypes
Flair color, eye color, hair texture, skin color, facial features, etc.
Medical genetics predictions
Kinship prediction
Biogeographic ancestry prediction
Analysis of contributes to multiple mixtures
Etc.

An integrated platform for SNPs and STR forensic analysis does not exist. A novel integration of multiple forensic analysis tools is presented that enable the fully automated analysis of raw high throughput sequences (HTS) directly from the sequencer, demultiplexing of sequence datasets to individual samples with DNA barcodes, allele calling of individual sequence reads, tallying results, and data quality filtering to create reference and mixture profiles. These sample profiles are automatically loaded into the platform database and searched against all known reference profiles using FastID or TachysSTR. Mixtures are automatically deconvoluted with the Plateau method to identify individual sub-profiles for individuals with no reference profiles, trace profiles and identified and characterized against reference trace exemplar profiles, saturated mixtures are automatically desaturated, etc. Reference profiles are characterized to predict individual gender, phenotype traits (hair color, hair texture, eye color, etc.), biogeographic ancestry, kinship relationships to other reference profiles, etc. The platform is designed with fully automated sample analysis requiring no input from an expert. Results are displayed graphically with interactive features like the Venn mixture deconvolution method, etc. This platform is designed to be extensible, web based, secure with user authentication, encypted passwords, etc. The platform includes a database to manage system data on panels and DNA profiles (references and mixtures). In short, everything described in this patent disclosure is integrated into a single system, named IdPrism.

Estimating Individual Contributions to DNA Mixtures

No methods exist for estimating the amount of DNA contributed to SNP mixtures by individuals. Three novel methods are described that enable estimation of contributed DNA by identified contributors and remaining unknown contributor(s). The first two methods take the average or median value of the major:minor SNPs attributed to an individual to proportional estimate the contributions for each contributor. The third method leverages the mathematical slope intercept to estimate individual contributions to mixtures.

Provided are three (3) methods for estimating amount contributed to mixtures by individuals
Median
Average
Slope intercept Fast P(RMNE) High Precision Statistical calculations for identification and mixture analysis encounter calculation precision errors as the number of loci increases. A novel reformulation of the random person (man) not excluded, P(RMNE), enables high precision calculations with high performance on a single computational thread. This method out performs standard high precision libraries and approximation methods (Taylor series approximations, Big Decimal library, etc.).

High Performance Kinship Comparisons

A novel method of encoding SNP alleles is provided to enable high performance kinship comparisons across reference profiles. Relatives share 0, 1, or 2 SNP alleles depending upon kinship relationship. This encoding enables fast comparisons of SNP loci and tallying of the number of SNPs with 0, 1, or 2 shared alleles. A parent and a child share at least one allele at all autosomal SNP loci. A grandparent and grandchild share half of these alleles in contiguous chromosomal blocks broken up by chromosomal cross-over events. Two siblings are expected to have roughly 25% of SNP loci with 2 shared alleles, 50% with 1 shared allele, and 25% with 0 shared alleles by chance.

Some features may include:
Encoding and method for high performance kinship analysis encoding all SNP alleles using 8 bits [ACGT][ACGT]
A high-performance method for kinship analysis by encoding all SNP alleles using 8 bits Saturated Mixture Analysis In some embodiments, a saturated mixture analysis approach is provided that includes a desaturation of saturated mixture to identify contributors to saturated mixtures. A SNP panel can be designed with multiple SNPs with an average minor allele frequency (mAF) for identifying multiple individuals in DNA mixtures. A panel with a population average mAF of 0.05 results in individuals with minor alleles at roughly 0.10 (2 times 0.05 times 0.95 or 2pq with p+q=1 and q=0.05) for autosomal SNP loci. These SNP panels will approach saturation of SNP loci in mixtures as the number of contributors approaches or exceeds 1/mAF (or 1/0.1 or 10 in this example). The ability to identify individual contributors to saturated mixtures diminishes as the total number of SNP loci for the mixture saturates with observed minor alleles. A novel method for desaturating saturated mixtures is proposed that enables identification of a subset of individual contributors to saturated mixtures. The SNP loci for the saturated mixture are sorted by increasing mAR and a subset of the saturated mixture SNPs with observed mAR are treated as major alleles for the subset of SNPs with the lowest mAR values; this enables the identification of higher DNA concentration contributors to saturated mixtures.

Trace Profile Detection

It is appreciated that there exists no methods to identify individuals who contribute trace profiles to SNP mixtures. A new method is proposed that leverages a subset of a reference profile with the highest minor allele ratios to match against trace profiles identified in SNP mixtures to identify trace contributes to SNP mixtures. In one implementation, a trace profile mixture analysis includes novel methods for identifying trace profile contributors to complex mixtures.

Minor Allele Count Method

One focus of SNP mixture analysis methods described herein use the minor allele ratio (mAR) in the classification of SNP alleles as major, major:minor, and minor:minor for reference profiles and mixture profiles. Analytical thresholds are used to differentiate between only major alleles present as a SNP loci (mAR approximately 0), a mixture of major and minor alleles (0<mAR<1), or only minor alleles present (mAR approximately 1). The minor allele count (mAC) provides an equivalent approach as an alternative to only using the mAR. SNP loci with low minor allele counts are more likely to be derived by polymerase or sequencer errors than low concentration contributed minor alleles. As provided herein, one minor allele count (mAC) approach includes an alternative data analysis approach that compliments the minor allele ratio (mAR) approach.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed herein with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. Where technical features in the figures, detailed description or any claim are followed by reference signs, the reference signs have been included for the sole purpose of increasing the intelligibility of the figures, detailed description, and/or claims. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure.

In the figures:

FIG. 15 depicts experimental results of a kinship analysis, in accordance with some embodiments of the technology described herein.

FIG. 27 is a graph depicting results from a mixture analysis using 468 SNPs with a minor allele frequency of approximately 0.05. Mixtures containing equal amounts of DNA from 8, 5, 3, 10 and 15 individuals were amplified using Fluidigm multiplexed PCR technology and sequenced on Ion Torrent PGM.

FIG. 29 is a diagram depicting results from a mixture analysis using 975 SNPs with a minor allele frequency of approximately 0.05. Mixtures containing equal amounts of DNA from 8, 10, 15, and 20 individuals were amplified using Ampliseq multiplexed PCR technology and sequenced on Ion Torrent PGM.

FIG. 33 shows one example of an STR mixture analysis of mixtures of 3, 4, 5, and 12 individual contributors.

Figure 37:
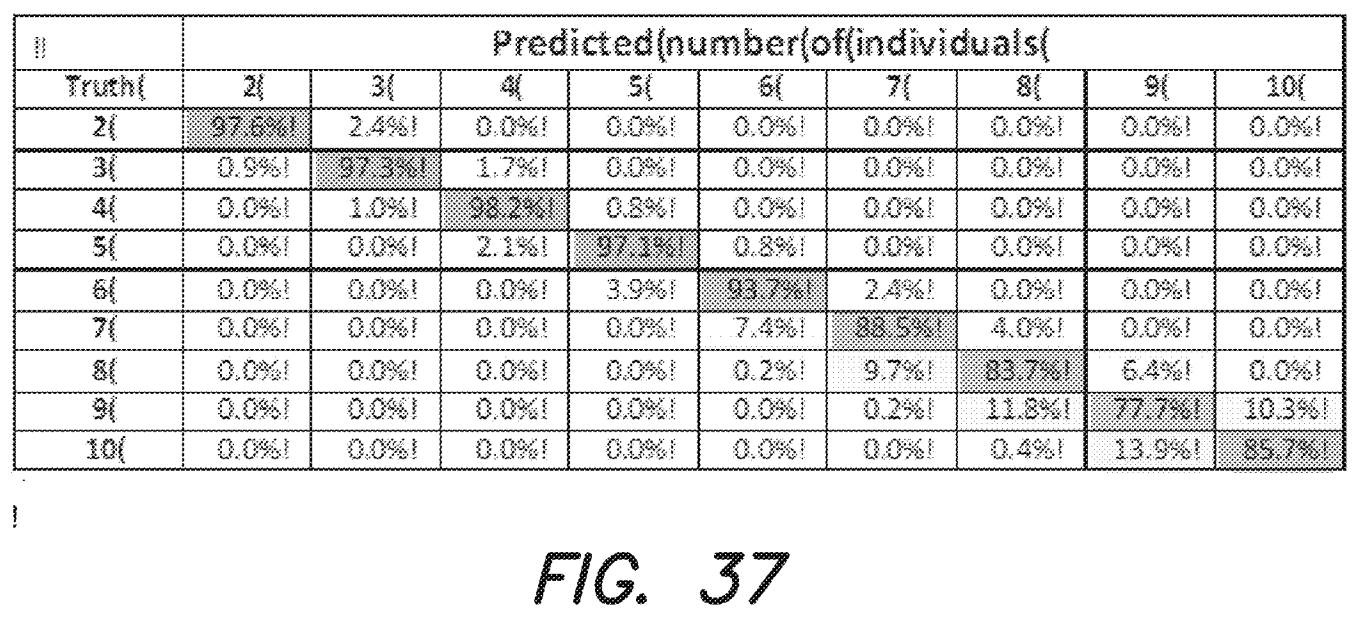

FIG. 37 shows a process for predicting the number of individuals in mixtures with SNP panels.

Figure 38:
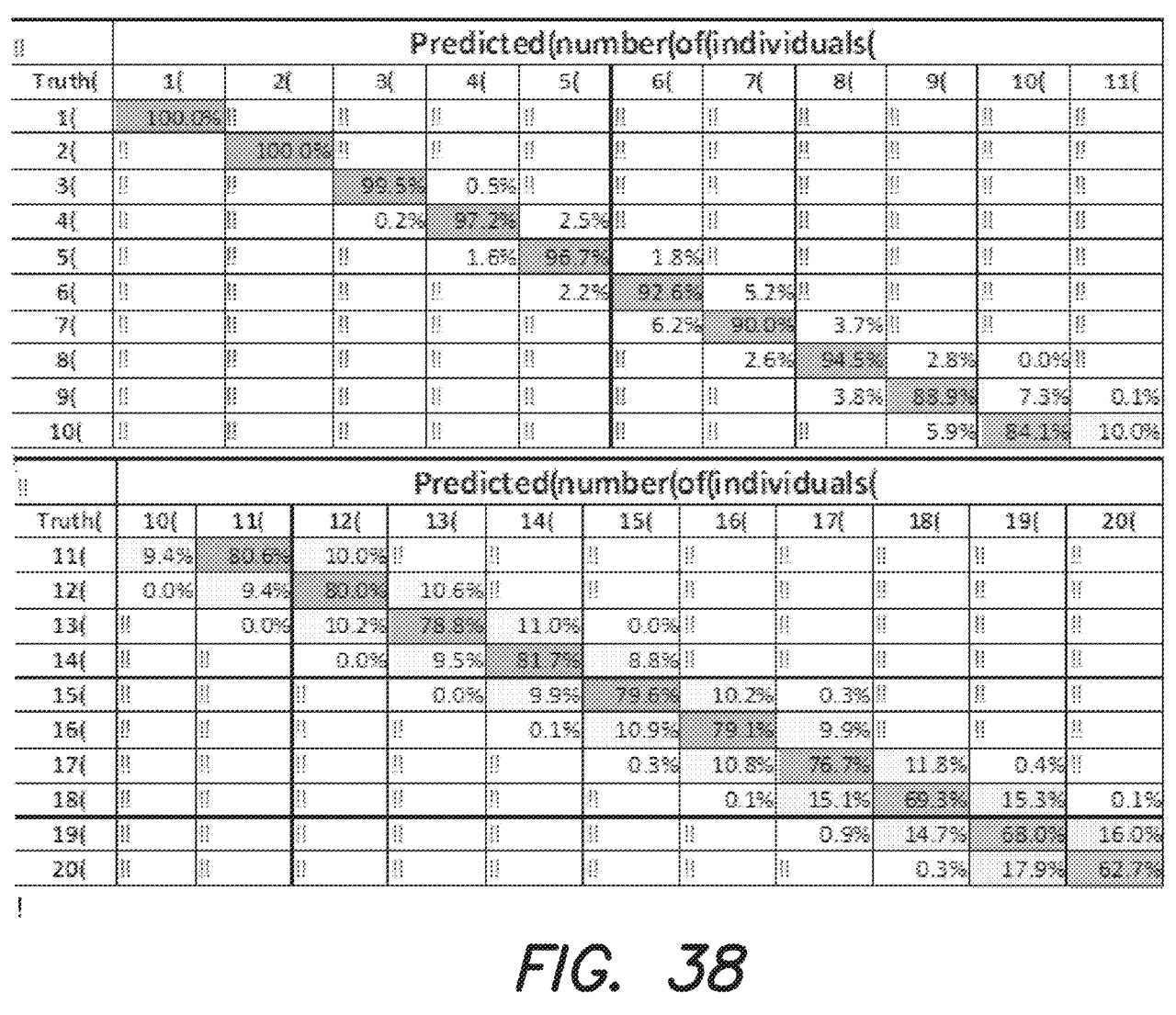

FIG. 38 shows a process for predicting the number of individuals in mixtures with STR panels.

FIG. 45B shows an example mixture 41 FastID search results against references and mixtures.

FIG. 45D shows an example mix41 Mixture-to-Mixture results.

FIG. 71 shows example HIS DNA Sequence Components.

FIG. 77 shows allele call (i.e., allele identification based on allele sizing) errors that result from conventional sequencing and analysis.

DETAILED DESCRIPTION

Figure 1:
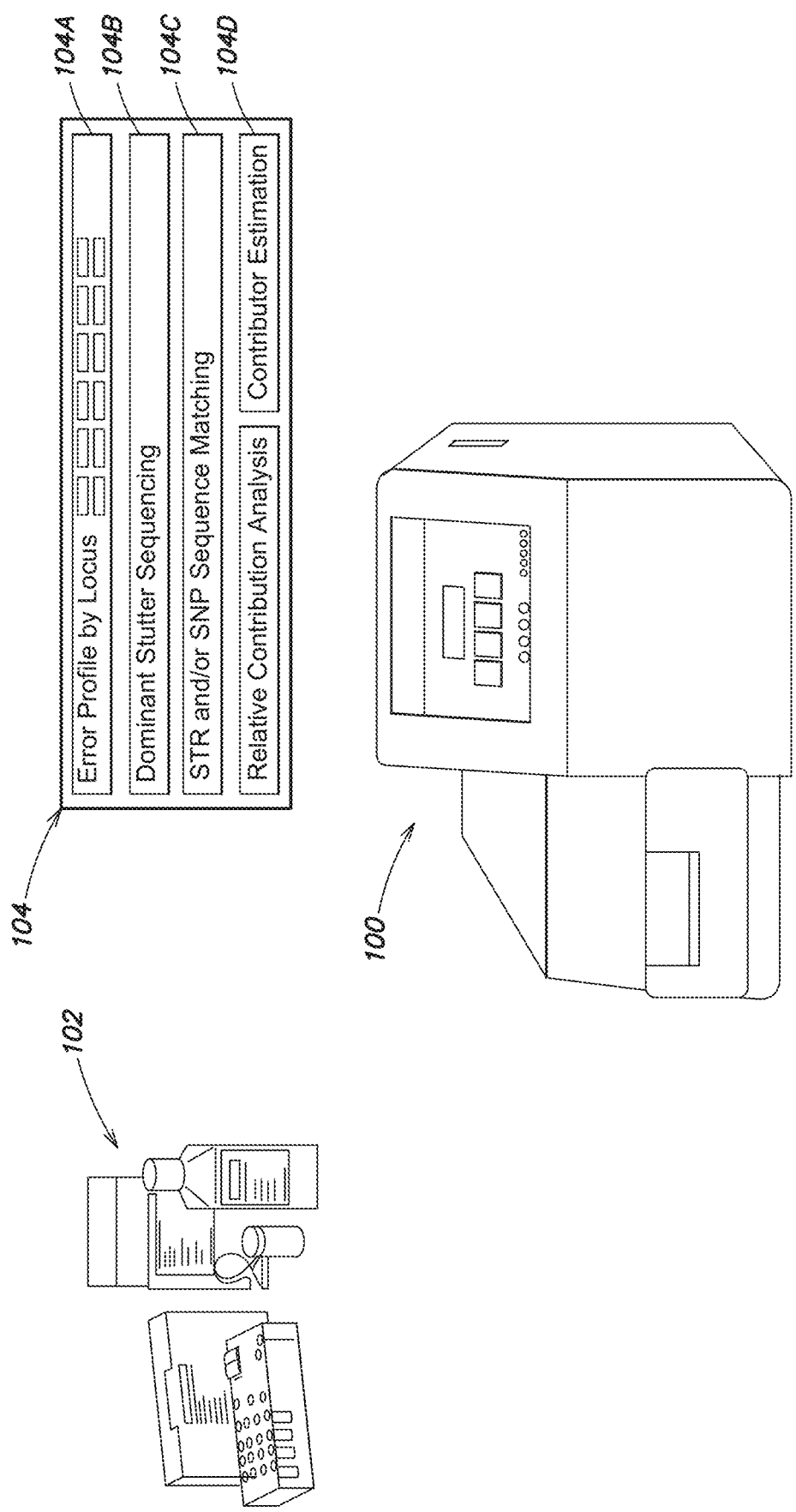
FIG. 1 illustrates a block diagram of a sample analysis system, according to one embodiment.

Systems and methods are provided for distinguishing STR (short tandem repeat) alleles from DNA polymerase artifacts created by DNA amplification when using PCR (polymerase chain reaction) techniques. Various embodiments of the systems and methods characterize the observed DNA polymerase errors on individual references per each locus to generate an error profile specific to each locus. Embodiments of the systems and methods analyze samples against the error profiles to distinguish real alleles from artifacts in individual reference samples and, in other examples, to distinguish real alleles from artifacts in samples that include mixtures of multiple individuals.

In some embodiments, the error profiling is configured to include tracking of −3, −2, −1, 0, +1, +2, and +3 allele length stutters, a respective rate of error for each polymerase and loci, as well as identifying a dominant −1 stutter sequence generated by the DNA polymerase for each loci (as error rates vary by locus and/or selected polymerase). Each integer for identifying allele length error (e.g., −1, −2, −3) represents introduction or deletion of a repeat sequence of length of 1 repeat unit. The 0 length allele stutters are individual base errors that randomly occur within the STR allele during PCR amplification. Discussed in greater detail below, results from methods and systems implementing various aspects demonstrate superior allele calls (i.e., identification of STRs) for individuals and mixture samples over conventional systems. Further embodiments extend the error profiles based on deeper sequencing depth (higher sequence counts) and incorporate, for example, −4, +4, etc., stutter artifacts.

Other aspects incorporate PCR amplification strength for different loci into sample analysis, improving accuracy over conventional identification approaches. In various embodiments, amplification strength modelling can be combined with other aspects to further increase accuracy. For example, estimating relative contributions of DNA of individuals in a DNA mixture can be enhanced based on estimates of relative proportions (e.g., normalized relative proportions) of STR allele strengths of individuals within the mixture. In another example, matching STR sequences rather than matching names based on allele length improves STR allele matching. In yet another embodiment, machine learning models on actual or in silico mixtures of individuals (e.g., from 2 to 30 contributors) enhances accuracy in predicting numbers of contributors. The machine learning models can be based on, trained on, or extrapolated from individual or combinations of STR and SNP profiles. Any of the embodiments and aspects can be combined to achieve increases in identification accuracy or improve estimates.

Examples of the methods, devices, and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

FIG. 1 is an example of a sample analysis system 100. The sample analysis system 100 illustrates a sequencing device in which a DNA sample can be introduced and analyzed. For example, the system 100 can be used in conjunction with PCR amplification for sequencing of PCR products (e.g., STRs and SNPs), sizing of PCR products, etc. System 100 can be configured as a standalone device, or as a multi-component system (e.g., with a sample amplification and sequencing component and a separate or integrated analysis component). According to various embodiments, sample or analysis kits 102 can be provided for users to capture biological samples and/or process samples through pre-analysis stages. The pre-analysis stages can include adding adapters, primers, polymerases, heating, and cooling, and any other known steps and approaches for PCR amplification/tagging of alleles in the samples. The kits can employ specific polymerases and the analysis of the resulting PCR products can include error profiles tailored to the agents employed (e.g., adapters, primers, polymerases, combinations of each, etc.) and respective loci being analyzed.

The FBI recently expanded its combined DNA index system (CODIS) from 13 loci (STR alleles) to 20 loci to better align with forensics used in Europe. Other systems may be used that analyze even greater numbers of loci. These various loci are identified and known by name as well as their genomic position and respective length in base pairs. Tables 1A-1B (collectively, Table 1) below shows observed polymerase errors rates for some loci. According to one embodiment, characterization of the PCR amplification artifacts observed across multiple individuals can be used to build profiles of expected artifacts specific to each locus (e.g., and each polymerase and PCR primer pairs). The analysis component shown at block 104 can be programmed with the error profiles for any number of agents used in PCR (or other amplification technique) and resolve allele identification based on leveraging the error profiles to distinguish real STR alleles from artifacts.

According to various embodiments, the analysis component shown at 104 can include any one or more of the illustrated analysis approaches. Further, the analysis component 104 can be integrated into a sequencing device 100 or can be executed by one or more separate systems. In some embodiments, each of the internal blocks 104A, 104B, 104C, 104D, and 104E can be executed on different systems. In various embodiments, the different systems can communicate respective results to other components/systems to improve accuracy. According to one embodiment, a DNA sequencing device or DNA analysis system can be enhanced to include allele error profiling by locus. In one example, each locus for analysis (e.g., CODIS loci, as well as additional loci) is modeled to establish an error profile. The modeling is executed based on comparing sequences established through PCR techniques against known or previously sequenced DNA. According to one embodiment, the deviations between the PCR established sequences and the known sequence provide an error model that the system (and e.g., component 104A) applies to unknown samples.

According to another embodiment, the analysis performed by block 104A relies on building error profiles for each locus based on multiple reference samples. For the multiple reference samples, the relevant portions (e.g., loci of interest) can be completely sequenced to provide an accurate baseline for evaluating any observed errors stemming from PCR amplification.

Building Per Locus Error Profiles

According to one embodiment, characterization of PCR amplification artifacts observed in multiple individuals enables the profiling of expected artifacts by STR locus (and/or agents used in PCR). For example, the system can be configured to model the observed patterns of STR stutter alleles. In one embodiment, the observed errors pattern can be shown to be dependent upon the number of PCR amplification cycles during sample preparation. Thus, the error profile per locus can also be applied to account for any number of amplification cycles. For example, the error profile can store error rate data associated with a data value for a number PCR cycles to which the error rate is associated.

Generally stated, the value in establishing an error profile for each locus (i.e., improving allele identification accuracy) can be observed in Table 1. For example, an error profile may be determined that is broken down into two components, the average error, and the variability of the error. Table 1a shows the mean locus error across samples, while Table 1b shows the standard deviation of the locus error across samples. Taking one convention system and resulting data, stutter alleles for −3, −2, −1, +1, +2, and +3 lengths were observed for some of the STR loci. Also 0 length allele variants were also observed for random DNA single nucleotide errors (at lower rate of error than deletions and additions).

One embodiment uses the observed errors across multiple reference samples to characterize errors by STR locus to generate per locus error profiles. The STR loci can be selected based on variations in DNA sequences between individuals (e.g., polymorphisms) that can be used in DNA analysis (e.g., in forensics cases) to determine identity. Table 1 A provides examples of observed error rates for 15 of the 20 STR loci that are used in conjunction with the FBI's CODIS database to identify individuals. Discussed in greater detail below, for both individual samples and mixture samples, distinguishing between real STR alleles and polymerase artifacts is accomplished by leveraging error profiles to distinguish real STR alleles from artifacts. Various embodiments improve the accuracy of distinguishing real STR alleles from artifacts—which can be key for DNA mixtures. And importantly improves the accuracy of DNA identification over conventional approaches.

TABLE 1A

| | Mean Error Characterization | | | | | | |
|---|---|---|---|---|---|---|---|
| Locus | −3 Stut | −2 Stut | −1 Stut | +0 Error | +1 Stut | +2 Stut | +3 Stut |
| D13S317 | 0.0035% | 0.108% | 3.29% | 2.37% | 1.04% | 0.011% | 0.00011% |
| D6S1043 | 0.046% | 0.595% | 7.71% | 0.66% | 1.42% | 2.7% | 0.0003% |
| CSF1PO | 0.0088% | 2.35% | 4.44% | 1.74% | 1.73% | 0.03% | 0.0005% |
| D7S820 | 0.017% | 0.312% | 5.58% | 0.884% | 1.46% | 0.021% | 0.0003% |
| vWA | 0.11% | 1.07% | 10.36% | 9.94% | 19.11% | 3.65% | 0.70% |
| D10S1248 | 0.13% | 1.21% | 11.00% | 0.592% | 0.512% | 0.003% | 0.00001% |
| D17S1301 | 0.33% | 2.02% | 14.84% | 2.27% | 1.28% | 0.02% | 0.0002% |
| TH01 | 0.2% | 0.433% | 6.58% | 0.520% | 0.363% | 0.001% | 0.000005% |
| FGA | 1.5% | 2.50% | 15.80% | 1.17% | 1.42% | 0.02% | 0.5% |
| D19S433 | 0.05% | 0.603% | 7.77% | 1.14% | 0.538% | 0.003% | 0.00002% |
| D20S482 | 0.13% | 1.21% | 11.02% | 0.669% | 2.12% | 0.04% | 0.001% |

TABLE 1B

Standard Deviation Error Characterization

| Locus | −3 Stut | −2 Stut | −1 Stut | +0 Error | +1 Stut | +2 Stut | +3 Stut |
| --- | --- | --- | --- | --- | --- | --- | --- |
| D13S317 | 0.002% | 0.058% | 1.21% | 1.73% | 0.596% | 0.0095% | 0.00013% |
| D6S1043 | 0.0421% | 0.422% | 3.66% | 1.73% | 0.596% | 0.195% | 0.00022% |
| CSF1PO | 0.0097% | 0.166% | 2.46% | 1.73% | 0.861% | 0.0222% | 0.00050% |

Various embodiments leverage the observed DNA polymerase error rates shown in Table 1 to build error profiles that can filter out such errors identifying unknown samples. For example, the error rate when viewed on a locus by locus basis shows the error rate (e.g., −1 & −2) is proportional when reduced to specific STR alleles. For example, the −2 is roughly the square of the −1 error rate. In some implementations, for example, where there is insufficient data to directly capture the −2 error rate, algorithm optimizations can be used to establish a −2 error rate (e.g., square a −1 error rate and use the square as the −2 error rate).

According to one modeling approach, the system 100 can be configured to establish and apply expected error profiles per analyzed loci. In further examples, the error profiles can be tailored or have database entries for an error rate per loci that are also specific to the agents used in processing (e.g., polymerase, tagging agent, adapter, etc.). FIG. 77 illustrates allele call (i.e., allele identification based on allele sizing) errors that result from conventional sequencing and analysis. Various embodiments of the present system identify and resolve such calling error by applying respective error profiles. According to one embodiment, the error profiles are applied by setting a threshold equal to the error rate plus a predefined number of standard deviations beyond the error rate. This is done to prevent edge cases from being falsely included. Allowing the number of standard deviations to be system defined (e.g., set by an administrative user) allows for setting the stringency of excluding false calls—and further allows users to dynamically tailor the precision based on the analysis being performed.

In some embodiments, the system can be configured to automatically assess various thresholds, for example, by perturbing the standard deviation setting and evaluating accuracy based on local minima analysis.

In FIG. 77, Illumina STR Peak calling errors for individual profiles (e.g., I6, I9, and I10) are shown. For example, allele name 15 (italics) is a false read for individual 6 (I6). Using error profiles of the +1 error for allele 14 and −1 for allele 16, the number of reads 379 are within an expected error profile, and should not result in calling of allele 15 for D20S482. Various embodiments, are configured to amply combination errors analysis to determine accurate results and reduce errors generated by prior art systems. After application of the combined error profile, the genotype for 16 is 14, 16 and not 14, 15, 16 as identified under conventional approaches.

Additional errors generated by conventional approaches include calling of allele 19 for D6S1043. Because the genomic sequences being analyzed via PCR and naming are known, the errors are readily apparent based on comparing results of the PCR and naming against the known sequences. Seen in again for I6, a combination error (+1 of allele 18 and −1 of allele 20) generated a false call for allele 19. 236 reads of allele 19 in the sample are within the combined error rate determined by the analysis system 100 (and/or analysis component 104A). For I9, allele 14 is also false call. As is allele 14 for I10, based on the 63 reads in the analyzed sample. The error rate for allele 14 is set at the average −1 error for CSF1PO plus three standard deviations from the error. This creates a combined error rate of 12%, which allele 14 falls within the boundary of. According to one embodiment, for each read output generated by the analysis system, the system evaluates the read output to determine whether the value could be generated as a result of error from other alleles. In some examples, the number of PCR cycles executed on a given sample is known, thus error profiles matching the number of cycles can be used. In other embodiments, increasing the number of PCR cycles increases the number of PCR artifacts, thus if a value for the number of reads does not exceed the expected rate of error for a single PCR cycle—the detected peak is determined to be an artifact and not an actual allele. Additionally, combination errors must be accounted for so as any allele is identified (e.g., number of reads for that allele is over an expected error number) the system is configured to account for error contributions for each of the identified alleles.

Figure 2:
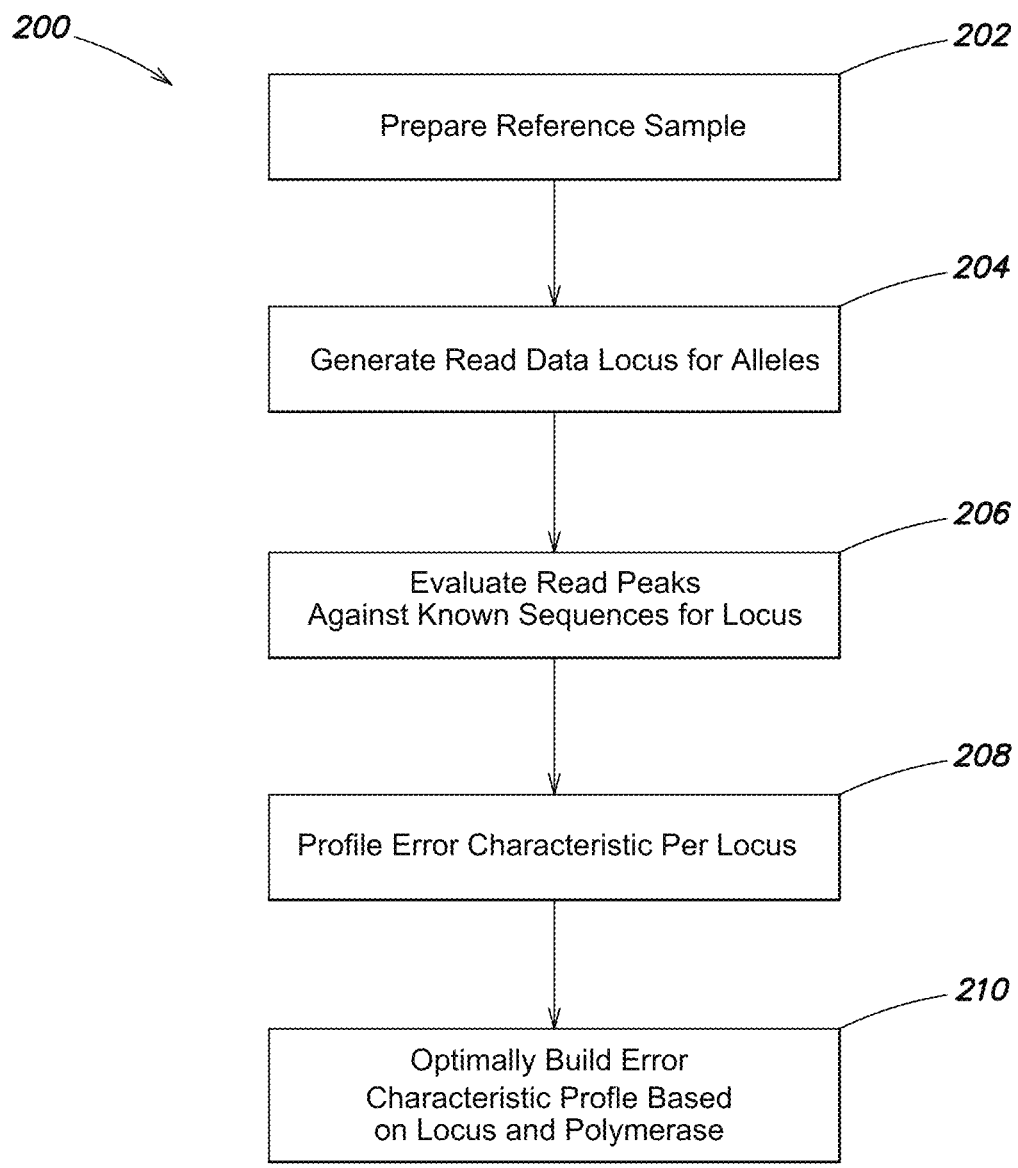
FIG. 2 illustrates an example process for building an error profile per locus, according to one embodiment.

FIG. 2 illustrates an example process 200 for building an error profile per locus. Process 200 begins at 202 with preparation of a sample for PCR analysis. For example, the sample is amplified, tagging agents are added, and read data is generated for loci in the sample, for example, based on capillary electrophoresis (CE). Each appearance of an allele is identified—typically based on a florescent signal obtained as the allele is eluted. Each appearance for an allele on each locus is recorded as a read, for example, captured at 204. The read data (e.g., peaks) is evaluated against known reference sequences for each locus to determine which reads are correct and which reads are the result of a PCR artifact (e.g., stutter) at 206. The rate of error is generated as part of profiling the error characteristics on each locus, for example at 208.

In some embodiments, the specific agents used during PCR (e.g., tags, polymerase, etc.) are captured in conjunction with the read data, for example at optional step 210. In some embodiments, the act of profiling error characteristics can include associating specific PCR primers with observed error patterns. Process 200 is executed repeatedly against number of reference samples to build error profile models. For example, confidence evaluations and fitting analysis can be used to determine accuracy of the models, and ensure that the error model meets a confidence threshold. In further embodiments, the error profile models can be refined over time based on incorporation/evaluation of new reference samples. The larger the number of reference samples analyzed, the greater the confidence value for the error profile that is developed.

Table 1 illustrates example error rates determined per locus, and each error rate per locus can be used to filter read data to separate stutter alleles from actual alleles. Multiple error profiles can be generated per locus, for example, to include difference agents and/or different numbers of PCR cycles. According to one embodiment, an analysis system can execute processed for eliminating error via locus based error profiles. The error profiles can be matched for specific analysis, for example, based on PC R primers being used and/or a number of PCR cycles executed on a given sample.

In one example, a DNA sequencing and/or analysis system can execute a process 300 (FIG. 3) to eliminate read error. According to one embodiment, process 300 filters allele reads (e.g., indicator of a specific allele locus) based on error profile information for each detected locus in a sample, and further can be configured to apply the error profile against reads based on respective instances of alleles for a given locus. In various examples, application of multiple error profiles or conditions can be used to eliminate combination read errors. For example, as shown in Table 1A, for I6 locus D20s482, allele name 14 is associated with a +1 error and allele name 16 is associated with a −1 error. In combination, the errors triggers a false call on the 15 Allele.

According to one embodiment, process 300 can be executed on data collected from analysis of a DNA sample to improve allele calling within the sample. With given read data for respective loci, process 300 can begin at 302 with identification of potential allele names within a given locus based on the read data. At 304, respective values for a number of reads are evaluated, for example, to determine if they are over a threshold number associated with the Allele name and locus. If the number of reads is over an initial threshold value 304 (YES), the number of reads can be tested against an adjusted threshold (e.g., adjust threshold at 308 and test again at 304). For example, at 306, additional alleles can be identified in the sample which may impact the threshold value used to confirm an artifact (e.g., 310) or confirm an allele (e.g., 312). For example, the threshold value can be adjusted or determined based on the presence of other named alleles (e.g., within a given locus).

In other implementations, the presence of read data on all potential alleles/allele names can be used to determine and/or generate a threshold that accounts for the presence of all the potential alleles, and a single evaluation may be used to confirm the presence of an allele versus an artifact, rather than cyclic or recursive analysis. In still other embodiments, confirmation of an artifact can also be used to tailor threshold values, by eliminating any error contribution that the actual presence of the allele would have required.

Referencing to FIG. 77, Allele name 14 and 16 are identified as being over a threshold value (even when assuming Allele name 15 is properly identified and thresholds increased based on potential error rates for each of 14, 15, and 16). In some examples, step 308 can include multiple adjustments and then tests of those threshold values. In further examples, step 308 can also include establishing threshold criteria for unambiguous thresholds where if exceed the named allele must be in the sample (e.g., assume all reads are real, incorporate errors for each read into the thresholds, and identify peaks that pass the adjusted threshold value). Process 300 can then re-evaluate any read data (e.g., via multiple adjustments to threshold values) that did not meet the unambiguous threshold by only considering error values from the named alleles that did pass the unambiguous threshold. In one embodiment, steps 304-308 are executed recursively to identify alleles and refine threshold values for determining a named allele is actually present in the sample. The logic for the allele calling is presented in the below pseudo-code example:

```
LOAD naming_dictionary
FOR locus in unique_loc
  SORT reads selected from locus
  FOR read in selected_reads
    IF number reads greater than minimum threshold AND no previous calls
      Call read
      Name Read
    ELSE
      Accumulate expected stutter from alleles within 3 units of distance
      IF reads greater than expected stutter reads
        Call read
        Name Read
      END IF
    END IF
  END FOR
END FOR
```

It should be appreciated that various embodiments of the example logic described above may be used, and the logic may be expressed in one or more programming languages, may include more or less steps, and/or may use a different structure.

Build Stutter Allele Sequence Profile

According to another embodiment, the system 100 can also be configured to learn (e.g., model) the dominant −1 stutter allele sequence for each allele within a locus to facilitate STR allele identification in mixtures (e.g., multi-contributor samples). According to one aspect, it is appreciated that learning the dominant −1 stutter allele sequence for each locus enables identification of the −1 stutter allele and enables the system to distinguish the dominant −1 stutter allele from STR alleles from other individuals (e.g., that have STR allele(s) with the same length and similar counts to −1 stutter alleles). When evaluating a mixture, if an allele has a reduced number of reads, one might assume that it is the stutter of a separate allele. However, if the allele in question does not fit the expected stutter pattern, it can be included as a sample present allele. In Table 3 below, both 32 alleles and the 33 allele plus others are distinct by sequence and are very unlikely stutter sequences and are called by this method. Various embodiments implement either of these approaches (e.g., error profiling and stutter allele sequencing) and/or combine these approaches to create novel tools for more accurate: (1) error profiling and (2) allele calling for samples (when analyzing both individual reference and DNA mixtures (multiple contributors).

TABLE 3

Enhanced STR Allele Calling Example

| Locus | Allele Name | Typed Allele? | Reads | MITLL Name | MITLL Called |
|---|---|---|---|---|---|
| D21S11 | 29 | Yes | 680 | 29 | Yes |
| D21S11 | 30 | Yes | 381 | 30" | Yes |
| D21S11 | 30 | Yes | 519 | 30' | Yes |
| D21S11 | 31 | No | 13 | 31_NC | No |
| D21S11 | 31 | No | 75 | 31 | Yes |
| D21S11 | 31.2 | No | 131 | 31.2_1 | Yes |
| D21S11 | 31.2 | No | 15 | 31.2_NC | No |
| D21S11 | 32 | No | 95 | 32_2 | Yes |
| D21S11 | 32 | No | 88 | 32_1 | Yes |
| D21S11 | 32.2 | Yes | 381 | 32.2 | Yes |
| D21S11 | 33 | No | 16 | 33_1 | Yes |

Figure 4:
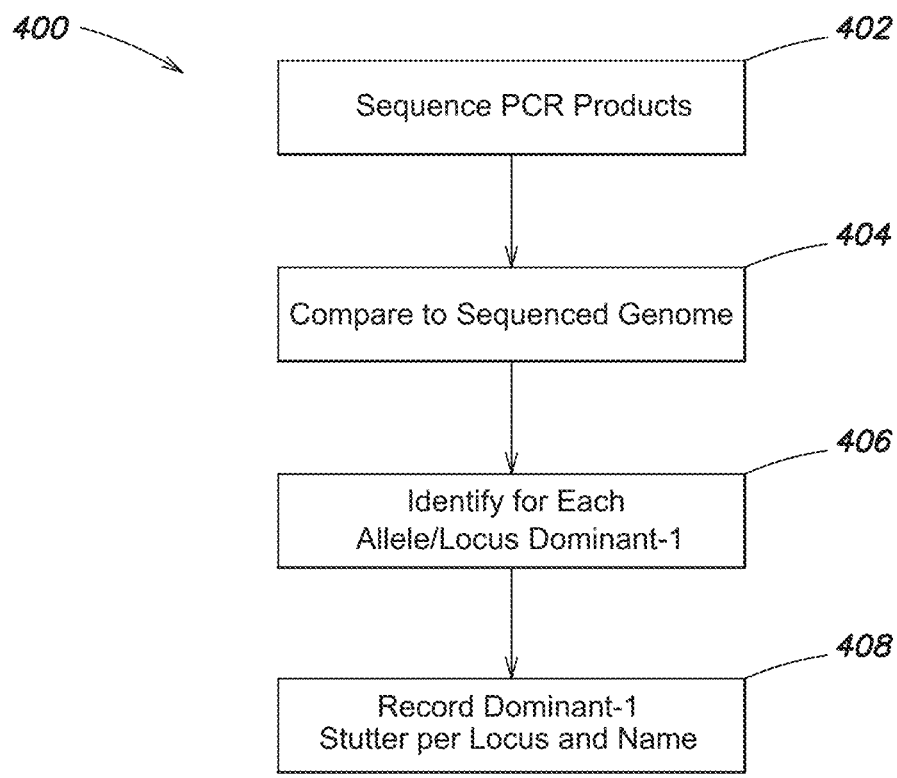
FIG. 4 illustrates an example process for defining a dominant stutter allele sequence, according to one embodiment.

FIG. 4 is an example process 400 for defining a dominant −1 stutter allele sequence. Process 400 begins at 402 with sequencing PCR products as discussed above. The sequenced PCR products can be compared to known sequences (e.g., on a reference sample having a known genomic sequence) at 404. For example, sequences of alleles having the same base pair length are compared to determine if the alleles match the references. Errors are reviewed and at 406, a dominant −1 stutter allele (e.g., a PCR artifact) can be identified for each real allele. For example, a −1 stutter reflects a single deletion of a STR for a specific allele name and locus. The deletion may also be accompanied by individual base pair errors. Regardless of the changes introduced during PCR, the most numerous error is identified at 406 by genomic sequence, and the sequence for each dominant −1 stutter is recorded at 408 for each allele and locus. In some embodiments, the data is recorded in conjunction with specific PCR primers, as different primers can generate different −1 dominant stutter sequences. Further embodiments include the dominant −1 stutter sequence produced by a first PCR primer and respective loci, a second PCR primer and respective loci, a third PCR primer and respective loci, and so on, to capture commonly used PCR primers and effect on the dominant −1 stutter allele for each allele and loci.

According to another embodiment, an analysis system (e.g. system 100) and/or an analysis component (e.g., 104 and/or 104B) is configured to identify a dominant sequence the dominant −1 stutter against an analyzed sample to remove for each allele at each locus data reads on the dominant −1 stutter. Various embodiments limit the error resolution to dominant −1 stutter alleles to improve processing over more invasive sequencing approaches. Limiting the analysis to the dominant −1 stutter, in some embodiments, significantly reduces the computational burden associated with matching, for example, more than one or all of the −1 stutter sequences. Further embodiments can be configured to address specific PCR primers, or accept as an input specification of PCR primers used during sample amplification. The dominant −1 stutter sequences are then employed by the system, if the PCR agents match.

According to various embodiments, execution of error profiling and/or dominant stutter sequencing resolves miscalled peaks observed in conventional allele calling for D20S482, D6S1043, CSF1PO, and D22S1045 shown in FIG. 77 and failed identifications/miscalled alleles in Table 4 (see e.g., Mix 1—THO01 8_NC; Mix—3 D2S1338 16_NC; Mix—3 D5S818 13_NC; and Mix—3 D8S1179 12 NC). Table 4 below presents a series of mixtures (Mix—1—Mix—3) where different mixtures contain a varied number of individuals contributing DNA at different concentrations.

TABLE 4

Enhancements in STR allele calling for DNA Mixture samples

| Sample | Locus | Allele Name | Current Test | Reads | Old name | Old Way | Notes |
|---|---|---|---|---|---|---|---|
| Mix---1 | D12S391 | 25_0 | Yes | 84 | 25 | No | False Negative |
| Mix---1 | D13S317 | 12_0 | Yes | 108 | 12 | No | False Negative |
| Mix---1 | D18S51 | 13_0 | Yes | 3740 | 13 | Yes | Reference |
| Mix---1 | D18S51 | 13.2_0 | Yes | 201 | 13.2 | No | False Negative |
| Mix---1 | D2S441 | 14_0 | Yes | 2077 | 14 | Yes | Reference |
| Mix---1 | D2S441 | 15_NC | No | 22 | 15 | No | Reference |
| Mix---1 | D2S441 | 16_0 | Yes | 201 | 16 | No | False Negative |
| Mix---1 | FGA | 22 | Yes | 1566 | 22 | Yes | Reference |
| Mix---1 | FGA | 23_NC | No | 34 | 23 | No | Reference |
| Mix---1 | FGA | 24 | Yes | 140 | 24 | No | False Negative |
| Mix---1 | TH01 | 8_NC | No | 557 | 8 | Yes | −1 stutter of 9 allele |
| Mix---1 | TH01 | 9 | Yes | 3975 | 9 | Yes | Reference |
| Mix---2 | D12S391 | 16_0 | Yes | 40 | 16 | No | False Negative |
| Mix---2 | D12S391 | 18_0 | Yes | 137 | 18 | Yes | Reference |
| Mix---2 | D13S317 | 12_0 | Yes | 52 | 12 | No | False Negative |
| Mix---2 | D18S51 | 13_0 | Yes | 1747 | 13 | Yes | Reference |
| Mix---2 | D18S51 | 13.2_0 | Yes | 78 | 13.2 | No | 13.2 not stutter of 13 allele |
| Mix---2 | D18S51 | 15_0 | Yes | 52 | 15 | No | not likely +2 stutter allele |
| Mix---2 | D2S1338 | 22_0 | Yes | 140 | 22 | No | 22_novel not likely −1 stutter |
| Mix---2 | D2S1338 | 23' | Yes | 331 | 23 | Yes | Reference |
| Mix---2 | D6S1043 | 18_0 | Yes | 139 | 18 | No | False Negative |
| Mix---2 | D6S1043 | 19_0 | Yes | 65 | 19 | No | False Negative |
| Mix---3 | D16S539 | 8 | Yes | 124 | 8 | No | False Negative |
| Mix---3 | D1S1656 | 16.3_0 | Yes | 46 | 16.3 | No | False Negative |
| Mix---3 | D21S11 | 28\|28.2 | Yes | 82 | 28 | No | False Negative |
| Mix---3 | D21S11 | 30" | Yes | 101 | 30 | No | False Negative |
| Mix---3 | D2S1338 | 16_NC | No | 315 | 16 | Yes | −1 stutter of 17 allele |
| Mix---3 | D2S1338 | 17 | Yes | 1539 | 17 | Yes | Reference |
| Mix---3 | D2S1338 | 22_0 | Yes | 410 | 22 | Yes | Reference |
| Mix---3 | D2S1338 | 22_1 | Yes | 80 | 22 | No | False Negative |
| Mix---3 | D5S818 | 12_0 | Yes | 342 | 12 | Yes | Reference |
| Mix---3 | D5S818 | 13_NC | No | 71 | 13 | Yes | +1 stutter of 12 allele |
| Mix---3 | D5S818 | 13_NC | No | 35 | 13 | Yes | +1 stutter of 12 allele |
| Mix---3 | D8S1179 | 12_NC | No | 672 | 12 | Yes | −1 stutter of 13 allele |
| Mix---3 | D8S1179 | 13 | Yes | 3975 | 13 | Yes | Reference | for each −1 allele at each locus. In additional embodiments, the analysis system (e.g., system 100) and/or analysis component 104 (e.g., 104 and/or 104B) is configured to match Shown in table 4 above, the STR sequence for the 22 allele is different from the 23' allele. A −1 alleles for the 23' allele should be a 22' allele. The 23' alleles has the third to the last repeat unit mutated from TTCC to GTCC where the 22 allele has a TTCC for the third to the last repeat unit.

Various embodiments implement mixture analysis based on comparing allele calling for both references and mixture samples and/or comparing the STR allele sequences from references with sequences present in the mixture sample.

Figure 5:
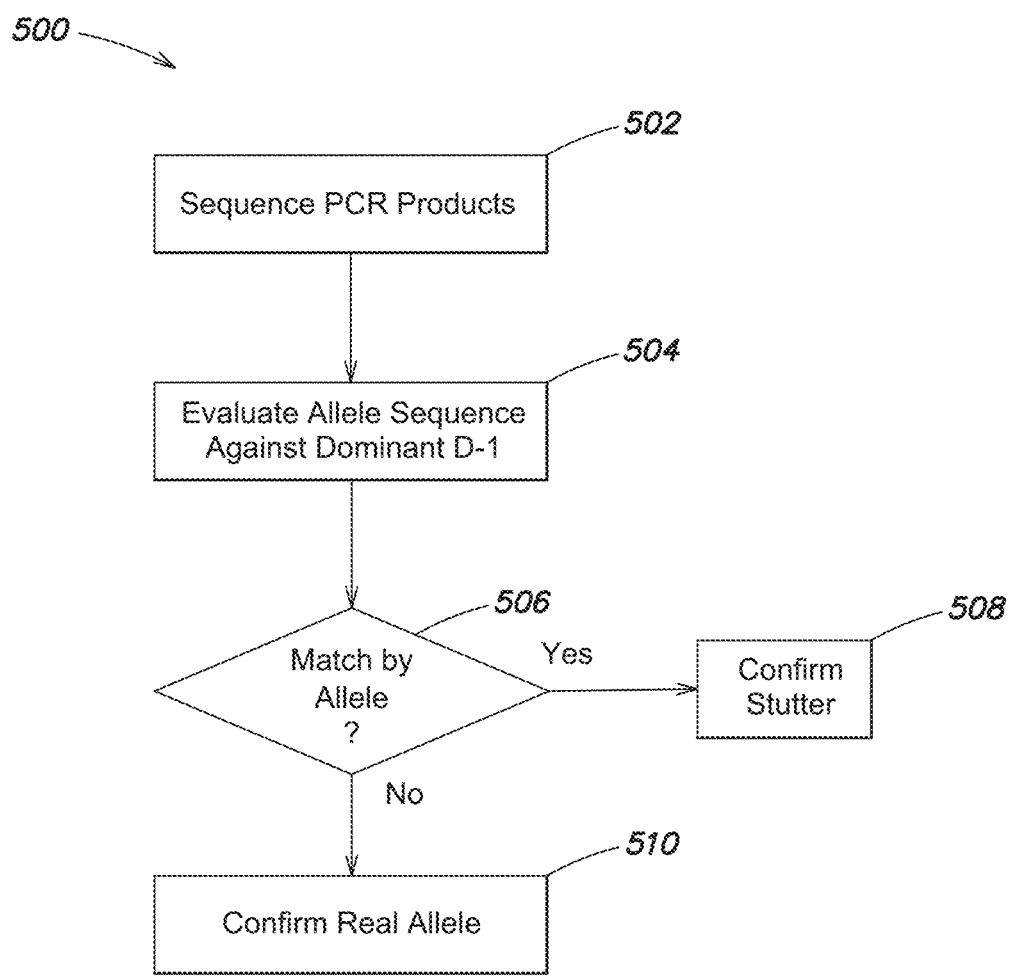
FIG. 5 is an example process for eliminating error induced by PCR amplification, according to one embodiment.

FIG. 5 is an example process 500 for eliminating error induced by PCR amplification. Process 500 can be executed by an analysis system (e.g. 100), an analysis component (e.g., 104), and/or an subcomponent (e.g., 104B) to improve accuracy in allele calling and ultimately identification. Process 500 begins at 502 with sequencing of PCR products as discussed above. Based on the results of the sequencing each read for a specific allele can be evaluated against dominant −1 stutter allele sequences at 504. In some examples, the dominant −1 stutter allele sequences are selected based on specific PCR primers used to process a sample under analysis. In other embodiments, the dominant −1 stutter sequence is retrieved from database records without need for determining the PCR primers used (e.g., agent agnostic sequence data or system is configured with dominant −1 stutter sequence using the same agents under analysis). If a match to a dominant −1 sequence is identified 506 (YES), then the data associated with that sequence can be confirmed as a stutter (i.e., not a genuine allele) and any data associated with the stutter can be excluded or discounted in confirming real alleles. For example, if the sequence obtained at 504 is evaluated and does not match 506 (NO), then process 500 can confirm it as a real allele at 510 or step 510 can include operations to confirm that the sequenced PCR product is a real allele. In one example, the 510 can include analysis of read data on the sequenced product to determine that the sequence is not within an error range (e.g., established by error profiles of other alleles).

Generate Allele Amplification Pattern

According to another aspect, analysis systems can be configured to leverage the strength of PCR amplification. PCR amplification strength varies by locus and is specific to the PCR primers used and other amplification condition factors. By determining and factoring strength of PCR amplification, various embodiments can be configured to improve identification accuracy. For example, the system can be configured to use PCR amplification strength to establish inclusion/exclusion criteria, where the inclusion/exclusion criteria is implemented on the system to establish an individual as a contributor to a DNA sample.

Figure 6:
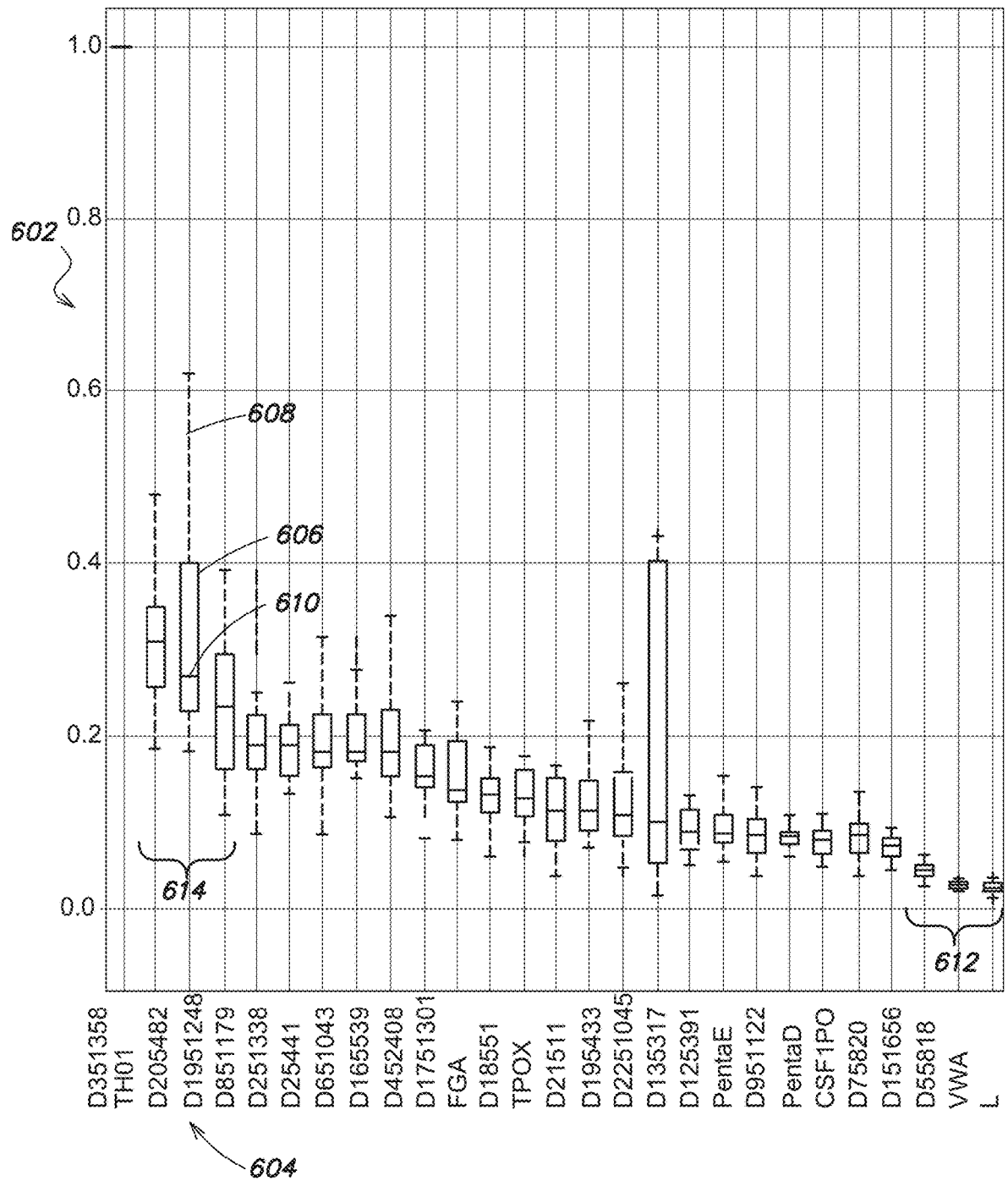
FIG. 6 is an example boxplot of STR allele PCR amplification strength, according to one embodiment.

Shown in FIG. 6 are the median percentage of reads against the maximum number of reads (602) for appearance of specific loci (604) detected in reference samples. For each locus a distribution bar is shown to illustrate variance in percent appearance across a reference sample population (e.g., at 606—showing the interquartile range of the distribution ($1^{st}$ to $3^{rd}$ quartile)). The maximum and minimum of the distributions for each loci are shown above and below the bar (e.g., at 608) indicating variability outside the upper and lower quartiles. The solid line within each bar (e.g., 610) illustrates a median value for each locus—which can be used in some embodiments as representative of an amplification strength (for example, other embodiments may use a mean value). In various embodiments, the strongest STR alleles (strongest by amplification strength) can be leveraged for inclusion/exclusion criteria for considering an individual as a candidate for having their DNA in an unknown mixture sample.

Under various sample conditions, the weakest STR alleles may not be observed in DNA mixtures for individuals. For example, if a contributor has a lower concentration of DNA in a sample, it is likely that STRs that have the weakest amplification will not even appear when analyzed for that individual. Various embodiments of the system employ this imbalance between STR loci as part of the analysis of DNA mixtures to improve identification accuracy over conventional systems. For example, under multiple contributor conditions the system can be configured to exclude the last three loci shown in FIG. 6 (e.g., at 612) from analysis—filtering the data being analyzed at this stage can also lead to computational efficiency over conventional implementation. It is realized that a high probability exists that low concentration contributors will not have some or all values for these loci, and rather than evaluate loci that will have no match because of low concentration (e.g. and lead to an improper conclusion that the individual is not a contributor), the system eliminates the low amplification strength loci, and performs a contributor analysis base on the remaining loci. The threshold and/or selection of loci to include or exclude can be dynamic, based on input into the system on specific PCR primers used and/or other amplification condition factors input into the system or as established by default settings.

According to another embodiment, exclusion of a potential contributor can be optimized based on the strongest amplification loci. For example, if a contributor does not have or match on the strongest amplification loci (e.g., shown in FIG. 6 at 614), then that contributor can be eliminated without further analysis.

Figure 7:
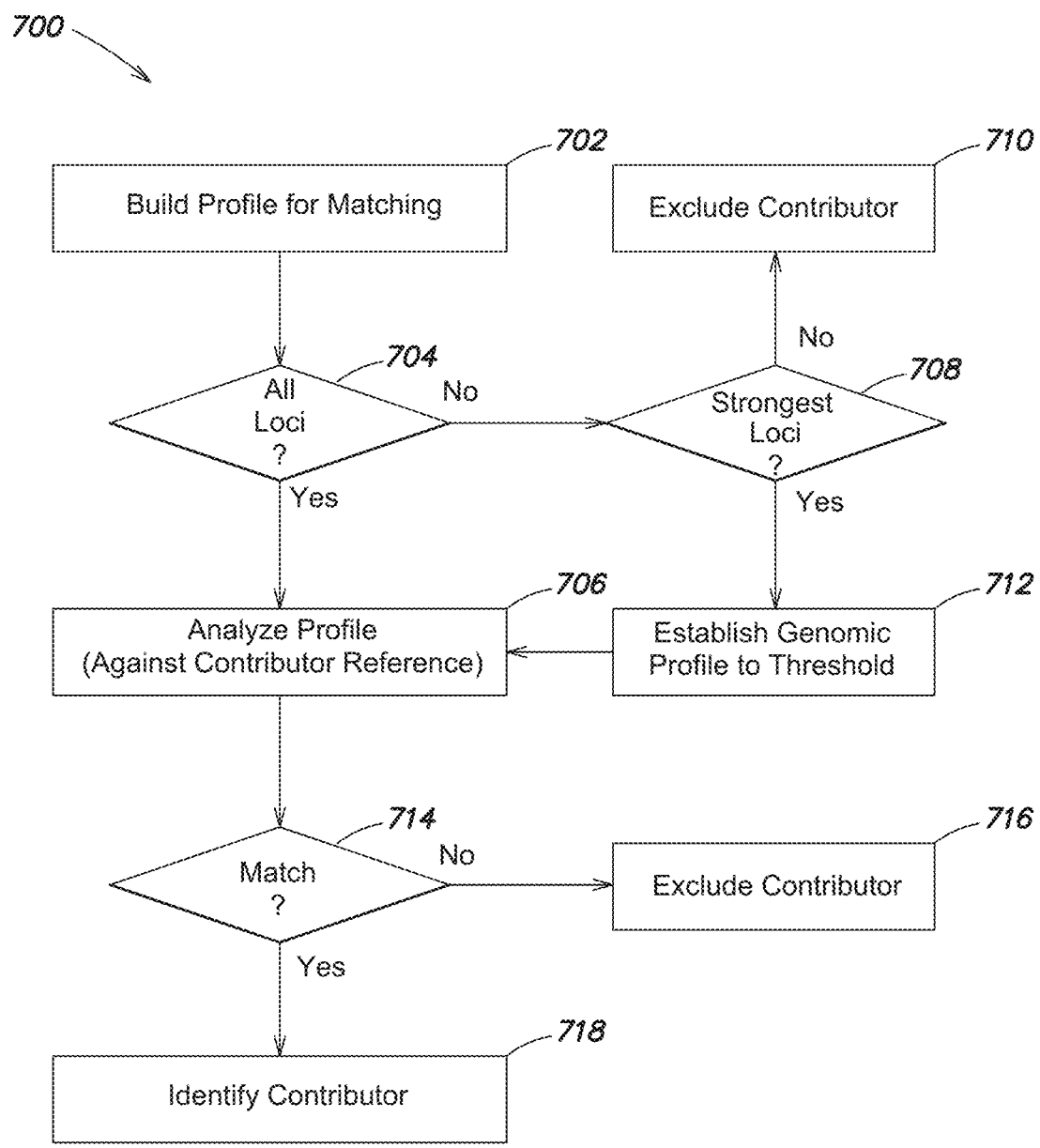
FIG. 7 is an example process for identifying a contributor in a sample, according to one embodiment.

FIG. 7 is an example process 700 for identifying (to a degree of probability) a contributor in a sample. Process 700 begins at 702 with building a profile for matching, for example, against a contributor reference. The profile for matching can be generated using any of the preceding technique to specifically identify alleles by name or sequence, and can execute one or more of the discussed approaches for improving accuracy. The results of the allele calling and/or allele sequencing can be analyzed to determine if all expected loci are present in the sample. If for example, a contributor's presence in the sample occurs at low concentration various low strength loci may not be detected. If the concentration is high in the sample, all the analyzed loci are more likely to be present 704 YES and analysis of contributor's profile can be made at 706. The analysis can be executed against a contributor reference or other profile. In some examples, a sample may be taken from a suspect to generate a contributor reference (via sequencing or allele naming) and perform the analysis at 706.

Where a contributor concentration is low, all loci may not be present, e.g., at 704 NO. Process 700 may then proceed with an exclusion operation to remove the candidate contributor from consideration at 708 based on whether the strongest loci are even present in the sample at 710. If the strongest amplification strength loci that should be present for a specific contributor are not present 708 NO, then that contributor can be eliminated from consideration at 710. In some embodiments, the exclusion execution can be a fast filter that achieves a negative result faster than and with fewer computation cycles than some conventional approaches. In other embodiments, the strongest loci analysis can be executed even before the all loci analysis at 704. In some examples, based on analysis of the strongest amplification loci, potential contributors can be eliminated as a first step of analyzing sample data and analysis only proceeds on potential contributors having at least the strongest amplification strength loci (e.g., and alleles) that are found in the sample under analysis.

If the strongest loci are present (and/or match alleles within the strongest loci) at 708 YES, process 700 can proceed with completing the genomic profile of the sample up to any established threshold at 712. The threshold can be tailored (e.g., by an administrator on the system, set by default, etc.) to exclude low amplification strength loci. In some examples, the process can be executed to determine that a number of loci do not appear at all or in significant quantity to establish the threshold (e.g., detect the bottom three amplification strength loci are not present, or detect sixth, fifth, and fourth lower strength loci are not present—and stop further analysis of weaker loci). This may occur as part of analysis at 706. In further embodiments, the process may process all potential loci in conjunction with a lowest amplification strength loci excluded profile and present analysis of both options. In a low concentration contributors example, side by side analysis can be provided that shows an exclusion in one setting and a match in another (e.g., using all loci—result: exclude contributor (based on not matching weak amplification strength loci); using threshold loci (exclude weak loci)—result: match and potentially provide the associated degree of probability of the match).

Analysis of the profile at 706 can continue with determination of a match (or probability of a match) at 714. If there is not a match 714 a potential contributor can be excluded at 716. If there is a match between the sample and a reference 714 YES, the contributor can be identified at 718 (e.g., identified to a degree of probability). Various analysis systems (e.g., 100) can execute process 700, for example, on samples to identify potential contributors. In further embodiments, process 700 can be executed by contribution analysis component (e.g., 104D) or other analysis systems to improved identification accuracy.

Analyze DNA Mixture with STR Sequences

According to another aspect, rather than comparing called allele names, an analysis system can be configured to match sequences of called STR alleles for individuals to a set of STR sequences found in DNA mixtures. Exact sequence matching can be used to match each called allele for respective individuals and respective sequences in DNA mixtures. According to one example, this is done by identifying the sequences corresponding to called alleles in a reference sample, and querying the mixture to determine if those same sequences are present in the sequenced DNA. If a sequence exactly matching the reference is present, it is considered a positive identification.

According to one embodiment, called STR alleles are sequenced for each individual contributor appearing in a DNA mixture. With known sequences the efficacy of prior art approaches can be tested and evaluated against various embodiments disclosed herein.

Shown in Table 4 below is a heat map organization of the results of conventional approaches for calling STR loci—the table shows the number of unmatched called alleles of the individual contributors (e.g., when called alleles for each individual of a group of individuals are separately analyzed) when compared in mixture under conventional approaches.

TABLE 4

| | I1 | I2 | I3 | I4 | I5 | I6 | I7 | I8 | I9 | I10 | I11 | I12 |
|---|---|---|---|---|---|---|---|---|---|---|---|---|
| Mix-1 | 18 | 26 | 25 | 22 | 19 | 28 | 26 | 4 | 0 | 22 | 25 | 29 |
| Mix-2 | 16 | 0 | 15 | 0 | 18 | 20 | 21 | 15 | 20 | 1 | 3 | 20 |
| Mix-3 | 7 | 9 | 6 | 5 | 4 | 9 | 4 | 3 | 8 | 7 | 9 | 6 |

Mix-1 is a two-person mixture where I9 has 9x greater DNA concentration than I8.
Mix-2 is a four-person mixture where I10 and I11 are present at 2:3 the concentration of I2 and I4. Mix-3 is an equimolar mixture composed of all individuals.
Shown above the colors are a scaled representation of the number of mismatches between a reference individual (x-axis) and a mixture (y-axis). A lighter color represents fewer mismatches while a darker color represents a greater number of mismatches.

Figure 9:
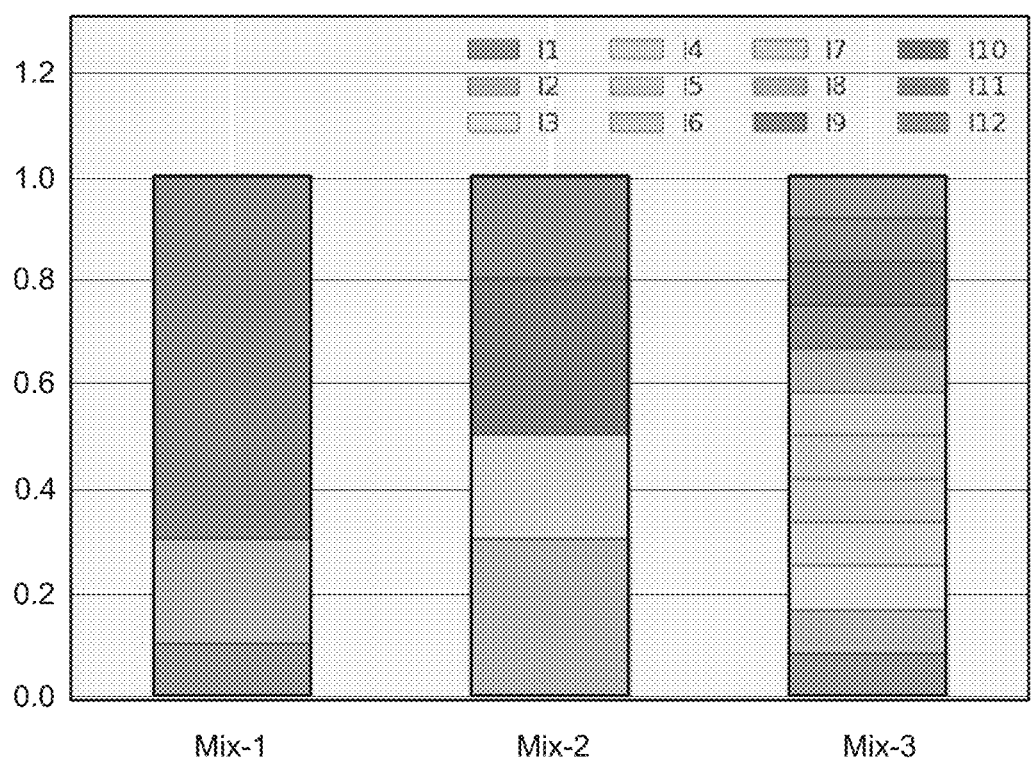
FIG. 9 illustrates actual mixture composition, according to one embodiment.

According to various embodiments, any reduction in the number of unmatched called alleles represents an increase in identification accuracy. Shown in FIG. 9 is the intended makeup of the mixtures 1, 2, and 3. Mixture 1 designed concentrations are 10% I1, 20% I8, and 70% I9. Mixture 2 designed concentrations are 20% I11, 30% I10, 20% I4, and 30% I2. Mixture 3 was designed to have equal proportions of each individual (e.g., 1-12).

Implementation Examples

In one embodiment, error patterning by loci is implemented within a python script (e.g., "STR_Noise Profiles Tool") that when executed is configured to characterize error patterns observed in high throughput sequencing (HTS) STR profiles. In an example execution, STR stutter alleles are observed for −3, −2, −1, +1, +2, and +3 STR allele lengths. It is observed that the higher the read counts for a specific locus, the higher the probability of observing the −2 and sometimes the −3 STR stutter peaks. Polymerase single base calling errors were also observed for the +0 STR allele lengths (see Table 5 below). Various embodiments characterizes these error patterns to create characterization profiles by locus that are used by analysis systems to improve accuracy of STR peak allele calling. For FIG. 77, miscalled peaks were observed in conventional allele calling for D20S482, D6S1043, CSF1PO, and D22S1045.

TABLE 5

Example STR alleles with +0 stutter alleles

| Locus | Allele Name | Typed Allele? | Reads |
|---|---|---|---|
| D12S391 | 19 | Yes | 980 |
| D12S391 | 19 | No | 30 |
| D12S391 | 20 | Yes | 825 |
| D12S391 | 20 | No | 11 |

According to another embodiment, additional methods can be implemented to improve matching alleles calls for both individuals and mixtures profiles. Table 4 shows the number of unmatched called alleles of individuals compared to mixtures for conventional allele calls in a heatmap. Table 6 shows the improved matching for alleles called by STR_Alleles—through implementation and execution of per loci error profiling. Table 7 illustrates further improvements in accuracy based on excluding the three weakest STR loci (i.e., weakest amplification strength loci) attributable based on amplification profiling of PCR agents and amplification conditions.

TABLE 6

Error Profiling Results for all autosomal STR loci

| | I1 | I2 | I3 | I4 | I5 | I6 | I7 | I8 | I9 | I10 | I11 | I12 |
|---|---|---|---|---|---|---|---|---|---|---|---|---|
| Mix-1 | 11 | 23 | 24 | 22 | 19 | 26 | 23 | 3 | 0 | 21 | 24 | 28 |
| Mix-2 | 15 | 0 | 15 | 0 | 18 | 19 | 20 | 15 | 20 | 0 | 2 | 20 |
| Mix-3 | 2 | 1 | 1 | 1 | 2 | 2 | 2 | 0 | 1 | 4 | 1 | 3 |

TABLE 7

Error Profiling Results with removal of three weakest STR loci

| Mix-1 | 6 | 19 | 20 | 18 | 15 | 21 | 17 | 0 | 0 | 18 | 22 | 24 |
| Mix-2 | 12 | 0 | 13 | 0 | 16 | 15 | 13 | 17 | 0 | 0 | 2 | 19 |
| Mix-3 | 0 | 1 | 1 | 0 | 1 | 1 | 0 | 0 | 1 | 4 | 0 | 2 |
| | I1 | I2 | I3 | I4 | I5 | I6 | I7 | I8 | I9 | I10 | I11 | I12 |

TABLE 8

STR sequence matching results (without three weakest STR loci)

| Mix-1 | 0 | 10 | 14 | 12 | 8 | 14 | 11 | 0 | 0 | 9 | 16 | 17 |
| Mix-2 | 8 | 0 | 8 | 0 | 8 | 9 | 10 | 6 | 6 | 0 | 0 | 14 |
| Mix-3 | 0 | 0 | 0 | 0 | 0 | 0 | 0 | 0 | 0 | 0 | 0 | 0 |
| | I1 | I2 | I3 | I4 | I5 | I6 | I7 | I8 | I9 | I10 | I11 | I12 |

According to some embodiments, the cells shown in Tables 6 and 7 appear without background fill where the match to the individual is sufficient for a high probability identification (e.g., sufficient for conviction). The improvement over Table 4 is readily apparent based on increase in the number of sufficient to identify cells. Further improvements are shown between Tables 6 and 7 in the reduction in the numbers of unmatched called alleles. Shown in Table 8, direct sequencing analysis (with three weakest loci removed) according to one embodiment provides the best alignment of called alleles with sequences in the DNA mixtures.

To establish relevance of various embodiments, standard mixture statistics are calculated. These statistics include the probability that a random man would not be excluded (PRMNE) from being identified as present in the mixture, and the likelihood ratio (LR) that the evidence supports a guilty verdict as opposed to an innocent one. Table 9 below shows the PRMNE and LR for Mix-1, Mix-2, and Mix-3.

TABLE 9

Forensic Statistics

| Mix | PRMNE | LR |
|---|---|---|
| Mix-1 | $3.087 \times 10^{-6}$ | 323,932 |
| Mix-2 | $1.78 \times 10^{-3}$ | 562.17 |
| Mix-3 | $3.854 \times 10^{-2}$ | 25.95 |

Generating DNA Concentration Estimates for Individuals in Mixtures

According to another aspect, various analysis systems can be configured to leverage the amplification strength profiles of STFR alleles (see FIG. 6) to estimate the relative concentration of DNA contributions by individuals in a mixture. Given a mixture sample, the distributions of loci and alleles that appear in the sample can be generated. The identified loci and STR alleles can be compared to amplification strength profiles to estimate a relative concentration for a number of individuals in a mixture. Generally, for alleles that are unique to specific contributors—the number of reads on those unique alleles can be used to indicate a concentration of that contributor. More specifically, the replication strength profile for all or a group of the alleles can be used to determine expected numbers of reads for each allele in a sample, and the expected number of reads can be extrapolated into an expected number of reads for two contributors, three contributors, four contributors, to upwards of 30 contributors modeled over various concentrations.

Each set of loci/allele combinations can be modeled such that for multiple contributor sample read distributions can be matched to an estimated concentration for each contributor.

Other properties of the amplification strength allow for the strength profile to be modeled and then applied in a comparison to an unknown sample. For example, for loci and alleles in common between a number of contributors these reads tend to aggregate (although in some examples they may show a smaller normalized number of reads than a single contributor sample), but the reads on alleles that are not found in common generate a unique signature for that sample that reflects relative concentration of the contributors. If a single individual provides the alleles (not in common to all the contributors) the strength profile provides an estimate of the number of reads that should be detected. Where the number is lower than that estimate—multiple contributors are indicated and relative concentrations can be determined. Each variation in the expected number of reads can be evaluated together to derive an estimate of relative concentration.

Figure 8:
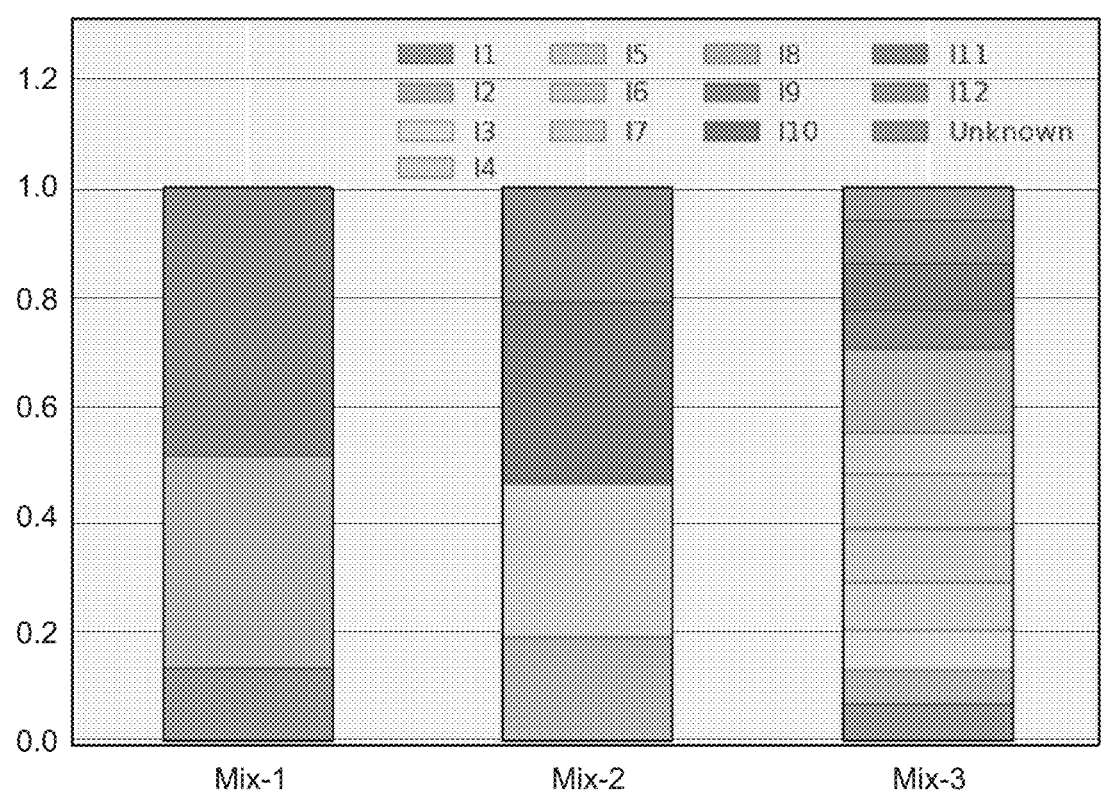
FIG. 8 illustrates mixture composition estimates, according to one embodiment.

In further embodiments, called alleles not matched to individuals can also be leveraged to estimate the amount of DNA from unknown contributors. For example, an analysis system (e.g., 100) and/or a an analysis component (e.g., 104E) can be configured to analyze a normalized ratio of the observed STR allele counts across STR loci to generate a relative estimate of original DNA concentrations, including estimation of an unknown portion of a sample. Shown in FIG. 8 are mixture composition estimated across twelve known individuals and an unknown. The system and/or analysis component estimates that Mix-1 is made up of three contributors having relative concentrations shown by the y-axis of FIG. 8. Shown in FIG. 8, the estimate for the original DNA concentration for individual 18 is actually higher than expected (FIG. 9—reflecting actual mixture elements). Observation of the differences between FIGS. 8 and 9 includes a reproducible increase that is observed for individual I8 in both Mix-1 and Mix-3. Thus refinement of the model can be used to eliminate the overestimate.

Generate Prediction of Number of Contributors

According to another aspect, an analysis system can be configured to calculate a predictive value for a number of contributors in a DNA sample. In one embodiment, the analysis system (e.g., 100) and/or an analysis component (e.g., 104E) is configured to leverage profiles of individuals to estimate a number of contributors appearing in a sample. For example, profiles of different STR loci reflect the different complexities of alleles represented for respective individuals and, for example, include significant allele sharing at some loci (e.g., TPDX—shown in FIG. 10). According to one embodiment, multiple in silico mixtures were created for mixtures of 2, 3, 4, 5, and so on up to 20 individuals. The various combination of the read values for different STR loci and different complexities of alleles are illustrated in part in FIG. 10. The different combinations of individuals and respective plots for number of alleles by locus that result are used to train a machine learning algorithm and build a tool (e.g., comparison model) for predicting the number of individuals in a mixture using the STR data obtained from analysis any mixture. The model creates a statistical separation based on features characterizing the number of unique alleles present across loci. These features are incorporated into a statistical model that separates unseen data based on these features. In one embodiment, a model is used to reflect the relationship between average number of STR alleles detected by locus (e.g., via a profile of STR Alleles detected by locus over set of loci) and the number of individuals appearing in the modeled data. The model can then be used by the system to evaluate unknown samples having unknown numbers of contributors to predict a number of individuals within the sample.

Tables 10A-B illustrates (for a known group of 20 individuals) predictions of a number of contributors for in silico generated mixtures of individual profiles (i.e., known individual STR allele profiles).

TABLE 10A

Predictions of individuals in STR mixtures

| Truth | Predicted number of individuals | | | | | | | | | | |
|---|---|---|---|---|---|---|---|---|---|---|---|
| | 1 | 2 | 3 | 4 | 5 | 6 | 7 | 8 | 9 | 10 | 11 |
| 1 | 100.0% | | | | | | | | | | |
| 2 | | 100.0% | | | | | | | | | |
| 3 | | | 99.5% | 0.5% | | | | | | | |
| 4 | | 0.2% | | 97.2% | 2.5% | | | | | | |
| 5 | | | | 1.6% | 96.7% | 1.8% | | | | | |
| 6 | | | | | 2.2% | 92.6% | 5.2% | | | | |
| 7 | | | | | | 6.2% | 90.0% | 3.7% | | | |
| 8 | | | | | | | 2.6% | 94.5% | 2.8% | 0.0% | |
| 9 | | | | | | | | 3.8% | 88.9% | 7.3% | 0.1% |
| 10 | | | | | | | | | 5.9% | 84.1% | 10.0% |

TABLE 10B

Continued Predictions of individuals in STR mixtures

| Truth | Predicted number of individuals | | | | | | | | | | |
|---|---|---|---|---|---|---|---|---|---|---|---|
| | 10 | 11 | 12 | 13 | 14 | 15 | 16 | 17 | 18 | 19 | 20 |
| 11 | 9.4% | 80.6% | 10.0% | | | | | | | | |
| 12 | 0.0% | 9.4% | 80.0% | 10.6% | | | | | | | |
| 13 | | 0.0% | 10.2% | 78.8% | 11.0% | 0.0% | | | | | |
| 14 | | | 0.0% | 9.5% | 81.7% | 8.8% | | | | | |
| 15 | | | | 0.0% | 9.9% | 79.6% | 10.2% | 0.3% | | | |
| 16 | | | | | 0.1% | 10.9% | 79.1% | 9.9% | | | |
| 17 | | | | | | 0.3% | 10.8% | 76.7% | 11.8% | 0.4% | |
| 18 | | | | | | | 0.1% | 15.1% | 69.3% | 15.3% | 0.1% |
| 19 | | | | | | | | 0.9% | 14.7% | 68.0% | 16.0% |
| 20 | | | | | | | | | 0.3% | 17.9% | 62.7% |

According to one embodiment, an analysis system is configured to apply the STR based prediction model to samples. Example data was captured from executing the prediction model on the mixture samples described above in FIG. 9. Table 11 illustrates the performance of the model. For example, Table 11 shows the results of contributor predictions based on a comparison of the model applied to allele profiles generated under conventional analysis approaches (e.g., ForenSeq) and when applied to called STR alleles by embodiments discussed herein (e.g., New Alleles). As shown in Table 11, algorithm performance is significantly more accurate when based on allele profiles generated with embodiments discussed herein, rather than under conventional approaches.

TABLE 11

| Mixture | ForenSeq Alleles | New Alleles | Truth |
|---|---|---|---|
| Mix-1 | 2 | 3 | 3 |
| Mix-2 | 4 | 4 | 4 |
| Mix-3 | 6 | 11 | 12 |

Further embodiments extend prediction modeling (prediction of number of contributors) into additional information based on SNP sequencing. According to various embodiments, analysis systems (e.g., 100) and/or analysis components (e.g., 104E) are configured to leverage profiles of individuals with sequenced SNPs to estimate a number of contributors in a sample based on SNP analysis. For example, multiple in silico mixtures were created for mixtures of 2, 3, 4, 5, 7, 8, 9 and 10 individuals. Sequencing of the SNPs in the sample was executed and the pattern of shared minor alleles was represented in a reduced dimensional space. Principal component analysis (PCA) was used to map the data along the dimensions of greatest variance. In place of using all dimensions, the number of dimensions was set such that the selected number of dimensions explains a predefined percentage of the variance in the data. The pattern was used to train a machine learning algorithm representative of the pattern. Various embodiments, implement the machine learning algorithm as an executable tool that predicts the number of individuals in a mixture responsive to analyzing sequenced SNPs of the sample. According to some embodiments, as there is less variance in individual SNPs, a larger number of sequenced loci are required to obtain similar performance (confidence values) to STR analysis discussed above. Table 12 illustrates the percent confidences in the predicted determination generated by embodiments executing the SNP based prediction tool based on sequencing 1500 SNPs within the mixture.

TABLE 12

| | Predicted number of individuals | | | | | | | | |
|---|---|---|---|---|---|---|---|---|---|
| Truth | 2 | 3 | 4 | 5 | 6 | 7 | 8 | 9 | 10 |
| 2 | 97.6% | 2.4% | 0.0% | 1.0% | 0.0% | 0.0% | 0.0% | 0.0% | 0.0% |
| 3 | 0.9% | 97.3% | 1.7% | 0.0% | 0.0% | 0.0% | 0.0% | 0.0% | 0.0% |
| 4 | 0.0% | 1.0% | 98.2% | 0.0% | 0.0% | 0.0% | 0.0% | 0.0% | 0.0% |
| 5 | 0.0% | 0.0% | 2.1% | 97.1% | 0.8% | 0.0% | 0.0% | 0.0% | 0.0% |
| 6 | 0.0% | 0.0% | 0.0% | 3.9% | 93.7% | 2.4% | 0.0% | 0.0% | 0.0% |
| 7 | 0.0% | 0.0% | 0.0% | 0.0% | 7.4% | 88.5% | 4.0% | 0.0% | 0.0% |
| 8 | 0.0% | 0.0% | 0.0% | 0.0% | 0.2% | 9.7% | 83.7% | 6.4% | 0.0% |
| 9 | 0.0% | 0.0% | 0.0% | 0.0% | 0.0% | 0.2% | 11.8% | 77.7% | 10.3% |
| 10 | 0.0% | 0.0% | 0.0% | 0.0% | 0.0% | 0.0% | 0.4% | 13.9% | 85.7% |

Further embodiments combine the underlying models of the SNP based prediction tool modeling and the STR based prediction tool to achieve greater accuracy and in some examples to reduce the number of SNPs required to achieve similar confidence levels.

Example Computer Systems

Various aspects and functions described herein may be implemented as specialized hardware or software components executing in one or more specialized computer systems. There are many examples of computer systems that are currently in use that could be specially programmed or specially configured. These examples include, among others, network appliances, personal computers, workstations, mainframes, networked clients, servers, media servers, application servers, database servers, and web servers. Other examples of computer systems may include mobile computing devices (e.g., smart phones, tablet computers, and personal digital assistants) and network equipment (e.g., load balancers, routers, and switches). Examples of particular models of mobile computing devices include iPhones, iPads, and iPod Touches running iOS operating systems available from Apple, Android devices like Samsung Galaxy Series, LG Nexus, and Motorola Droid X, Blackberry devices available from Blackberry Limited, and Windows Phone devices. Further, aspects may be located on a single computer system or may be distributed among a plurality of computer systems connected to one or more communications networks.

Figure 11:
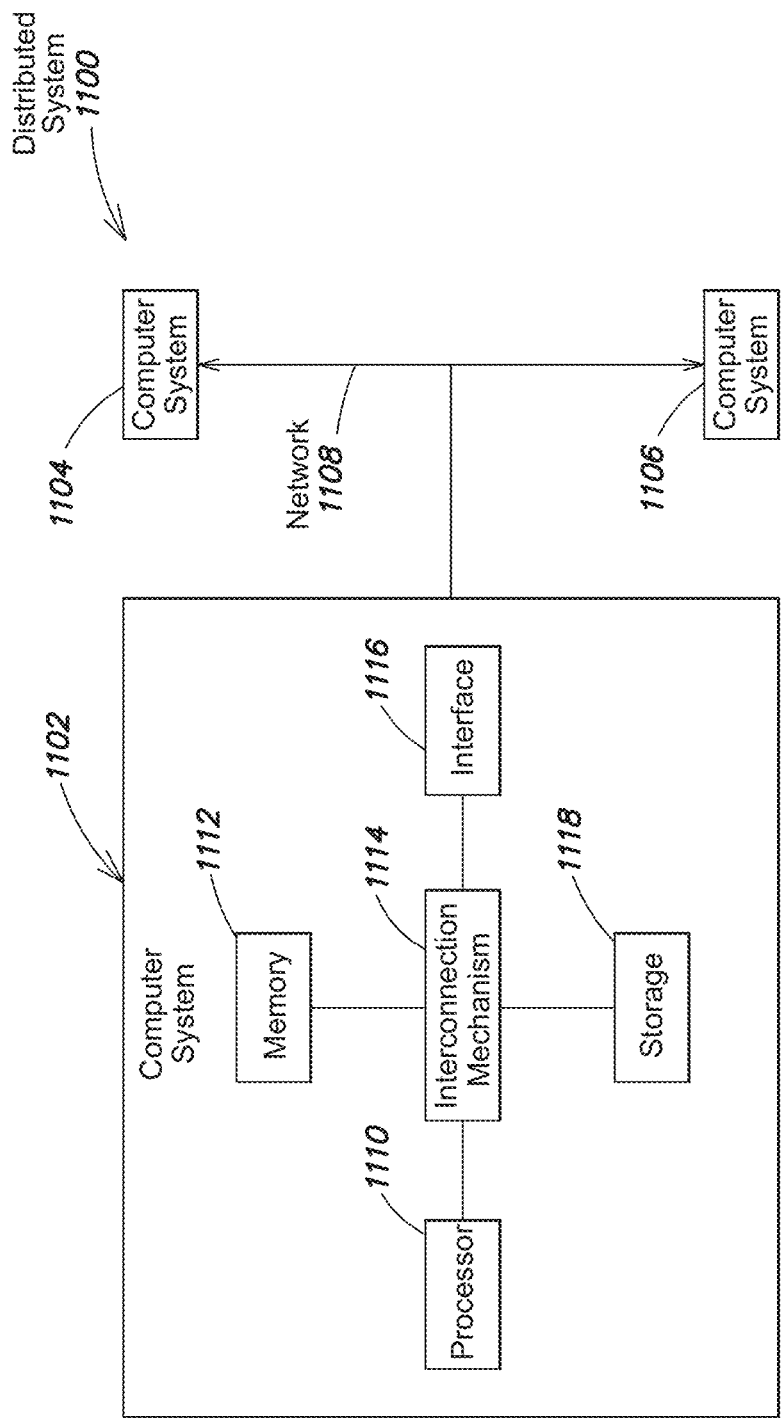
FIG. 11 is a block diagram of an example distributed database system in which various aspects of the present invention can be practiced.

For example, various aspects, functions, and processes including read error correction, dominant allele error sequencing and profiling, building and evaluating per locus error profiles, concentration estimation based on amplification strength profiling and evaluation, number of contributor predictions based on amplification strength evaluation, etc., may be distributed among one or more computer systems configured to provide a service to one or more client computers, or to perform an overall task as part of a distributed system, such as the distributed computer system 1100 shown in FIG. 11. Additionally, aspects may be performed on a client-server or multi-tier system that includes components distributed among one or more server systems that perform various functions. Consequently, embodiments are not limited to executing on any particular system or group of systems. Further, aspects, functions, and processes may be implemented in software, hardware or firmware, or any combination thereof. Thus, aspects, functions, and processes may be implemented within methods, acts, systems, system elements and components using a variety of hardware and software configurations, and examples are not limited to any particular distributed architecture, network, or communication protocol.

Referring to FIG. 11, there is illustrated a block diagram of a distributed computer system 1100, in which various aspects and functions are practiced. As shown, the distributed computer system 1100 includes one or more computer systems that exchange information. More specifically, the distributed computer system 1100 includes computer systems 1102, 1104, and 1106. As shown, the computer systems 1102, 1104, and 1106 are interconnected by, and may exchange data through, a communication network 1108. The network 1108 may include any communication network through which computer systems may exchange data. To exchange data using the network 1108, the computer systems 1102, 1104, and 1106 and the network 1108 may use various methods, protocols and standards, including, among others, Fiber Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST, and Web Services. To ensure data transfer is secure, the computer systems 1102, 1104, and 1106 may transmit data via the network 1108 using a variety of security measures including, for example, SSL or VPN technologies. While the distributed computer system 1100 illustrates three networked computer systems, the distributed computer system 1100 is not so limited and may include any number of computer systems and computing devices, networked using any medium and communication protocol.

As illustrated in FIG. 11, the computer system 1102 includes a processor 1110, a memory 1112, an interconnection element 1114, an interface 1116 and data storage element 1118. To implement at least some of the aspects, functions, and processes disclosed herein, the processor 1110 performs a series of instructions that result in manipulated data. The processor 1110 may be any type of processor, multiprocessor or controller. Example processors may include a commercially available processor such as an Intel Xeon, Itanium, Core, Celeron, or Pentium processor; an AMD Opteron processor; an Apple A4 or A5 processor; a Sun UltraSPARC processor; an IBM Power5+ processor; an IBM mainframe chip; or a quantum computer. The processor 1110 is connected to other system components, including one or more memory devices 1112, by the interconnection element 1114.

The memory 1112 stores programs (e.g., sequences of instructions coded to be executable by the processor 1110) and data during operation of the computer system 1102. Thus, the memory 1112 may be a relatively high performance, volatile, random access memory such as a dynamic random access memory ("DRAM") or static memory ("SRAM"). However, the memory 1112 may include any device for storing data, such as a disk drive or other nonvolatile storage device. Various examples may organize the memory 1112 into particularized and, in some cases, unique structures to perform the functions disclosed herein. These data structures may be sized and organized to store values for particular data and types of data.

Components of the computer system 1102 are coupled by an interconnection element such as the interconnection element 1114. The interconnection element 1114 may include any communication coupling between system components such as one or more physical busses in conformance with specialized or standard computing bus technologies such as IDE, SCSI, PCI and InfiniBand. The interconnection element 1114 enables communications, including instructions and data, to be exchanged between system components of the computer system 1102.

The computer system 1102 also includes one or more interface devices 1116 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 1102 to exchange information and to communicate with external entities, such as users and other systems.

The data storage element 1118 includes a computer readable and writeable nonvolatile, or non-transitory, data storage medium in which instructions are stored that define a program or other object that is executed by the processor 1110. The data storage element 1118 also may include information that is recorded, on or in, the medium, and that is processed by the processor 1110 during execution of the program. More specifically, the information may be stored in one or more data structures specifically configured to conserve storage space or increase data exchange performance. The instructions may be persistently stored as encoded signals, and the instructions may cause the processor 1110 to perform any of the functions described herein. The medium may, for example, be optical disk, magnetic disk or flash memory, among others. In operation, the processor 1110 or some other controller causes data to be read from the nonvolatile recording medium into another memory, such as the memory 1112, that allows for faster access to the information by the processor 1110 than does the storage medium included in the data storage element 1118. The memory may be located in the data storage element 1118 or in the memory 1112, however, the processor 1110 manipulates the data within the memory, and then copies the data to the storage medium associated with the data storage element 1118 after processing is completed. A variety of components may manage data movement between the storage medium and other memory elements and examples are not limited to particular data management components. Further, examples are not limited to a particular memory system or data storage system.

Although the computer system 1102 is shown by way of example as one type of computer system which may be specially configured and upon which various aspects and functions may be practiced, aspects and functions are not limited to being implemented on the computer system 1102 as shown in FIG. 11. Various aspects and functions may be practiced on one or more specially configured computers and having a different architectures or components than that shown in FIG. 11. For instance, the computer system 1102 may include specially programmed, special-purpose hardware, such as an application-specific integrated circuit ("ASIC") tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 1102 may be a computer system including an operating system that manages at least a portion of the hardware elements included in the computer system 1102. In some examples, a processor or controller, such as the processor 1110, executes an operating system. Examples of a particular operating system that may be executed include a Windows-based operating system, such as, Windows NT, Windows 2000 (Windows ME), Windows XP, Windows Vista or Windows 7, 8, or 10 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Oracle Corporation. or a UNIX operating systems available from various sources. Many other operating systems may be used, and examples are not limited to any particular operating system.

The processor 1110 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C# (C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user space application) or in a commonly shared data structure (such as an application registry that is defined by an operating system). In addition, some examples provide for both system and user interfaces that allow external entities to modify the parameters and thereby configure the behavior of the components.

Improved Computer Systems and Algorithms

In the United States of America, the Federal Bureau of Investigation has a database of over 15 million DNA samples in the National DNA Index System (NDIS). Conventional forensic techniques involve comparing STR profiles between samples and individuals whose samples are in the NDIS. The inventor has appreciated that samples with more than one contributor are difficult or impossible to analyze using only STR profiles. The inventor has further appreciated that conventional protocols for searching the NDIS are time consuming, expensive, and often require manual evaluation of the results. Accordingly, the inventor has developed techniques to address these shortcomings of conventional forensic identification techniques. For example, the techniques described herein may be scaled to enable comparisons of large numbers of samples (hundreds of thousands to millions) against databases of tens of millions of samples with performance improvements on the order of 100 to 1000 times faster than traditional approaches.

In some embodiments, techniques described herein provide faster implementations for database comparisons in nucleic acid analysis by encoding one or more features of a nucleic acid sequence using a lossy encoding developed by the inventor, which retains information that may be used to identify one or more individuals while eliminating extraneous information. Encoding a nucleic acid sequence using such a lossy encoding facilitates rapid comparison of the encoded sequence with DNA samples in the NDIS or similar database. As a result, the techniques described herein may be used to rapidly compare multiple samples (each of which may include genetic information from multiple contributors) to information stored in the NDIS database.

In some embodiments, techniques described herein provide for faster implementations due to the reduction of nucleic acid sequence information to a binary encoding. The binary encoding can be rapidly compared to a database of previously generated binary encodings using native bitwise instructions (e.g., XOR, AND, NAND, NOT, OR, population count instruction, etc.) For example, in some aspects, these techniques can be used in single nucleotide polymorphism (SNP, pronounced "snip") analysis. In some embodiments, by implementing the coding scheme set forth in Table 13 below, any occurrence of a minor allele in a nucleic acid sequence may be encoded as a "1" bit.

TABLE 13

Binary Encoding of SNP Alleles

| Alleles | Binary Encoding |
|---------|-----------------|
| MM      | 0               |
| Mm      | 1               |
| mM      | 1               |
| mm      | 1               |

In some embodiments, techniques described herein may be used to compare an individual sample to another individual sample. For example, in some embodiments, a first individual sample may contain nucleic acid sequence information for a first individual who is homozygous for a minor allele at a specific genetic locus, indicating the presence of a SNP. As described in the above, a homozygous minor allele ("mm") may be encoded as a "1" bit. In some embodiments, the encoding of the SNP of the first individual may be compared to one or more encodings of individual samples. In some embodiments, a comparison of the first individual encoding to another individual encoding is executed using an "XOR" instruction.

In some embodiments, the comparison using the XOR instruction results in an indication of whether the two individual samples differ in the occurrence of the SNP. For example, in some embodiments, the XOR between the first individual ("1") and an individual who has a SNP at the same specific genetic locus ("1") would produce a "0" bit. In some embodiments, the XOR between the first individual ("1") and an individual who does not have a SNP at the same specific genetic locus ("0") would produce a "1" bit. In some embodiments, a population count instruction may be used to tally the "1" bits resulting from the XOR instruction. Thus, in some embodiments, a greater value resulting from the population count instruction may provide a greater confidence that the individuals being compared are different.

In some embodiments, techniques described herein may be used to compare an individual sample to a mixture of samples. In some embodiments, the comparison of the individual to the mixture is performed using an XOR instruction as described above. In some embodiments, the result of the XOR instruction is "anded" to the individual sample using an "AND" instruction. In some embodiments, the AND instruction results in an indication of whether the mixture does not have the same SNP as the individual. For example, in some embodiments, an XOR result of "1" indicates that the individual and the mixture differ with respect to the presence of a SNP. However, in some embodiments, the individual might not have a SNP while the mixture does have a SNP. In such embodiments, the occurrence of the SNP in the mixture could be the result of a contributor other than the individual. Thus, in some embodiments, the AND instruction allows for an indication of when the individual has a SNP and the mixture does not. In some embodiments, a population count instruction can be used to tally the "1" bits resulting from the AND instruction.

In some embodiments, techniques described herein provide advantages over STR analysis in the profiling of a nucleic acid sample by implementing SNP analysis. Such a SNP analysis may be useful for comparisons of sequence information obtained from a nucleic acid sample having more than one contributor against a database of samples.

Some embodiments are directed to a method comprising using at least one computer hardware processor to perform: receiving sequence information obtained from a nucleic acid sample, wherein the sequence information comprises a plurality of genetic loci, the plurality of genetic loci including a first genetic locus; generating, based on the received sequence information, an encoding for the nucleic acid sample at least in part by encoding the first genetic locus using a first value when the first genetic locus is homozygous for a major allele and using a second value different from the first value when the first genetic locus is not homozygous for the major allele; comparing the generated encoding of the nucleic acid sample with a plurality of previously-generated encodings for a respective plurality of nucleic acid samples; and when it is determined that, as a result of the comparing, the generated encoding of the nucleic acid sample matches at least one encoding in the plurality of previously-generated encodings, the at least one encoding being associated with at least one person, providing an indication that the nucleic acid sample is consistent with the at least one person. In some embodiments, the comparing is performed using bitwise instructions native to the at least one computer hardware processor executing the method.

In some embodiments, generating the encoding comprises generating a lossy encoding. In some embodiments, the lossy encoding retains information related to one or more features of a nucleic acid sequence that may be useful for identifying an individual. For example, in some embodiments, the lossy encoding encodes information related to a SNP. A SNP is a single-nucleotide substitution of one base (e.g., cytosine, thymine, uracil, adenine, or guanine) for another at a specific position, or locus, in a genome, where the substitution is present in a population to an appreciable extent (e.g., more than 1% of the population).

In some embodiments, the presence or absence of a SNP in a nucleic acid sequence may by itself be used to identify an individual. Thus, in some embodiments, the lossy encoding may encode a sequence by encoding only information indicative of the presence or absence of a SNP in a nucleic acid sequence. In some embodiments, the lossy encoding loses information related to specific nucleotide composition. In some embodiments, the loss of information related to specific nucleotide composition allows the encodings to be implemented in methods described herein at speeds greater than the corresponding nucleic acid sequence information (e.g., greater than the raw data).

In some embodiments, generating the encoding comprises generating a binary encoding. In some embodiments, the first value is a binary value. In some embodiments, the first value consists of a first bit and the second value consists of a second bit different from the first bit. In some embodiments, the first bit is zero. In some embodiments, the first bit is zero and the second bit is one. In some embodiments, only two different values may be used for generating an encoding, for example, if the encoding is intended only to retain information related to the presence or absence of a particular feature.

For example, when encoding nucleic acid sequence information based on the presence or absence of a SNP, the absence of a SNP may be encoded by using a first value (e.g., 0) when a locus is homozygous for a major allele. Alternatively, the presence of a SNP may be encoded by using a second value (e.g., 1) when the locus is not homozygous for a major allele (e.g., the locus is homozygous for a minor allele or the locus is heterozygous).

A variant of the similar nucleic acid sequence located at a given locus is called an allele. As with most multicellular organisms, humans have two sets of chromosomes. These chromosomes are referred to as homologous chromosomes, having the same genes in the same loci. If both alleles at a locus on the homologous chromosomes are the same, they and the organism are homozygous with respect to that gene or location. If the alleles are different, they and the organism are heterozygous with respect to that gene or location.

In a given population, the allele occurring with the greatest frequency at a given locus is referred to as the major allele. Alternative variants at this same locus are referred to as minor alleles. If a major allele is present at a specific locus in both homologous chromosomes, the locus is said to be homozygous for a major allele. If a minor allele is present at a specific locus in both homologous chromosomes, the locus is said to be homozygous for a minor allele. If a pair of homologous chromosomes contains a major allele at a specific locus in one chromosome and a minor allele at the corresponding locus in the other chromosome, the locus is said to be heterozygous.

In some embodiments, the received sequence information obtained from the nucleic acid sample comprises sequence information for only one person (e.g., one contributor). In some embodiments, the received sequence information obtained from the nucleic acid sample comprises sequence information for more than one person (e.g., more than one contributor). In some embodiments, when the generated encoding of the nucleic acid sample matches two different encodings in the plurality of previously-generated encodings, the two different encodings being associated with two different people, the method further comprises providing an indication that the nucleic acid sample is consistent with the two different people.

In some embodiments, generating the encoding comprises using the second value when the first genetic locus is homozygous for a minor allele or the first genetic locus is heterozygous. In some embodiments, the presence of the second value in the generated encoding indicates the presence of a SNP at the first genetic locus. In some embodiments, the use of binary bits to identify SNPs is advantageous because it simplifies and condenses the sequence information into an encoding capable of much faster implementations. In some embodiments, the use of binary bits to encode SNPs is advantageous because it allows for the binning of SNP indicators (e.g., the locus is homozygous for a minor allele or the locus is heterozygous) and non-SNP indicators (e.g., the locus is homozygous for a major allele).

In some embodiments, in methods described herein, the generating further comprises encoding each of the plurality of genetic loci using the first value or the second value. In some embodiments, a plurality of genetic loci are pre-selected for encoding. In some embodiments, the plurality of genetic loci are pre-selected based on known population genetics. Population genetics, in some embodiments, may provide information related to the distribution and change in the frequency of alleles within populations.

In some embodiments, systems described herein may be used to execute methods described herein. In some embodiments, the system comprises: at least one database storing a plurality of encodings for a respective plurality of nucleic acid samples; at least one computer hardware processor; at least one non-transitory computer-readable storage medium storing processor-executable instructions that, when executed by the at least one computer hardware processor, cause the at least one computer hardware processor to perform: receiving sequence information obtained from a nucleic acid sample, wherein the sequence information comprises a plurality of genetic loci, the plurality of genetic loci including a first genetic locus; generating, based on the received sequence information, an encoding for the nucleic acid sample at least in part by encoding the first genetic locus using a first value when the first genetic locus is homozygous for a major allele and using a second value different from the first value when the first genetic locus is not homozygous for the major allele; comparing the generated encoding of the nucleic acid sample with the plurality of encodings stored in the at least one database; and when it is determined that, as a result of the comparing, the generated encoding of the nucleic acid sample matches at least one encoding in the plurality of encodings stored in the at least one database, the at least one encoding being associated with at least one person, providing an indication that the nucleic acid sample is consistent with the at least one person.

In some embodiments, the at least one computer hardware processor is configured to perform a plurality of native bitwise instructions. In some embodiments, native bitwise instructions include a population count bitwise instruction, an "XOR" bitwise instruction, and an "AND" bitwise instruction. Additionally or alternatively, native bitwise instructions include a bitwise OR instruction, a bitwise NAND instruction, a bitwise NOT instruction, an arithmetic shift instruction, a logical shift instruction, a circular shift instruction. and/or any other suitable bitwise instructions that the at least one computer hardware processor is configured to execute, as aspects of the technology described herein are not limited in this respect.

Some embodiments are directed to a method comprising using at least one computer hardware processor to perform: receiving sequence information obtained from a nucleic acid sample, wherein the sequence information comprises at least one short tandem repeat (STR) locus, the at least one STR locus comprising a unit of nucleotides repeated a number of times; generating, based on the received sequence information, an encoding for the nucleic acid sample at least in part by encoding the at least one STR locus using a value that corresponds to the number of times the unit of nucleotides is repeated; comparing the generated encoding of the nucleic acid sample with a plurality of previously-generated encodings for a respective plurality of nucleic acid samples; and when it is determined that, as a result of the comparing, the generated encoding of the nucleic acid sample matches at least one encoding in the plurality of previously-generated encodings, the at least one encoding being associated with at least one person, providing an indication that the nucleic acid sample is consistent with the at least one person. In some embodiments, the comparing is performed using bitwise instructions native to the at least one computer hardware processor executing the method.

In some embodiments, generating the encoding comprises generating a lossy encoding. In some embodiments, the lossy encoding retains information related to one or more features of a nucleic acid sequence that may be useful for identifying an individual. In some embodiments, the lossy encoding encodes information related to an STR. An STR is a tract of repetitive sequence in which a unit of nucleotides (e.g., ranging in length from 2-13 base pairs) is repeated, anywhere from a few times to hundreds of times in a row. The number of times the unit of nucleotides is repeated in a particular STR can vary from one individual to another. Thus, in some embodiments, the number of times the unit of nucleotides is repeated in a particular STR may be used to identify an individual.

In some embodiments, the lossy encoding may encode a sequence by encoding only information indicative of the number of times the unit of nucleotides is repeated in a particular STR. Thus, in some embodiments, the lossy encoding may be indicative of the number of repeating units in the particular STR and/or the identity of the particular STR variant, but the lossy encoding cannot by itself be used to identify nucleotide composition of the particular STR. In some embodiments, the loss of information related to specific nucleotide composition allows the encodings to be implemented in methods described herein at speeds greater than the corresponding nucleic acid sequence information.

In some embodiments, more than two different values may be used when generating an encoding, for example, if the encoding is intended to retain information related to more than one feature of a nucleic acid sequence. For example, in some embodiments, it may be desirable to encode information related to more than one STR locus. As any given STR locus may be one of a limited number of variants, encoding more than one STR locus may increase the uniqueness of the encoding. Thus, in some embodiments, the certainty with which one or more individuals may be identified from a nucleic acid sample scales with the number of values used to encode the nucleic acid sequence information obtained from the nucleic acid sample.

In a binary encoding, the number of bits used to encode a particular feature may depend on the number of possible values for the particular feature. In the foregoing example illustrating generating an encoding that encodes for the presence or absence of a SNP, a single bit (e.g., 1 or 0) may be used since the number of possible outcomes is limited to two values ("presence" or "absence"). In some embodiments, a single bit (e.g., 1 or 0) may be used to encode for the presence or absence of a particular variant at an STR locus. In some embodiments, it may be advantageous to use multiple bits for encoding an STR locus, as a given STR locus typically comprises multiple variants.

The number of values encoded by a given number of bits follows the formula: 2n, where n is the number of bits. For example, a one bit encoding (21=2) may be used to encode either of two values (e.g., 1 or 0). As such, a two bit encoding (22=4) may be used to encode any one of four values (e.g., 00, 01, 10, or 11), a three bit encoding may be used to encode any one of eight values (23=8), a four bit encoding may be used to encode any one of sixteen values (24=16), a five bit encoding may be used to encode any one of 32 values (25=32), etc. Thus, the maximum number of STR locus variants that may be assigned unique values using a binary encoding of length n is less than or equal to 2n. In other words, a binary encoding of length n may be used to encode, uniquely, up to 2n values.

In some embodiments, the value may correspond to the absolute number of times the unit of nucleotides is repeated in the STR locus. The absolute number of repeats may greatly vary across STR loci. For example, some STR loci may consist of a unit of nucleotides repeated only a few times while other STR loci may consist of a unit of nucleotides repeated hundreds of times. Thus, when it is desirable to generate an encoding using a value that directly corresponds to the absolute number of repeats in the locus, this variation in repeat number may be taken into consideration when selecting the number of bits to be used. In some embodiments, the value may consist of 1 bit, between 1-3 bits, between 2-4 bits, between 3-5 hits, between 4-6 bits, between 5-7 bits, between 6-8 bits, between 7-9 bits, between 8-10 bits, 10 bits, or more than 10 bits. In some embodiments, the value may consist of 5 bits.

Although the absolute number of repeats may greatly vary across STR loci to include relatively large numbers, the actual number of variants at any given locus may be small by comparison. Typically, each STR allele can be shared by 5-20% of individuals. Thus, in some embodiments, it may be advantageous to encode an STR locus using a value that directly corresponds to an identifier for a particular variant at the locus. As the number of possible values is minimized in this approach, the encoding may provide for faster implementations. In some embodiments, the value may be one of between 2-30 possible values (e.g., one of 2 possible values, one of between 2-12 possible values, one of between 10-20 possible values, one of between 20-30 possible values, or one of 30 possible values). In some embodiments, the value is one of between 5-25 possible values (e.g., one of 5 possible values, one of between 5-15 possible values, one of between 10-20 possible values, one of between 15-20 possible values, or one of 25 possible values). In some embodiments, the value is one of around 20 possible values (e.g., one of 15, 16, 17, 18, 19, 20, 21, 22, 23, 24, or 25 possible values).

In some embodiments, an STR encoding may be generated based on the common known STR alleles for a given STR locus. In some embodiments, a "1" bit may be used in the STR encoding that is unique to a particular allele at an STR locus. For example, the STR locus TPDX may comprise a number of repeating [AATG] units which may vary from individual to individual. Table 14 below lists examples of different TPDX alleles, along with 16-bit encodings that could be used to represent each allele.

TABLE 14

Examples of TPOX alleles and corresponding encodings

| Allele | Number of repeats | Encoding |
|---|---|---|
| [AATG]$_6$ | 6 | 0000000000000001 |
| [AATG]$_7$ | 7 | 0000000000000010 |
| [AATG]$_8$ | 8 | 0000000000000100 |
| [AATG]$_9$ | 9 | 0000000000001000 |
| [AATG]$_{10}$ | 10 | 0000000000010000 |
| [AATG]$_{11}$ | 11 | 0000000000100000 |
| [AATG]$_{12}$ | 12 | 0000000001000000 |
| [AATG]$_{13}$ | 13 | 0000000010000000 |
| [AATG]$_{14}$ | 14 | 0000000100000000 |
| [AATG]$_n$ | Other alleles | 0000001000000000 |

As shown in Table 14, in some embodiments, a unique value may be assigned to each of one or more known common STR alleles. In some embodiments, an encoding for a particular STR locus may be generated for a sample comprising a mixture of contributors. In some embodiments, an encoding may be generated that encodes each allele present in nucleic acid sequence information. For example, a mixed sample having alleles with 7, 9, and 12 repeats may be encoded as "0000000001001010" according to the representative encodings shown in Table 14.

In some embodiments, the at least one genetic locus is pre-selected for encoding. In some embodiments, the at least one STR locus is selected from the core STR loci of the CODIS database or equivalent. CODIS is an index of pointers to assist US public crime laboratories to compare and exchange genetic profiles (e.g., DNA profiles). A record in the CODIS database, known as a CODIS DNA profile, consists of an individual's genetic profile, together with the sample's identifier and an identifier of the laboratory responsible for the profile.

CODIS identifies genetic markers at the following STR loci: the original set: D3S1358, vWA, FGA, D8S1179, D21S11, D18551, D5S818, D13S317, D7S820, D16S539, THO1, TPDX, CSF1PO, and AMEL; and the additional set: D1S1656, D2S441, D2S1338, D10S1248, D12S391, D19S433, and D22S1045 (the "COINS STR loci"). In some embodiments, the at least one STR locus is selected from the CODIS STR loci. In some embodiments, the at least one STR locus is selected from Table 15 below.

TABLE 15

| STR Loci | | | |
|---|---|---|---|
| CSF1PO (US core locus) | D22S1045 (European recommended locus) | D6S1043 | DYS464 |
| FGA (FIBRA) (US core locus) | DYS19 (European core Y-STR; SWGDAM recommended) | CD4 | DY5635 |
| TH01 (US core locus) | DYS385 a/b (European core Y-STR; SWGDAM recommended) | F13A1 | Y-GATA-A4 |
| TPOX (US core locus) | DYS389 I/II (European core Y-STR; SWGDAM recommended) | F13B | Y-GATA-A7.1 |
| VWA (US core locus) | DYS390 (European core Y-STR; SWGDAM recommended) | FES/FPS | Y-GATA-A7.2 |
| D3S1358 (US core locus) | DYS391 (European core Y-STR; SWGDAM recommended) | HPRTB | Y-GATA-A10 |
| D5S818 (US core locus) | DYS392 (European core Y-STR; SWGDAM recommended) | LPL | Y-GATA-H4 |
| D7S820 (US core locus) | DYS393 (European core Y-STR; SWGDAM recommended) | Penta D | ACTBP2 (SE33) |
| D8S1179 (US core locus) | DYS438 (SWGDAM recommended) | Penta E | Amelogenin |
| D13S317 (US core locus) | DYS439 (SWGDAM recommended) | D6S1043 | D3S1359 |
| D16S539 (US core locus) | SE33 (German core locus) | D14S1434 | D7S809 |
| D18S51 (US core locus) | CD4 | DYS388 | D8S347 |
| D21S11 (US core locus) | F13A1 | DYS434 | D11S554 |
| D2S1338 (European locus) | F13B | DYS437 | D13S308 |
| D19S433 (European locus) | FES/FPS | DYS447 | FABP |
| D1S1656 (European recommended locus) | HPRTB | DYS448 | FOLP23 (DHFRP2) |
| D2S441 (European recommended locus) | LPL | DYS456 | |
| D10S1248 (European recommended locus) | Penta D | DYS458 | |
| D12S391 (European recommended locus) | Penta E | DYS460 | |

In some embodiments, it may be advantageous to encode more than one STR locus in order to increase the uniqueness of a genetic profile being encoded. Thus, in some embodiments, the encoding encodes at least two STR loci. In some embodiments, the encoding encodes a plurality of the CODIS STR loci. In some embodiments, the encoding encodes all of the CODIS STR loci. In some embodiments, the encoding encodes a plurality of STR loci independently selected from the STR loci recited in Table 15.

In some embodiments, systems described herein may be used to execute methods described herein. In some embodiments, the system comprises: at least one database storing a plurality of encodings for a respective plurality of nucleic acid samples; at least one computer hardware processor; at least one non-transitory computer-readable storage medium storing processor-executable instructions that, when executed by the at least one computer hardware processor, cause the at least one computer hardware processor to perform: receiving sequence information obtained from a nucleic acid sample, wherein the sequence information comprises at least one short tandem repeat (STR) locus, the at least one STR locus comprising a unit of nucleotides repeated a number of times; generating, based on the received sequence information, an encoding for the nucleic acid sample at least in part by encoding the at least one STR locus using a value that corresponds to the number of times the unit of nucleotides is repeated; comparing the generated encoding of the nucleic acid sample with a plurality of previously-generated encodings for a respective plurality of nucleic acid samples; and when it is determined that, as a result of the comparing, the generated encoding of the nucleic acid sample matches at least one encoding in the plurality of previously-generated encodings, the at least one encoding being associated with at least one person, providing an indication that the nucleic acid sample is consistent with the at least one person.

In some embodiments, the at least one computer hardware processor is configured to perform a plurality of native bitwise instructions. In some embodiments, native bitwise instructions include a population count bitwise instruction, an "XOR" bitwise instruction, and an "AND" bitwise instruction. Additionally or alternatively, native bitwise instructions include a bitwise OR instruction, a bitwise NAND instruction, a bitwise NOT instruction, an arithmetic shift instruction, a logical shift instruction, a circular shift instruction, and/or any other suitable bitwise instructions that the at least one computer hardware processor is configured to execute, as aspects of the technology described herein are not limited in this respect.

Figure 12A:
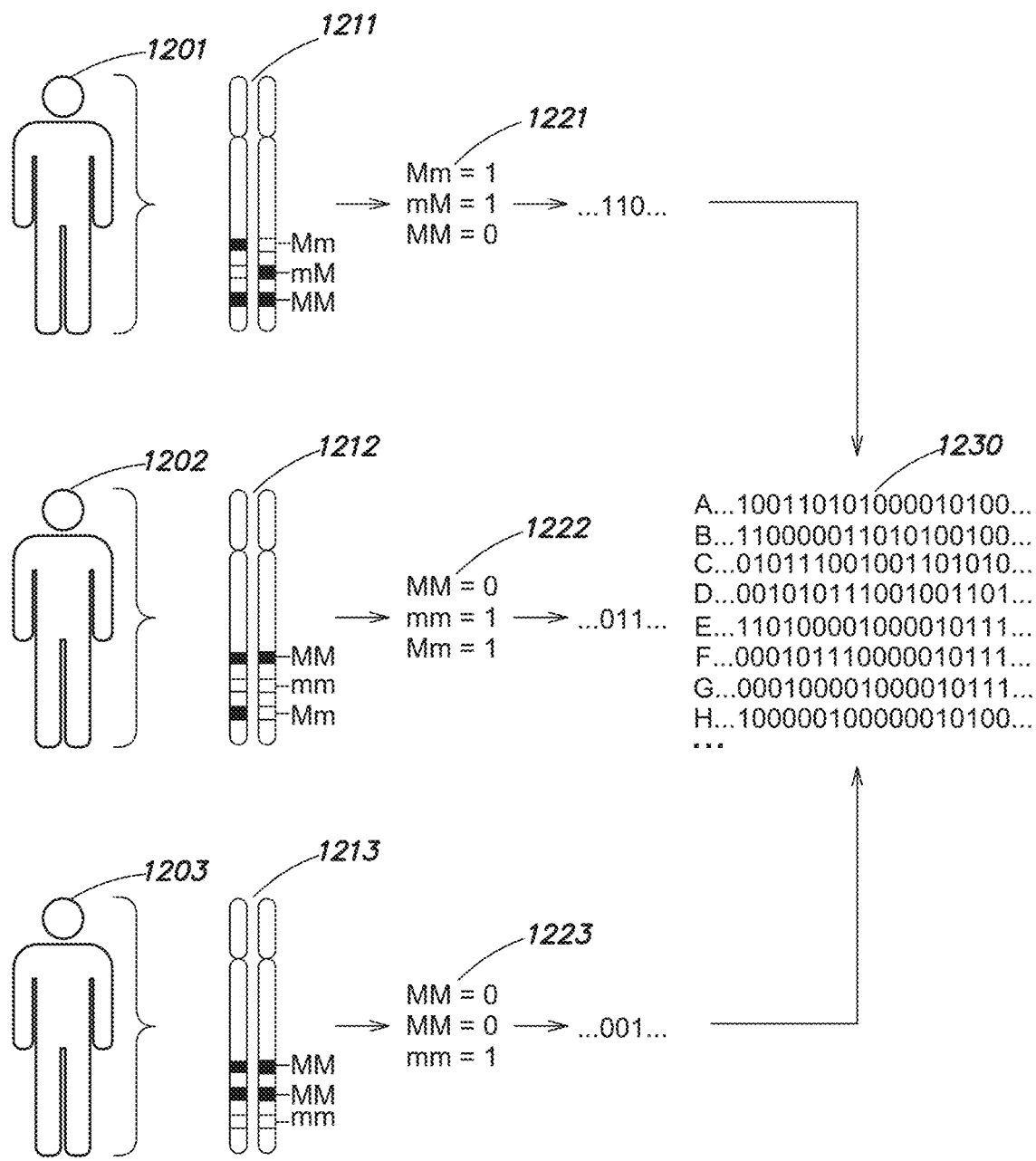
FIGS. 12A and 12B are diagrams illustrating identifying an individual from a nucleic acid sample containing genetic material from multiple individuals, in accordance with some embodiments of the technology described herein.

FIG. 12A depicts an example of generating encodings based on sequencing information (e.g., genetic profiles) of different individuals. A first individual 1201 has homologous chromosomes 1211 with three specific loci shown. For each locus, each chromosome is shown as having a major allele (black box) or a minor allele (white box). As shown, individual 1201 has a first locus comprising heterozygous allele "Mm," a second locus comprising heterozygous allele "mM," and a third locus comprising homozygous major allele "MM." According to some methods provided herein, these loci can be encoded according to 1221, where "0" encodes a locus that is homozygous for a major allele and "1" encodes a locus that is not homozygous for a major allele. Thus, for the first individual 1201, the three loci can be represented by the encoding "110."

In order to distinguish individual genetic profiles or sequencing information representative of one or more individuals, specific loci may be analyzed. For example, a second individual 1202 has homologous chromosomes 1212 with three loci corresponding to the sites depicted in homologous chromosomes 1211. The first locus comprises homozygous major allele "MM," the second locus comprises homozygous minor allele "mm," and the third locus comprises heterozygous allele "Mm." These loci are encoded according to 1222 to generate an encoding of "011" for these loci. Similarly, an encoding for the corresponding three loci can be generated for a third individual 1203 having homologous chromosomes 1213. Having two homozygous major alleles and one homozygous minor allele, sequencing information for the third individual 1203 is encoded according to 1223 to generate an encoding of "001" for the three loci. As shown in FIG. 12A, the encodings can be compiled into a database of encodings 1230.

In some embodiments, it may be advantageous to select a set of loci and/or SNPs for inclusion in the analysis if the SNP is (1) relatively rare (has a low minor allele frequency, or "mAF"), (2) is not well-correlated with ancestry, (3) is physically far enough from another SNP within any chromosome that they do not tend to be inherited together, and, optionally, (4) is not related to health status. For example, in the context of a forensic investigation, the loci and/or SNPs selected for inclusion may be SNPs most often found in healthy individuals. However, in the context of SNP analysis of a medical or biological sample, for instance, to diagnose and/or prognose cancer, it may be desirable to include loci and/or SNPs, for example, that predict unregulated or deregulated cell proliferation, neovascularization, and metastasis.

It should be appreciated that an encoding generated based on nucleic acid sequencing information is not limited to three values, as shown in FIG. 12A. It should also be appreciated that generating an encoding is not necessarily limited to nucleic acid sequencing information that is representative of a single contributor (e.g., one person). In some embodiments, one encoding may comprise sequencing information for more than one contributor (e.g., more than one person). For example, a nucleic acid sample may comprise a mixture of genetic profiles. Upon subjecting the nucleic acid sample to nucleic acid sequencing, allele variation at a specific locus may be indicative of a mixture of genetic profiles.

Figure 12B:
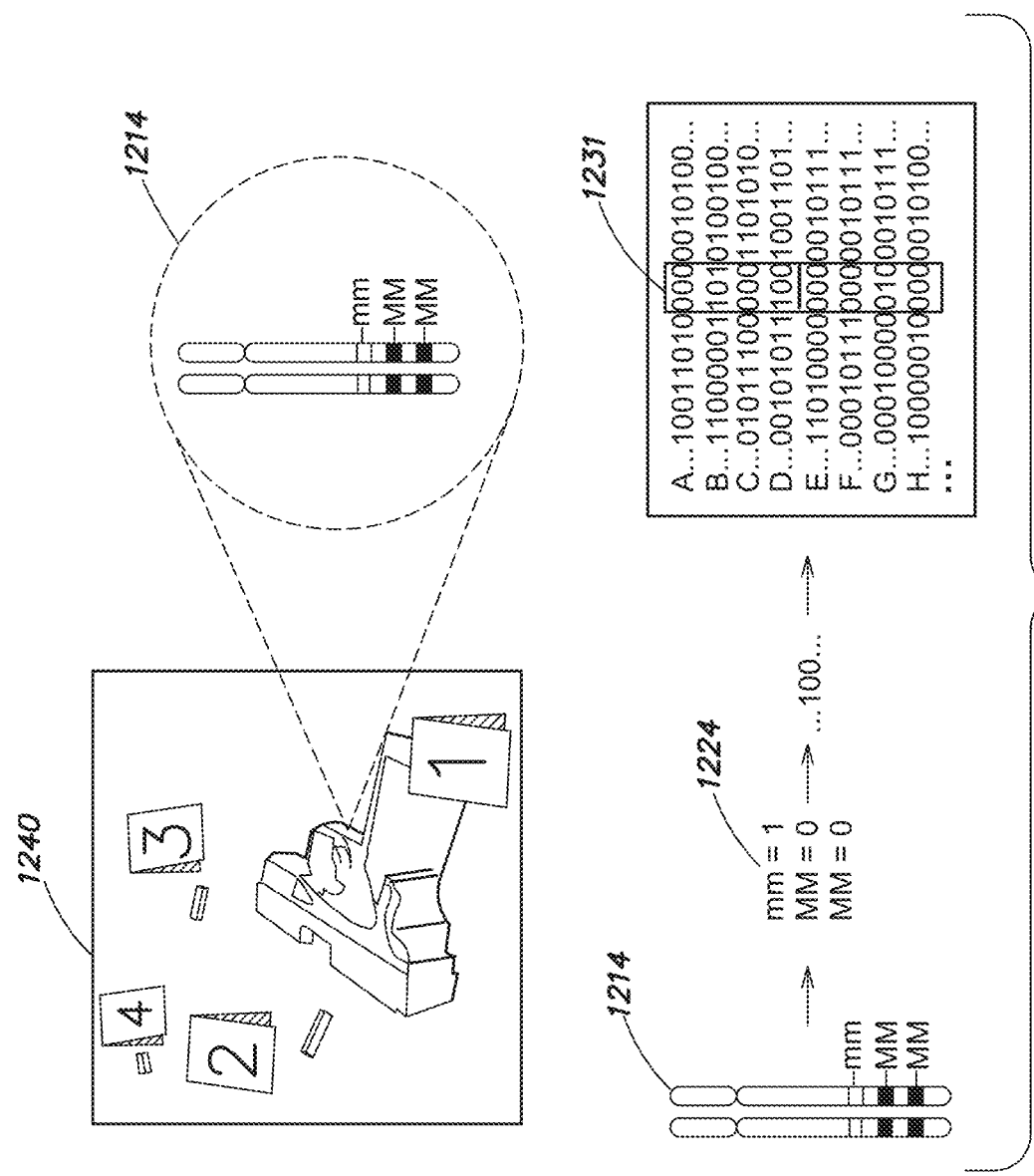

Methods and systems of the disclosure may provide superior properties over the existing methods of building and deconvoluting genetic profiles in a forensic setting. FIG. 12B depicts a crime scene 1240 in which a nucleic acid sample comprising nucleic acid 114 was obtained. An encoding may be generated based on the allele zygosity at specific loci. For example, a first locus comprising a homozygous minor allele and a second and third locus comprising homozygous major alleles are encoded according to 1224 as "100." The encoding generated for the nucleic acid sample may subsequently be compared to a database 1231 comprising a plurality of encodings to potentially identify a matching encoding, e.g., encoding "D."

Figure 13:
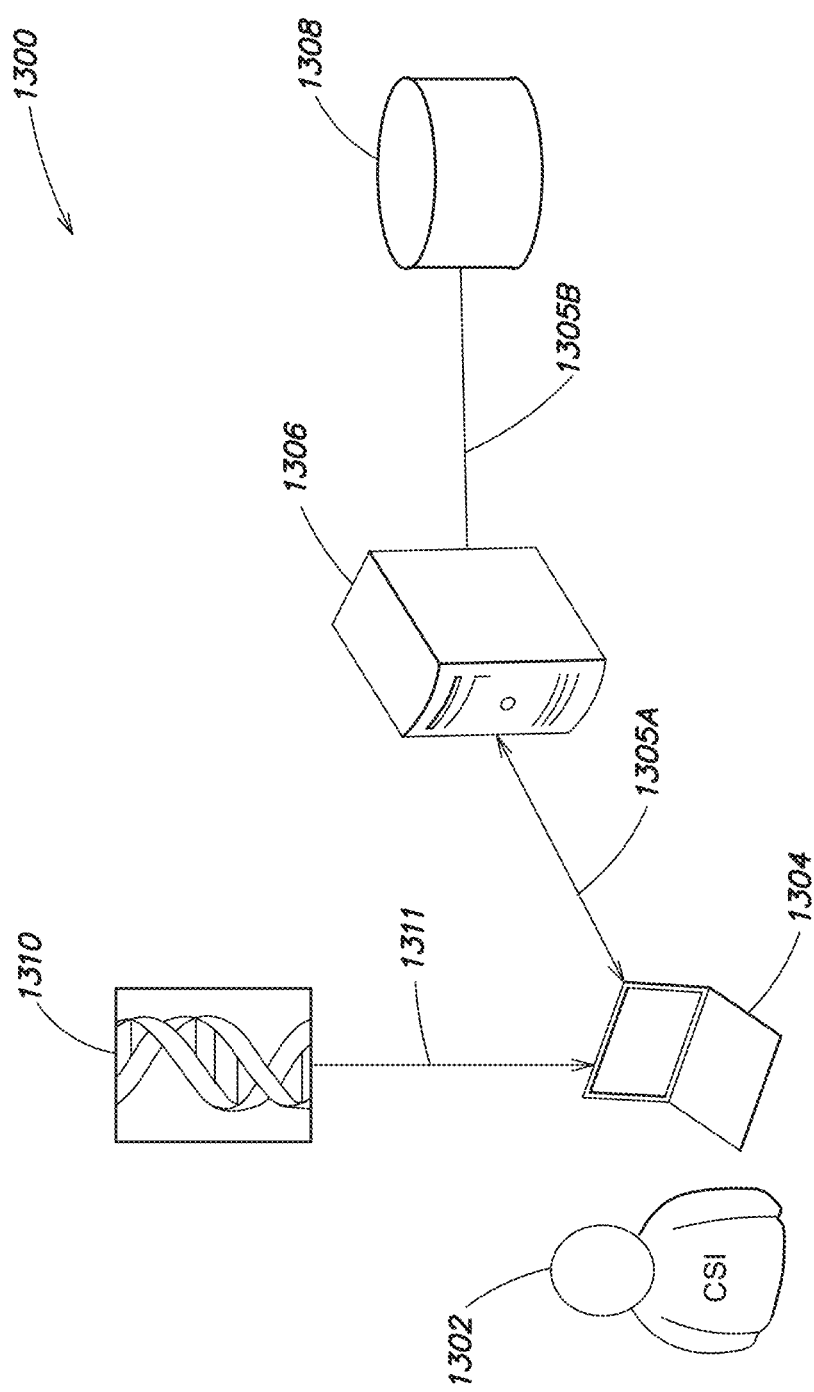
FIG. 13 depicts an illustrative environment in which embodiments of the present technology may operate.

FIG. 13 shows a non-limiting illustrative environment 1300 in which embodiments described herein may operate. In the illustrative environment, an individual 1302 may use any suitable device 1304 to conduct methods described herein. For instance, the device 1304 may be a laptop computer, a mobile device, a desktop computer, a desktop monitor, or any other device that is compatible with the methods described herein.

In the illustrated embodiment, sequence information 1310 is received by the device 1304 via connection 1311, which may include wired and/or wireless connection. For example, device 1304 can receive sequence information 1310 via wired and/or wireless internet connection (e.g., via e-mail, via online data storage, etc.). Connection 1311 is also contemplated to include non-internet (e.g., offline) connections, such as connection to external data storage media.

In this embodiment, device 1304 is communicatively coupled to one or more computers (e.g., servers) each configured to perform processing related to generating an encoding of sequence information and/or comparing the generated encoding with a plurality of previously generated encodings. As shown, device 1304 is coupled to a single server 1306 via wired and/or wireless connection 1305A, though in other embodiments any suitable number of servers may be used and distributed in any manner. For instance, in some embodiments, at least ten, at least one hundred, at least one thousand, or at least ten thousand servers may be used. For embodiments in which multiple servers are used, the servers may not be located in the same physical location and may be distributed across multiple physical locations.

Each server, such as server 1306, may be configured (alone or in combination with one or more other servers) to perform processing related to generating an encoding of sequence information and/or comparing the generated encoding with a plurality of previously generated encodings. In some embodiments, one or more of the servers may be configured to store processor-executable instructions. In some embodiments, device 1304 may be configured to store processor-executable instructions. In some embodiments, one or more of the servers may be configured to execute one or more instructions related to the steps of generating the encoding of sequence information and/or comparing the generated encoding with a plurality of previously generated encodings. In some embodiments, the device 1304 may be configured to execute one or more instructions related to the steps of generating the encoding of sequence information and/or comparing the generated encoding with a plurality of previously generated encodings.

In the illustrated embodiment, the server 1306 is connected to a storage device 1308 via wired and/or wireless connection 1305B. Storage device(s) 1308 may be any suitable storage device(s) or article(s) of manufacture capable of storing information. For example, storage device (s) 208 may be any non-transitory computer readable storage medium or media such as a computer memory (RAM and/or ROM), one or more hard disk drives, one or more optical disks (CDs and/or DVDs), one or more magnetic tapes, one or more flash memories, one or more circuit configurations in Field Programmable Gate Arrays and/or any other suitable device(s).

In the illustrated embodiment, one or more of device 1304, server 1306, and storage device(s) 1308 can be configured to execute and/or support one or more instructions related to the steps of generating the encoding of sequence information and/or comparing the generated encoding with a plurality of previously generated encodings. In some embodiments, one or more of device 1304, server 1306, and storage device(s) 1308 can be configured to perform a plurality of native bitwise instructions. In some embodiments, native bitwise instructions include a population count bitwise instruction, an "XOR" bitwise instruction, and an "AND" bitwise instruction. Additionally or alternatively, native bitwise instructions include a bitwise OR instruction, a bitwise NAND instruction, a bitwise NOT instruction, an arithmetic shift instruction, a logical shift instruction, a circular shift instruction, and/or any other suitable bitwise instructions that the at least one computer hardware processor is configured to execute, as aspects of the technology described herein are not limited in this respect.

FIG. 3A shows an illustrative process 300 comprising steps of generating an encoding of sequence information based on allele zygosity and comparing the generated encoding with a plurality of previously generated encodings. Process 300 may be performed, at least in part, by one or more of device 1304, server 1306, and storage device(s) 1308.

Process 1400 begins in act 1402, where sequence information obtained from a nucleic acid sample is received. The received sequence information comprises a plurality of genetic loci, including a first genetic locus. In some embodiments, the received sequence information may comprise sequence information for only one person. In some embodiments, the received sequence information may comprise sequence information for more than one person.

Next, process 1400 proceeds to decision block 1404, where it is determined whether the first genetic locus of the sequence information received in 1402 is homozygous for a major allele. As described herein, a genetic locus is homozygous for a major allele when an allele occurring with the greatest frequency in a given population is present in both homologous chromosomes at that locus.

The determination of whether the first genetic locus is homozygous for a major allele may be made in any suitable way. For example, the determination may be made that the first genetic locus is not homozygous for a major allele if the first genetic locus is homozygous for a minor allele or if the first genetic locus is heterozygous. In some embodiments, the determination may be made at least in part by comparing the locus to publically available genetic information for a given population.

If it is determined, in decision block 1404, that the first genetic locus is homozygous for a major allele, process 1400 proceeds to act 1406, where the first genetic locus is encoded using a first value. If it is determined, in decision block 1404, that the first genetic locus is not homozygous for a major allele, process 1400 proceeds to act 1408, where the first genetic locus is encoded using a second value.

In some embodiments, the act (e.g., 1406 or 1408) of generating an encoding comprises generating a lossy encoding. A "lossy encoding" can represent the compression of data into a form which, when it is re-expanded, does not contain all of the original information. In some embodiments, the act (e.g., 1406 or 1408) of generating an encoding comprises generating a binary value. In some embodiments, the act 1406 of encoding the first genetic locus using a first value comprises encoding the first genetic locus using a first bit. In some embodiments, the act 1408 of encoding the first genetic locus using a second value comprises encoding the first genetic locus using a second bit. In some embodiments, the act 1406 of encoding the first genetic locus using a first bit comprises encoding the first genetic locus using a "0". In some embodiments, the act 1408 of encoding the first genetic locus using a second bit comprises encoding the first genetic locus using a "1".

After the encoding process in act 1406 or act 1408, process 1400 proceeds to act 1410, where the generated encoding of the nucleic acid sample is compared with a plurality of previously generated encodings for a respective plurality of nucleic acid samples. In some embodiments, the comparing is performed using bitwise instructions native to at least one computer hardware processor executing the process 1400.

After the comparing step in act 1410, process 1400 proceeds to decision block 1412, where it is determined, as a result of the comparing in act 1410, whether the generated encoding of the nucleic acid sample matches the at least one of the plurality of previously generated encodings for the respective plurality of nucleic acid samples.

If it is determined, in decision block 1412, that, as a result of the comparing in act 1410, the generated encoding of the nucleic acid sample matches at least one encoding in the plurality of previously generated encodings, the at least one encoding being associated with at least one person, then process 1400 proceeds to act 1414, where an indication is provided that the nucleic acid sample is consistent with the at least one person.

In some embodiments, the generated encoding of the nucleic acid sample matches two different encodings in the plurality of previously generated encodings, the two different encodings being associated with two different people. In such embodiments, act 1414 comprises providing an indication that the nucleic acid sample is consistent with the two different people.

During process 1400, decision block 1404 and acts 1406 and 1408 may advantageously be repeated for any number of subsequent loci (e.g., a second genetic locus, a third genetic locus, etc.) in the received sequence information to generate an encoding comprising more than one value. Such an embodiment may be useful, for example, when implementing SNP analysis. By analyzing loci that are known to occur at a specific frequency in a given population, accuracy will be increased in the determining step represented in decision block 1412.

For example, FIG. 1A depicts an individual 102 with three loci that correspond to a first site that is homozygous for a major allele ("MM"), a second site that is homozygous for a minor allele ("mm"), and a third site that is heterozygous ("Mm"). Using process 1400, one could generate an encoding for the three loci of "011." FIG. 1A further depicts an individual 1203 with three loci that correspond to a first site that is homozygous for a major allele ("MM"), a second site that is homozygous for a major allele ("MM"), and a third site that is homozygous for a minor allele ("mm"). Using process 300, one could generate an encoding for the three loci of "001."

In some embodiments, an encoding of "1" can indicate the presence of a SNP. Thus, in the foregoing example with individual 102 ("011") and individual 1203 ("001"), it could be said that both individuals have a SNP at the third site of the three loci while neither individual has a SNP at the first site. However, individual 1202 may be distinguished from individual 1203 in that the former has a SNP at the second site of the three loci. As the number of encoded loci increases, there is a decrease in the probability) that sequence information for any given individual will match the encoding.

It should be appreciated that systems and methods provided herein are not limited to SNP analysis, which is illustrated in the above example. In some aspects, techniques described herein may be used for STR analysis. For example, an encoding can be generated based on one or more of the defined core STR loci of the CODIS database or equivalent. Sequencing information obtained from a nucleic acid sample may comprise one or more of these core STR loci, and an encoding may be generated for one or more of the loci.

Figure 14A:
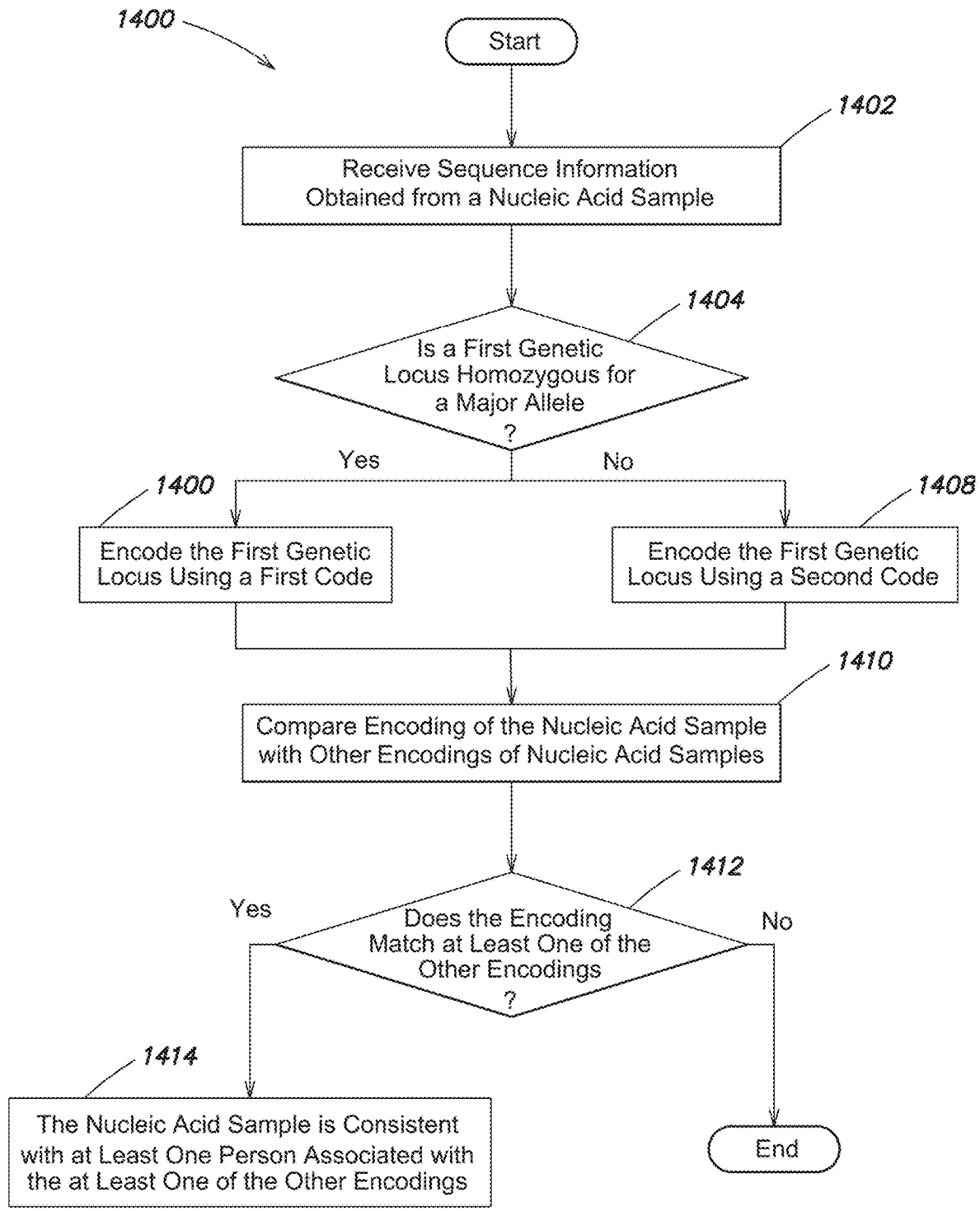
FIGS. 14A and 14B are flow charts of illustrative processes for encoding sequence information obtained from a nucleic acid sample and comparing the resultant encoding with encodings of other nucleic acid samples, in accordance with some embodiments of the technology described herein.
Figure 14B:
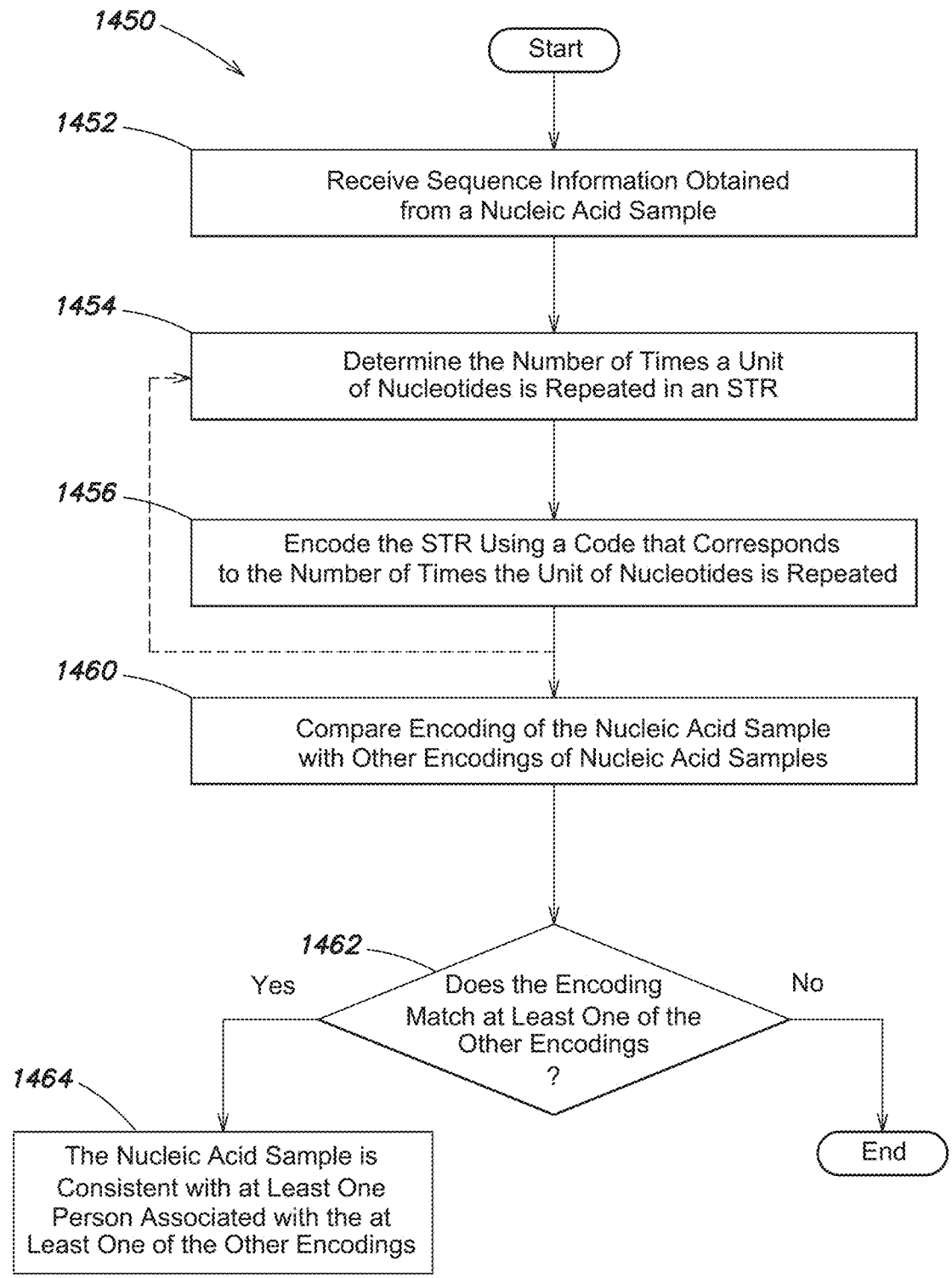

FIG. 14B shows an illustrative process 1450 for forensic identification using STR analysis, in accordance with some embodiments of the technology described herein. The process 1450 includes generating an encoding of sequence information based on the number of repeated motifs in an STR and comparing the generated encoding with a plurality of previously generated encodings. Process 1450 may be performed by any suitable computing device(s). For example process 1450 may be performed by one or more of device 204, server 206, and storage device(s) 208.

Process 1450 begins in act 1452, where sequence information obtained from a nucleic acid sample is received. In some embodiments, the received sequence information may consist of sequence information for only one person. In some embodiments, the received sequence information may consist of sequence information for more than one person. The received sequence information may comprise at least one STR locus, which may comprise a unit of nucleotides repeated a number of times. As described previously, an STR is a tract of repetitive nucleic acid sequence in which certain units of nucleotides (ranging in length from 2-5 base pairs) are repeated, typically 5-50 times.

Next, process 1450 proceeds to act 1454, where the number of times the unit of nucleotides is repeated in the STR is determined for the STR locus of the sequence information received in 1452. In some embodiments, the STR locus may comprise a single unit of nucleotides that is repeated some number of times. In some embodiments, the STR locus comprises multiple units of nucleotides that are each independently repeated some number of times.

For example, the STR locus D8S1179 (chromosomal location: 8q24.13) is one of the genetic markers of the CODIS loci. In some individuals, D8S1179 consists of a single unit of nucleotides (e.g., "TCTA") repeated some number of times, which may be represented as [TCTA]n, where n denotes the number of times the unit is repeated. In other individuals, D8S1179 consists of multiple units of nucleotides repeated some number of times, for example, as represented by the formula [TCTA]n[TCTG]n[TCTA]n, where each instance of n can independently vary (e.g., the STR locus can be [TCTA]1[TCTG]1[TCTA]11, [TCTA]2[TCTG]1[TCTA]13, etc.).

When the STR consists of multiple units of nucleotides repeated some number of times, the number determined in act 1451 can be made in any suitable way. As described in the above example, D8S1179 can consist of repeat structures [TCTA]n and [TCTA]n[TCTG]n[TCTA]n. In some embodiments, a practitioner of the technology described herein may choose to determine the value of the latter structure by summing each value for n (e.g., the number of times determined in act 1454 for [TCTA]2[TCTG]1[TCTA]13 is 2+1+13, or 16). In some embodiments, the practitioner may choose to exclude certain units from the number determined in act 1454 (e.g., TCTG is excluded from consideration and the number of times determined for [TCTA]2[TCTG]1[TCTA]13 is 2+13, or 15).

Once the number is determined in act 1454, process 1450 proceeds to act 1456, where an encoding is generated using a value that corresponds to the number of times the unit of nucleotides is repeated. It should be appreciated that process 1450 is one illustrative embodiment of the technology described herein, and that an encoding may be generated to encode any characteristic of an STR locus. For example, in some embodiments, an encoding may be generated that encodes one or more of the following in an STR: sequence length of the unit of nucleotides that is repeated (e.g., using a value that corresponds to a value of 4 for [TCTA]n); number of times the unit of nucleotides is repeated (e.g., using a value that corresponds to the value of n in [TCTA]n); and overall sequence length of the STR (e.g., using a value that corresponds to the product of 4 and n in [TCTA]n).

After the encoding process in act 1456, process 1450 proceeds to act 1460, where the generated encoding of the nucleic acid sample is compared with a plurality of previously generated encodings for a respective plurality of nucleic acid samples. In some embodiments, the comparing is performed using bitwise instructions native to at least one computer hardware processor executing the process 1450.

After the comparing step in act 1460, process 1450 proceeds to decision block 1462, where it is determined, as a result of the comparing in act 1460, whether the generated encoding of the nucleic acid sample matches the at least one of the plurality of previously generated encodings for the respective plurality of nucleic acid samples.

If it is determined, in decision block 1462, that, as a result of the comparing in act 1460, the generated encoding of the nucleic acid sample matches at least one encoding in the plurality of previously generated encodings, the at least one encoding being associated with at least one person, then process 1450 proceeds to act 1464, where an indication is provided that the nucleic acid sample is consistent with the at least one person.

In some embodiments, the generated encoding of the nucleic acid sample matches two different encodings in the plurality of previously generated encodings, the two different encodings being associated with two different people. In such embodiments, act 1464 comprises providing an indication that the nucleic acid sample is consistent with the two different people.

During process 1450, acts 1454 and 1456 can advantageously be repeated (as indicated by the dashed line) for any number of subsequent STR loci in the received sequence information to generate an encoding comprising more than one value. Such an embodiment may be desirable, for example, when implementing STR analysis. By analyzing STR loci that are known to occur at a specific frequency in a given population, accuracy will be increased in the determining step represented in decision block 1462.

EXAMPLES

Example 1: SNP Allele Comparisons

The DNA bases are encoded as A, C, G, and T. A SNP typically has a major allele that is most common in a population of people and a minor allele with a lower allele frequency than the major allele. Most SNPs have typically only two alleles, but more alleles are possible. Let M represent a major allele and m represent a minor allele. With two alleles for a SNP, then there are four possibilities for the SNP for an individual: MM, Mm, mM, and mm. For comparing two individuals, Table 16 shows the possible allele combinations. To compare a set of SNPs, size N, between two individuals, 2×N allele comparisons are needed with care to treat Mm and mM as two common alleles.

TABLE 16

Possible SNP Allele Comparisons between Two Individuals

| Individual 1 | Individual 2 | # of Common Alleles |
|---|---|---|
| MM | MM | 2 |
| Mm | MM | 1 |
| mM | MM | 1 |
| mm | MM | 0 |
| MM | Mm | 1 |
| Mm | Mm | 2 |
| mM | Mm | 2 |
| mm | Mm | 1 |
| MM | mM | 1 |
| Mm | mM | 2 |
| mM | mM | 2 |
| mm | mM | 1 |
| MM | mm | 0 |
| Mm | mm | 1 |
| mM | mm | 1 |
| mm | mm | 2 |

The logic binary bit operators for XOR and AND are shown in Tables 17 and 18.

TABLE 17

Logic XOR Operator

| Bit 1 | Bit 2 | Operator | Result |
|---|---|---|---|
| 0 | 0 | XOR | 0 |
| 0 | 1 | XOR | 1 |
| 1 | 0 | XOR | 1 |
| 1 | 1 | XOR | 0 |

TABLE 18

Logic AND Operator

| Bit 1 | Bit 2 | Operator | Result |
|---|---|---|---|
| 0 | 0 | AND | 0 |
| 0 | 1 | AND | 0 |
| 1 | 0 | AND | 0 |
| 1 | 1 | AND | 1 |

SNP alleles may be mapped to a single binary bit for rapid comparisons between two samples. Table 19 illustrates the binary encoding of alleles.

TABLE 19

Binary Encoding of SNP Alleles

| Alleles | Binary Encoding |
|---|---|
| MM | 0 |
| Mm | 1 |
| mm | 1 |

Panels (or sets) of SNPs can be encoded as hex strings for easier representation of SNPs with four different SNP alleles for a sample represented by one hexadecimal letter. An example of encoding four SNPs loci as a hexadecimal representation are shown in Table 8, with encodings shown in Table 9. Note that 64 or 256 SNP loci can be encoded in 64-bit and 256-bit computer hardware registers.

TABLE 20

Hex Encoding of Four SNP Alleles

| Base 10 | Base 16-Hex | Base 2-Binary |
|---|---|---|
| 0 | 0 | 0000 |
| 1 | 1 | 0001 |
| 2 | 2 | 0010 |
| 3 | 3 | 0011 |
| 4 | 4 | 0100 |
| 5 | 5 | 0101 |
| 6 | 6 | 0110 |
| 7 | 7 | 0111 |
| 8 | 8 | 1000 |
| 9 | 9 | 1001 |
| 10 | A | 1010 |
| 11 | B | 1011 |
| 12 | C | 1100 |
| 13 | D | 1101 |
| 14 | E | 1110 |
| 15 | F | 1111 |

TABLE 21

Sample Minor Alleles of Individuals and Mixtures

| Sample | Minor Alleles encoded as Hexadecimal digits |
|---|---|
| Ind-1 | 06001440004808200000202000000000601000086000420000000003 |
| Ind-2 | 000000000020480500008400140200a000000000005961008040100 |
| Ind-2 | 000000000020480500008408140200a000001000005961008040140 |
| Ind-3 | 020000000040000000040400100000020000000008000002000000 |
| Ind-3 | 02000000000000000004040010000002000000000800000200000040 |
| Mix-1 | 002000000020580500408408140a00a000001000005961008042170 |
| Mix-2 | 0000490980004000000006000020010825000e0000044400021080290212100040028000004048400410440840010000a209840000000105 |
| Mix-3 | 1210004002800000404840004104408400010000a2098400000001050 |
| Mix-4 | 32288040038100200804462a5000568220205c485c38048398000440 |

Two samples for individuals can be compared by mapping the binary representation of SNP alleles onto hardware bit representations and comparing the samples directly with the computer hardware XOR (exclusive OR) instruction. The 1 bits in the result represents all of positions where there is a difference in the minor alleles between the two individuals, see Tables 22 and 23. The computer hardware population count instruction tallies all of the 1 bits in the result to identify (count) all of the minor allele differences between the two samples. In Table 22, the first replicate for individual 2 has three dropped minor alleles as compared to the second replicate. In Table 23, each replicate has a single minor allele difference from the other replicate.

TABLE 22

Comparison of Replicate Samples for Individual 2

| Sample | Minor Alleles encoded as Hexadecimal digits |
|---|---|
| Ind-2 | 000000000020480500008400140200a000000000005961008040100 |
| Ind-2 | 000000000020480500008408140200a000001000005961008040140 |
| XOR | 00000000000000000000008000000000000001000000000000000400 |
| Pop. count | 3 |

TABLE 23

Comparison of Replicate Samples for Individual 3

| Sample | Minor Alleles encoded as Hexadecimal digits |
|---|---|
| Ind-3 | 020000000040000000040400100000020000000008000002000000 |
| Ind-3 | 02000000000000000004040010000002000000000800000200000040 |
| XOR | 0000000000400000000000000000000000000000000000000000040 |
| Pop. count | 2 |

Using this approach and parallelization, it is possible to compare very large numbers of samples rapidly on typical symmetric multiprocessing (SMP) computers, a laptop, or any computing device.

To compare an individual sample to a mixture sample, the XOR result can be bit masked to only consider the minor alleles of the individual by anding (logical AND operation) the XOR result to the individual profile with the hardware AND instruction. Table 24 illustrates the comparison of Individual 3 with Mixture 4 with one minor allele mismatch between the individual and the mixture.

TABLE 24

Comparison of Individual 3 with Mixture 4

| Sample | Minor Alleles encoded as Hexadecimal digits |
|---|---|
| Ind-3 | 02000000000400000000404001000000020000000000800000200000000 |
| Mix-4 | 32288040038100200804462a5000568220205c485c38048398000440 |
| XOR | 3028804003c100200800422a4000568020205c485438048198000440 |
| AND | 00000000004000000000000000000000000000000000000000000000 |
| Pop. count | 1 |

A traditional comparison of SNP loci requires 2×N allele comparisons. For a 64-bit computer, the number of operations are reduced to the scale of N/64 operations. For very large sets of samples, the method may out perform a traditional approach by a factor of 100-to 1,000-fold.

A second method is a variant of the above method using the massively parallel computing hardware in standard graphics processing units (GPUs) like the Tesla K80. The graphics memory of the CPU can be loaded with target samples and multiple batches of query samples can be rapidly compared using the CPU hardware instructions for XOR, AND, and population count. Using the parallel hardware of the CPU, hundreds of samples can be compared to thousands of samples using the CPU XOR and AND operations. This approach may outperform a traditional approach by a factor of 10,000-to 100,000-fold.

A third method leverages the Bigtable approach that gave rise to Big Data NO SQL databases. A traditional approach maps alleles for each sample in a table. An inverted table approach maps the alleles to the samples. A tally of the most frequently occurring sample names for a set of minor alleles for a sample yields an ordered list of best possible matches between the sample and entries in the database. This is a Big Data alternative method using NO SQL and New SQL database technologies.

Example 2: Search Method Identifies Relatives

In FIG. 15, a sample (ZR5HE:IX-23) was searched against hundreds of other samples. The results indicate no additional samples for this individual, but did detect both a 2nd degree (ZR5HE:IX-22) and a 3rd degree relative (OELSG:IX-21).

Figure 16A:
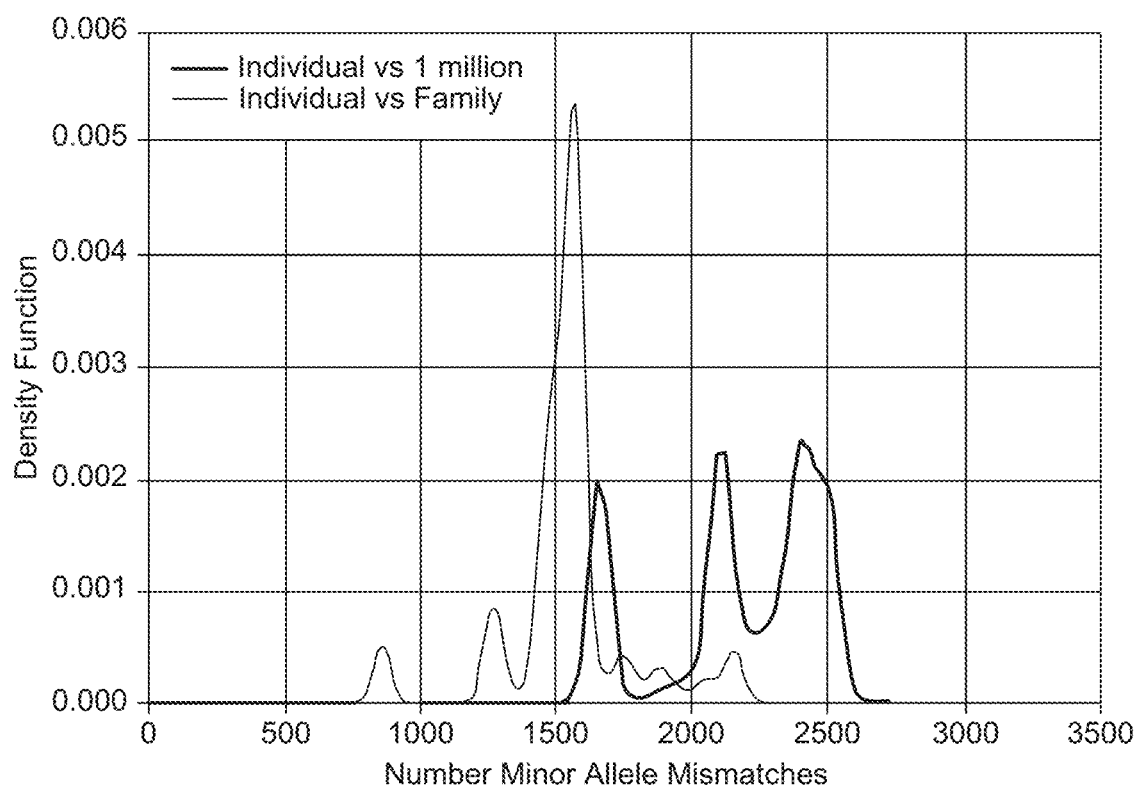
FIG. 16A depicts an illustrative chart showing a comparison between an individual versus four generations of relatives and an individual versus 1 million unrelated individuals using 12,456 SNPs with mAF 0.01 to 0.2 (note: height of data not to scale), in accordance with some embodiments of the technology described herein.
Figure 16B:
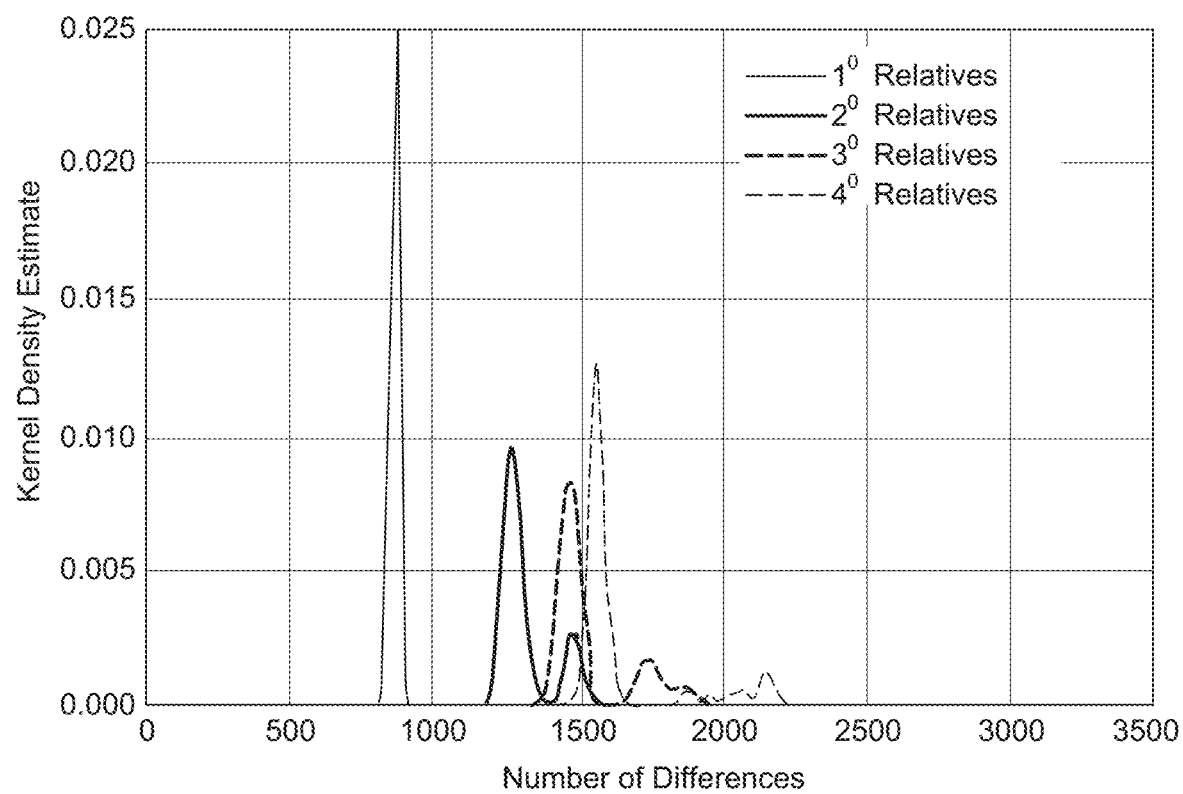
FIG. 16B depicts an illustrative comparison of the individual in FIG. 5A versus four generations of relatives (e.g., descendants) using 12,456 SNPs with mAF 0.01-0.2 (note: height of data not to scale), in accordance with some embodiments of the technology described herein.

A similar comparison is graphed in FIGS. 16A-16B using data from 4 generations of relatives (descendants) shown in green and 1 million unrelated individuals. In FIG. 16A, the first peak on the left in the green line indicate 1st degree relatives, 2nd peak represents 2nd degree relatives, 3rd peak represents 3rd degree relatives—this is illustrated in detail in FIG. 16B. The blue line indicates random matches to 1 million individuals with four different ethnic backgrounds with the first peak on the left indicating individuals with a shared ethnic background.

Figure 17A:
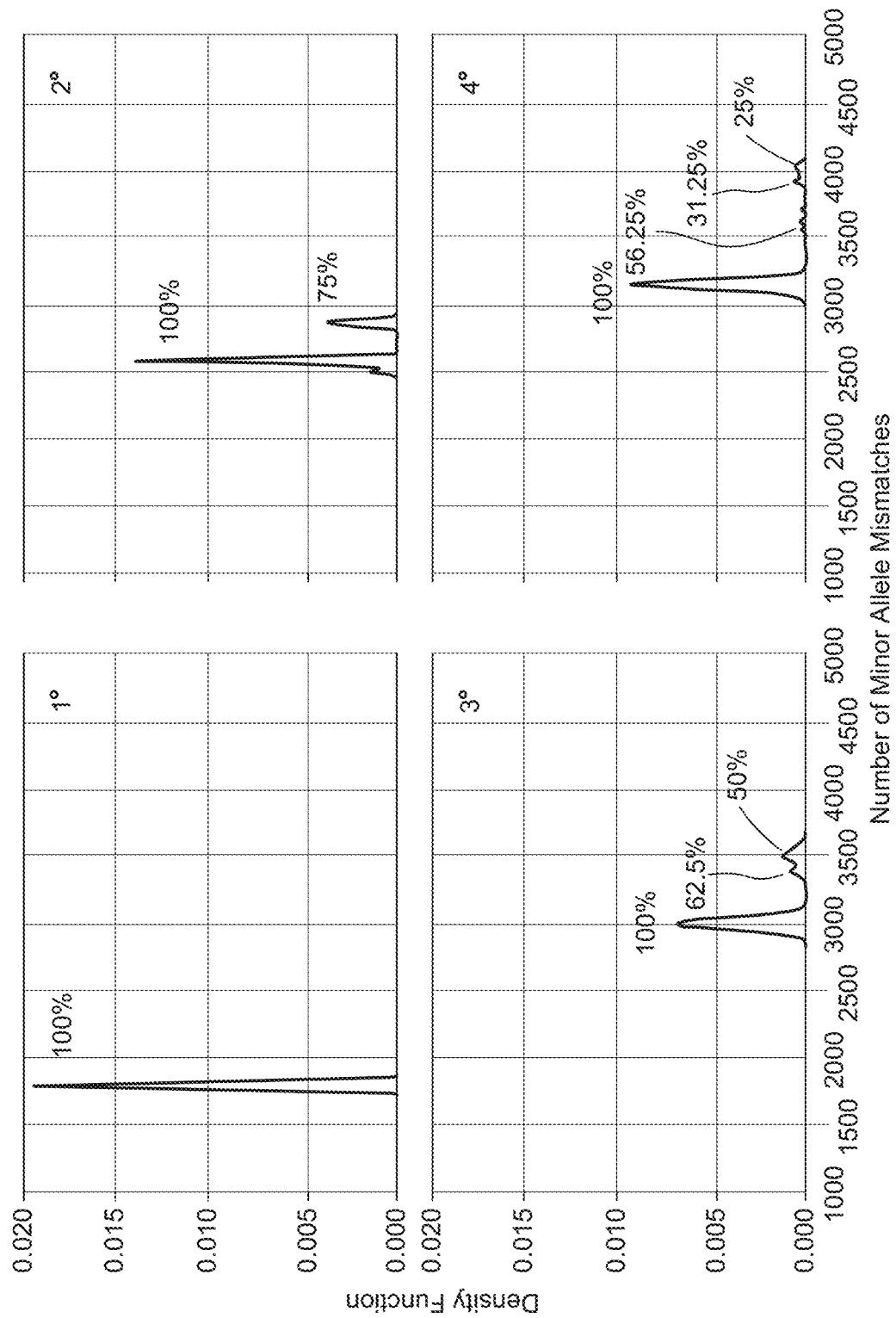
FIG. 17A depicts a chart illustrating a kernel density estimation (KDE) for 12,456 SNPs with a mAF between 0.01 and 0.2, in accordance with some embodiments of the technology described herein.
Figure 17B:
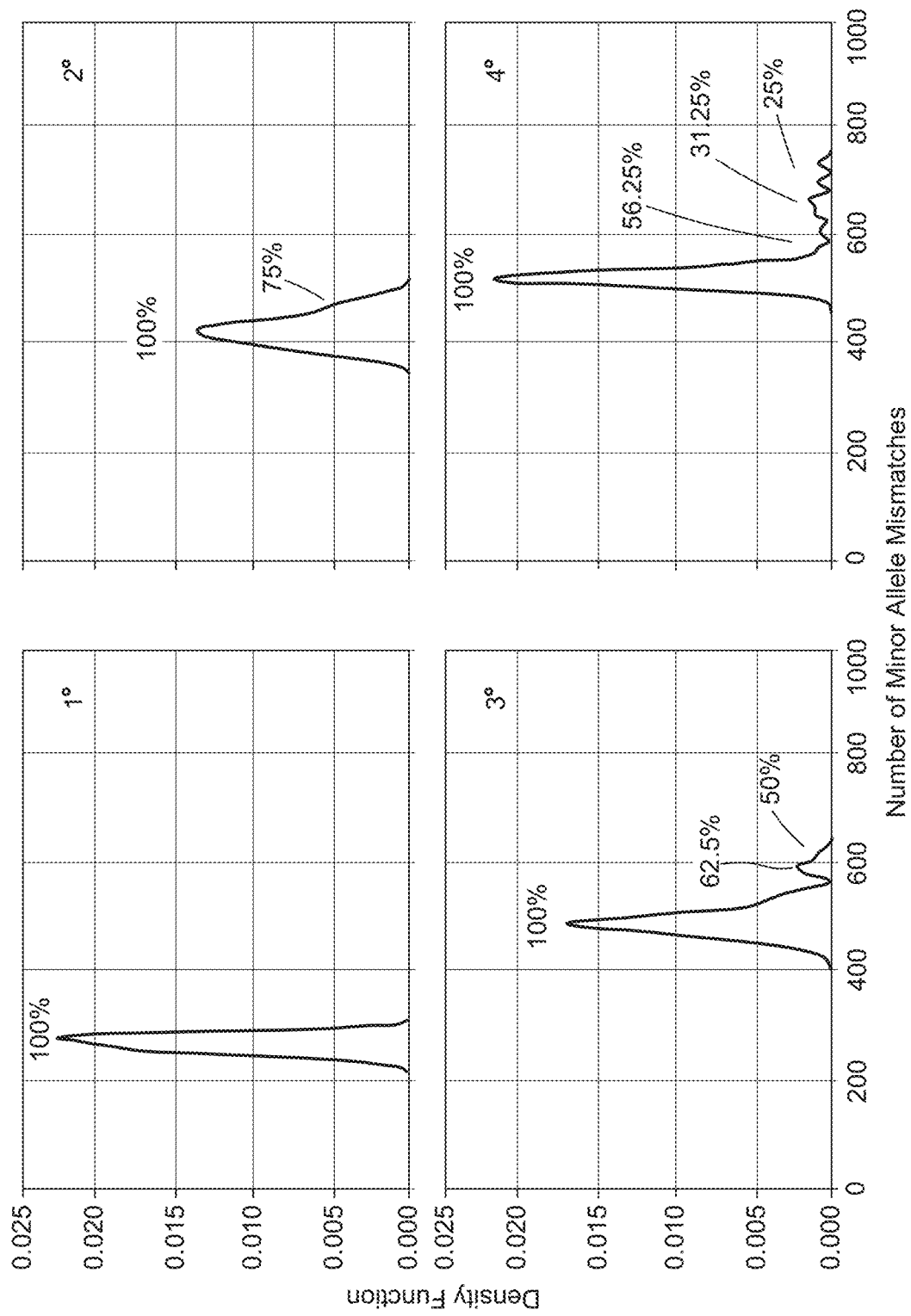
FIG. 17B depicts a chart illustrating the KDE for 3,453 SNPs with a mAF between 0.01 and 0.1, in accordance with some embodiments of the technology described herein.

In FIG. 16B for the 3rd degree relatives shown in the red line, there are smaller peaks to the right of the main red peak indicating 3rd degree relatives with different ethnic backgrounds due to admixture. The left most main peak, represents individuals with the same ethnic background as the individual of interest—this is examined in FIGS. 17A-17B with labeling of percent sharing of ethnic background with the person being searched.

Figure 18:
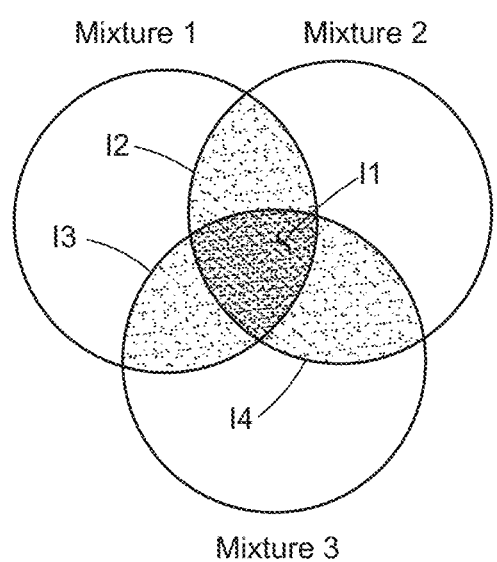
FIG. 18 is a diagram illustrating the identification of individuals by comparing mixtures. I1, I2, I3, and I4 represent individuals common between the different overlaps in the three mixtures, in accordance with some embodiments of the technology described herein.

The comparison method enables the comparisons of (a) individuals vs. individuals, (b) individuals versus mixtures, (c) mixtures versus individuals, and (d) mixtures versus mixtures. FIG. 18 illustrates how individuals can be identified by comparing mixtures. The methods of the disclosure, including the SNP panels described herein, provide superior properties when compared to existing methods of building and/or deconvoluting a DNA profile. Prior to the development of the methods of the disclosure, Voskoboinik and Darvasi published methods for deconvoluting complex DNA mixtures, (see, Voskoboinik, L. and Darvasi, A. Forensic Identification of an Individual in Complex DNA Mixtures. 2011. Forensic Science International: Genetics 5:428-435) however, there are important differences between the methods of Voskoboinik and Darvasi and the methods of the disclosure. For example, fundamentally, the methods of the disclosure are quantitative. The quantitative methods of the disclosure allow the user to both build an individual DNA profile from a complex DNA mixture as well as deconvolute a complex DNA mixture to component profiles without any prior knowledge of any DNA sequence or genetic marker present of any contributor to any complex DNA mixture under analysis.

In further contrast to the methods of Voskoboinik and Darvasi, the methods of the disclosure include multiple complex DNA mixtures to build an individual DNA profile. The methods of the disclosure for building an individual DNA profile detect the presence or absence of a particular SNP in each complex DNA mixture. The set of SNPs that are present in each of the complex DNA mixtures, also referred to as an overlapping population of SNPs, an intersection of the complex DNA mixtures, or a product of the multiplication of the complex DNA mixtures, represents those SNPs belonging to common contributors to each of the complex DNA mixtures in addition to those SNPs that are present in each mixture by chance. As the number of complex DNA mixtures included in the analysis increases, the accuracy with which the methods identify common contributors to each mixtures increases because the probability that each common SNP occurs in each mixture by chance alone becomes vanishingly small (i.e. rapidly approaches zero).

In further contrast to the methods of Voskoboinik and Darvasi, and in contrast to the methods of the disclosure for building individual DNA profiles, the methods of the disclosure for deconvolution or resolution of a component and/or individual contributor from a complex DNA mixture may be performed by analyzing a single complex DNA mixture. In certain embodiments of the methods of the disclosure for deconvolution or resolution of a component and/or individual contributor from a complex DNA mixture, the method may analyze more than one complex DNA mixture. The methods of the disclosure for deconvoluting or resolving a complex DNA mixtures into one or more components detect a signal amplitude of each SNP of a SNP panel to distinguish major versus minor contributors to the complex DNA mixture. These methods can detect differences in signal amplitude across a high-dynamic range. For example, these methods can resolve a DNA profile of a minor contributor to the mixture when as little as 0.001% to 49% of the DNA in the complex mixture belongs to the minor contributor. The resolution of DNA profiles using these methods increases as the number of SNP loci increase in the SNP panel used.

As used herein, the term complex DNA mixture refers to a DNA mixture comprised of DNA from one, two, or more contributors. Preferably, the complex DNA mixtures of the methods described herein include DNA from at least 1, 2, 3, 4, 5, 6, 7, 8, 9, 10, 11, 12, 13, 14, 15, 16, 17, 18, 19, 20, or more contributors. In practice and in theory, there is no upper limit to the number of contributors to a complex DNA mixture of the disclosure. Moreover, with respect to methods of building an individual DNA profile, there is no upper limit to either the number of contributors to a complex DNA mixture or the number of complex DNA mixtures analyzed to build the individual DNA profile. For example, with respect to methods of building an individual DNA profile, the number of complex DNA mixtures that may be included in the analysis may be at least 1, 2, 3, 4, 5, 6, 7, 8, 9, 10, 11, 12, 13, 14, 15. 16, 17, 18, 19, 20, or more contributors.

Selection of SNP Markers

A single nucleotide polymorphism (SNP) is a single position in the genome that tends to vary between individuals. Millions of SNPs have been identified in the human genome. Not all of these SNPs are appropriate for analyzing mixtures of DNA.

When selecting a set of loci and/or SNPs for inclusion in a SNP panel of the disclosure, it is best if the SNP is (1) relatively rare (has a low minor allele frequency), (2) is not well-correlated with ancestry, (3) is physically far enough from another SNP within any chromosome that they do not tend to be inherited together, and, optionally, (4) is not related to health status. For example, in the context of a forensic investigation, the loci and/or SNPs selected for inclusion may be SNPs most often found in healthy individuals. However, in the context of analysis of medical or biological sample or a genetically heterogeneous medical or biological sample, for instance, to diagnose and/or prognose cancer. it may be desirable to include Loci and/or SNPs, for example, that predict unregulated or deregulated cell proliferation, neovascularization, and metastasis.

As a panel for analysis of complex DNA mixtures, it is important to assemble a collection of SNPs that is large enough to provide the statistical power for identifying an individual in a mixture, but is small enough to be easily run on the sequencing instrument available. For analysis of the loci and/or SNPs of the SNP panels described herein, any sequencing instrument may be used. Exemplary, but non-limiting, systems for amplifying large numbers of SNPs include: Fluidigm Access Array and Life Technology Ampliseq. Each of these methods utilizes proprietary design principles to identify PCR primers that can amplify a subset of the desired SNPs. Both of these systems are available to the public.

Four exemplary panels of SNPs are described herein. Three of these panels were used for mixture analysis: the 480 panel; the 975 panel; the OptMix panel. The OptMix panel is a subset of the Kinship panel, which was designed to assess the degree of relatedness between two people from DNA samples.

As used in the following descriptions, a FST (Fixation Index) is a measurement of how closely any given SNP correlates with ancestry. For example, a low FST indicates that the allele correlates poorly with ancestry. Moreover, a mAF (minor allele frequency) describes the frequency that an allele is present on a chromosome in a population.

Any one of the following panels, including any SNP panel of the disclosure, may be subject to an empirical screening process. An empirical screening process may include one or more of the following steps in any combination:

Delete loci that tend to give ambiguous results (e.g. mAR not at expected values in reference samples), Delete loci that tend to produce a low number of reads (for example, <10% of the average number of reads/locus), Delete loci that produce impossible results in known family tree, and/or Delete loci that tend to generate data from only one strand of DNA.

The 480 panel: Amplification was performed using Fluidigm Access Array. Loci were selected as follows:

FST <0.06: Poor correlation between ancestry and genotype on ALFRED database (see, for example, Pakstis et al. Hum Genet (2010) 127:315-324)

Average Heterozygosity=0.058-0.13 on ALFRED (should correspond to mAF~0.03-0.07)

No health related data on SNP in the NIH/NCBI dbSNP database mAF=0.03-0.07 on dbSNP database Average Heterozygosity=0.058-0.13 on dbSNP (should correspond to MAF~0.03-0.07), meaning that the alleles are relatively rare in the population Elimination of duplicate SNPs and ambiguously mapped SNPs.

Minimum distance between alleles of 500,000 bases (of NCBI build 37, Tian C, et al. (2008) PLoS Genetics 4(1): 29-39)=1430 SNPs.

Selected 950 SNPs, 530 of which were compatible with Fluidigm DNA amplification platform The 975 panel: Amplification was performed using Ampliseq. Same process as described for the 480-panel, however, include all 1430 SNPs rather than selecting from this group the 950 SNPs used in the 480-panel.

Kinship panel: Amplification was performed using Ampliseq. Similar criteria as described for the 480-SNP panel, with the following distinctions:

a low mAF, and in certain embodiments, between 0.01 and 0.3

Distance between loci >110,000 by

OptMix panel: Amplification was performed using Ampliseq. Similar criteria as described for the Kinship panel, with the following distinctions:

Distance between loci >500,000 mAF<0.06

Delete loci that tend to give ambiguous results (mAR not at expected values in reference samples)

Delete loci that tend to produce a low number of reads (<10% of the average number of reads/locus)

Delete loci that produce impossible results in known family tree

Delete loci that tend to generate data from only one strand of DNA.

Table 25 provides a list of SNPs included in the an embodiment of the OptMix Panel of the disclosure.

| SNP# | SNP Reference |
|---|---|
| 1 | rs10014900 |
| 2 | rs16872711 |
| 3 | rs3026840 |
| 4 | rs10015135 |
| 5 | rs16874072 |
| 6 | rs3087374 |
| 7 | rs1001742 |
| 8 | rs16874114 |
| 9 | rs3092829 |
| 10 | rs1003469 |
| 11 | rs16876526 |
| 12 | rs3106532 |
| 13 | rs10042810 |
| 14 | rs16878072 |
| 15 | rs3108124 |
| 16 | rs10042938 |
| 17 | rs16878691 |
| 18 | rs3109091 |
| 19 | rs10045099 |
| 20 | rs16879548 |
| 21 | rs3127158 |
| 22 | rs10054189 |
| 23 | rs16879674 |
| 24 | rs3136795 |
| 25 | rs10059981 |
| 26 | rs16882710 |
| 27 | rs3138158 |
| 28 | rs10066520 |
| 29 | rs16884281 |
| 30 | rs314756 |
| 31 | rs10079950 |
| 32 | rs16885867 |
| 33 | rs319884 |
| 34 | rs1008461 |
| 35 | rs16894006 |
| 36 | rs3213395 |
| 37 | rs10093823 |
| 38 | rs16895698 |
| 39 | rs3214070 |
| 40 | rs1009682 |
| 41 | rs16899390 |
| 42 | rs3218995 |
| 43 | rs10097827 |
| 44 | rs16906840 |
| 45 | rs324882 |
| 46 | rs10099140 |
| 47 | rs16907089 |
| 48 | rs325609 |
| 49 | rs10116365 |
| 50 | rs16907395 |
| 51 | rs347433 |
| 52 | rs10125854 |
| 53 | rs16912069 |
| 54 | rs354255 |
| 55 | rs1013579 |
| 56 | rs16912603 |
| 57 | rs356296 |
| 58 | rs10164423 |
| 59 | rs16916228 |
| 60 | rs35677470 |
| 61 | rs10178469 |
| 62 | rs16917429 |
| 63 | rs3732596 |
| 64 | rs10179948 |
| 65 | rs16918105 |
| 66 | rs3732868 |
| 67 | rs10185703 |
| 68 | rs16918622 |
| 69 | rs3733472 |
| 70 | rs1019540 |
| 71 | rs16920971 |
| 72 | rs3733709 |
| 73 | rs10196787 |
| 74 | rs16928182 |
| 75 | rs3734690 |
| 76 | rs10201330 |
| 77 | rs16928482 |
| 78 | rs3739446 |
| 79 | rs10206295 |
| 80 | rs16928989 |
| 81 | rs3739916 |
| 82 | rs10216611 |
| 83 | rs16933296 |
| 84 | rs3741571 |
| 85 | rs10228665 |
| 86 | rs16941516 |
| 87 | rs3742209 |
| 88 | rs10229451 |
| 89 | rs16942885 |
| 90 | rs3743175 |
| 91 | rs10237037 |

-continued

| SNP# | SNP Reference |
|---|---|
| 92 | rs16945135 |
| 93 | rs3744453 |
| 94 | rs10247070 |
| 95 | rs16947335 |
| 96 | rs3751474 |
| 97 | rs1024787 |
| 98 | rs16947417 |
| 99 | rs3754913 |
| 100 | rs10249706 |
| 101 | rs16948164 |
| 102 | rs3759732 |
| 103 | rs10258384 |
| 104 | rs16948633 |
| 105 | rs3764459 |
| 106 | rs10259889 |
| 107 | rs16949858 |
| 108 | rs3765148 |
| 109 | rs10280153 |
| 110 | rs16950754 |
| 111 | rs3769071 |
| 112 | rs10280515 |
| 113 | rs16951027 |
| 114 | rs3773371 |
| 115 | rs10413635 |
| 116 | rs16961669 |
| 117 | rs3775534 |
| 118 | rs10439364 |
| 119 | rs16964136 |
| 120 | rs3780660 |
| 121 | rs1044281 |
| 122 | rs16964707 |
| 123 | rs3787158 |
| 124 | rs10445895 |
| 125 | rs16966016 |
| 126 | rs3789257 |
| 127 | rs10456051 |
| 128 | rs16967852 |
| 129 | rs3790262 |
| 130 | rs10474648 |
| 131 | rs16971135 |
| 132 | rs3792491 |
| 133 | rs10483173 |
| 134 | rs16973356 |
| 135 | rs3793354 |
| 136 | rs10484358 |
| 137 | rs16976488 |
| 138 | rs3795244 |
| 139 | rs10484658 |
| 140 | rs16977658 |
| 141 | rs3795348 |
| 142 | rs10485047 |
| 143 | rs16979618 |
| 144 | rs3796352 |
| 145 | rs10485311 |
| 146 | rs16985057 |
| 147 | rs3798012 |
| 148 | rs10485490 |
| 149 | rs16986694 |
| 150 | rs3799007 |
| 151 | rs10485548 |
| 152 | rs16989572 |
| 153 | rs3810840 |
| 154 | rs10485764 |
| 155 | rs16989682 |
| 156 | rs3810925 |
| 157 | rs10486523 |
| 158 | rs16990450 |
| 159 | rs3812852 |
| 160 | rs10487308 |
| 161 | rs16990824 |
| 162 | rs3813474 |
| 163 | rs10488002 |
| 164 | rs16991498 |
| 165 | rs3819971 |
| 166 | rs10488501 |
| 167 | rs16997765 |

-continued

| SNP# | SNP Reference |
|---|---|
| 168 | rs3824534 |
| 169 | rs10488698 |
| 170 | rs17006704 |
| 171 | rs3857470 |
| 172 | rs10488723 |
| 173 | rs1700688 |
| 174 | rs3857487 |
| 175 | rs10488758 |
| 176 | rs17007024 |
| 177 | rs389089 |
| 178 | rs10488831 |
| 179 | rs17008011 |
| 180 | rs3915009 |
| 181 | rs10489168 |
| 182 | rs17009521 |
| 183 | rs3917118 |
| 184 | rs10492034 |
| 185 | rs17010346 |
| 186 | rs3920484 |
| 187 | rs10492176 |
| 188 | rs17013082 |
| 189 | rs3945008 |
| 190 | rs10492251 |
| 191 | rs17014898 |
| 192 | rs3948463 |
| 193 | rs10492273 |
| 194 | rs17020274 |
| 195 | rs3967819 |
| 196 | rs10492340 |
| 197 | rs17020633 |
| 198 | rs4073420 |
| 199 | rs10492523 |
| 200 | rs17021617 |
| 201 | rs4130603 |
| 202 | rs10492683 |
| 203 | rs17023499 |
| 204 | rs4142466 |
| 205 | rs10493050 |
| 206 | rs17028543 |
| 207 | rs4149418 |
| 208 | rs10493204 |
| 209 | rs17030351 |
| 210 | rs415135 |
| 211 | rs10494246 |
| 212 | rs17031645 |
| 213 | rs4151467 |
| 214 | rs10494795 |
| 215 | rs17036738 |
| 216 | rs4236939 |
| 217 | rs10494933 |
| 218 | rs17038089 |
| 219 | rs4242335 |
| 220 | rs10495982 |
| 221 | rs17039555 |
| 222 | rs4253449 |
| 223 | rs10496694 |
| 224 | rs17043820 |
| 225 | rs4271931 |
| 226 | rs10497363 |
| 227 | rs17044733 |
| 228 | rs4316524 |
| 229 | rs10497796 |
| 230 | rs17045327 |
| 231 | rs4318657 |
| 232 | rs10497880 |
| 233 | rs17046580 |
| 234 | rs438323 |
| 235 | rs10498177 |
| 236 | rs17047517 |
| 237 | rs4386077 |
| 238 | rs10501273 |
| 239 | rs17048581 |
| 240 | rs4388439 |
| 241 | rs10502273 |
| 242 | rs17049231 |
| 243 | rs439012 |

| SNP# | SNP Reference | | SNP# | SNP Reference |
|---|---|---|---|---|
| 244 | rs10502421 | | 320 | rs17088873 |
| 245 | rs17050809 | | 321 | rs451505 |
| 246 | rs4393596 | | 322 | rs10516481 |
| 247 | rs10502634 | | 323 | rs17089231 |
| 248 | rs17053338 | | 324 | rs4540898 |
| 249 | rs4394199 | | 325 | rs10517293 |
| 250 | rs10503042 | | 326 | rs17089348 |
| 251 | rs17054660 | | 327 | rs4541963 |
| 252 | rs4394904 | | 328 | rs10518156 |
| 253 | rs10503375 | | 329 | rs17099016 |
| 254 | rs17055965 | | 330 | rs4542003 |
| 255 | rs4405494 | | 331 | rs10518233 |
| 256 | rs10503703 | | 332 | rs17100629 |
| 257 | rs17056745 | | 333 | rs4545048 |
| 258 | rs441624 | | 334 | rs10518580 |
| 259 | rs10504514 | | 335 | rs17101019 |
| 260 | rs17058466 | | 336 | rs45573433 |
| 261 | rs4426962 | | 337 | rs10518890 |
| 262 | rs10504646 | | 338 | rs17101326 |
| 263 | rs17059415 | | 339 | rs45574736 |
| 264 | rs4429602 | | 340 | rs10520293 |
| 265 | rs10505465 | | 341 | rs17101375 |
| 266 | rs17061334 | | 342 | rs4558436 |
| 267 | rs4438580 | | 343 | rs10520879 |
| 268 | rs10505743 | | 344 | rs17101479 |
| 269 | rs17061779 | | 345 | rs4559766 |
| 270 | rs4440352 | | 346 | rs10521400 |
| 271 | rs10506991 | | 347 | rs17112145 |
| 272 | rs17062602 | | 348 | rs457417 |
| 273 | rs4442208 | | 349 | rs10521761 |
| 274 | rs10507309 | | 350 | rs17116121 |
| 275 | rs17063732 | | 351 | rs4575127 |
| 276 | rs4443280 | | 352 | rs1055300 |
| 277 | rs10507372 | | 353 | rs17116968 |
| 278 | rs17063897 | | 354 | rs4588690 |
| 279 | rs4445380 | | 355 | rs10743150 |
| 280 | rs10507969 | | 356 | rs17117895 |
| 281 | rs17066802 | | 357 | rs4602844 |
| 282 | rs4451134 | | 358 | rs10782775 |
| 283 | rs10510180 | | 359 | rs17118223 |
| 284 | rs17069342 | | 360 | rs4614050 |
| 285 | rs4452447 | | 361 | rs1079384 |
| 286 | rs10510527 | | 362 | rs17123673 |
| 287 | rs17070015 | | 363 | rs4622794 |
| 288 | rs4461068 | | 364 | rs10811817 |
| 289 | rs10510709 | | 365 | rs17125182 |
| 290 | rs17071395 | | 366 | rs4624663 |
| 291 | rs4469289 | | 367 | rs10841280 |
| 292 | rs10510790 | | 368 | rs17125478 |
| 293 | rs17071680 | | 369 | rs4639045 |
| 294 | rs4478182 | | 370 | rs10858044 |
| 295 | rs10511062 | | 371 | rs17127960 |
| 296 | rs17072430 | | 372 | rs4639092 |
| 297 | rs4480127 | | 373 | rs10866057 |
| 298 | rs10511671 | | 374 | rs17128116 |
| 299 | rs17072652 | | 375 | rs4641724 |
| 300 | rs4483642 | | 376 | rs10894631 |
| 301 | rs10512455 | | 377 | rs17133162 |
| 302 | rs17074679 | | 378 | rs4646583 |
| 303 | rs4489951 | | 379 | rs10894740 |
| 304 | rs10512749 | | 380 | rs17140460 |
| 305 | rs17079205 | | 381 | rs4647255 |
| 306 | rs449077 | | 382 | rs10902671 |
| 307 | rs10513169 | | 383 | rs17141070 |
| 308 | rs17082035 | | 384 | rs4651133 |
| 309 | rs4500099 | | 385 | rs10925642 |
| 310 | rs10513316 | | 386 | rs17141233 |
| 311 | rs17082406 | | 387 | rs4656427 |
| 312 | rs4504735 | | 388 | rs10928474 |
| 313 | rs10513600 | | 389 | rs17147659 |
| 314 | rs17082882 | | 390 | rs4663621 |
| 315 | rs450652 | | 391 | rs10934891 |
| 316 | rs10513684 | | 392 | rs17147932 |
| 317 | rs17085668 | | 393 | rs4663942 |
| 318 | rs4513926 | | 394 | rs10939840 |
| 319 | rs10515282 | | 395 | rs17148348 |

| SNP# | SNP Reference |
|---|---|
| 396 | rs4686131 |
| 397 | rs10977642 |
| 398 | rs17154851 |
| 399 | rs4687402 |
| 400 | rs10985311 |
| 401 | rs17157492 |
| 402 | rs4692073 |
| 403 | rs10991911 |
| 404 | rs17161478 |
| 405 | rs4696333 |
| 406 | rs10993282 |
| 407 | rs17167011 |
| 408 | rs470330 |
| 409 | rs11021359 |
| 410 | rs17170870 |
| 411 | rs4713842 |
| 412 | rs11023830 |
| 413 | rs17170899 |
| 414 | rs4726191 |
| 415 | rs11047406 |
| 416 | rs17172001 |
| 417 | rs4737839 |
| 418 | rs11048174 |
| 419 | rs17174781 |
| 420 | rs4741012 |
| 421 | rs11052670 |
| 422 | rs17179483 |
| 423 | rs4741126 |
| 424 | rs1105608 |
| 425 | rs17181902 |
| 426 | rs4741411 |
| 427 | rs1106228 |
| 428 | rs17182699 |
| 429 | rs4744157 |
| 430 | rs11062739 |
| 431 | rs17184553 |
| 432 | rs4744244 |
| 433 | rs1106665 |
| 434 | rs17191796 |
| 435 | rs474503 |
| 436 | rs11071515 |
| 437 | rs17192622 |
| 438 | rs4760319 |
| 439 | rs11079203 |
| 440 | rs17193986 |
| 441 | rs4763862 |
| 442 | rs11111200 |
| 443 | rs17194266 |
| 444 | rs4767004 |
| 445 | rs11124126 |
| 446 | rs17194872 |
| 447 | rs477188 |
| 448 | rs11126472 |
| 449 | rs17195147 |
| 450 | rs4771973 |
| 451 | rs11127757 |
| 452 | rs17195948 |
| 453 | rs477377 |
| 454 | rs11128026 |
| 455 | rs17196895 |
| 456 | rs4777085 |
| 457 | rs11129773 |
| 458 | rs17199261 |
| 459 | rs4777309 |
| 460 | rs11162827 |
| 461 | rs17200082 |
| 462 | rs4781565 |
| 463 | rs11180595 |
| 464 | rs17210682 |
| 465 | rs4783491 |
| 466 | rs11182474 |
| 467 | rs17224880 |
| 468 | rs4783514 |
| 469 | rs11211099 |
| 470 | rs17229226 |
| 471 | rs4783754 |
| 472 | rs11222339 |
| 473 | rs17244884 |
| 474 | rs4784320 |
| 475 | rs1126700 |
| 476 | rs17245425 |
| 477 | rs4784929 |
| 478 | rs11488811 |
| 479 | rs17246669 |
| 480 | rs4786719 |
| 481 | rs11520742 |
| 482 | rs17251406 |
| 483 | rs4807536 |
| 484 | rs11542344 |
| 485 | rs17252590 |
| 486 | rs4808178 |
| 487 | rs11544160 |
| 488 | rs17254871 |
| 489 | rs4809130 |
| 490 | rs11548494 |
| 491 | rs17254960 |
| 492 | rs4823695 |
| 493 | rs11562750 |
| 494 | rs17262881 |
| 495 | rs4831375 |
| 496 | rs11562980 |
| 497 | rs17269545 |
| 498 | rs4831658 |
| 499 | rs11564538 |
| 500 | rs17273416 |
| 501 | rs4831958 |
| 502 | rs11568350 |
| 503 | rs17274750 |
| 504 | rs4834703 |
| 505 | rs11570210 |
| 506 | rs17283159 |
| 507 | rs4840584 |
| 508 | rs11571789 |
| 509 | rs17284014 |
| 510 | rs4842 |
| 511 | rs11575584 |
| 512 | rs17291465 |
| 513 | rs4843143 |
| 514 | rs11576325 |
| 515 | rs17295966 |
| 516 | rs4844553 |
| 517 | rs11577260 |
| 518 | rs17298178 |
| 519 | rs4869255 |
| 520 | rs11578034 |
| 521 | rs17304921 |
| 522 | rs4871381 |
| 523 | rs11581207 |
| 524 | rs17307316 |
| 525 | rs4873279 |
| 526 | rs11581921 |
| 527 | rs17309944 |
| 528 | rs4878199 |
| 529 | rs11588833 |
| 530 | rs17311688 |
| 531 | rs4878412 |
| 532 | rs11589338 |
| 533 | rs1731480 |
| 534 | rs4879653 |
| 535 | rs11589793 |
| 536 | rs17319875 |
| 537 | rs4887337 |
| 538 | rs11600347 |
| 539 | rs17320054 |
| 540 | rs4888184 |
| 541 | rs11602057 |
| 542 | rs17325358 |
| 543 | rs4888320 |
| 544 | rs11608551 |
| 545 | rs17326309 |
| 546 | rs4906888 |
| 547 | rs11621563 |

| SNP# | SNP Reference |
|---|---|
| 548 | rs17336463 |
| 549 | rs4910467 |
| 550 | rs11622927 |
| 551 | rs17340555 |
| 552 | rs4926242 |
| 553 | rs11624540 |
| 554 | rs17343939 |
| 555 | rs4938408 |
| 556 | rs11625631 |
| 557 | rs17346526 |
| 558 | rs4951362 |
| 559 | rs11627476 |
| 560 | rs17358566 |
| 561 | rs4963129 |
| 562 | rs11642466 |
| 563 | rs17359728 |
| 564 | rs4968363 |
| 565 | rs11645010 |
| 566 | rs17365315 |
| 567 | rs497022 |
| 568 | rs11646999 |
| 569 | rs17366009 |
| 570 | rs4970525 |
| 571 | rs11647070 |
| 572 | rs17367196 |
| 573 | rs4976464 |
| 574 | rs11647470 |
| 575 | rs17367381 |
| 576 | rs4988232 |
| 577 | rs11651481 |
| 578 | rs17370763 |
| 579 | rs5030244 |
| 580 | rs11651563 |
| 581 | rs17374803 |
| 582 | rs5030390 |
| 583 | rs1165210 |
| 584 | rs17377506 |
| 585 | rs503335 |
| 586 | rs11652516 |
| 587 | rs17379925 |
| 588 | rs509587 |
| 589 | rs11653803 |
| 590 | rs17381374 |
| 591 | rs527787 |
| 592 | rs11653892 |
| 593 | rs17382424 |
| 594 | rs5442 |
| 595 | rs11656279 |
| 596 | rs17384316 |
| 597 | rs548511 |
| 598 | rs11661682 |
| 599 | rs17387100 |
| 600 | rs5744936 |
| 601 | rs11661898 |
| 602 | rs17387806 |
| 603 | rs5749893 |
| 604 | rs11663494 |
| 605 | rs17403673 |
| 606 | rs5907387 |
| 607 | rs11665253 |
| 608 | rs17406856 |
| 609 | rs5918275 |
| 610 | rs11669586 |
| 611 | rs17411140 |
| 612 | rs5921853 |
| 613 | rs11674112 |
| 614 | rs17421546 |
| 615 | rs5935536 |
| 616 | rs11675968 |
| 617 | rs17424123 |
| 618 | rs5936094 |
| 619 | rs11678166 |
| 620 | rs17434692 |
| 621 | rs5942641 |
| 622 | rs11680177 |
| 623 | rs17438763 |
| 624 | rs5967140 |
| 625 | rs11683295 |
| 626 | rs17441007 |
| 627 | rs6011358 |
| 628 | rs11684620 |
| 629 | rs17444098 |
| 630 | rs6026904 |
| 631 | rs11684843 |
| 632 | rs17446795 |
| 633 | rs6043427 |
| 634 | rs11695814 |
| 635 | rs17449595 |
| 636 | rs6078334 |
| 637 | rs11707445 |
| 638 | rs17450051 |
| 639 | rs6081988 |
| 640 | rs11716445 |
| 641 | rs17451753 |
| 642 | rs6082883 |
| 643 | rs11716837 |
| 644 | rs17460146 |
| 645 | rs6086303 |
| 646 | rs11717945 |
| 647 | rs17463584 |
| 648 | rs6096168 |
| 649 | rs11724347 |
| 650 | rs17472165 |
| 651 | rs6113989 |
| 652 | rs11740355 |
| 653 | rs17473570 |
| 654 | rs6114608 |
| 655 | rs11744078 |
| 656 | rs17473628 |
| 657 | rs6117860 |
| 658 | rs11749678 |
| 659 | rs17475620 |
| 660 | rs6125 |
| 661 | rs11751671 |
| 662 | rs17479518 |
| 663 | rs619865 |
| 664 | rs11753585 |
| 665 | rs174827 |
| 666 | rs626260 |
| 667 | rs11753634 |
| 668 | rs17484734 |
| 669 | rs6435814 |
| 670 | rs11754129 |
| 671 | rs17487852 |
| 672 | rs6437962 |
| 673 | rs11755699 |
| 674 | rs17491203 |
| 675 | rs6452575 |
| 676 | rs11757369 |
| 677 | rs17493272 |
| 678 | rs6457967 |
| 679 | rs11758916 |
| 680 | rs17493678 |
| 681 | rs6535246 |
| 682 | rs11759295 |
| 683 | rs17496224 |
| 684 | rs6549310 |
| 685 | rs11760660 |
| 686 | rs17500235 |
| 687 | rs655485 |
| 688 | rs11761850 |
| 689 | rs17500922 |
| 690 | rs6557015 |
| 691 | rs11769445 |
| 692 | rs17501221 |
| 693 | rs6578113 |
| 694 | rs11776754 |
| 695 | rs17509254 |
| 696 | rs6590745 |
| 697 | rs11786927 |
| 698 | rs17510512 |
| 699 | rs659561 |

-continued

| SNP# | SNP Reference |
|---|---|
| 700 | rs11787606 |
| 701 | rs17513439 |
| 702 | rs663978 |
| 703 | rs11791817 |
| 704 | rs17527704 |
| 705 | rs6664438 |
| 706 | rs11794589 |
| 707 | rs17532490 |
| 708 | rs6671579 |
| 709 | rs11800419 |
| 710 | rs17535206 |
| 711 | rs667747 |
| 712 | rs11837627 |
| 713 | rs17541818 |
| 714 | rs6686449 |
| 715 | rs11842055 |
| 716 | rs17545756 |
| 717 | rs6689451 |
| 718 | rs11844932 |
| 719 | rs17546921 |
| 720 | rs6693750 |
| 721 | rs11847307 |
| 722 | rs17565060 |
| 723 | rs6695549 |
| 724 | rs11853050 |
| 725 | rs17566482 |
| 726 | rs6696761 |
| 727 | rs11853234 |
| 728 | rs17572451 |
| 729 | rs6703198 |
| 730 | rs11856276 |
| 731 | rs17574203 |
| 732 | rs6709780 |
| 733 | rs11858624 |
| 734 | rs17575888 |
| 735 | rs6722904 |
| 736 | rs1186850 |
| 737 | rs17576753 |
| 738 | rs6723017 |
| 739 | rs11871106 |
| 740 | rs17578880 |
| 741 | rs6726796 |
| 742 | rs11877476 |
| 743 | rs17579009 |
| 744 | rs6727383 |
| 745 | rs11890866 |
| 746 | rs17583195 |
| 747 | rs6733228 |
| 748 | rs11896614 |
| 749 | rs17583400 |
| 750 | rs6745277 |
| 751 | rs11903679 |
| 752 | rs17585302 |
| 753 | rs6747682 |
| 754 | rs11907142 |
| 755 | rs17588988 |
| 756 | rs6752056 |
| 757 | rs11908623 |
| 758 | rs17588991 |
| 759 | rs6753302 |
| 760 | rs11917524 |
| 761 | rs17593120 |
| 762 | rs6793666 |
| 763 | rs11921124 |
| 764 | rs17594577 |
| 765 | rs6796955 |
| 766 | rs11925530 |
| 767 | rs17594632 |
| 768 | rs680997 |
| 769 | rs11927897 |
| 770 | rs17601960 |
| 771 | rs6818342 |
| 772 | rs11946455 |
| 773 | rs17602721 |
| 774 | rs682605 |
| 775 | rs11947297 |

-continued

| SNP# | SNP Reference |
|---|---|
| 776 | rs17603351 |
| 777 | rs683191 |
| 778 | rs11948396 |
| 779 | rs17605851 |
| 780 | rs6831965 |
| 781 | rs11956152 |
| 782 | rs17606924 |
| 783 | rs6858087 |
| 784 | rs11969288 |
| 785 | rs17612883 |
| 786 | rs6865858 |
| 787 | rs11976853 |
| 788 | rs17613128 |
| 789 | rs6872306 |
| 790 | rs11982601 |
| 791 | rs17615452 |
| 792 | rs6885006 |
| 793 | rs11984145 |
| 794 | rs17618789 |
| 795 | rs6890344 |
| 796 | rs1199677 |
| 797 | rs17620193 |
| 798 | rs6896121 |
| 799 | rs12001157 |
| 800 | rs17622586 |
| 801 | rs6904307 |
| 802 | rs1202440 |
| 803 | rs17626856 |
| 804 | rs6908035 |
| 805 | rs12026065 |
| 806 | rs17628000 |
| 807 | rs6922765 |
| 808 | rs1203847 |
| 809 | rs17628482 |
| 810 | rs6925857 |
| 811 | rs1207696 |
| 812 | rs17628639 |
| 813 | rs6926332 |
| 814 | rs12081722 |
| 815 | rs17629030 |
| 816 | rs6928457 |
| 817 | rs12087089 |
| 818 | rs17630660 |
| 819 | rs6929656 |
| 820 | rs12099166 |
| 821 | rs17637745 |
| 822 | rs6931360 |
| 823 | rs12104610 |
| 824 | rs17642142 |
| 825 | rs6940742 |
| 826 | rs12105526 |
| 827 | rs17642472 |
| 828 | rs6951835 |
| 829 | rs12110710 |
| 830 | rs17646665 |
| 831 | rs695867 |
| 832 | rs12112460 |
| 833 | rs17646831 |
| 834 | rs6973676 |
| 835 | rs12113398 |
| 836 | rs17647618 |
| 837 | rs6987972 |
| 838 | rs12119464 |
| 839 | rs17653330 |
| 840 | rs6988595 |
| 841 | rs12119469 |
| 842 | rs17659820 |
| 843 | rs6994108 |
| 844 | rs12119861 |
| 845 | rs17662563 |
| 846 | rs699575 |
| 847 | rs12123578 |
| 848 | rs17666538 |
| 849 | rs699838 |
| 850 | rs12123883 |
| 851 | rs17667896 |

| SNP# | SNP Reference |
|------|---------------|
| 852 | rs7001242 |
| 853 | rs12125585 |
| 854 | rs17671350 |
| 855 | rs7010463 |
| 856 | rs12125927 |
| 857 | rs17675800 |
| 858 | rs7012787 |
| 859 | rs12127106 |
| 860 | rs17683284 |
| 861 | rs7037276 |
| 862 | rs12130351 |
| 863 | rs17685879 |
| 864 | rs7039190 |
| 865 | rs12137025 |
| 866 | rs17686437 |
| 867 | rs7040099 |
| 868 | rs12137988 |
| 869 | rs17690120 |
| 870 | rs704084 |
| 871 | rs12144375 |
| 872 | rs17695385 |
| 873 | rs7043864 |
| 874 | rs12145172 |
| 875 | rs17699960 |
| 876 | rs704471 |
| 877 | rs12152235 |
| 878 | rs17700494 |
| 879 | rs7056552 |
| 880 | rs12185903 |
| 881 | rs17704073 |
| 882 | rs7065 |
| 883 | rs12190581 |
| 884 | rs17704348 |
| 885 | rs7106019 |
| 886 | rs12191763 |
| 887 | rs17705765 |
| 888 | rs7110525 |
| 889 | rs12197456 |
| 890 | rs17708107 |
| 891 | rs7130376 |
| 892 | rs12197916 |
| 893 | rs17715481 |
| 894 | rs7135097 |
| 895 | rs12198650 |
| 896 | rs17719439 |
| 897 | rs7143124 |
| 898 | rs12200000 |
| 899 | rs17722347 |
| 900 | rs7150108 |
| 901 | rs12200541 |
| 902 | rs17728587 |
| 903 | rs7154172 |
| 904 | rs12204289 |
| 905 | rs17728589 |
| 906 | rs7155712 |
| 907 | rs12204295 |
| 908 | rs17729322 |
| 909 | rs7174536 |
| 910 | rs12206238 |
| 911 | rs17730920 |
| 912 | rs7174822 |
| 913 | rs12207718 |
| 914 | rs17732565 |
| 915 | rs7177722 |
| 916 | rs12210807 |
| 917 | rs17740495 |
| 918 | rs7178197 |
| 919 | rs12216694 |
| 920 | rs17742216 |
| 921 | rs7182555 |
| 922 | rs1222321 |
| 923 | rs17748089 |
| 924 | rs718938 |
| 925 | rs12258 |
| 926 | rs17756220 |
| 927 | rs719489 |
| 928 | rs12281746 |
| 929 | rs17760393 |
| 930 | rs7196459 |
| 931 | rs1228454 |
| 932 | rs17763463 |
| 933 | rs7197032 |
| 934 | rs12291238 |
| 935 | rs17763689 |
| 936 | rs7228843 |
| 937 | rs12295055 |
| 938 | rs17764093 |
| 939 | rs723303 |
| 940 | rs12305001 |
| 941 | rs17766637 |
| 942 | rs7234082 |
| 943 | rs12308116 |
| 944 | rs17771867 |
| 945 | rs7234088 |
| 946 | rs12314695 |
| 947 | rs17776169 |
| 948 | rs7242585 |
| 949 | rs12320850 |
| 950 | rs17776453 |
| 951 | rs7243360 |
| 952 | rs12326937 |
| 953 | rs17779007 |
| 954 | rs7253363 |
| 955 | rs12334642 |
| 956 | rs17779334 |
| 957 | rs725859 |
| 958 | rs12335930 |
| 959 | rs17779811 |
| 960 | rs7267617 |
| 961 | rs12360927 |
| 962 | rs17783089 |
| 963 | rs7268671 |
| 964 | rs12362898 |
| 965 | rs17783214 |
| 966 | rs7285825 |
| 967 | rs12369757 |
| 968 | rs17784833 |
| 969 | rs7287435 |
| 970 | rs12374525 |
| 971 | rs17790824 |
| 972 | rs7290510 |
| 973 | rs12422191 |
| 974 | rs17792616 |
| 975 | rs7297610 |
| 976 | rs12424873 |
| 977 | rs17799872 |
| 978 | rs7298274 |
| 979 | rs12425125 |
| 980 | rs17802089 |
| 981 | rs7299484 |
| 982 | rs12445722 |
| 983 | rs17804092 |
| 984 | rs7301769 |
| 985 | rs12451772 |
| 986 | rs17808754 |
| 987 | rs7302032 |
| 988 | rs12451779 |
| 989 | rs17811445 |
| 990 | rs7303903 |
| 991 | rs12454851 |
| 992 | rs17811959 |
| 993 | rs7305388 |
| 994 | rs12461121 |
| 995 | rs17813471 |
| 996 | rs7306642 |
| 997 | rs12478448 |
| 998 | rs17816202 |
| 999 | rs7307415 |
| 1000 | rs12486110 |
| 1001 | rs17823341 |
| 1002 | rs7309212 |
| 1003 | rs12496209 |

-continued

| SNP# | SNP Reference |
|---|---|
| 1004 | rs17825523 |
| 1005 | rs7309966 |
| 1006 | rs12496664 |
| 1007 | rs17826483 |
| 1008 | rs7311374 |
| 1009 | rs12496794 |
| 1010 | rs17830827 |
| 1011 | rs7313153 |
| 1012 | rs12524615 |
| 1013 | rs17839705 |
| 1014 | rs7315708 |
| 1015 | rs12531526 |
| 1016 | rs1799001 |
| 1017 | rs7318463 |
| 1018 | rs12531665 |
| 1019 | rs1799963 |
| 1020 | rs7319265 |
| 1021 | rs12534694 |
| 1022 | rs180054 |
| 1023 | rs7321929 |
| 1024 | rs12549829 |
| 1025 | rs1800689 |
| 1026 | rs7323443 |
| 1027 | rs12551673 |
| 1028 | rs1804527 |
| 1029 | rs732867 |
| 1030 | rs12558663 |
| 1031 | rs1805395 |
| 1032 | rs7328941 |
| 1033 | rs12562819 |
| 1034 | rs1805494 |
| 1035 | rs7331460 |
| 1036 | rs12591311 |
| 1037 | rs1809201 |
| 1038 | rs735331 |
| 1039 | rs12595041 |
| 1040 | rs181504 |
| 1041 | rs7355718 |
| 1042 | rs12599182 |
| 1043 | rs181536 |
| 1044 | rs7372560 |
| 1045 | rs12602254 |
| 1046 | rs1860790 |
| 1047 | rs7421179 |
| 1048 | rs12625154 |
| 1049 | rs1861782 |
| 1050 | rs7434449 |
| 1051 | rs12634358 |
| 1052 | rs1864951 |
| 1053 | rs746434 |
| 1054 | rs12654591 |
| 1055 | rs1867645 |
| 1056 | rs7464987 |
| 1057 | rs12657498 |
| 1058 | rs1870016 |
| 1059 | rs746748 |
| 1060 | rs12660137 |
| 1061 | rs1870105 |
| 1062 | rs747360 |
| 1063 | rs12660488 |
| 1064 | rs1883187 |
| 1065 | rs7525133 |
| 1066 | rs12684931 |
| 1067 | rs1891530 |
| 1068 | rs7526164 |
| 1069 | rs12705676 |
| 1070 | rs1892889 |
| 1071 | rs7527203 |
| 1072 | rs12707672 |
| 1073 | rs1919555 |
| 1074 | rs7555023 |
| 1075 | rs12708330 |
| 1076 | rs1939470 |
| 1077 | rs7555782 |
| 1078 | rs12713406 |
| 1079 | rs1955511 |

-continued

| SNP# | SNP Reference |
|---|---|
| 1080 | rs7566539 |
| 1081 | rs12734773 |
| 1082 | rs1957478 |
| 1083 | rs7568769 |
| 1084 | rs12760956 |
| 1085 | rs1958958 |
| 1086 | rs7572401 |
| 1087 | rs12800255 |
| 1088 | rs1961758 |
| 1089 | rs757326 |
| 1090 | rs12802741 |
| 1091 | rs196594 |
| 1092 | rs757578 |
| 1093 | rs1281189 |
| 1094 | rs1972384 |
| 1095 | rs7578670 |
| 1096 | rs12819272 |
| 1097 | rs1980908 |
| 1098 | rs7585125 |
| 1099 | rs12829100 |
| 1100 | rs1990734 |
| 1101 | rs7596265 |
| 1102 | rs12872212 |
| 1103 | rs1991027 |
| 1104 | rs7599440 |
| 1105 | rs12881445 |
| 1106 | rs1994945 |
| 1107 | rs7602743 |
| 1108 | rs12882445 |
| 1109 | rs1996624 |
| 1110 | rs7615158 |
| 1111 | rs12888471 |
| 1112 | rs1997786 |
| 1113 | rs7615580 |
| 1114 | rs12896281 |
| 1115 | rs1999543 |
| 1116 | rs7617405 |
| 1117 | rs12898407 |
| 1118 | rs2001146 |
| 1119 | rs7619267 |
| 1120 | rs12910083 |
| 1121 | rs2002176 |
| 1122 | rs762143 |
| 1123 | rs12914140 |
| 1124 | rs2004016 |
| 1125 | rs7627687 |
| 1126 | rs12927245 |
| 1127 | rs200577 |
| 1128 | rs763378 |
| 1129 | rs12929714 |
| 1130 | rs2015035 |
| 1131 | rs7636142 |
| 1132 | rs12965811 |
| 1133 | rs2018899 |
| 1134 | rs763876 |
| 1135 | rs12984558 |
| 1136 | rs2028241 |
| 1137 | rs7644726 |
| 1138 | rs13002508 |
| 1139 | rs2031183 |
| 1140 | rs7653164 |
| 1141 | rs13025811 |
| 1142 | rs203217 |
| 1143 | rs7665448 |
| 1144 | rs13027062 |
| 1145 | rs2036801 |
| 1146 | rs7671873 |
| 1147 | rs13027536 |
| 1148 | rs2039979 |
| 1149 | rs7675915 |
| 1150 | rs13030450 |
| 1151 | rs2053648 |
| 1152 | rs7678445 |
| 1153 | rs13034777 |
| 1154 | rs2055502 |
| 1155 | rs768543 |

| SNP# | SNP Reference |
|---|---|
| 1156 | rs13035893 |
| 1157 | rs2058708 |
| 1158 | rs7686178 |
| 1159 | rs13036818 |
| 1160 | rs2059004 |
| 1161 | rs770936 |
| 1162 | rs13050655 |
| 1163 | rs2059041 |
| 1164 | rs7720612 |
| 1165 | rs13064568 |
| 1166 | rs2063273 |
| 1167 | rs7732337 |
| 1168 | rs13067311 |
| 1169 | rs2064923 |
| 1170 | rs7733891 |
| 1171 | rs13067800 |
| 1172 | rs2067478 |
| 1173 | rs7734751 |
| 1174 | rs13072299 |
| 1175 | rs2067794 |
| 1176 | rs774983 |
| 1177 | rs13077577 |
| 1178 | rs2069329 |
| 1179 | rs7752412 |
| 1180 | rs13089058 |
| 1181 | rs2073418 |
| 1182 | rs7758412 |
| 1183 | rs13098826 |
| 1184 | rs2073550 |
| 1185 | rs7765980 |
| 1186 | rs13108289 |
| 1187 | rs2102540 |
| 1188 | rs7780223 |
| 1189 | rs13110639 |
| 1190 | rs2108798 |
| 1191 | rs7785 |
| 1192 | rs13136209 |
| 1193 | rs2122627 |
| 1194 | rs7817848 |
| 1195 | rs13153283 |
| 1196 | rs2125290 |
| 1197 | rs7818567 |
| 1198 | rs1316883 |
| 1199 | rs2143557 |
| 1200 | rs783396 |
| 1201 | rs13172853 |
| 1202 | rs2149265 |
| 1203 | rs7837373 |
| 1204 | rs13175238 |
| 1205 | rs2153944 |
| 1206 | rs7842261 |
| 1207 | rs13177772 |
| 1208 | rs2156460 |
| 1209 | rs7846685 |
| 1210 | rs13193527 |
| 1211 | rs216313 |
| 1212 | rs7858958 |
| 1213 | rs13193570 |
| 1214 | rs216365 |
| 1215 | rs7860480 |
| 1216 | rs13205436 |
| 1217 | rs2164824 |
| 1218 | rs7861928 |
| 1219 | rs13207257 |
| 1220 | rs2165893 |
| 1221 | rs7937072 |
| 1222 | rs13208509 |
| 1223 | rs2168458 |
| 1224 | rs795527 |
| 1225 | rs13220676 |
| 1226 | rs2173967 |
| 1227 | rs7959782 |
| 1228 | rs13220781 |
| 1229 | rs219463 |
| 1230 | rs7966147 |
| 1231 | rs13223286 |
| 1232 | rs221007 |
| 1233 | rs7966281 |
| 1234 | rs13224682 |
| 1235 | rs2219989 |
| 1236 | rs7978767 |
| 1237 | rs13226 |
| 1238 | rs2225607 |
| 1239 | rs7994080 |
| 1240 | rs1323851 |
| 1241 | rs2229862 |
| 1242 | rs7996474 |
| 1243 | rs13241783 |
| 1244 | rs2234931 |
| 1245 | rs7997230 |
| 1246 | rs13244143 |
| 1247 | rs224053 |
| 1248 | rs7997459 |
| 1249 | rs13245368 |
| 1250 | rs2240982 |
| 1251 | rs7998952 |
| 1252 | rs1324619 |
| 1253 | rs224199 |
| 1254 | rs8007208 |
| 1255 | rs13253897 |
| 1256 | rs2245642 |
| 1257 | rs8014003 |
| 1258 | rs13253939 |
| 1259 | rs2267389 |
| 1260 | rs8017738 |
| 1261 | rs1325957 |
| 1262 | rs2273720 |
| 1263 | rs8037890 |
| 1264 | rs1326016 |
| 1265 | rs2275084 |
| 1266 | rs8043874 |
| 1267 | rs13263868 |
| 1268 | rs2275335 |
| 1269 | rs8049613 |
| 1270 | rs13264275 |
| 1271 | rs2275690 |
| 1272 | rs8065724 |
| 1273 | rs13264895 |
| 1274 | rs2276878 |
| 1275 | rs806711 |
| 1276 | rs13267988 |
| 1277 | rs2277472 |
| 1278 | rs806850 |
| 1279 | rs13278854 |
| 1280 | rs2279047 |
| 1281 | rs8069038 |
| 1282 | rs13286656 |
| 1283 | rs2279854 |
| 1284 | rs8069917 |
| 1285 | rs13288168 |
| 1286 | rs2279955 |
| 1287 | rs8070360 |
| 1288 | rs1329672 |
| 1289 | rs2282087 |
| 1290 | rs8087023 |
| 1291 | rs13299805 |
| 1292 | rs2282137 |
| 1293 | rs8088185 |
| 1294 | rs1332180 |
| 1295 | rs228342 |
| 1296 | rs8093902 |
| 1297 | rs13345127 |
| 1298 | rs2286007 |
| 1299 | rs8108440 |
| 1300 | rs1336563 |
| 1301 | rs2289722 |
| 1302 | rs8110782 |
| 1303 | rs13375691 |
| 1304 | rs2290986 |
| 1305 | rs8118581 |
| 1306 | rs13379247 |
| 1307 | rs2291287 |

| SNP# | SNP Reference |
|---|---|
| 1308 | rs8125465 |
| 1309 | rs13380855 |
| 1310 | rs2291366 |
| 1311 | rs8132970 |
| 1312 | rs13381425 |
| 1313 | rs2291399 |
| 1314 | rs8182247 |
| 1315 | rs13386519 |
| 1316 | rs2291909 |
| 1317 | rs8187858 |
| 1318 | rs13392744 |
| 1319 | rs2293139 |
| 1320 | rs823955 |
| 1321 | rs13393621 |
| 1322 | rs2294777 |
| 1323 | rs831438 |
| 1324 | rs13396013 |
| 1325 | rs2296213 |
| 1326 | rs844125 |
| 1327 | rs13401220 |
| 1328 | rs2297781 |
| 1329 | rs848223 |
| 1330 | rs13404171 |
| 1331 | rs2298116 |
| 1332 | rs853006 |
| 1333 | rs13404991 |
| 1334 | rs2299105 |
| 1335 | rs865635 |
| 1336 | rs13422055 |
| 1337 | rs2299554 |
| 1338 | rs870735 |
| 1339 | rs13426621 |
| 1340 | rs2304579 |
| 1341 | rs873727 |
| 1342 | rs13428359 |
| 1343 | rs2319850 |
| 1344 | rs878184 |
| 1345 | rs13431961 |
| 1346 | rs2330986 |
| 1347 | rs883580 |
| 1348 | rs13435689 |
| 1349 | rs2331902 |
| 1350 | rs885446 |
| 1351 | rs1346520 |
| 1352 | rs233551 |
| 1353 | rs888610 |
| 1354 | rs1351770 |
| 1355 | rs2343541 |
| 1356 | rs8923 |
| 1357 | rs1360809 |
| 1358 | rs2345724 |
| 1359 | rs896331 |
| 1360 | rs1362689 |
| 1361 | rs2370876 |
| 1362 | rs908436 |
| 1363 | rs1363670 |
| 1364 | rs2390945 |
| 1365 | rs914346 |
| 1366 | rs1366477 |
| 1367 | rs2400700 |
| 1368 | rs917836 |
| 1369 | rs1371428 |
| 1370 | rs2416879 |
| 1371 | rs9289100 |
| 1372 | rs1372587 |
| 1373 | rs242343 |
| 1374 | rs9298315 |
| 1375 | rs1382154 |
| 1376 | rs2423740 |
| 1377 | rs9307306 |
| 1378 | rs1384755 |
| 1379 | rs2423866 |
| 1380 | rs9316876 |
| 1381 | rs1388068 |
| 1382 | rs2428936 |
| 1383 | rs9324996 |
| 1384 | rs138840 |
| 1385 | rs2432969 |
| 1386 | rs9327649 |
| 1387 | rs1390559 |
| 1388 | rs2436941 |
| 1389 | rs9328420 |
| 1390 | rs1391817 |
| 1391 | rs2448175 |
| 1392 | rs934127 |
| 1393 | rs1424802 |
| 1394 | rs2457435 |
| 1395 | rs9352581 |
| 1396 | rs1425215 |
| 1397 | rs2465024 |
| 1398 | rs9355427 |
| 1399 | rs1428088 |
| 1400 | rs247230 |
| 1401 | rs938152 |
| 1402 | rs1434093 |
| 1403 | rs2490565 |
| 1404 | rs9402098 |
| 1405 | rs1436750 |
| 1406 | rs2495210 |
| 1407 | rs941879 |
| 1408 | rs1439530 |
| 1409 | rs2512642 |
| 1410 | rs943588 |
| 1411 | rs1442360 |
| 1412 | rs251789 |
| 1413 | rs9450117 |
| 1414 | rs1442404 |
| 1415 | rs2566478 |
| 1416 | rs946411 |
| 1417 | rs1447681 |
| 1418 | rs2568970 |
| 1419 | rs9479837 |
| 1420 | rs1461607 |
| 1421 | rs2575066 |
| 1422 | rs948588 |
| 1423 | rs1470219 |
| 1424 | rs2579643 |
| 1425 | rs9488000 |
| 1426 | rs1472080 |
| 1427 | rs2580189 |
| 1428 | rs9491304 |
| 1429 | rs1475201 |
| 1430 | rs2580869 |
| 1431 | rs9494944 |
| 1432 | rs1480390 |
| 1433 | rs2595647 |
| 1434 | rs9503907 |
| 1435 | rs1487232 |
| 1436 | rs260693 |
| 1437 | rs9509571 |
| 1438 | rs1491716 |
| 1439 | rs2610690 |
| 1440 | rs9511259 |
| 1441 | rs1492210 |
| 1442 | rs2624485 |
| 1443 | rs951704 |
| 1444 | rs1524641 |
| 1445 | rs2633958 |
| 1446 | rs951752 |
| 1447 | rs1530272 |
| 1448 | rs265271 |
| 1449 | rs9523176 |
| 1450 | rs1534813 |
| 1451 | rs2658161 |
| 1452 | rs9524558 |
| 1453 | rs1540087 |
| 1454 | rs2666205 |
| 1455 | rs9526984 |
| 1456 | rs1550879 |
| 1457 | rs2669331 |
| 1458 | rs9531337 |
| 1459 | rs1552596 |

| SNP# | SNP Reference |
|---|---|
| 1460 | rs268309 |
| 1461 | rs953726 |
| 1462 | rs1553930 |
| 1463 | rs26887 |
| 1464 | rs9538430 |
| 1465 | rs1556384 |
| 1466 | rs269243 |
| 1467 | rs954039 |
| 1468 | rs1558253 |
| 1469 | rs2702185 |
| 1470 | rs9546594 |
| 1471 | rs1560585 |
| 1472 | rs270996 |
| 1473 | rs9581919 |
| 1474 | rs1561629 |
| 1475 | rs2713946 |
| 1476 | rs9589238 |
| 1477 | rs1562030 |
| 1478 | rs272128 |
| 1479 | rs9591472 |
| 1480 | rs1563981 |
| 1481 | rs2732043 |
| 1482 | rs9600990 |
| 1483 | rs1564419 |
| 1484 | rs27429 |
| 1485 | rs9601690 |
| 1486 | rs1564693 |
| 1487 | rs2747151 |
| 1488 | rs9608554 |
| 1489 | rs1571704 |
| 1490 | rs2762829 |
| 1491 | rs9610900 |
| 1492 | rs1574005 |
| 1493 | rs2764724 |
| 1494 | rs9642144 |
| 1495 | rs1584091 |
| 1496 | rs2782517 |
| 1497 | rs9668398 |
| 1498 | rs1592903 |
| 1499 | rs2806204 |
| 1500 | rs9673539 |
| 1501 | rs162683 |
| 1502 | rs2819017 |
| 1503 | rs9693094 |
| 1504 | rs1652364 |
| 1505 | rs2825336 |
| 1506 | rs973236 |
| 1507 | rs166892 |
| 1508 | rs2829949 |
| 1509 | rs9809356 |
| 1510 | rs16827018 |
| 1511 | rs2833355 |
| 1512 | rs9812240 |
| 1513 | rs16832634 |
| 1514 | rs2833927 |
| 1515 | rs9816026 |
| 1516 | rs16833306 |
| 1517 | rs2835239 |
| 1518 | rs9824384 |
| 1519 | rs16843177 |
| 1520 | rs28360135 |
| 1521 | rs9830198 |
| 1522 | rs16850869 |
| 1523 | rs2837742 |
| 1524 | rs9831161 |
| 1525 | rs16852780 |
| 1526 | rs2838443 |
| 1527 | rs9839647 |
| 1528 | rs16852915 |
| 1529 | rs2843705 |
| 1530 | rs9842772 |
| 1531 | rs16853650 |
| 1532 | rs284633 |
| 1533 | rs9846767 |
| 1534 | rs16856148 |
| 1535 | rs286913 |
| 1536 | rs9860789 |
| 1537 | rs16856802 |
| 1538 | rs288266 |
| 1539 | rs9879860 |
| 1540 | rs16858692 |
| 1541 | rs2889718 |
| 1542 | rs9883072 |
| 1543 | rs16858789 |
| 1544 | rs289698 |
| 1545 | rs989215 |
| 1546 | rs16859945 |
| 1547 | rs2904523 |
| 1548 | rs9894393 |
| 1549 | rs16860912 |
| 1550 | rs291939 |
| 1551 | rs9897758 |
| 1552 | rs16861659 |
| 1553 | rs2948653 |
| 1554 | rs9913935 |
| 1555 | rs16865908 |
| 1556 | rs2974020 |
| 1557 | rs994426 |
| 1558 | rs16867729 |
| 1559 | rs2978565 |
| 1560 | rs9946654 |
| 1561 | rs16868772 |
| 1562 | rs300259 |
| 1563 | rs9948159 |
| 1564 | rs16869867 |
| 1565 | rs3008483 |
| 1566 | rs9958933 |
| 1567 | rs16871128 |
| 1568 | rs3025153 |

Any panel generated using one or more of the criteria provided herein, or any one of the above-listed panels, may be combined with one or more SNPs that predict or correlate with, any other SNP that predicts or correlates with a characteristic used to differentiate individuals. For example, any panel generated using one or more of the criteria provided herein, or any one of the above-listed panels, may be combined with one or more SNPs that predict or correlate with, any other SNP that predicts or correlates with the occurrence of an externally visible trait, biogeographic ancestry and/or kinship to provide a more extensive DNA profile. Moreover, any panel generated using one or more of the criteria provided herein, or any one of the above-listed panels, may be combined with one or more SNPs that predict or correlate with, any other SNP that predicts or correlates with the occurrence of a biological disease or condition, including, but not limited to, youth, age, an increased risk for developing a disease or condition (for example, increased risk of developing cancer or mental senility), blood type, proliferative disease (including cancer), metabolic disease, inflammatory disease, neurological disease, cardiovascular disease, immunological disease (including, autoimmune conditions), respiratory disease, liver disease, kidney disease, intestinal disease and/or infectious disease.

Resolving Individual Contributors in Complex DNA Mixtures

Voskoboinik and Darvasi described a theoretical method to detect known individuals in complex DNA mixtures by using a panel of 500 to 1,000 SNPs with minor allele frequency of around 0.05. They showed that a known individual can be reliably detected with low false match probability in DNA mixtures of up to 10 people.

By way of illustration, a 1,000 SNP panel for a given individual (referred to as subject 1), is depicted in FIG. 1, in which the location of a black line indicates the presence of a minor allele SNP at that locus. This resultant pattern of black lines is statistically unique to this individual to within a vanishingly small number (<10-40). A mixture of 5 peoples' DNA, including subject 1, when analyzed with this "barcoding" method appears as shown in FIG. 2. The barcode pattern is more filled in, that is, more loci have a minor allele SNP present because of the combined contribution of the 5 people. Using the methods described by Voskoboinik and Darvasi, if subject 1's SNP profile is known, the methods of the disclosure can reliably detect the presence of subject 1 in this mixture with a low false match probability (<10-15). A substantial limitation of the approach of Voskoboinik and Darvasi arises when the user doesn't have a reference SNP profile to compare to the DNA mixture, but wants to determine the individual contributors' SNP profiles for direct comparison to other forensic reference samples/profiles.

The central principle underlying the methods of the disclosure is the ability to confirm the contributions of common unknown individuals to multiple complex DNA mixtures when DNA SNP profile of any of the individual contributors is not known a-priori. This ability provides more than just a significant improvement over existing methods (e.g. Voskoboinik and Darvasi), but rather a new capacity to analyze mixtures that would have been impossible to resolve prior to the development of the SNP panels and methods of the disclosure.

Figure 3:
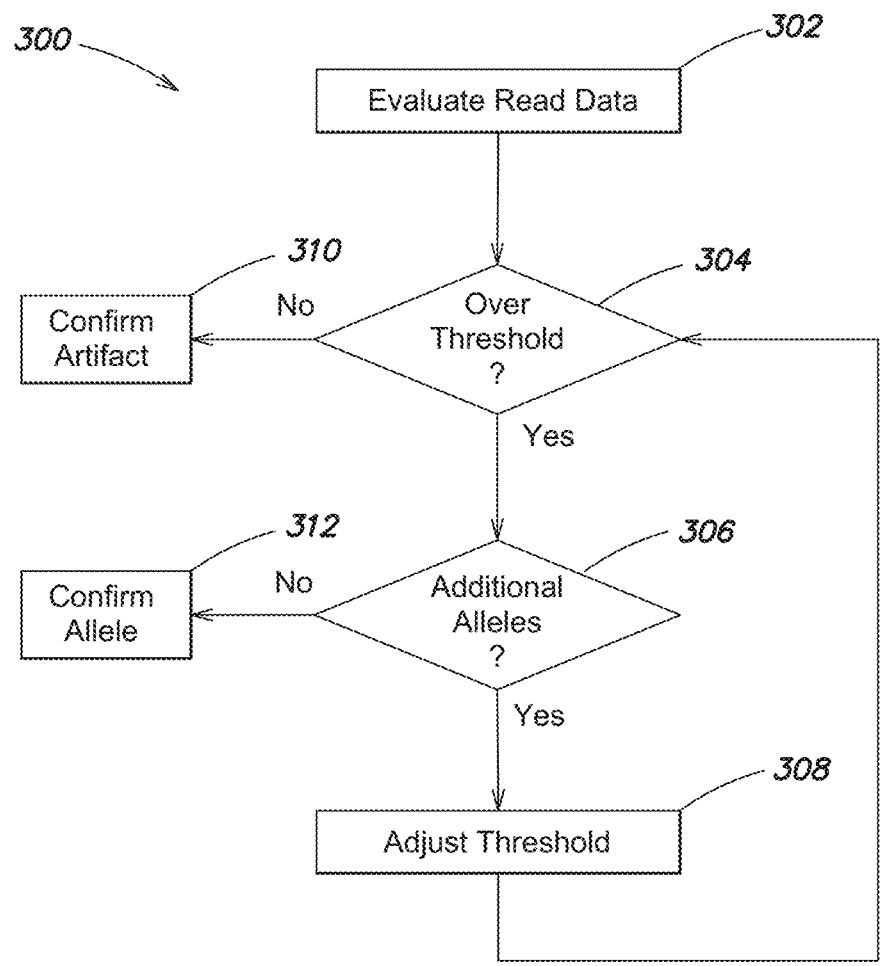
FIG. 3 illustrates an example process for eliminating read error, according to one embodiment.

The methods of the disclosure measure the intersection, or overlapping population of genetic markers, e.g. minor allele SNPs, across multiple DNA mixtures. Due to statistical random chance, a certain number of SNPs will be shared by different individuals. For any SNP at a given loci, the probability that it will be shared by chance across multiple mixtures decreases as the number of mixtures considered increases if each individual is only occurs in one of the considered mixtures. However, if the same individual is a DNA contributor in all of the mixtures, then the probable number of shared loci across those mixtures will increase and should include some or all of the shared individual contributor's minor alleles. For example, after comparing five 5-person DNA mixtures with one common contributor across them, subject 1's 127 SNP profile can be reliably reproduced to within 11 SNPs (shown in FIG. 3). The image depicted in FIG. 3 is identical to subject 1's profile shown in FIG. 1, the profile depicted in FIG. 3 having only 11 extra SNPs.

The methods of the disclosure use vector multiplication to find common SNPs across data sets (for instance, each complex DNA mixture may be considered a data set) to build an individual profile from an analysis of multiple complex DNA mixtures. According to these methods, the presence of a minor allele SNP is represented by the value 1 and its absence by a zero in the data. For example, to compare three DNA mixtures, these methods multiply the first two mixtures' SNP panels together, and then multiply that product by the third mixture to find the common minor allele SNPs shared among all three mixtures. By counting the number of shared SNPs, these methods can estimate whether the data sets (or complex DNA mixtures) have zero, one or more contributors in common.

Significantly, the methods of the disclosure provide an ability to build individual profiles from complex DNA mixtures without any "known" individual profiles or data from any of the contributors to the complex DNA mixture. This important feature of the methods of the disclosure enable the user to build individual profiles from complex DNA mixtures that would have been impossible prior to the development of the SNP panels and methods described herein.

Direct Devolution of Complex DNA Mixtures to Individuals

Using single nucleotide polymorphisms (SNPs) sequenced from a panel of loci on the human genome, the disclosure provides a method for direct deconvolution of a complex DNA mixture to individual contributors and/or components. According to embodiments of these methods, at each locus, a minor allele ratio (mAR) is calculated as the number of sequences called with that locus' minor allele, divided by the total number of observed sequences at that locus. For an individual DNA profile, mARs typically fall around 0 (homozygous major), 0.5 (heterozygous) or 1.0 (homozygous minor). For a mixture of DNA contributors, mAR ranges between 0 and 1.0. Within mixtures, the observed mAR values directly correlate with the number of contributing individuals and their relative DNA molar concentrations. These correlations can be leveraged to identify the presence of and/or separate individual contributors' DNA profiles.

FIG. 4 demonstrates a typical mAR plot for a mixture of two individual DNA profiles, combined in a DNA molar ratio of 4:1. Two partial DNA profiles are visible in FIG. 4. Both contributors' homozygous major alleles fall around a mAR of 0.0. Minor alleles separate into two bands centered on mAR=0.1 and mAR=0.5, corresponding to the two non-equimolar contributors. These unique, individual profiles can be independently extracted and compared against reference DNA profiles or additional deconvoluted mixtures for identification. If an extracted minor allele band matches a reference SNP profile with high confidence, the individual contributor is identified. If the band has a high proportion of minor allele matches with a band extracted from a different mixture, this suggests that there is a common contributor to both mixtures and the two allele bands can be combined to provide a more complete DNA profile for that unknown contributor than could be obtained from analysis of a single mixture. This principle is demonstrated in FIG. 5.

Calculating Probability of Random Man not Excluded

In parallel to deconvolution, the forensic standard false inclusion metric, the probability of a random man not excluded, P(RMNE), can be calculated directly from the profiles generated from the methods of the disclosure. P(RMNE) quantifies the likelihood of falsely identifying a random individual from the population present in the mixture. For example, homozygous major allele profiles are extracted and, in conjunction with population-averaged minor-allele frequencies, define the parameters for a P(RMNE) calculation.

The disclosure provides a model to declare and/or determine whether an individual is present within a mixture while accounting for mismatched alleles. Minor allele calls are compared between an interrogatory sample and a mixture, declaring each locus a match or mismatch. To account for potential sources of non-trivial error, the method provides a detection module that allow for one or more mismatches. For this reason, an individual as a whole is declared "present in mixture" if the number of mismatches is small, or declared "absent from mixture" if the number of allele mismatches is large. Selection of an optimal minor allele mismatch level involves balancing true detection sensitivity and false-positive inclusions.

If at any particular locus, both the individual and the mixture contain a minor allele, a match is declared for that locus. However, if an individual presents with one or more minor alleles at a particular locus but the mixture appears homozygous major, a mismatch is called. The rare case where a mixture is called homozygous minor at a locus is also considered; a match is called for a homozygous minor or heterozygous individual, and a mismatch otherwise.

A model to evaluate P(RMNE) for any number of allowed allele mismatches, considering variance in mAF between loci, has been developed. To ensure a precise calculation of the P(RMNE) value, four methods are calculated and compared:
   Direct Evaluation of the probability distribution function (pdf)
   Approximation of the pdf via a binomial distribution (see also Voskoboinik and Darvasi)
   Exact calculation of the pdf utilizing the Discrete Fourier Transform—Characteristic Function (DFT-CF) method, and
   A Monte Carlo simulation.

Previously, the probability of a random man not excluded has been formulated by Voskoboinik and Darvasi as:

$$P(RMNE) = \prod_{i=0}^{S}(1-p_i)^2 \approx \overline{P}^{2S} \tag{1}$$

A mixed DNA sample is genotyped at N SNP loci where S is the number of homozygous major loci in a mixture, is the population estimated mAF of allele i and is the average mAF taken across all S loci. This model of false inclusion assumes all minor allele-containing loci must match between a reference and a mixture. If all N-S alleles match, then a reference DNA sample will be called homozygous major with probability at every locus called homozygous major in the mixture. A subject can be excluded from a mixture at a particular locus if they have a minor allele when that locus is homozygous major in the mixture. Exclusion due to homozygous minor loci in the mixture is about three orders of magnitude less likely than exclusion due to homozygous major loci (Voskoboinik and Darvasi). Allele mismatches are not considered in this equation. As mentioned by Voskoboinik and Darvasi and described previously, averaging minor allele frequencies using the approximation in equation 1 boosts computational speed of evaluating P(RMNE), at the cost of a reduction in the model's accuracy. This approximation of P(RMNE) in equation 1 is valid for small mixtures with no sequencing error. However, the model is not accurate enough for forensic admissibility. A more precise model considering allele mismatches and allele specific mAFs is required.

Rather than fix an estimated allele call error rate as in Voskoboinik and Darvasi the approximation in equation 1 can be improved to include allele mismatches by rewriting as a binomial distribution:

$$P_M(RMNE) \approx \sum_{k=0}^{M} \overline{P}^{2k}(1-\overline{P})^{2(S-k)}\binom{S}{k} \tag{2}$$

Where M is the maximum number of allowed mismatching loci. M greater than zero results from any number of deficiencies in the genotyping process such as drop out, low copy number, amplification, sequencing errors and others. For equation 2, P(RMNE) is approximated as a Binomial distribution with a "probability of success" equal to the average minor allele frequency across all forensically valid loci, Using this improvement over equation 1, PM(RMNE) can be quickly evaluated for all M less than S. Given a desired probability of false inclusion tolerance t, a threshold can be placed on the maximum number of allowed allele mismatches, M, such that PM(RMNE)<t.

The probability of a random man not excluded can be further improved to include both locus-dependent mAFs, the inclusion of possible mismatches where the mixture is homozygous minor and the suspect is not, and an arbitrary number of allele mismatches:

$$P_M(RMNE) = \sum_{k=0}^{M}\left[\prod_{A_k}\prod_{i \in A_k}(1-p_i)^2 \prod_{i \in A_k^c}(1-(1-p_i^2)) + \prod_{B_k}\prod_{i \in B_k}p_i^2 \prod_{i \in B_k^c}(1-p_i^2)\right] \tag{3}$$

Where represents all sets of (S-k) loci wherein both the individual and the mixture are called homozygous major and represents all sets of k loci wherein the individual is called with one or more minor alleles and the mixture is called homozygous major. Similarly, let Q equal the number of alleles wherein the mixture is called homozygous minor (mAR>0.99). represents all sets of (Q-k) loci wherein both the individual and the mixture are called homozygous minor and represents all sets of k loci wherein the individual is called with less than two minor alleles and the mixture is called homozygous minor. In practice, Q is observed as zero and equation 3 reduces to:

$$P_M(RMNE) = \sum_{k=0}^{M}\prod_{A_k}\prod_{i \in A_k}(1-p_i)^2 \prod_{i \in A_k^c}(2*p_i - p_i^2) \tag{4}$$

The cumulative distribution function (cdf), evaluated over a range of M mismatched loci, presented in equation 4 is equivalent to the Poisson-Binomial distribution where the probability of a homozygous major allele call, defines the probability of success for trial i. Equations 3 and 4 directly calculate the probability that a random individual, with T minor alleles, has M mismatching and T-M matching minor allele loci for all combinations of possible mismatching alleles. This is a powerful tool allowing a user to immediately quantify, for a given mixture, how the choice of the number of allowed mismatched loci due to all sources of analytical error affects the likelihood that a random individual would be falsely called "present in mixture", or the P(RMNE). This will also lend confidence to the judicial system that P(RMNE) is being accurately calculated for imperfectly matching data.

While this generalization adds precision to previous models, equation 4 requires computing all combinations of M mismatching loci over S-M homozygous major loci must be considered. This creates a large computational running time prohibiting calculation for large k. To be precise, the cost of evaluating this distribution function for M mismatching loci is—a polynomial algorithm. Calculating this probability distribution function for M=4 and N=299 on a MacBook Pro with 4 GB of RAM and an Intel 2.7 GHz i7 takes upwards of an hour.

To mitigate the long running time of direct calculation but retain the fidelity of the Poission-Binomial model, the DFT-CF method of evaluating the Poisson-Binomial distribution is utilized (see also Hong, Yili. Computational Statistics & Data Analysis, Volume 59, March 2013, Pages 41-51). It is an exact method, simultaneously evaluating the above probability distribution function for all in running time. The same MacBook Pro is able to evaluate the RMNE for any number of mismatches in seconds. A faster formulation for P(RMNE) with higher precision has been formulated (MIT 19461L).

EXAMPLES

Example 1: Selection of SNP Markers

Four exemplary panels of SNPs are described herein. Three of these panels were used for mixture analysis: the 480 panel; the 975 panel; the OptMix panel. The OptMix panel is a subset of the Kinship panel, which was designed to assess the degree of relatedness between two people from DNA samples.

The 480 panel: Amplification was performed using Fluidigm Access Array. Loci were selected as follows:

FST <0.06: Poor correlation between ancestry and genotype on ALFRED database

Average Heterozygosity=0.058-0.13 on ALFRED (should correspond to MAF~0.03-0.07)

No health related data on SNP in the NIH/NCBI dbSNP database mAF=0.03-0.07 on dbSNP database Average heterozygosity=0.058-0.13 on dbSNP (should correspond to MAF 0.03-0.07), meaning that the alleles are relatively rare in the population Elimination of duplicate SNPs and ambiguously mapped SNPs.

Minimum distance between alleles of 500,000 bases (of NCBI build 37)=1430 SNPs.

Selected 950 SNPs, 530 of which were compatible with Fluidigm DNA amplification platform The 975 panel: Amplification was performed using Ampliseq. Same process as described for the 480-panel, however, include all 1430 SNPs rather than selecting from this group the 950 SNPs used in the 480-panel.

Kinship panel: Amplification was performed using Ampliseq. Similar criteria as described for the 480-SNP panel, with the following distinctions:

mAF between 0.01 and 0.3

Distance between loci >110,000 bp

OptMix panel: Amplification was performed using Ampliseq. Similar criteria as described for the Kinship panel, with the following distinctions:

Distance between loci >500,000 mAF<0.06

Delete loci that tend to give ambiguous results (mAR not at expected values in reference samples)

Delete loci that tend to produce a low number of reads (<10% of the average number of reads/locus)

Delete loci that produce impossible results in known family tree

Delete loci that tend to generate data from only one strand of DNA.

Example 2: Deconvoluting/Resolving Complex DNA Mixtures

The forensic standard false inclusion metric, the probability of a random man not excluded, P(RMNE), can be calculated directly from the profiles generated from the methods of the disclosure. P(RMNE) quantifies the likelihood of falsely identifying a random individual from the population present in the mixture. For example, homozygous major allele profiles are extracted and, in conjunction with population-averaged minor-allele frequencies, define the parameters for a P(RMNE) calculation. The mathematical formula for this calculation is shown in FIG. 6.

Figure 10:
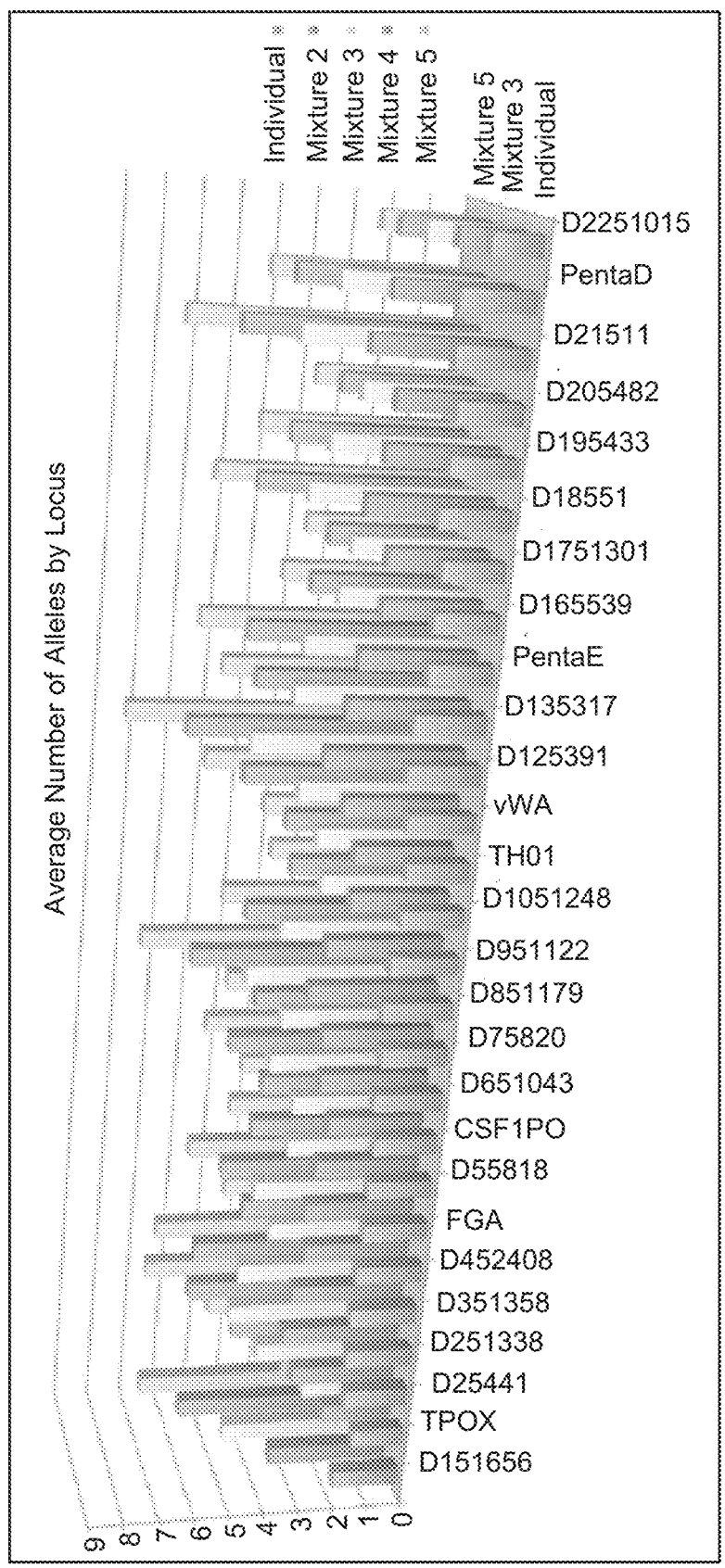
FIG. 10 illustrates a plot of the average number of alleles by locus for one to five contributors to STR mixture, according to one embodiment.

FIG. 9 shows the results from a mixture analysis using 468 SNPs with a minor allele frequency of approximately 0.05. For this analysis, mixtures containing equal amounts of DNA from 8, 5, 3, 10 and 15 individuals were amplified using Fluidigm multiplexed PCR technology and sequenced on Ion Torrent PGM. Calculations of probability of detection vs. P(RMNE) demonstrate that a P(RMNE) of less than 10-9 can be achieved in a 3-5 person mixture with minimal detriment to the probability of detection (Pd) (FIG. 10).

FIG. 11 shows the results from a mixture analysis using 975 SNPs with a minor allele frequency of approximately 0.05. Mixtures containing equal amounts of DNA from 8, 10, 15, and 20 individuals were amplified using Ampliseq multiplexed PCR technology and sequenced on Ion Torrent PGM. Calculations of probability of detection vs. P(RMNE) demonstrate that a P(RMNE) of less than 10-9 can be achieved in a 8-10 person mixture with a Pd of 1 (FIG. 12).

REFERENCES

Ballantyne, K. N. et al., 2012, For. Sci. Int. Gen., 6:208-218.
Buckleton, J. S. et al. Forensic DNA Evidence Interpretation, CRC Press, Boca Raton, 2005.
Eriksson, N. et al., PLOS Genetics, 2010, e1000993.
Hong, Yili. On computing the distribution function for the Poisson binomial distribution. Computational Statistics & Data Analysis, Volume 59, March 2013, Pages 41-51, ISSN 0167-9473.
Kidd, K. K. et al., 2012, For. Sci. Int. Gen., 6:646-652.
Liu, F. et al., PLOS Genetics, 2012, e1002932.
Nassir, R. et al., 2009, BMC Genetics, 10:39.
Pakstis et al. Hum Genet (2010) 127:315-324.
Tian C, et al. (2008) PLoS Genetics 4(1): 29-39.
Voskoboinik, L. and Darvasi, A. Forensic Identification of an Individual in Complex DNA Mixtures. 2011. Forensic Science International: Genetics 5:428-435.
Walsh, S. et al., 2011, For. Sci. Int. Gen., 5:170-180.

All publications, patents and sequence database entries mentioned herein, including those items listed below, are hereby incorporated by reference for the teachings referenced herein as if each individual publication or patent was specifically and individually indicated to be incorporated by reference. In case of conflict, the present application, including any definitions herein, will control.

Advanced DNA Forensics Software Platform

According to various embodiments, one or more functions may be performed using a DNA forensics software platform as more fully described below. It is appreciated that DNA forensics is transitioning from sizing of short tandem repeat (STR) alleles to high throughput sequencing (HTS) of STRs and/or single nucleotide polymorphisms (SNPs). DNA microarrays also provide an inexpensive method for rapidly characterizing hundreds of thousands to millions of SNPs in a sample. The significant increase in number of DNA loci cannot be handled by current forensics solutions. Below is described describes an advanced DNA forensics software platform that enables one or more of the following functions:

(1) Identification
(2) Kinship identification
(3) Mixture Analysis (4) Saturated Mixture Analysis
(5) Identification of Trace Profiles
(6) Biogeographic Ancestry (BGA) prediction
(7) Phenotype/Externally Visible Trait (EVT) prediction
(8) Geolocation
(9) Medical Genetics
(10) Mixture Deconvolution
(11) Mixture-to-Mixture Analysis
(12) Identification of Unknowns
(13) sample annotation
(14) multi-site networking
(15) data security
(16) system backup, and more (FIG. 1). Key concepts are the integration of advanced DNA forensics modules into a unified system with a local database that coordinates with other sites. One example system architecture uses a web-based solution with web services. FIG. 13 shows an advanced DNA forensics system modules and example architecture.

Details

Forensics samples can be characterized by HTS sequencing pipelines or DNA microarrays 1. FIG. 2 illustrates the high level steps of sample sequencing and HTS raw data processing to detect sequence variants. FIG. 14 shows and example sample characterization pipeline according to various embodiments.

Genomic Sequence Variants

Human cells contain nuclear DNA and mitochondrial DNA. Cells typically have multiple mitochondria per cell. Unrelated individuals typically have on the order of four million single nucleotide polymorphisms (SNPs) variations, differences in short tandem repeats (STRs) sequences, copy-number variations (CNVs), and other types of sequence differences. Multiple technologies have been developed to characterize DNA sequence variants. These individual sequence variants have important forensics applications.

Whole Genome Shotgun (WGS) DNA Sequencing

High Throughput Sequencing (HTS) whole genome sequencing (WGS) generates random coverage of the nuclear genome. WGS methods generate sequences to cover the target's genome with X-level of coverage. The depth of coverage and sequence quality determine the detectability of variants and the accuracy of the sequence data. Some WGS datasets with shorter sequence lengths may not be long enough to characterize some of the longer STR alleles.

Exome Sequencing

HTS exome sequencing targets the exons of genes and nearby flanking sequences. Gene, promoter, splicing, and coding sequence variants may impact gene expression, splicing, or function. Characterizing functional variants for individuals is restricted in some jurisdictions for forensics applications. Advanced DNA forensics system can have capabilities for characterizing functional variants that can be disabled/hidden depending upon legal jurisdictions.

DNA MicroArray Sequencing

DNA microarrays can characterize four million or more SNPs and identify CNVs in samples. Phasing of linked SNPs is possible to create individual chromosome haplotypes and microhaplotypes. Haplotypes and microhaplotypes have applications in kinship and biogeographic ancestry prediction. This is an alternate technology to HTS variant characterization method.

HTS Single Nucleotide Polymorphism (SNP) DNA Forensics

HTS can detect SNP variants and linked variants (microhaplotypes). SNP or combined SNP and STR panels have been designed for thousands to tens of thousands of loci[2].

Short Tandem Repeats (STRs) Forensics

Capillary electrophoresis sizing of STRs is the current standard for DNA forensics. Sizing STRs works well for samples from individuals and some mixtures with two contributors. A few mixtures with three or four contributors have been able to be analyzed, but it advised against analysis for DNA forensics. FITS sequencing of STRs determines STR allele sequences and linked variants. Encountered issues are variants in flanking sequences, novel STR alleles, sequencing artifacts, sequencing errors, and PCR artifacts[3]. Known and novel STR alleles should need to be named consistently. Known STR alleles for some loci can be obtained from the NIST STRbase[4]. Illumina currently markets the ForenSeq panel[5,6] of combined STRs and SNPs.

Insertion/Deletion DNA Forensics

Like SNPs, insertions or deletions of DNA can be used as variants for differentiating individuals.

Mitochondrial DNA (mtDNA) Forensics

Whole or targeted mitochondrial genomes can be sequenced[7]. Mitochondrial DNA is valuable for the analysis of degraded DNA samples for suspect or remains identification, kinship analysis, and biogeographic ancestry prediction.

Microhaplotypes

Closely linked variants define microhaplotypes[8] that can be used as genetic markers.

Data Processing

In certain specific embodiments, the advanced DNA forensics system processes the variants characterized by multiple technologies: CE sized STRs, microarrays, FITS data, etc. Some of the data formats to be supported include: BAM (binary sequence alignment/map) or FASTQ, Variant Call Format (VCF), Illumina GenomeStudio software data export, Illumina ForenSeq Excel files, etc.

HTS Analysis Pipeline

The HTS data analysis pipeline takes as input both BAM and FASTQ files for variant characterization for targeted SNP and STR loci. Sequence data will come from Ion Torrent/Thermal Fisher, Illumina, Roche, PacBio, Oxford, etc., sequencers. The analysis pipeline identifies SNP and STR alleles, sequence counts, counts by strand, and linked SNP variants (microhaplotypes) in flanking sequences.

Experiments & Samples

High throughput sequencers can generate from 4 million to over 8 billion sequences per run. The number of samples sequenced at a time varies from a single sequence to multiple parallel lanes of multiplexed samples. Individual samples within a multiplexed experiment are marked by short DNA barcodes added to the 5' and sometimes 3' ends of DNA for samples. Samples may be reference samples from known individuals or unknown samples collected from objects, clothing, food, etc. Sample annotation on samples can be collected and managed within the advanced forensics DNA software platform or may be managed in external systems with sample names or reference links connecting the characterized samples with forensics DNA samples. Annotation on individuals may be extensive, including name, age, appearance, photographs, fingerprints, known relatives, etc. Sample annotation can also contain information on site of collection, location coordinates, date of collection, photographs, etc.

Applications

When samples are characterized by different techniques, sample profiles from one data source can be compared with data from other sources when sufficient numbers of shared loci exist.

Identification

Search a sample against the set of known individual reference profiles to identify matches to known samples/individuals. Searching of SNP or STR sample profiles will be implemented. Searching of sample profiles across different panels is possible when a sufficient number of loci are common in both panels.

Implementation: The MIT application "Extremely Fast Forensics HTS DNA SNP and STR Sequence Analysis" (MIT case #18133L, Appendices A and B) shows an example of the identification search methodology.

Mixture Analysis/Mixture Search

Search a reference sample against a set or database of profiled mixture samples to determine if an individual contributed DNA to the mixture sample (reference-to-mixture)9. Search a mixture against a set or database of profiled reference samples to determine the contributors to the mixture (mixture-to-references). Search a mixture against a set or database of profiled mixture samples to determine the mixture samples with common individual contributors (mixture-to-mixtures). MIT case #18133L method implements each of these mixture analysis methods: reference-to-mixtures, mixture-to-references, and mixture-to-mixtures. FIG. 3 illustrates mixture analysis with STR sequences for 3 (Mix03p), 4 (Mix04p), 5 (Mix05p), and 12 (Mix12p) contributor mixtures with counts of called reference STR alleles not matched in each mixture. FIG. 15 shows one example of an STR mixture analysis.

Analysis of Saturated Mixtures

Identification of one or more individuals in saturated mixtures (mixtures with large numbers of DNA contributors such that more than 70% of the SNPs have observed minor alleles) by leveraging differences in DNA contributor concentration differences to identify profiles of major DNA contributors to the saturated mixture (MIT 19785L, Appendix D).

Identification of Individuals with only Trace DNA Profiles present in DNA mixtures An individual may contribute one, two, or more, or a fraction of a cell's DNA to a forensic sample. These are referred to as trace profiles. The advanced forensics system contains methods for identification of trace profiles within DNA mixtures and identifying them as unknown or matching them to known reference samples (MIT 19786L, Appendix L).

Mixture Deconvolution Methods

Advanced DNA forensics of mixtures includes multiple methods to identify individuals in mixtures without known reference samples.

The Plateau mixture deconvolution method (e.g., discussed herein) leverages imbalances in DNA concentrations between contributors to determine individual profiles. This method applies to mixture profiles of SNPs or STRs. FIG. 16 illustrates the Plateau method applied to a mixture of two individuals with DNA concentrations of 100 to 1.

The Venn mixture deconvolution method (e.g., Appendix N) applies Venn set logic to DNA mixtures to identify individuals or overlapping individuals between one, two, or more mixtures. FIG. 17 illustrates a Venn method applied to four mixtures with the identification of four of the six DNA contributors.

The Venn Matrix mixture deconvolution method (MIT 19092L Appendix E) first leverages identification of individuals within a set of mixtures, subtracting their profiles, and then applying the Venn mixture deconvolution method to identify novel mixture contributors with no known reference samples.

Detection of Unknowns

The Venn, Plateau, and Venn Matrix methods can identify unknown profiles in DNA mixtures (MIT 19127L, Appendix G).

Mixture-to-Mixture Analysis—Multiple samples & sites Analysis (e.g., MIT 19093L, Appendix F)

Frequently, people of forensic interest appear in multiple samples and/or locations. The mixture-to-mixtures analysis approach enables the visualization of overlap between individuals and multiple mixtures (as shown in FIG. 18).

Estimating Number of Individuals in mixtures

Figure 19:
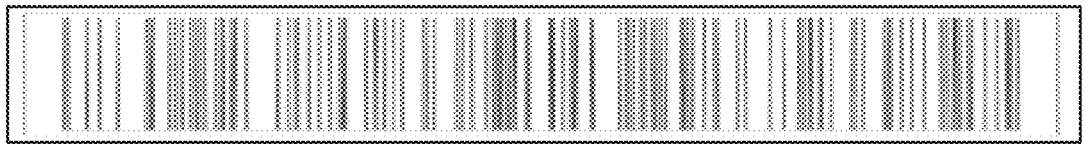
FIG. 19 is a schematic depiction of a DNA profile or barcode based upon a 1,000 SNP panel for a given individual (referred to as subject 1) in which the location of a black line indicates the presence of a minor allele SNP at that locus.
Figure 20:
FIG. 20 is a schematic depiction of a DNA profile or barcode based upon a 1,000 SNP panel for a mixture of 5 peoples' DNA, including subject 1.

Forensic analysts need to identify the number of contributors to DNA mixtures for proper estimation of statistical significance of profile matches for some analytical methods. Due to variability between individuals and chance, this is a difficult problem. The amount of trace DNA left by individuals on touch samples include high DNA shedders, variable DNA shedders, and low DNA shedders. Low DNA shedders can be difficult to detected or undetectable in some touch samples. Machine learning algorithms can estimate the number of contributors in mixtures based on either SNP profiles (FIG. 19) or STR profiles (FIG. 20).

Estimating the relative contributions of individuals of DNA to mixtures

Figure 21:
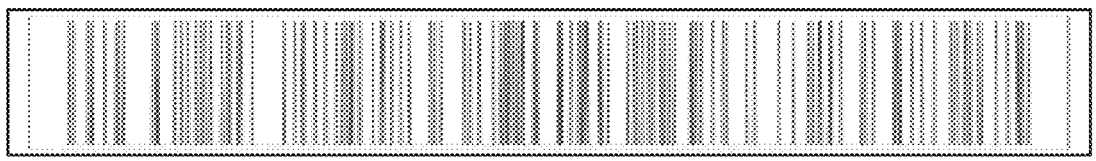
FIG. 21 is a schematic depiction of a DNA profile or barcode reproduced using the methods of the disclosure to compare five 5-person DNA mixtures with one common contributor across them. Subject 1's 127 SNP profile can be reliably reproduced to within 11 SNPs (compared to the DNA profile for subject 1 shown in FIG. 12).

The relative concentrations of contributors to a forensics sample can be estimated using the relative strengths of the amplified alleles (FIG. 21). Three additional methods for estimating DNA contributor DNA concentrations are described in Appendix H (MIT 19399L).

Gender Prediction

The gender of an individual can be predicted for single contributor samples by examining SNP or STR loci on the X and Y chromosomes outside of the pseudoautosomal regions (PAR) shared by the sex chromosomes. Females will have 1 or 2 alleles (major:major, major:minor, and minor:minor); and males for these loci should only have 1 allele. For non-PAR Y chromosome loci, females should not have any read counts and males should have 1 allele. Duplication events on the Y chromosome are common and some Y loci may have 2 alleles for males. Unusual combinations of sex chromosomes should also be considered for women who might have 1 or 3 X chromosomes (Turner syndrome:X—1:2,000 to 1:5,000 or Triple X syndrome:XXX—1:1,000) or men with 2 X or 2 Y chromosomes (Klinefelter syndrome: XXY 1:500 to 1:1,000 and XYY—1:1,000).

Kinship

Shared DNA by inheritance can be used to predict kinship between related individuals. Autosomal, mitochondrial, X and Y chromosome inheritance, and microhaplotype sharing of alleles can inform kinship predictions. Mothers pass their mtDNA genome to all of their children. Fathers pass their Y chromosome and in some cultures their last name to their sons. A child inherits half of their genetics from each of their parents. The KinLinks application illustrates application of kinship prediction using HTS SNP panels10. Two methods for rapid (MIT 19709L, Appendix K) and precise Bayesian (Appendix 0) predictions of kinship are also disclosed.

Surname Prediction

In some instances, it is possible to predict likely last names of individuals directly from Y chromosome loci profiles 11.

Biogeographic Ancestry (BGA)

Figure 22:
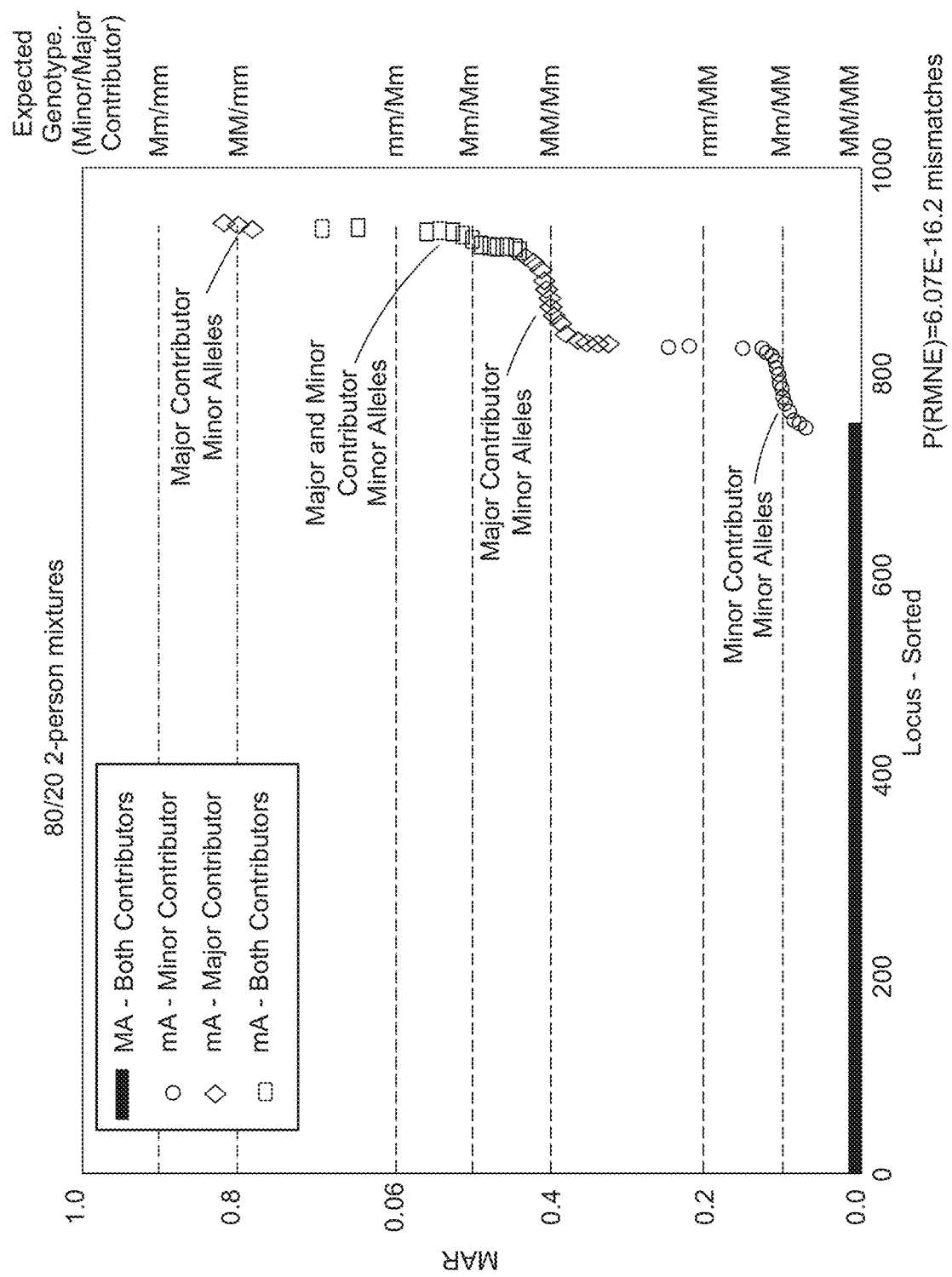
FIG. 22 is a graph depicting, an analysis of mAR of a two-person mixture, sequenced using a panel of 975 SNP loci. The minor and major contributor's allele signatures are immediately apparent. Expected genotypes mARs are labeled as mm (homozygous minor), mM (heterozygous) and MM (homozygous major) on the right. P(RMNE) has been calculated using the major allele profiles as 6.07E-16.

Being able to predict the biogeographic ancestry (BGA) of an individual from a DNA sample (FIG. 22) has multiple forensics applications from remains identification to narrowing suspect profiles with exclusion of non-matching ethnicities.

Externally Visible Traits (EVTs)/Phenotype

Appearance and phenotype are determined by genetic variants. Variants have been characterized for predicting eye color, hair color, hair texture, nose structure, and additional facial features. Attempts are underway to predict facial appearance from DNA. Daniel describes the SNaPshot system for forensic phenotyping including BGA prediction.

Medical Genetics

Medical conditions also have forensics applications, but may not be permissible to ascertain in some legal jurisdictions. Some sequence variants contribute directly to medical conditions. For example, knowing that a suspect is lactose intolerant may enable to reduction of candidate suspects to a smaller set.

Geolocation

DNA from microorganisms (bacteria, archaea, fungi), plants, insects, and animals may be present in samples. The geographic distribution of these organisms may enable the geolocation prediction of sample origin or sample history.

Statistics

Linkage disequilibrium between two DNA loci indicates linkage of alleles by population structure or physical linkage nearby on the same chromosome.

Random match probability (RMP) is the probability that two unrelated individuals have identical genotypes by chance alone.

Random-Man-Not-Excluded P(RMNE) or Combined Probability of Inclusion (CPI) attempts to explain the occurrence of the observed alleles on a statistical basis, treating each allele independently using population allele frequencies.

Likelihood Ratios (LR)13—ratio of probabilities that the DNA in the profile is from the suspect over the probability of the profile is from a random individual.

Minor Allele Count method

The counts of minor allele reads (MAC) can be used as an equivalent or an alternative to the minor allele ratio (mAR) approach described in this document (MIT 19787L, Appendix M).

System Details

The advanced DNA forensics system may include the following system features:
 User authentication & authorization
 Usage logging
 Parameter setting tracking of settings used
 User controls
 Parameter settings
 Algorithm role access
 BGA, EVTs, Medical genetics
 Disable features in some locations
 User role-based access control
 System Operating modes
 Research—all settings available
 Forensics—certain settings locked down so that user must use validated settings for sample analysis
 Networking between sites
 Data can be exchanged between network sites using web services
 System maintenance
 User administration interfaces for maintaining system, updates
 System troubleshooting, logs
 Data backup, export, and import
 Data encryption
 Data export
 CODIS compatible output format Database Design The standard of universally unique identifier (UUID)14 will be adopted to enable distributed instances to uniquely identify information without any central coordination. If the UUID is used as a primary database table key, there is an additional performance consideration when inserting new database table records with the UUIDs likely in random order versus the standard incrementing order that comes with an auto-incrementing integer primary key. To avoid this, each database table will be designed with both an auto-incrementing integer primary key followed immediately by a UUID primary key with associated index table. All foreign keys (references by other database tables) will be to the UUID primary key and not to the integer primary key. This design strategy enables easy data exchange between sites without impacting database performance. The result is that all data at each site will be uniquely identified and portable to any other site.

Figure 23:
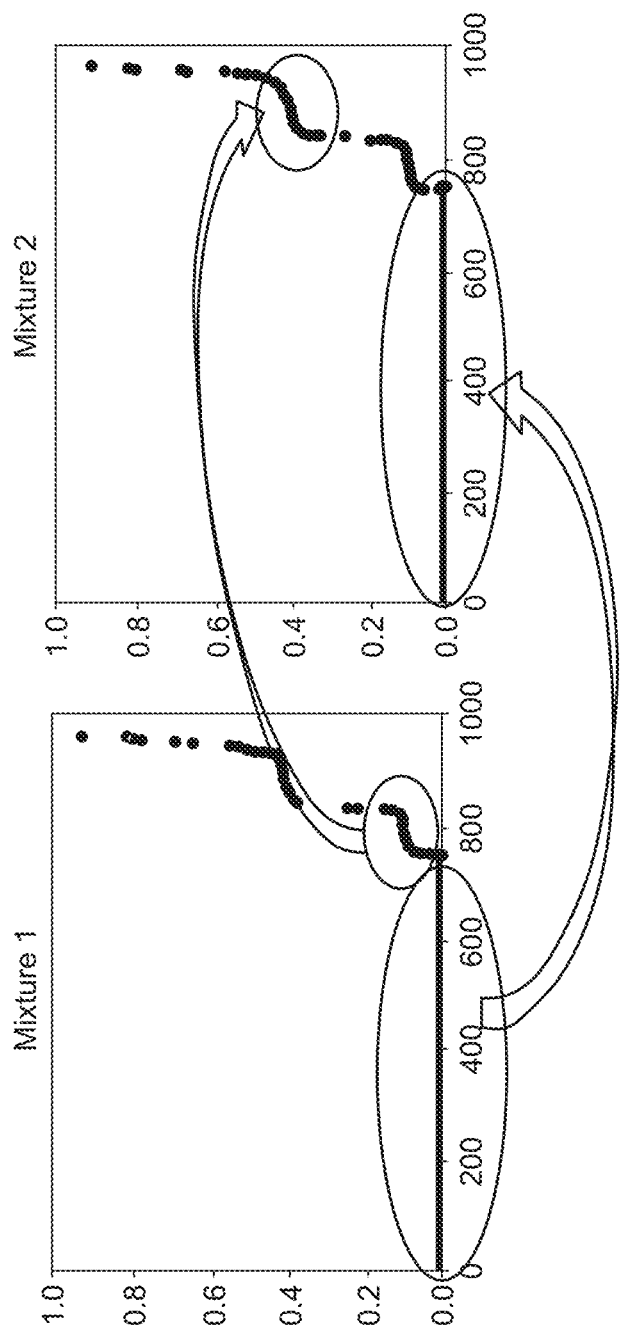
FIG. 23 is a pair of graphs depicting a theoretical match of a suspect's SNP profile in two mixtures. Major allele (orange, bottom arrow) and Minor allele (blue, top arrow) SNP profiles are extracted and compared across mixtures. Partially matching sub-profiles are circled. A collection of matching sub-profiles can be added in union to provide a larger DNA profile.
Figure 24:
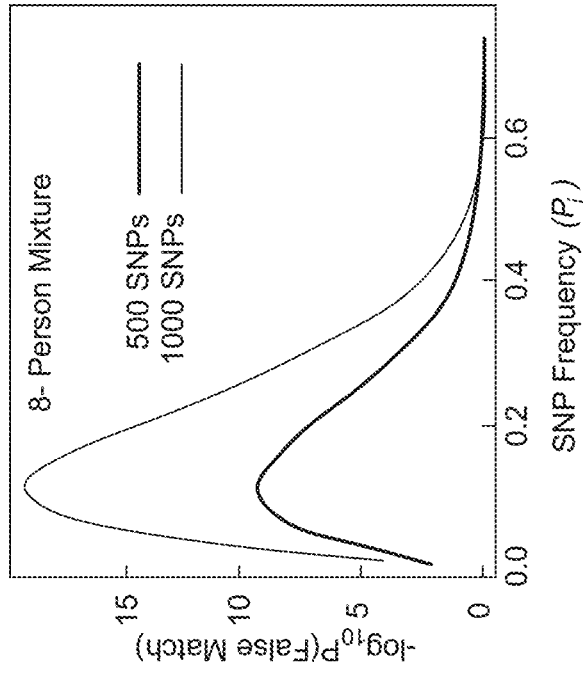
FIG. 24 is a schematic depiction of the probability of a Random Man Not Excluded P(RMNE) as exemplified in a graph plotting the probability of a false match against SNP frequency of a mixture containing DNA from 8 individuals and a SNP panel having either 500 or 1000 SNPs.
Figure 25:
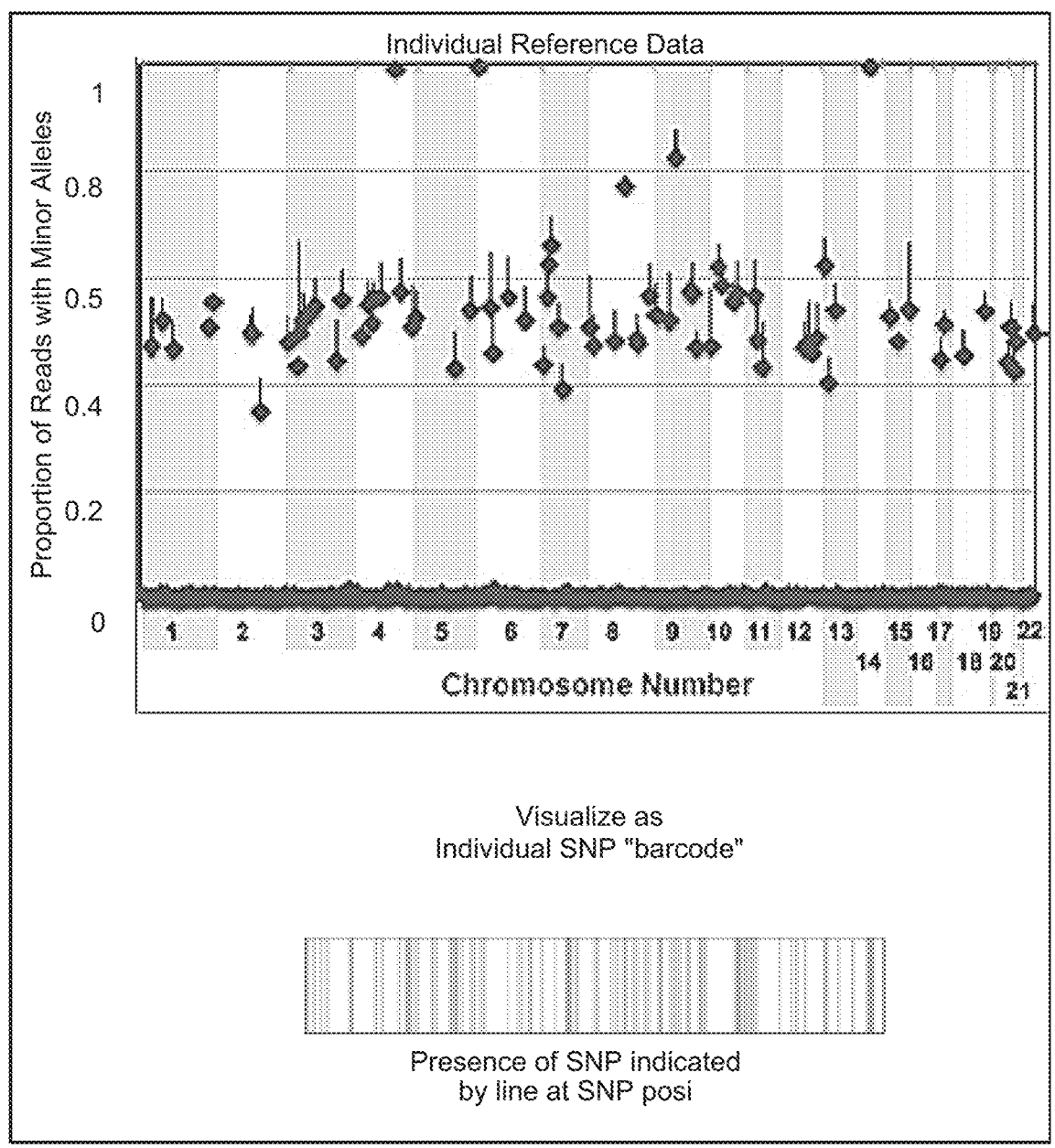
FIG. 25 is a graph depicting individual reference data from a SNP panel and a depiction of the same data as an individual SNP "barcode".
Figure 26:
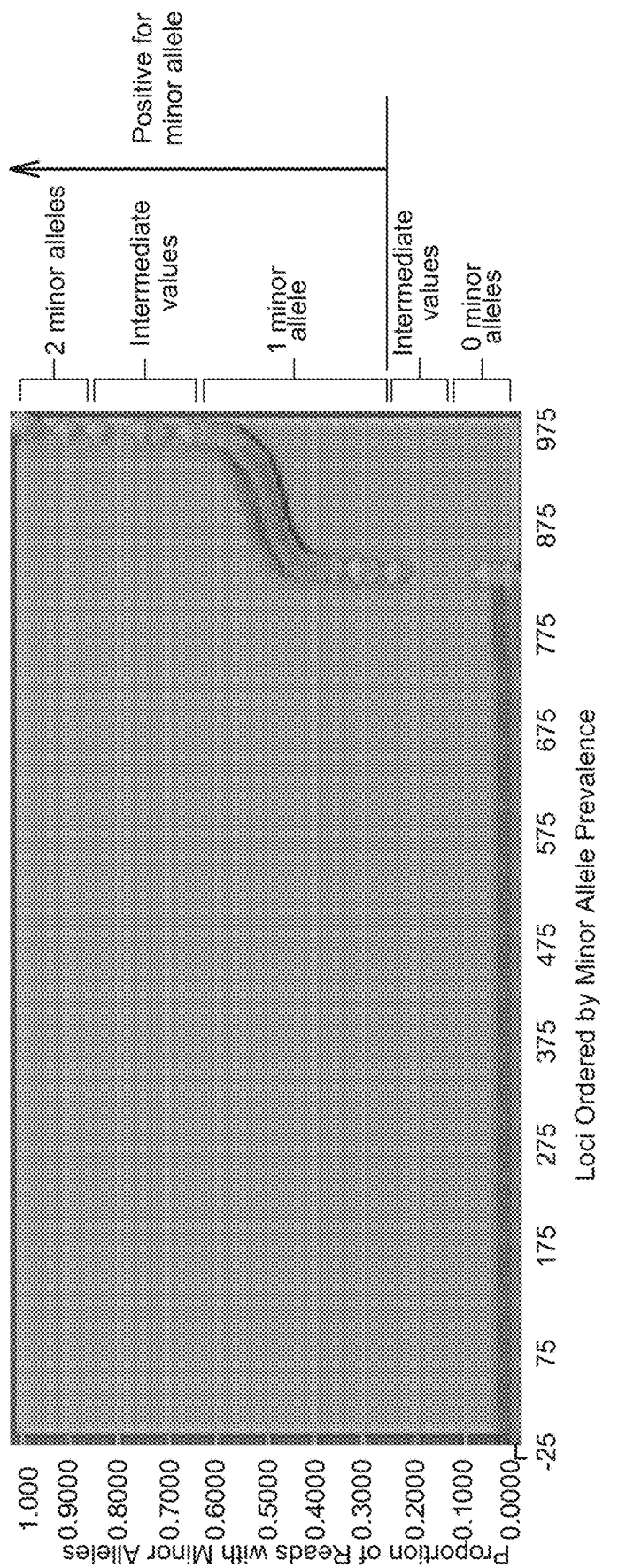
FIG. 26 is a graph depicting the determination of the threshold for calling a minor allele using the ratio of the minor allele calls to the total number of reads at a locus. In this example, a subject is determined to have a minor allele at a locus if the ratio of the minor allele calls to total calls exceeds 0.25. There are ratios with intermediate values that can make it difficult to clearly distinguish homozygous major from heterozygous genotypes, and heterozygous from homozygous minor genotypes. These intermediate values may result from amplification error, sequence error, or copy number variants, and may be corrected by optimization of the analysis algorithm or use of alternate loci.
Figure 28:
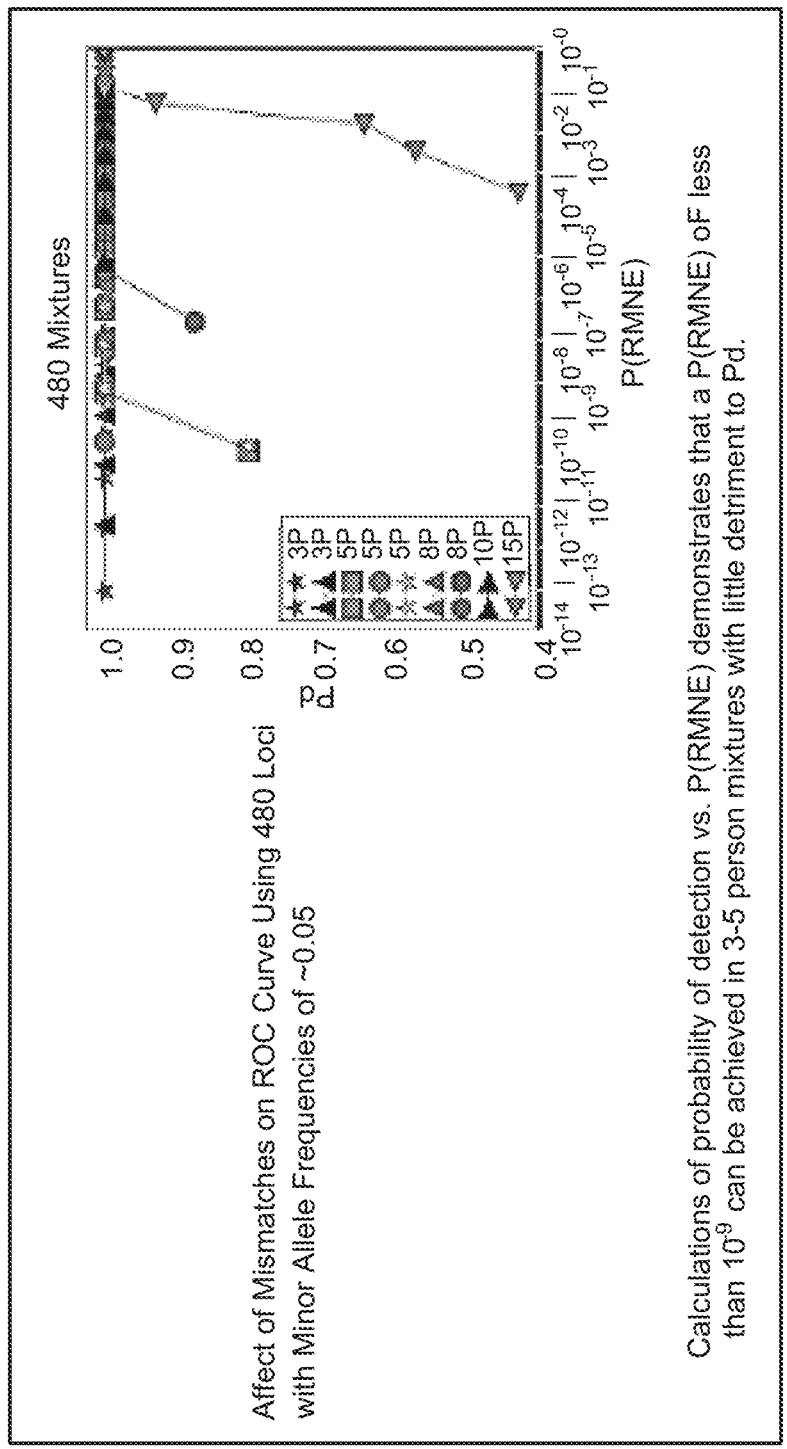
FIG. 28 is a graph depicting the effect of mismatches on receiver operating characteristic (ROC) Curve using 480 loci with minor allele frequencies of approximately 0.05. Calculations of probability of detection vs. P(RMNE) demonstrate that a P(RMNE) of less than 10-9 can be achieved in a 3-5 person mixture with minimal detriment to the probability of detection (Pd).
Figure 30:
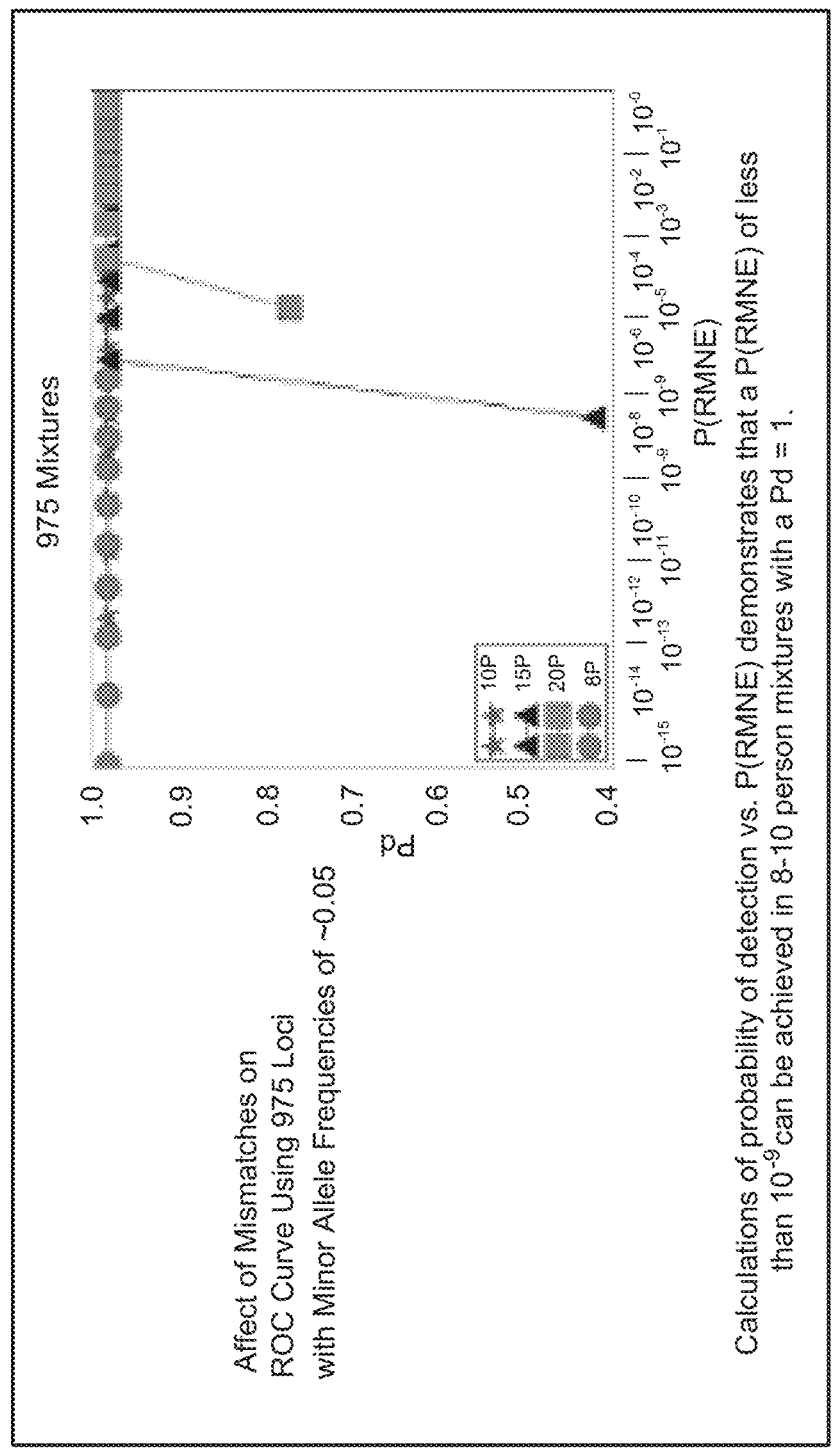
FIG. 30 is a diagram depicting the effect of mismatches on ROC Curve using 975 loci with minor allele frequencies of approximately 0.05. Calculations of probability of detection vs. P(RMNE) demonstrate that a P(RMNE) of less than 10-9 can be achieved in a 8-10 person mixture with a Pd of 1.
Figure 31:
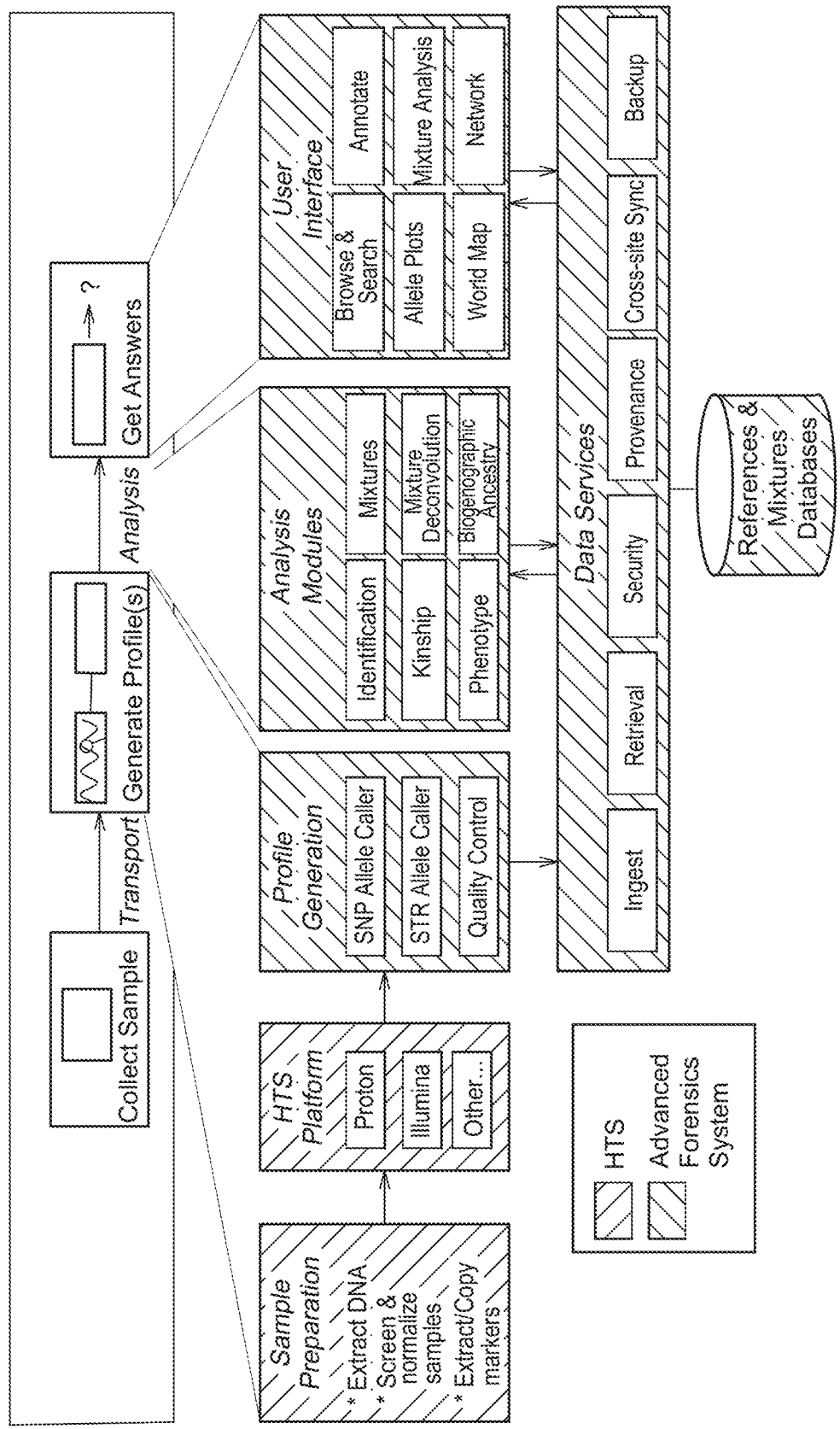
FIG. 31 shows an advanced DNA forensics system modules and example architecture.
Figure 32:
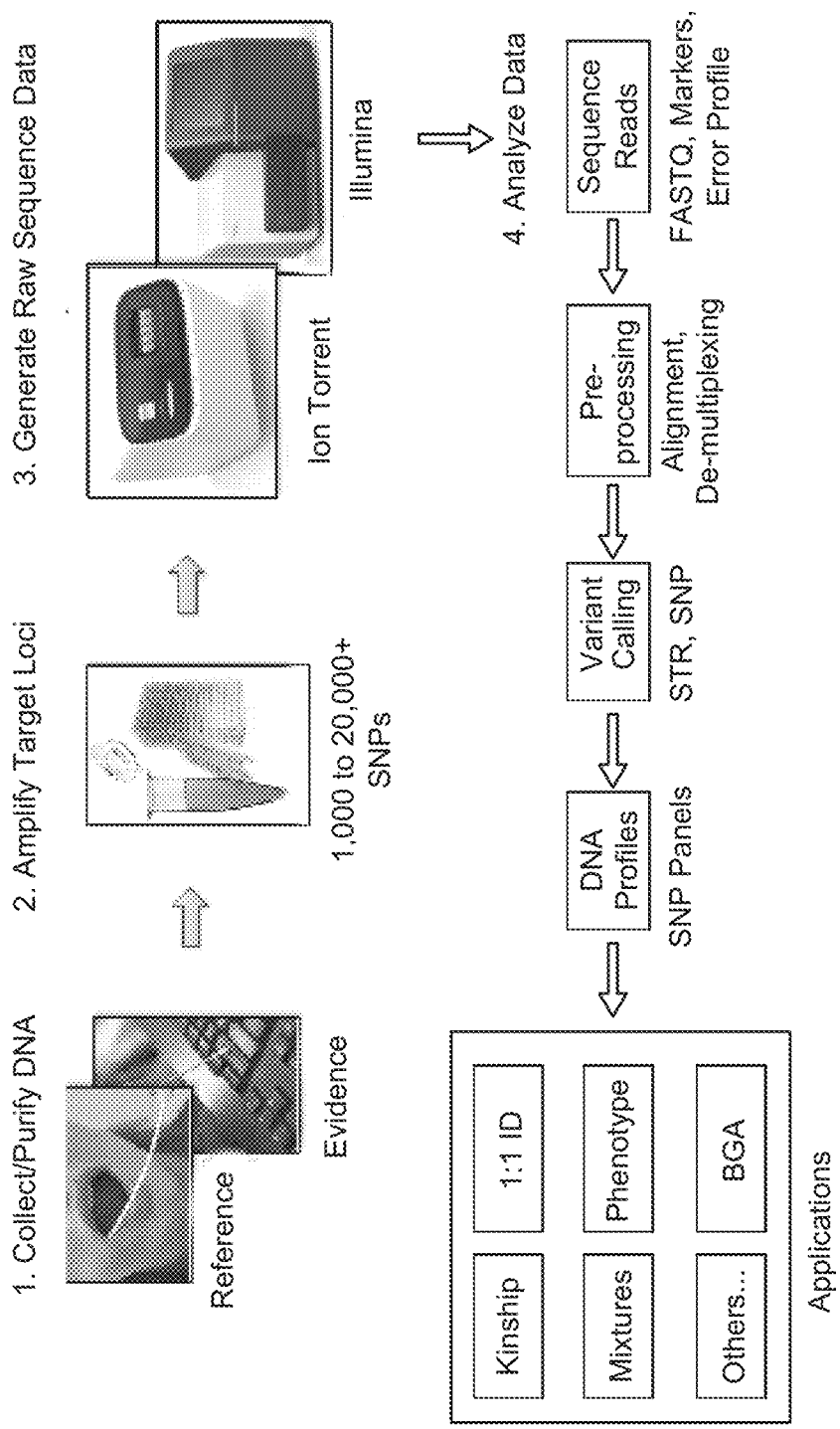
FIG. 32 shows and example sample characterization pipeline according to various embodiments.
Figure 34:
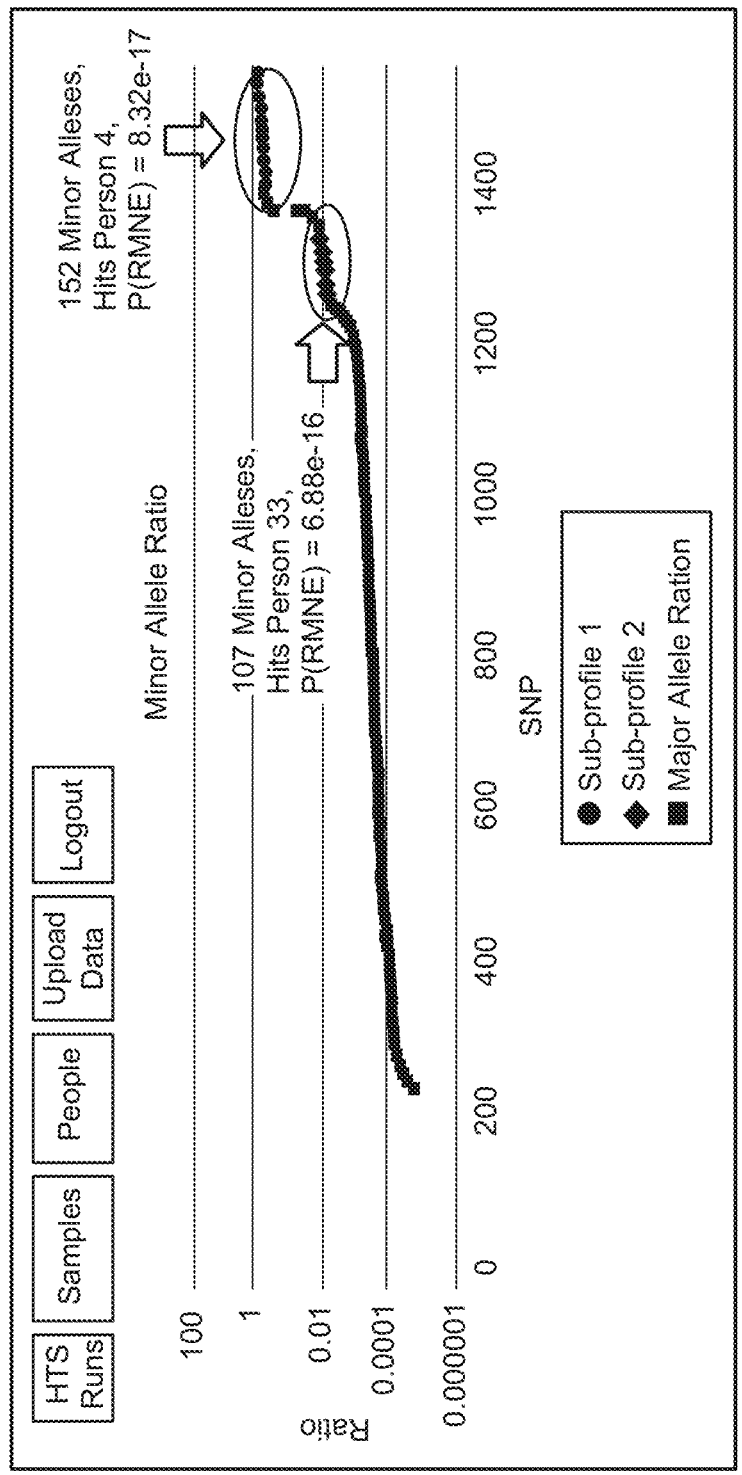
FIG. 34 shows an example Plateau mixture deconvolution method according to various embodiments.
Figure 35:
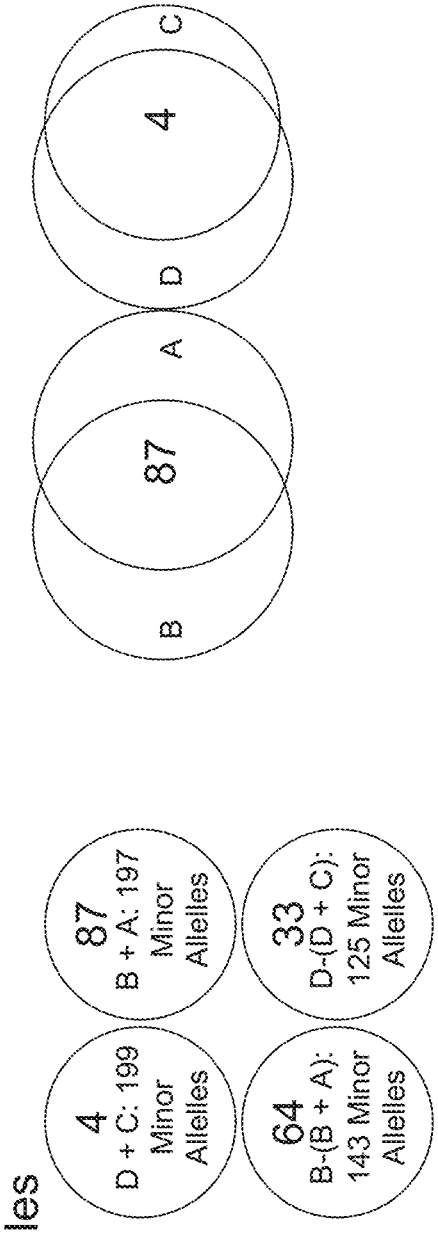
FIG. 35 shows an example Venn mixture deconvolution method according to various embodiments.
Figure 36:
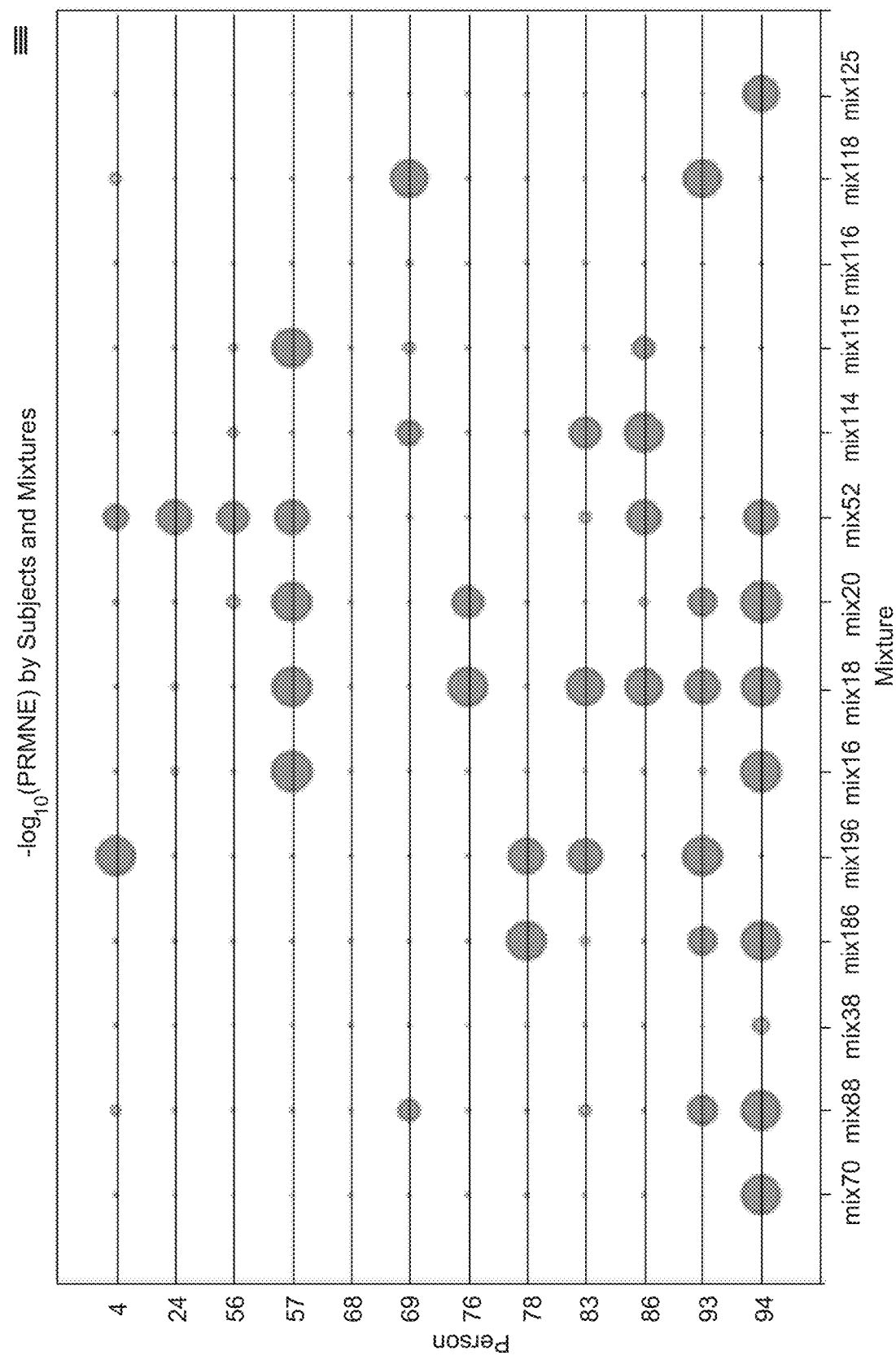
FIG. 36 shows an example mixture-to-mixture analysis method according to various embodiments.
Figure 39:
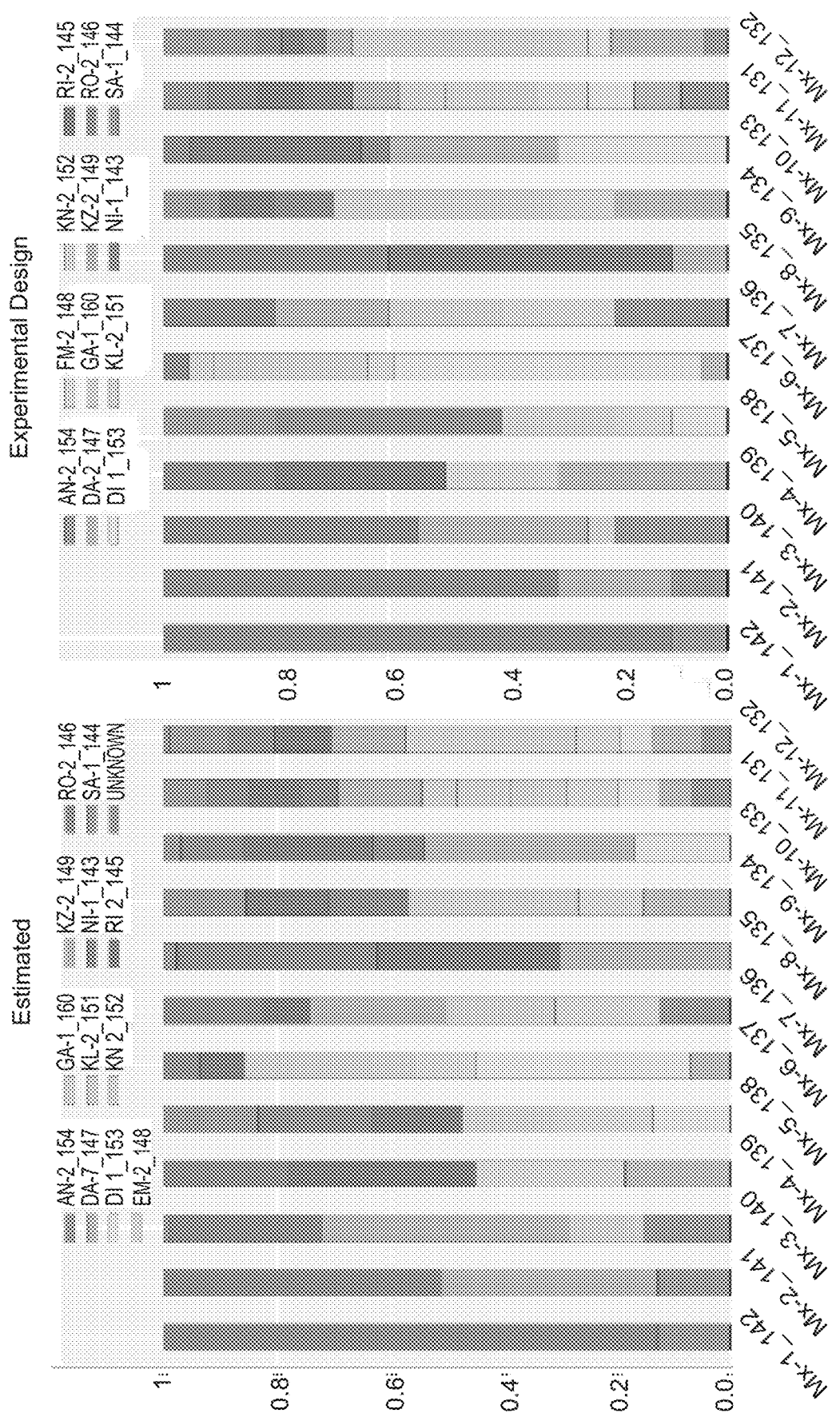
FIG. 39 shows estimating the relative contributions of individuals to DNA STR mixtures.
Figure 40:
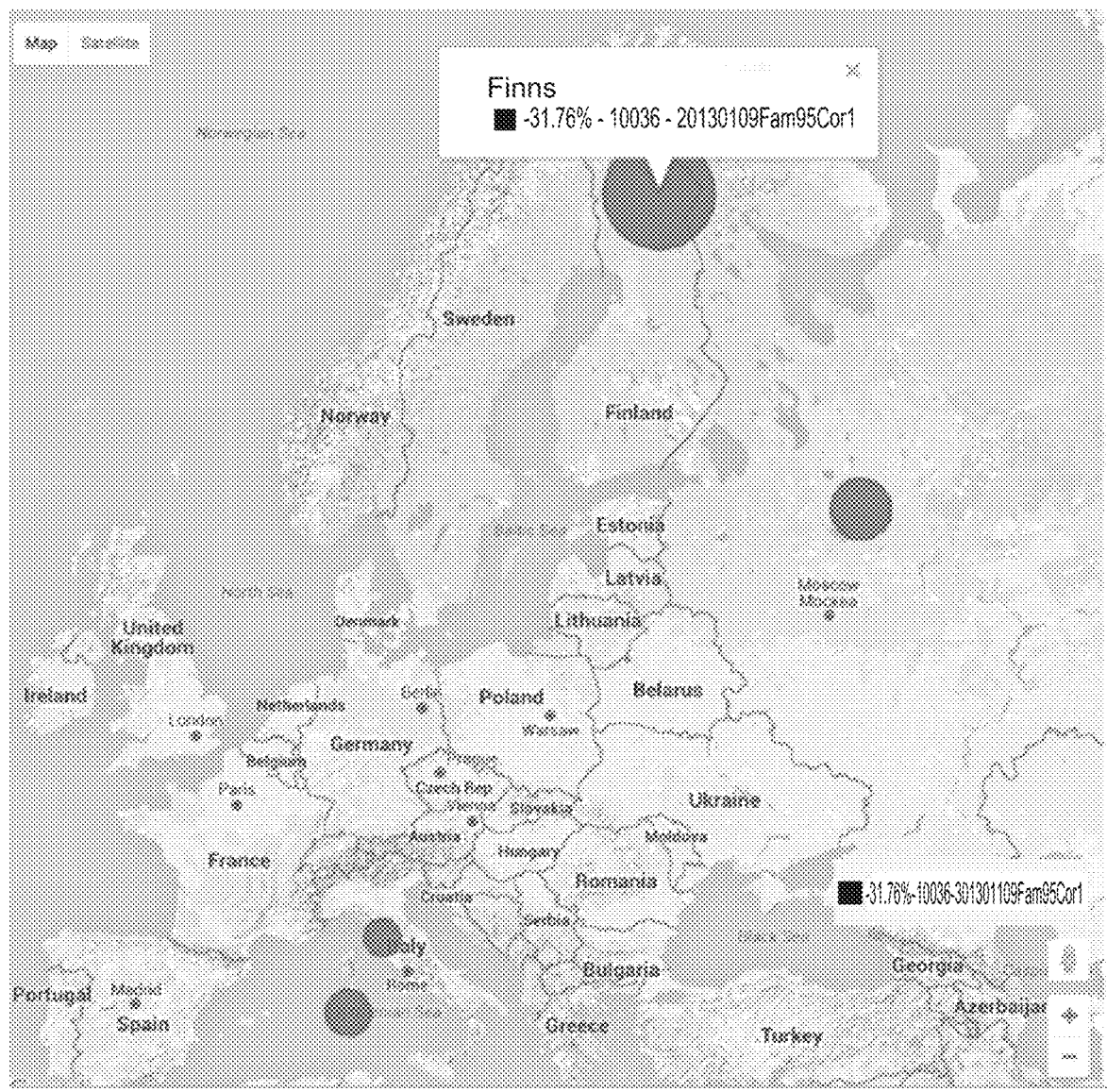
FIG. 40 shows a BGA for an individual using Google maps.
Figure 41A:
FIGS. 41A-41C show database tables that may be used to implement an advanced DNA forensics system.
Figure 41B:
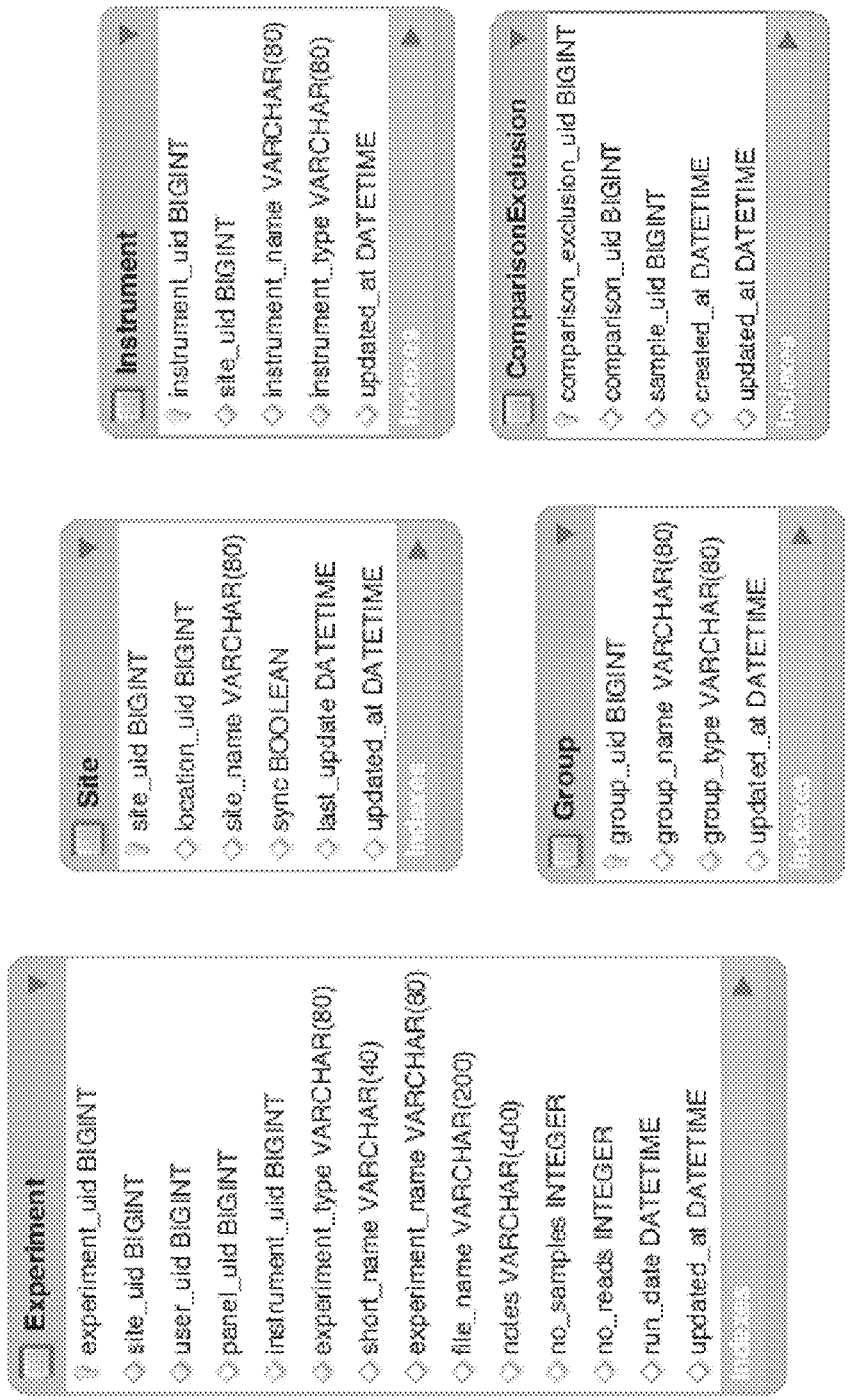
Figure 41C:
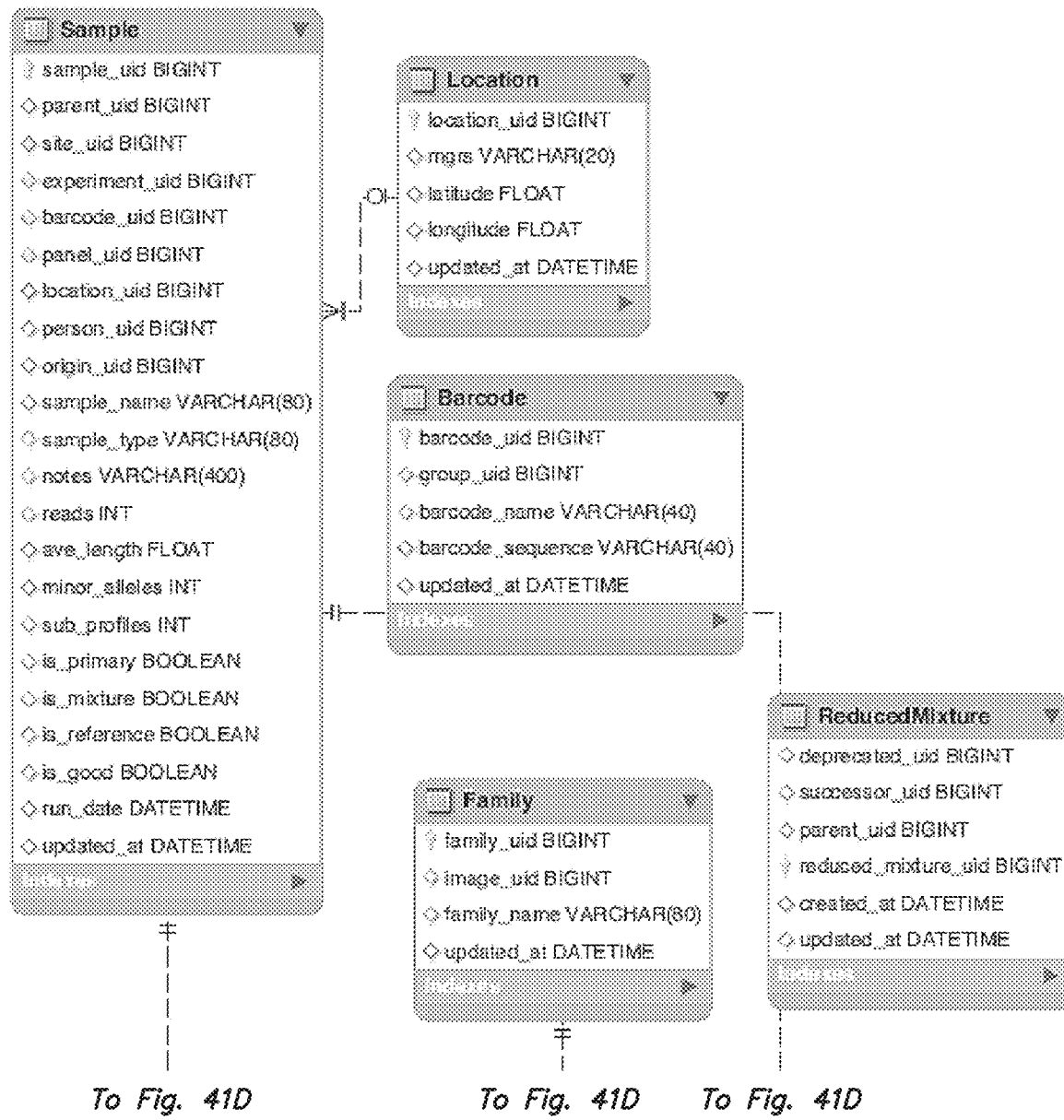
Figure 41D:
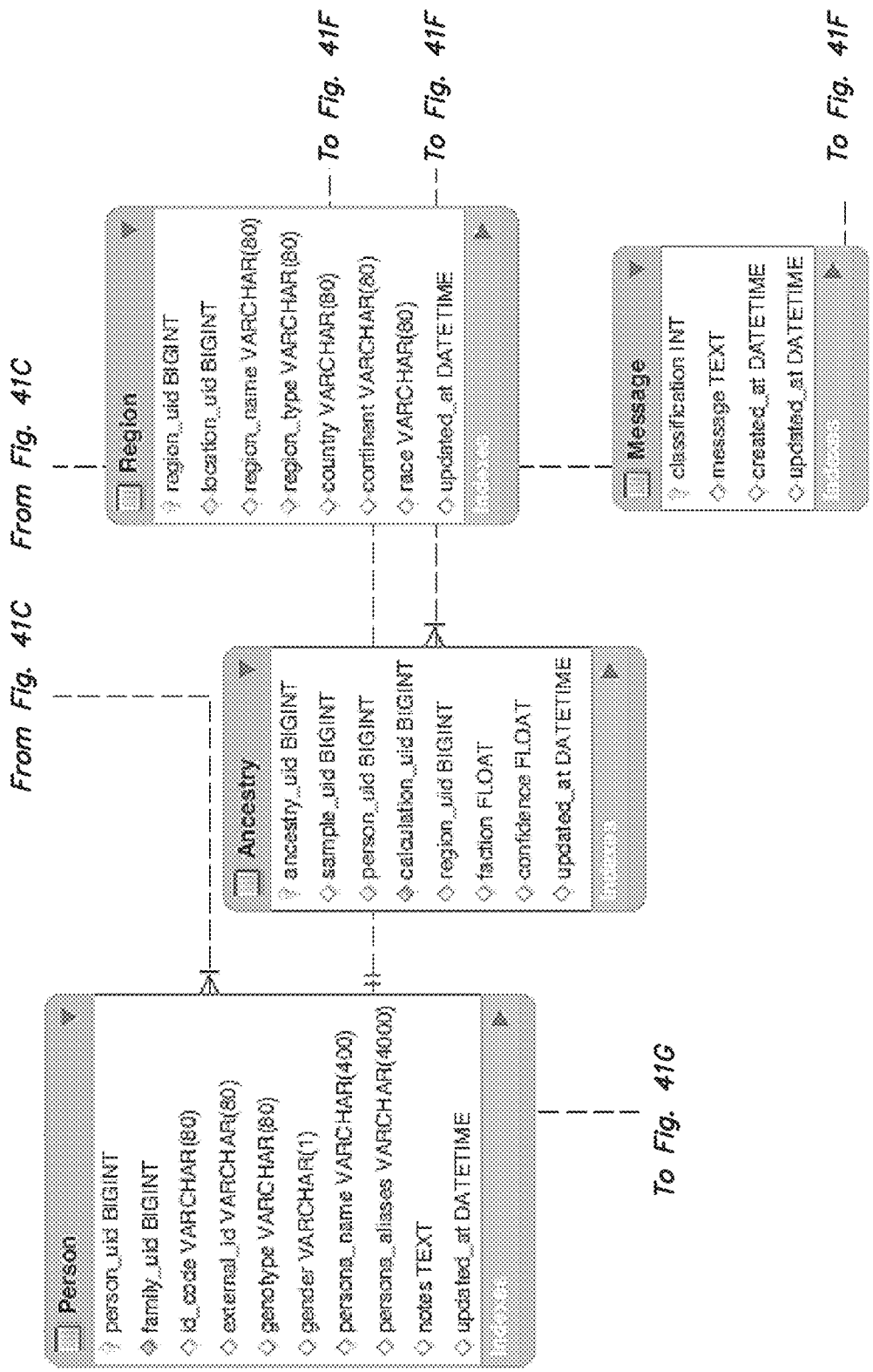
Figure 41E:
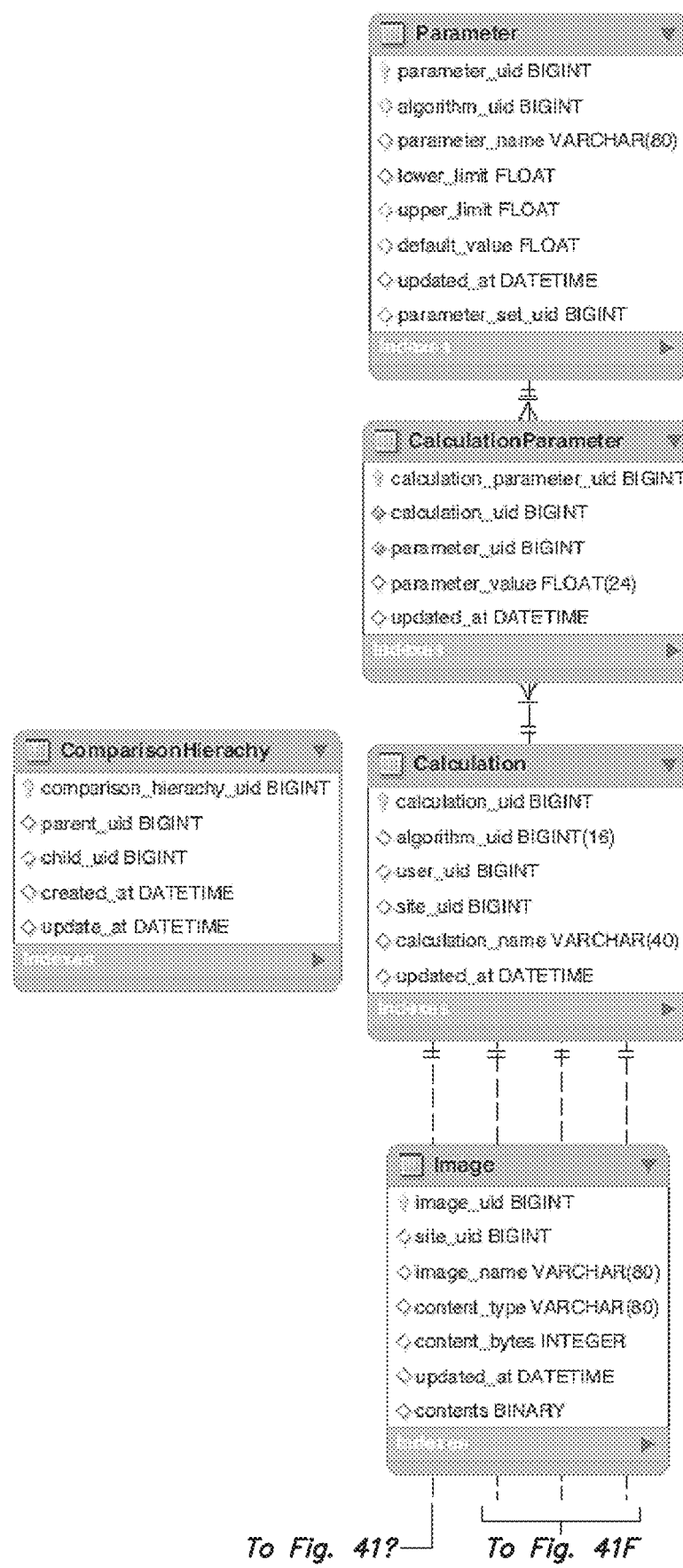
Figure 41F:
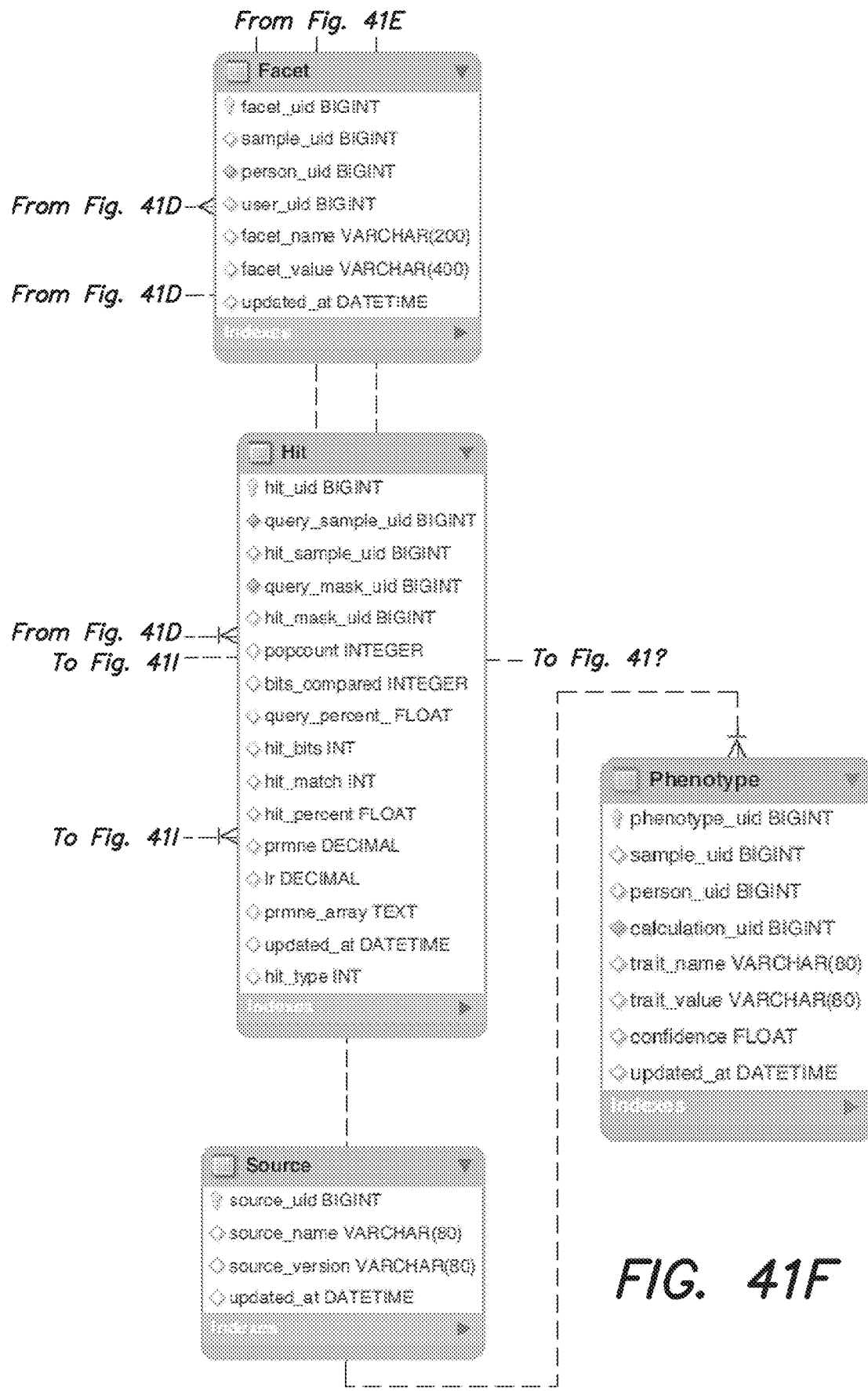
Figure 41G:
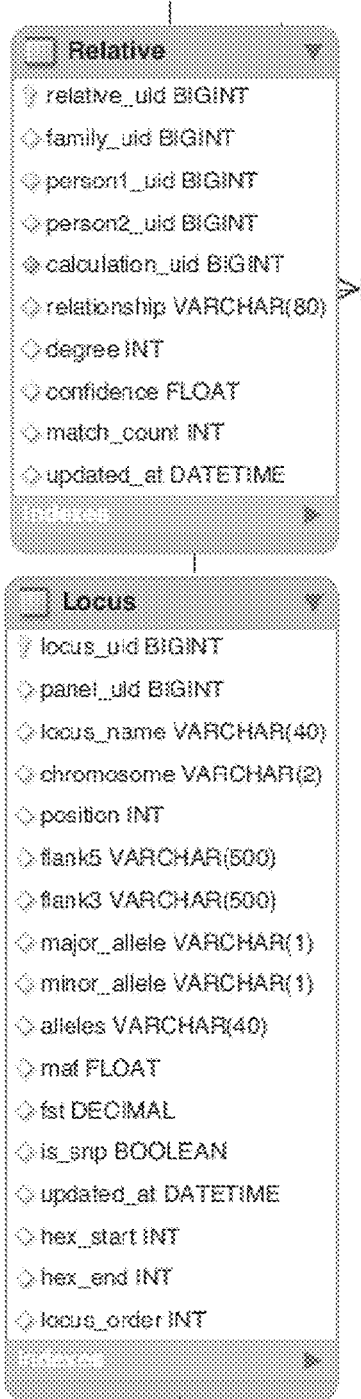
Figure 41G:
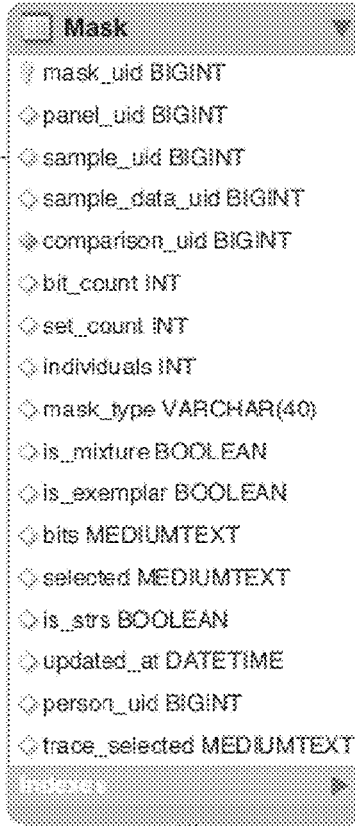
Figure 41G:
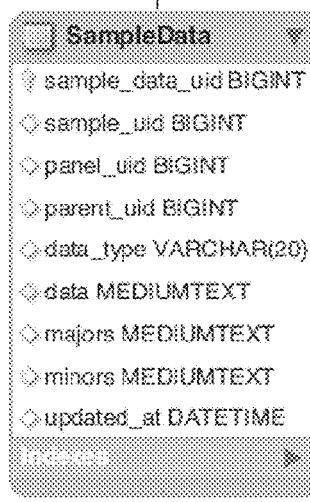
Figure 41H:
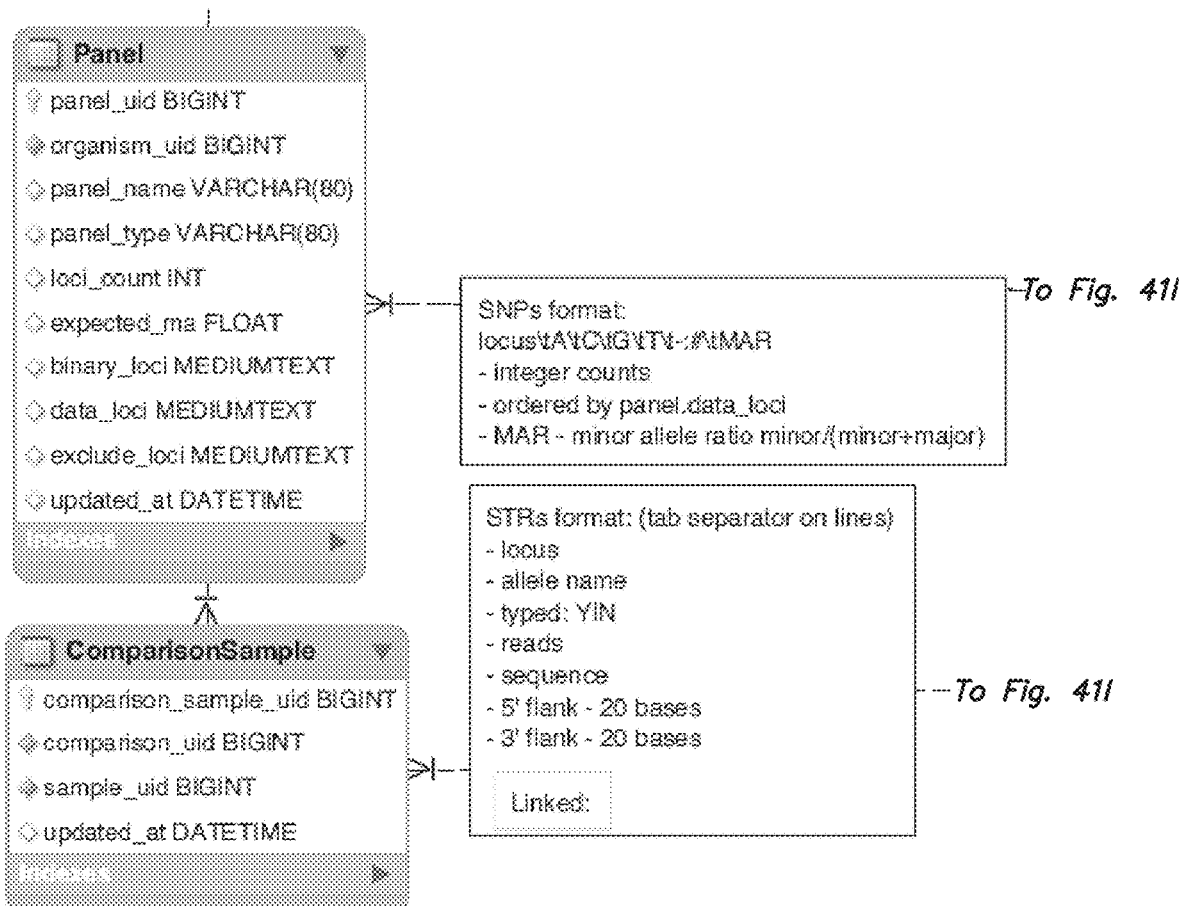
Figure 41I:
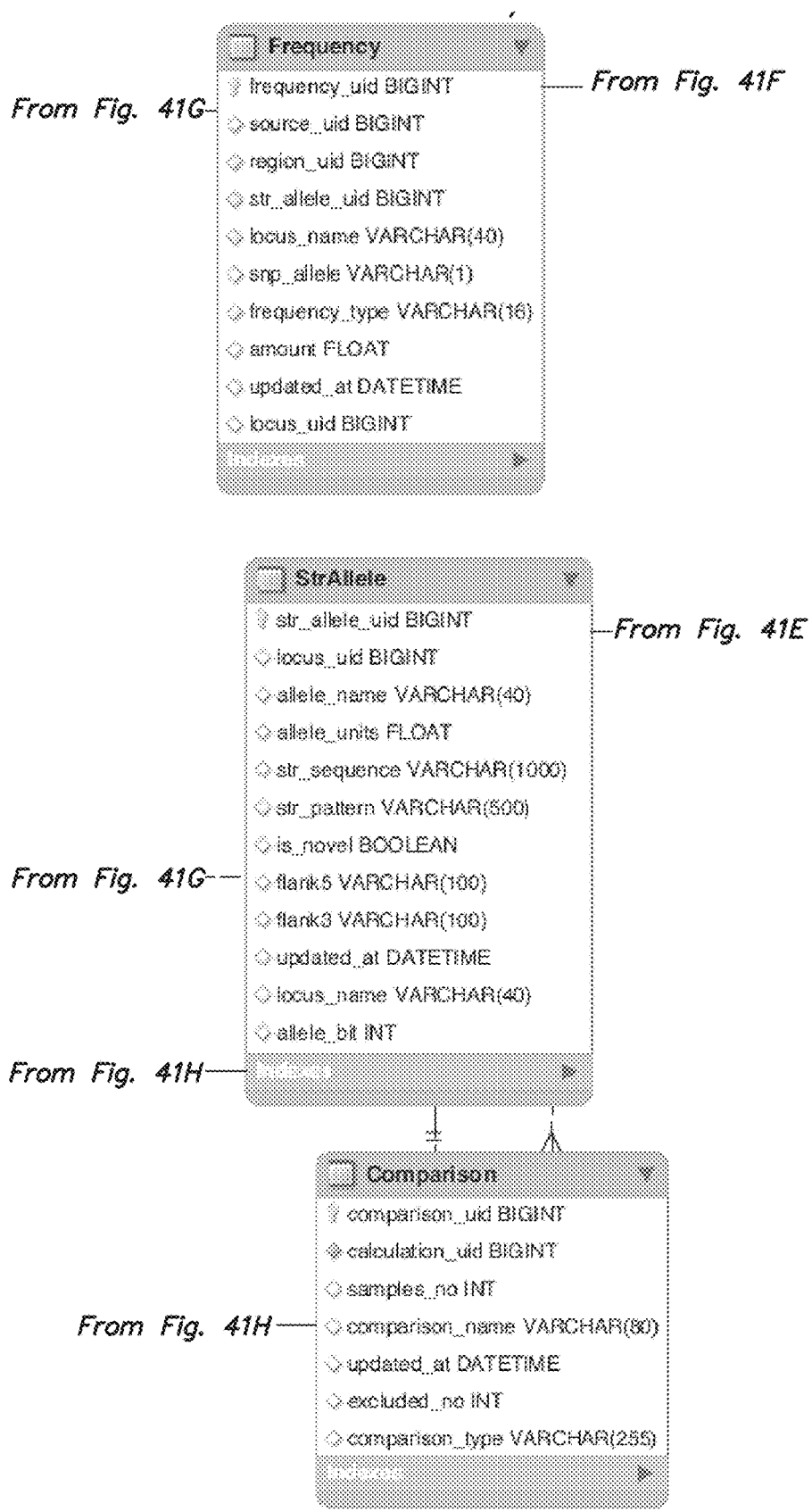
Figure 41J:
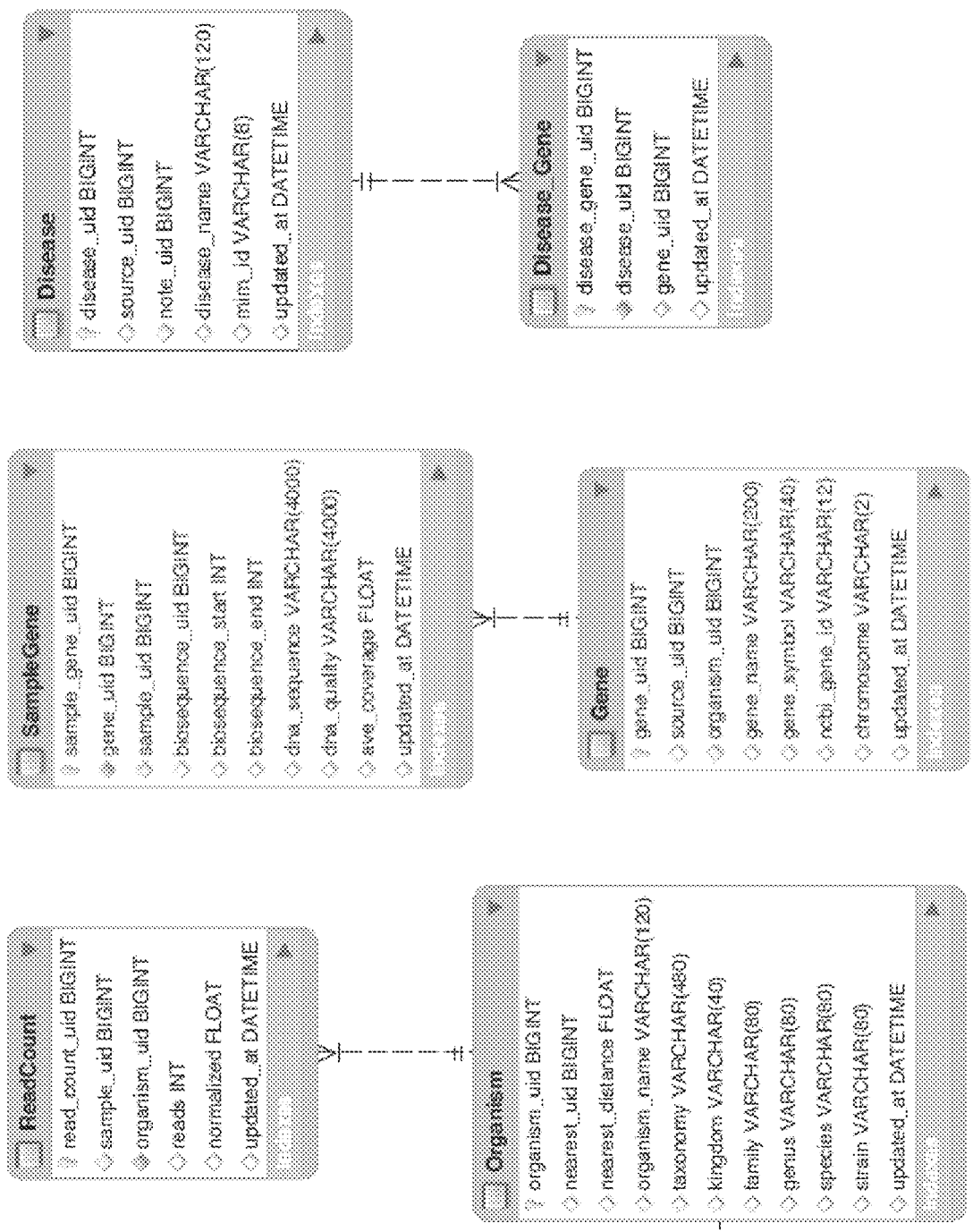
Figure 41K:
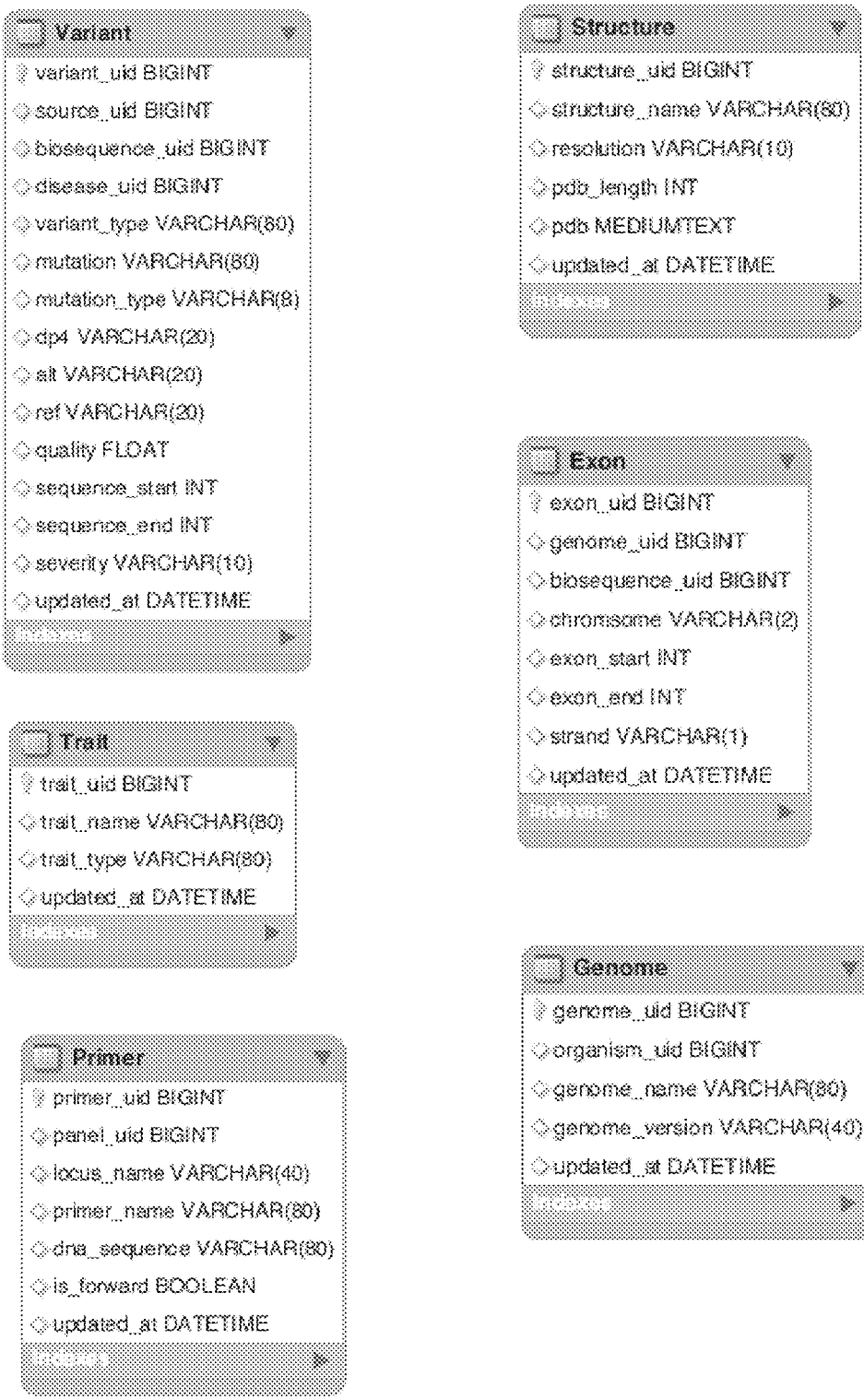
Figure 41L:
Figure 41L:
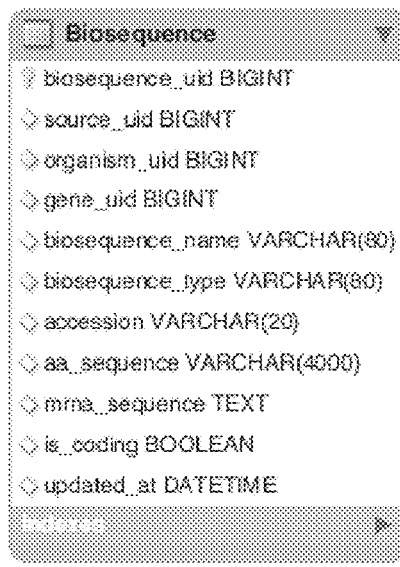
Figure 41L:

The initial data model concepts are illustrated next and in FIG. 23A-C. The "Ref:" subfields are references to other data models.
 Site—geographic BIP-IT designation
 Ref: location
 Site name
 User—BIP-IT user; site-specific
 Ref: site
 User name, account, etc.
 Log—activity log
 Ref: user
 Action & timestamp
 Data files/Results—data files
 Ref: site
 File details
 Instrument
 Instrument name, type
 Experiment—supports multiplexing of samples
 Ref: site
 Name, type, notes, run date
 Barcode—DNA sequence identifier for a multiplexed sample
 Name, sequence
 Sample—individual DNA sample—reference, mixture, etc.
 Ref: site, experiment, barcode
 Name, type, details
 Person—an individual within a DNA sample
 External id(s)—to enable higher level data fusion with other systems
 Genotype—XY, XX, XYY, etc.
 Location—coordinates
 Latitude, longitude, MGRS (military grid reference system)
 Algorithm—software algorithm
 Name, version, updated at
 Parameter—parameters for software algorithms
 Ref: algorithm
 Name, limits, default value
 Folder—file system like folders for tracking samples of interest
 Ref: site, user
 Name
 Relative—relationship between two individuals
 Ref: two People, algorithm
 Relationship, related, degree, confidence
 Ancestry—biogeographic ancestry prediction
 Ref: person, region, algorithm
 Fraction, confidence Region—geographic region or ethnic/racial group
Ref: location
Name, type, country, continent
Phenotype—externally visible trait prediction
Ref: algorithm
Trait name, trait value, prediction, confidence
Locus—genetic location
Name, chromosome, position
Panel—collection of genetic loci
Name, type, SNP count, STR count, loci
STR Allele—identified STR alleles
Ref: locus, STR
Name, sequence, STR pattern (regular expression), is novel
Sample Data
Ref: sample, panel
Sample data—SNPs & STRs, data type
Mask
Ref: sample, panel, sample data
Sample data bit mask
Population Frequencies—population frequencies for SNPs and STRs
Ref: source, locus, region
Frequency
Linked—linking, phasing, and micro-haplotypes of genetic markers
Ref: sample
Organisms (Geolocation)—non-human organisms identified in sample
Name, taxonomy
Hit
Ref: sample1, sample2, mask1, mask2
Comparison details
Source
Name
Disease
Disease name, Online Mendelian Inheritance in Man15 (MIM ID)
Gene
Ref: source, organism
Name, symbol, NCBI gene ID, chromosome
Disease Gene
Ref: disease, gene
Biosequence
Ref: organism
Type, accession, protein sequence, mRNA sequence
Structure
Ref: organism
Structure name, PDB entry, resolution
Residue
Ref: structure
Residue, structure atoms
Genetics—additional data
Mapping tables—linking data between tables Various embodiments and aspects may be practiced alone or in combination with any other aspects or embodiments described herein.

Detecting Multiple Individuals with High Confidence in Saturated Mixtures

High throughput sequencing of DNA single nucleotide polymorphism (SNP) panels has significant advantages for analysis of DNA mixtures. Isaacson et al. (Robust detection of individual forensic profiles in DNA mixtures. Forensic Science International: Genetics 14, 31-37) describe how to analyze complex DNA mixtures with many individual contributors. This approach leverages SNPs with low minor allele to major allele population ratios. For very high numbers of individual contributors, the number of minor alleles present in the mixture saturates most SNP loci. This creates challenges for current mixture analysis approaches resulting in no detection of contributing individuals or lower significance of detections. Detection of individuals in saturated mixtures is an unsolved forensics community need. Various embodiments described herein provide techniques for confidently identifying individuals in saturated DNA mixtures.

Most SNPs have two alleles which occur with different allele frequencies in a population. The most common allele for a given SNP is called the major allele, and the least common allele is called the minor allele. The DNA profile of an individual can be matched to a DNA mixture by comparing the individual's minor alleles to the mixture. When a sufficient number of the SNP loci where the individual has a minor allele also have the minor allele in the mixture, then that individual can be identified in the mixture. The confidence of this identification is inversely proportional to the number of loci where the individual has a minor allele but the mixture only contains major alleles, or likely mismatches.

A DNA mixture is said to be saturated if it has a minor allele at so many of its SNP loci that nearly any individual could be identified in the mixture. In this case, current mixture analysis cannot identify any individuals with high confidence.

Individuals frequently contribute different amounts of DNA to DNA mixtures. As a result, the number of reads of a minor allele at a given SNP locus is proportional to the contribution percentages of each person in the mixture who has a minor allele at that locus. Therefore, the SNP loci with the highest number of minor allele reads are the loci where the top contributors to the mixture have minor alleles. The minor allele loci of the lower contributors are proportionally lower when not shared by other individuals in the mixture. This is because the minor allele loci unique to each low contributor occur with low minor allele reads, the SNP loci where multiple low contributors have a minor allele occur with moderate minor allele reads, and the SNP loci where one or more low contributors share a minor allele with one or more high contributors occur with high minor allele reads. Finally, it can be inferred that high contributors have major alleles at SNP loci with low minor allele reads in the mixture, since these loci would appear with high minor allele reads in the mixture if one or more high contributors had the minor allele at these loci. The mixture minor allele reads represent an approximate sum of individual minor alleles contributed to the mixture weighted by the DNA concentrations of the individuals.

Because high contributors have major alleles at the loci with low minor allele reads in the mixture, treating these mixture minor alleles as major alleles for these high contributors is a close approximation of the contributed alleles. Note that low DNA contributors likely have chance sharing of minor alleles with high contributors.

This method of mixture desaturation works by converting the bottom k minor alleles by minor allele count in the mixture to major alleles, such that the mixture has N % major alleles. For a mixture with $M$ major allele positions on a panel of P loci, $k=NP-M$. More individuals are identified at low N, whereas fewer individuals are identified with higher confidence at high N. Ns between 45% and 80% work well. Table 1 shows the value performance of N=45% desaturation compared to current mixture analysis on saturated mixtures.

TABLE 26

Performance of N = 45% mixture desaturation.

| Reference | V1D5J: IX-30 | mix55fabric | mix162 | mix160 | mix186 | URK5V: IX-32 | URK5V: IX-25 | mix52 | mix88 | mix187 | mix51 |
|---|---|---|---|---|---|---|---|---|---|---|---|
| 24 | 1 | 1 | 1 | 1 | 1 | 1 | *1.26E-10* | 2.31E-54 | 1 | 1 | *8.00E-73* |
| 86 | 1 | 1 | 1 | 1 | 1 | 1 | 1 | *1.98E-52* | 1 | 1 | 1 |
| 94 | 1 | 6.28E-69 | 1 | 6.22E-16 | 8.09E-72 | *1..25E-09* | 1 | 2.30E-29 | 6.25E-72 | 1 | 3.34E-47 |
| 57 | 1 | 2.88E-66 | 5.47E-19 | 6.61E-32 | 1 | 1 | 3.45E-11 | 4.60E-15 | 1 | 1 | 4.89E-49 |
| 93 | 1 | 8.39E-83 | 1 | 3.88E-44 | 6.24E-22 | 1 | 6.45E-17 | 1 | 2.69E-24 | 1.25E-34 | 7.13E-20 |
| 69 | 1 | 1 | 6.89E-44 | 7.59E-59 | 1 | 1.95E-10 | 7.97E-20 | 1 | *1.58E-17* | 5.88E-19 | 1 |
| 68 | 1 | 1 | 1 | 1 | 1 | 1.63E-12 | 7.97E-20 | 1 | 1 | 1 | 1 |
| 76 | 3.79E-10 | 1 | 1 | 1 | 1 | 1.02E-10 | 5.87E-19 | 1 | 1 | 1 | 1 |
| 78 | 1 | 1 | 1 | 1 | 7.67E-46 | 1 | 1.22E-17 | 1 | 1 | 1 | 1 |
| 83 | 1 | 1 | 1 | 1 | 1 | 1 | 5.37E-12 | 1 | 1 | 1 | 1 |
| 4 | 1 | 6.48E-15 | 2.73E-58 | 3.78E-73 | 1 | 1 | *1.51E-10* | 1 | 1 | 2.50E-15 | 1 |
| NA01246 | 4.22E-19 | 1 | 1 | 1 | 1 | 1 | 1 | 1 | 1 | 1 | 1 |
| NA08106 | 1.86E-15 | 1 | 1 | 1 | 1 | 1 | 1 | 1 | 1 | 1 | 1 |
| 19 | 5.73E-14 | 1 | 1 | 1 | 1 | 5.88E-23 | 1 | 1 | 1 | 1 | 1 |
| NA10069 | 1.08E-10 | 1 | 1 | 1 | 1 | 1 | 1 | 1 | 1 | 1 | 1 |

Italic cells show new reference to mixture hits detected with desaturation, and the cells contain the probability that the random man is not excluded (PRMNE) of the match. The bold cells contain reference to mixture hits that were identified using both current mixture analysis and mixture desaturation.

Figure 42:
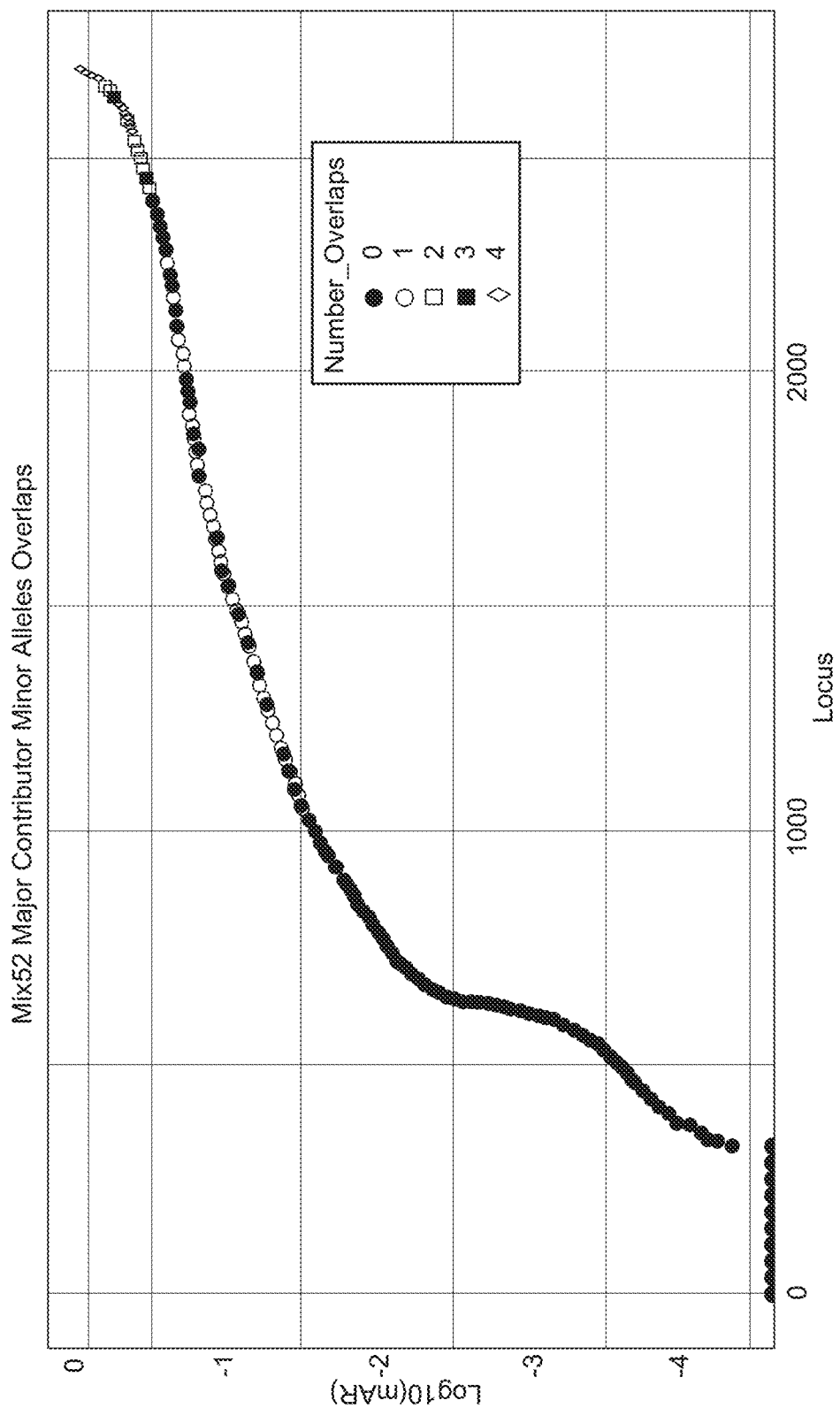
FIG. 42 shows the distribution of the minor allele loci of four high contributors in a mixture.
Figure 43:
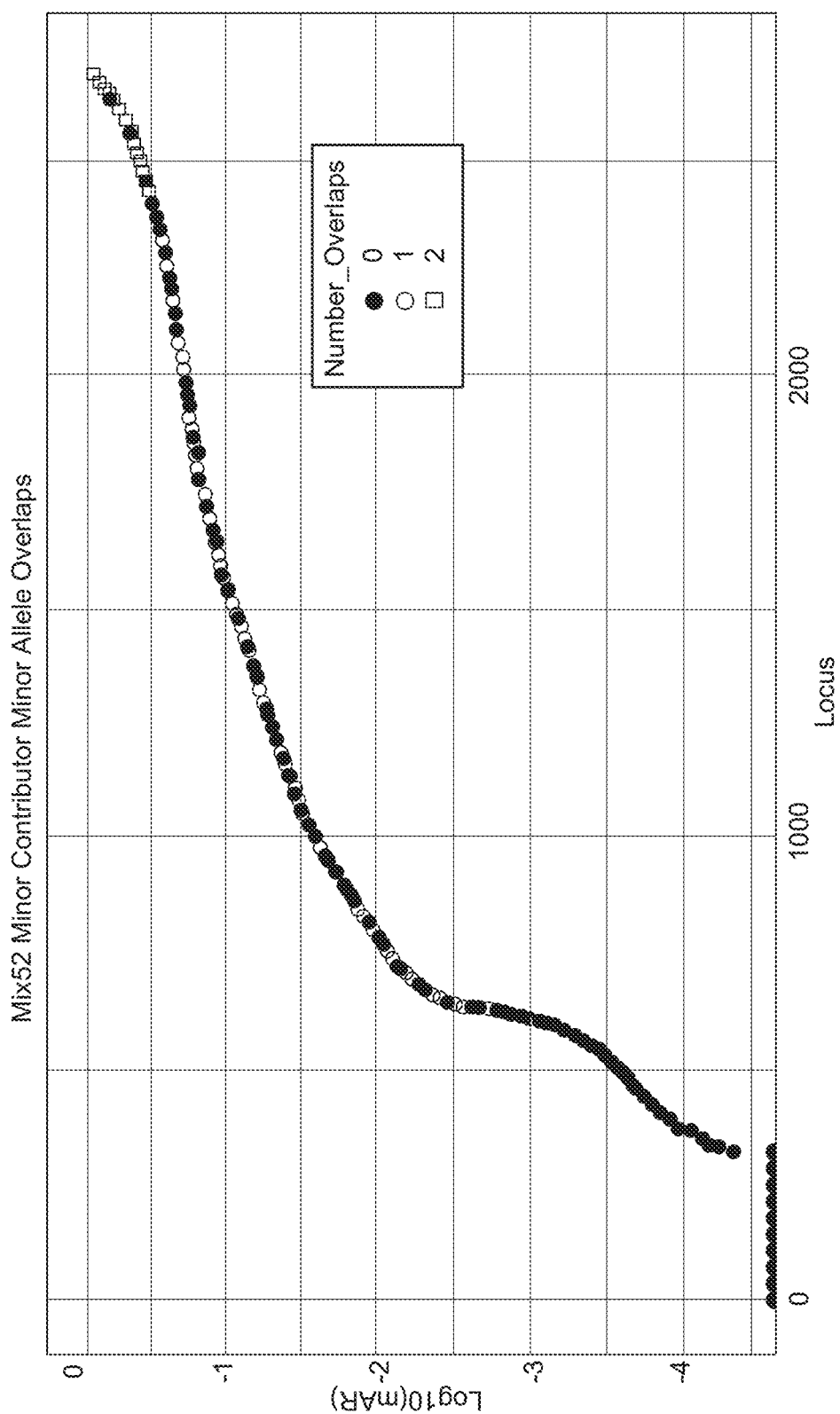
FIG. 43 shows the distribution of minor allele loci of two minor contributors in a mixture.

The minor allele ratio (mAR) at a SNP locus is defined as the number of minor allele reads divided by the total reads at that locus. The mixture de-saturation method described using the minor allele reads can also use the mAR. Loci with high mAR in the mixture are the loci where one or more high contributors has a minor allele, and all of each high contributor's minor allele loci have high mAR in the mixture. However, the minor allele loci of low contributors are more evenly distributed in the mixture. FIGS. 42 and 43 illustrate this distribution of loci using mAR. In particular, FIG. 42 shows the distribution of the minor allele loci of four high contributors in a mixture. Loci are rank ordered by mAR values. Loci colored purple are loci where no high contributor has a minor allele. Green, blue, grey and red loci are where one, two, three, or four high contributors have the minor allele, respectively. Notice that non-purple loci exist with high MAR in the mixture. FIG. 43 shows the distribution of minor allele loci of two minor contributors in a mixture. Blue, red, and green loci have zero, one, and two minor contributors that possess a minor allele at that locus, respectively. Notice how these loci are more evenly distributed in the mixture compared to those of the major contributors.

Venn Matrix Method for Complex DNA Mixture Deconvolution

Figure 44:
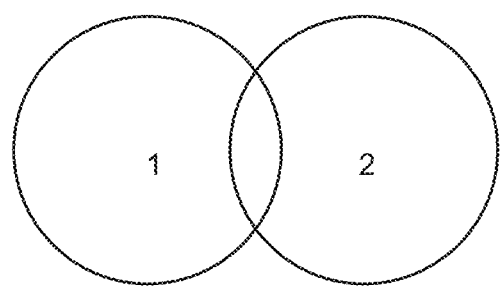
FIG. 44 illustrates that two unrelated are likely to share a set of alleles in common by chance alone.

In some embodiments, a Venn Matrix method may be used to analyze complex mixtures. In one implementation, search results of a mixture against known references, unknown sub-profiles previously identified, and other mixtures to select a set of mixtures that likely overlap for deconvolution of complex DNA mixtures. Starting with the FastID search results for a mixture, select all known individuals and unknown sub-profiles for this mixture and all potentially overlapping mixtures also identified by FastID. Next, subtract these individuals and sub-profiles from each of the set of potentially overlapping mixtures (if identified in that mixture) creating sets of reduced mixtures. This subtraction reduces the potential set of alleles that might be in common between two mixtures by chance alone. Next, apply the Venn deconvolution method (MIT 16637) to the set of reduced mixtures. Finally, apply the Mixture-to-Mixture matrix visualization (MIT new: DNA Mixture-to-Mixture Analysis) to the integrated results of the set of mixtures mapped onto individual references and unknown sub-profiles. This approach works for both short tandem repeats (STRs) and single nucleotide polymorphisms (SNPs) complex DNA mixtures. According to some embodiments, the Venn method enables the identification of individuals and groups of individuals common in two or more complex DNA mixtures. Previously, no guidance has been provided to determine which mixtures to consider for deconvolution. FIG. 44 illustrates that two unrelated are likely to share a set of alleles in common by chance alone. The chance overlap between two individuals can be estimated for SNP and STR DNA loci. For SNP loci, each individual typically has two alleles (e.g., AA, AG, GG or alternative DNA base combinations), with each of the alleles inherited from each parent. Table 1 illustrates the possibilities for SNP sharing between two unrelated individuals at one locus. For resolution of more individuals in a complex mixture, a minor allele ratio (MAR) close to 0.05 is ideal [Isaacson, et al. 2014]. For SNPs with this MAR, an individual will have approximately 10% of the positions (2 alleles×0.05 MAR) with one minor allele and 1% with two minor alleles (10% x 10%). This creates a sparse barcode pattern of minor alleles for each individual that has a low probability of random sharing with unrelated individuals (10%×10%=1%). This can be expressed as $f_1$ as the fraction of SNPs with minor alleles for individual 1 and $f_2$ for individual 2. The expected sharing of minor alleles, E, is $E=f_1 \times f_2$. This formula also applies to DNA mixtures for estimating the expected amount of chance minor allele sharing between two mixtures. The chance overlap between two STR samples can be estimated by summing the observed allele frequencies at each locus as $f_i$. An example of observed STR allele frequencies in the U.S. population is shown in Table 27.

TABLE 27

Example of Possible SNP Allele Sharing between 2 Individuals

|  | AA | AG | GG |
|---|---|---|---|
| AA | 2 | 1 | 0 |
| AG | 1 | 2 | 1 |
| GG | 0 | 1 | 2 |

DNA Mixture-to-Mixture Analysis

In some embodiments, a novel method may be used for analyzing DNA overlaps between one DNA mixture and other DNA mixtures with shared DNA contributors. Two or more DNA mixtures can have no common contributors, and any detected common DNA alleles result from chance. When two or more DNA mixtures have common contributors, the overlap between the mixtures will be enriched above chance by the alleles of the common contributors. The Lincoln FastID or equivalent methods enable the comparisons of samples, both individual reference samples and complex DNA mixtures (e.g., samples from crime scenes, clothing, money, weapons, etc.). Included in these results are identifications of overlaps between mixtures. The Lincoln Venn Mixture Deconvolution method can identify sub-profiles of one or more individuals common to two or more mixtures. A DNA mixture may match zero or more reference samples, zero or more DNA mixtures. When a mixture matches one or more mixtures, visualization of identified reference sample matches, identified sub-profiles, and novel unknown sub-profiles, the entire set of results can be visualized side-by-side in a scatter plot/bubble chart or matrix for immediate insights into the individuals (both known and unknown) common to the set of overlapping mixtures (crime scenes). This is done by organizing the reference hits for each mixture into a matrix of matches between mixtures and individuals. The significance of the matching results (e.g., probability of random man not excluded P(RMNE), likelihood ratio (LR), etc.) can be encoded into the visualization by symbol shape and size. The mixture-to-mixture analysis approaches applies to SNPs, STRs, DNA microarray profiles, etc.

Criminal justice DNA forensics currently relies upon DNA analysis of allele lengths by sizing of a set of short tandem repeats (STRs). The United States is expanding from 13 to 20 DNA loci to facilitate alignment with DNA forensics used in Europe. Advances in DNA sequencing technologies will shift DNA forensics from sizing STR alleles to sequencing both STR and single nucleotide polymorphisms (SNPs). Inclusion of SNPs enables additional advanced capabilities, including analysis of DNA mixtures with two or more contributors. Current STR sizing has very limited DNA mixture analysis resolution with difficulties with differences in DNA concentrations and mixtures with more than two contributors. MIT Lincoln Laboratory has pioneered advanced DNA mixture analysis with both STR panels and SNP panels (with up to 15,000 SNPs). Methods have been developed that can correctly identify 12 contributors in STR mixtures and multiple individuals in mixtures of 15 to 20 individuals with SNP panels.

DNA Mixture Analysis

Figure 45A:
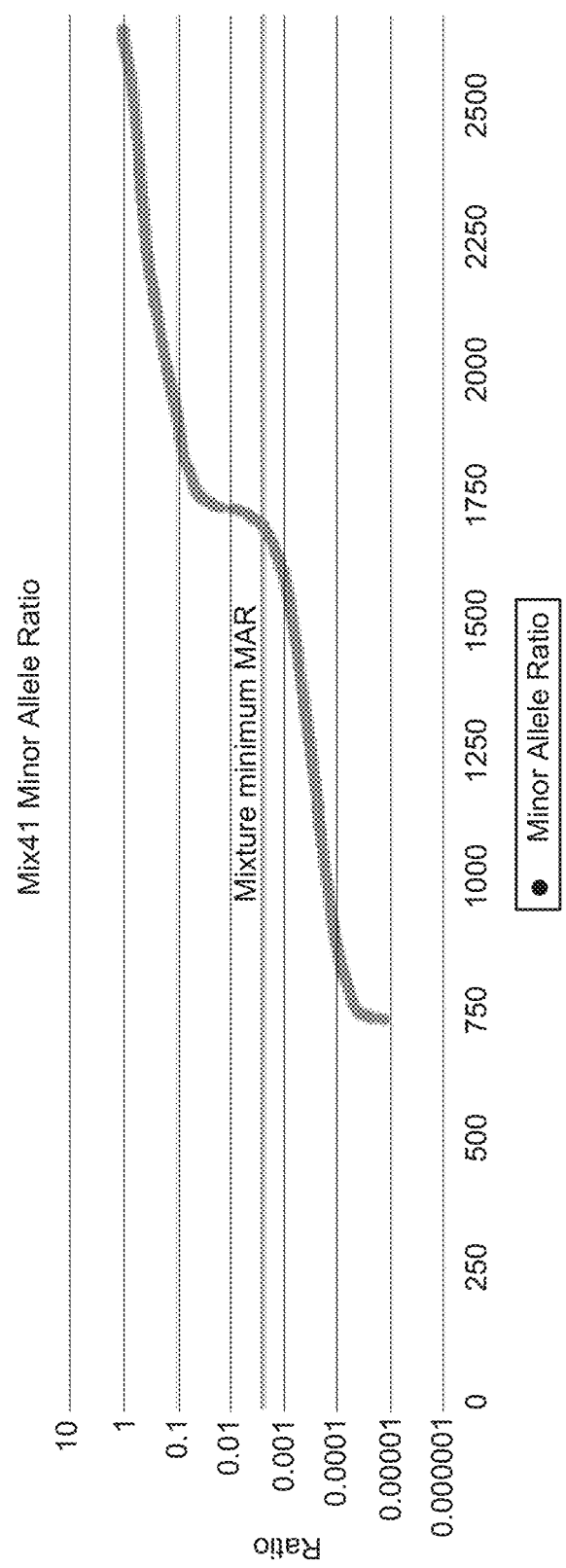
FIG. 45A shows an example mixture 41 plot of minor allele ratios.
Figure 45C:
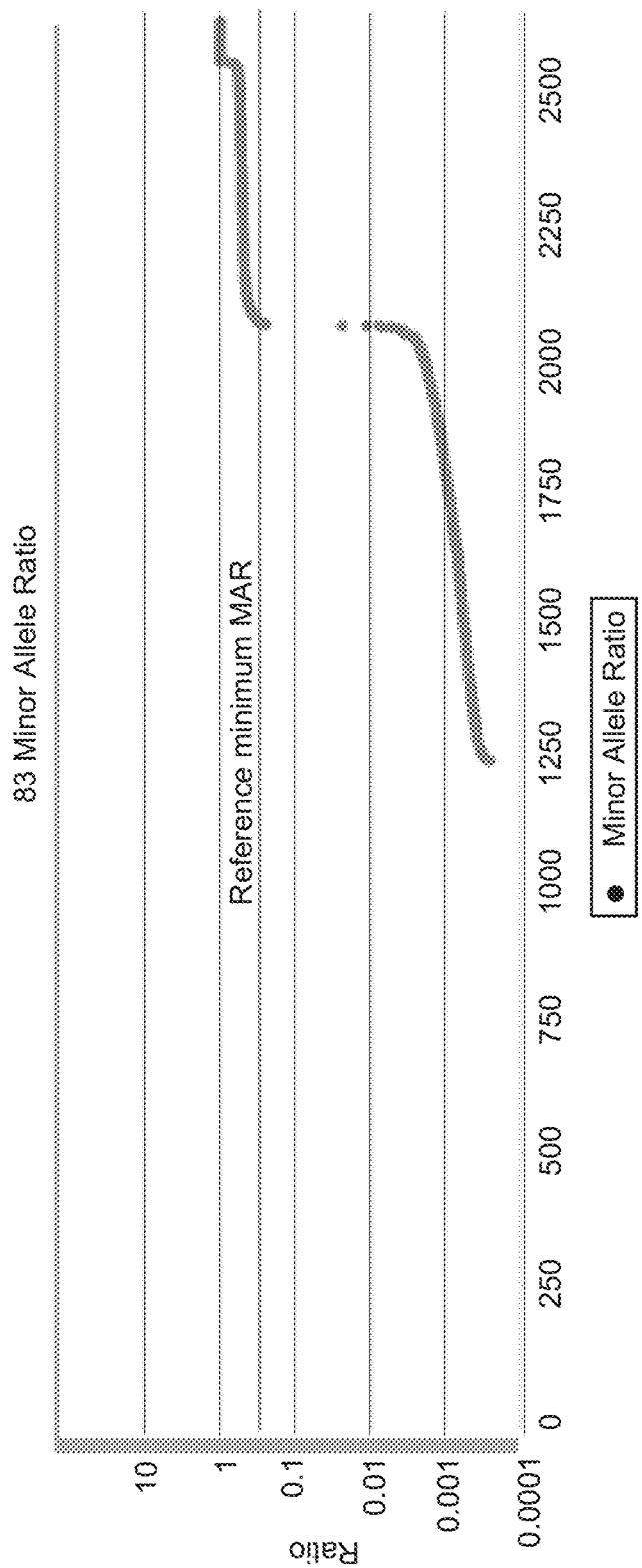
FIG. 45C shows an example reference 83 plot of minor allele ratios.
Figure 45D:
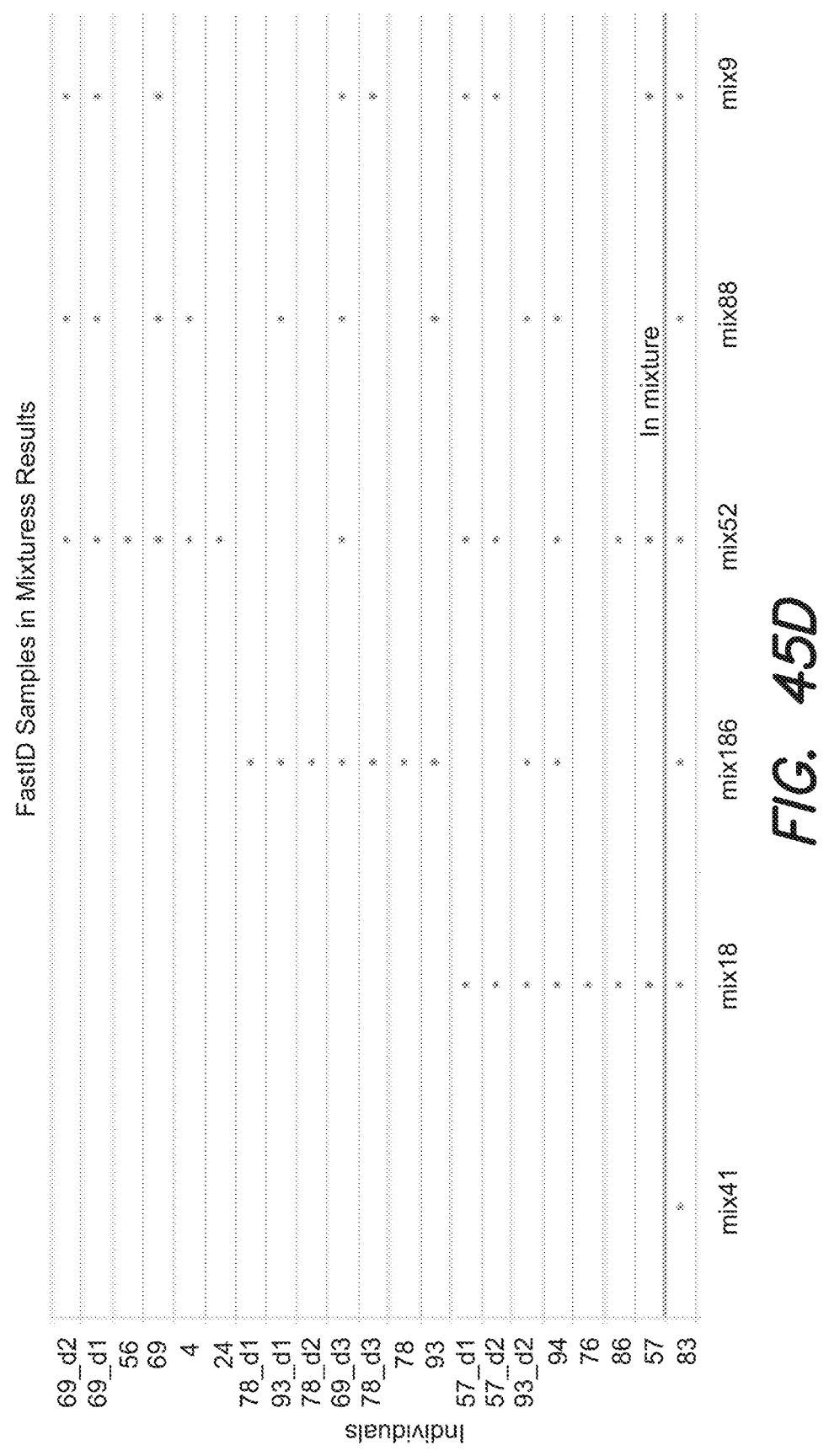

A sample with DNA from one contributor will be a partial or full profile for the individual. FIG. 45 illustrates an example mixture, mix41. The profile of minor alleles is illustrated in FIG. 45A. The FastID search results against references and mixtures are shown in FIG. 45B. The profile for individual 83 is matched for all except for 3 SNP minor alleles. FIG. 45C shows the minor allele ratio profile for individual 83; it has fewer minor alleles than mix41 indicating that mix41 has additional contributors. Mixture 41 also matches against five other mixtures, mix9, mix18, mix52, mix88, and mix186. In FIG. 45D, the individuals identified by FastID search results are plot in a matrix of individuals versus mixtures scatter plot. Note that there are multiple reference samples of individuals 69, 78, and 93. In FIG. 1d, it becomes immediately clear that the overlap of mix41 and the other five mixtures all include individual 83.

The approach enables the visualization and analysis of mixture-to-mixture overlaps. This example can be extended to include identified sub-profiles from mixtures and unknown individuals.

Identifying Unknowns in DNA Mixtures

Unknowns are individuals whose DNA is present in forensic samples and there is no reference sample for this individual in the set of individuals with profiles in the reference database. A forensics DNA sample can contain DNA from 0, 1, or more individuals. Trace amounts of DNA may result in only a partial profile for an individual. The following are methods to detect unknowns in forensics samples:

- A sample consistent with having a profile of an individual based on the amplified loci but having no matches to known individuals is a candidate profile for an unknown.
- A mixture of two or more individuals where some but not all of the individuals are known contains unknowns. Subtracting the known profiles from the mixture leaves the signature profiles for the unknowns.
- The Venn method can be used to deconvolve a set of mixtures and references to identify unknown individuals.
- The Plateau method can be used to deconvolve mixtures into sub-profiles of known and/or unknown individuals.
- The Venn Matrix method can be used to deconvolve a set of mixtures and references to identify unknown individuals.

Sample from Unknown Contributor

Figure 46:
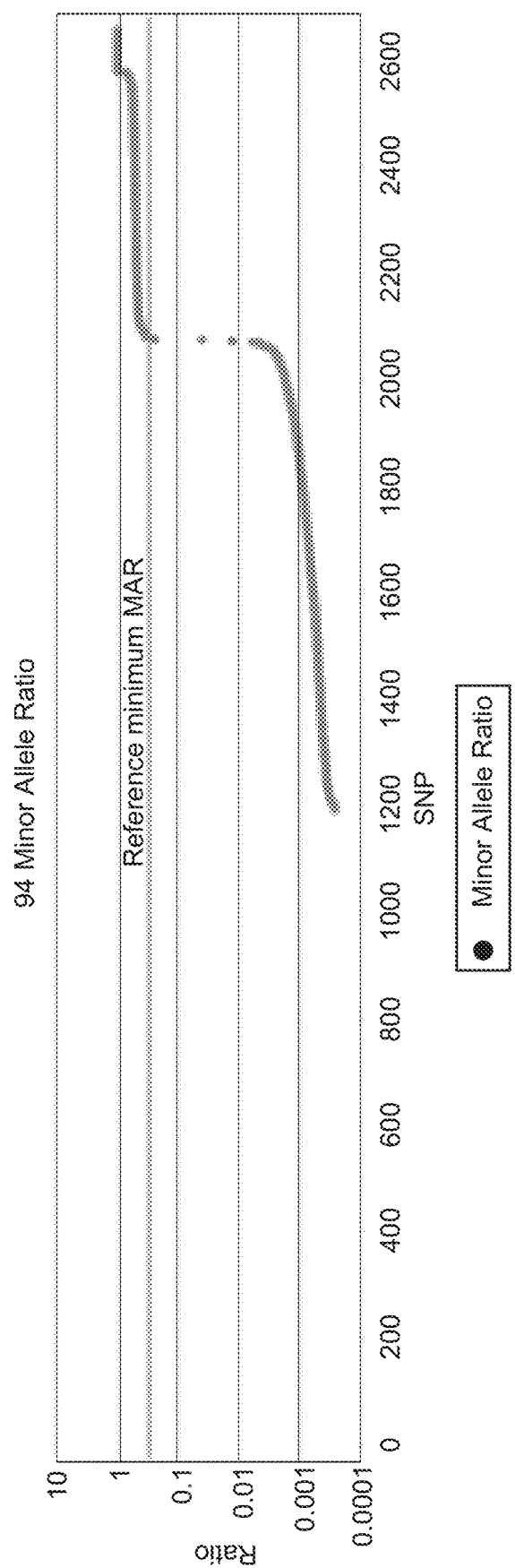
FIG. 46 shows an example SNP Panel with 2,655 loci example profile for an individual.
Figure 47:
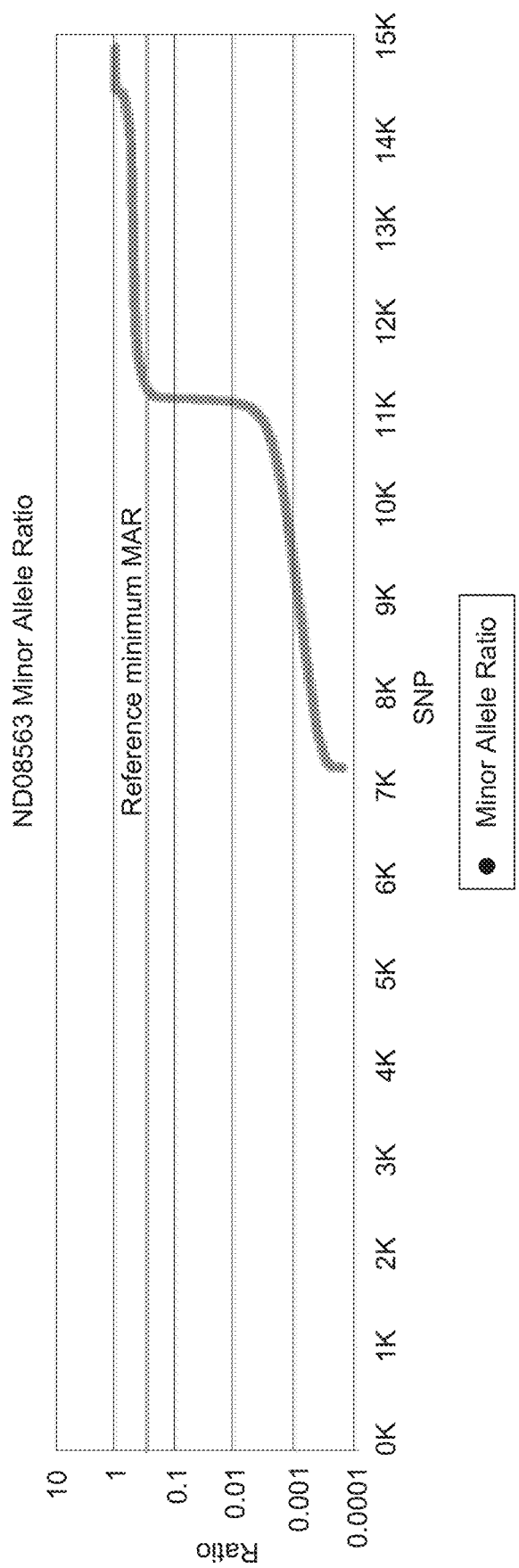
FIG. 47 shows an example SNP Panel with 14,933 loci example profile for an individual.
Figure 48:
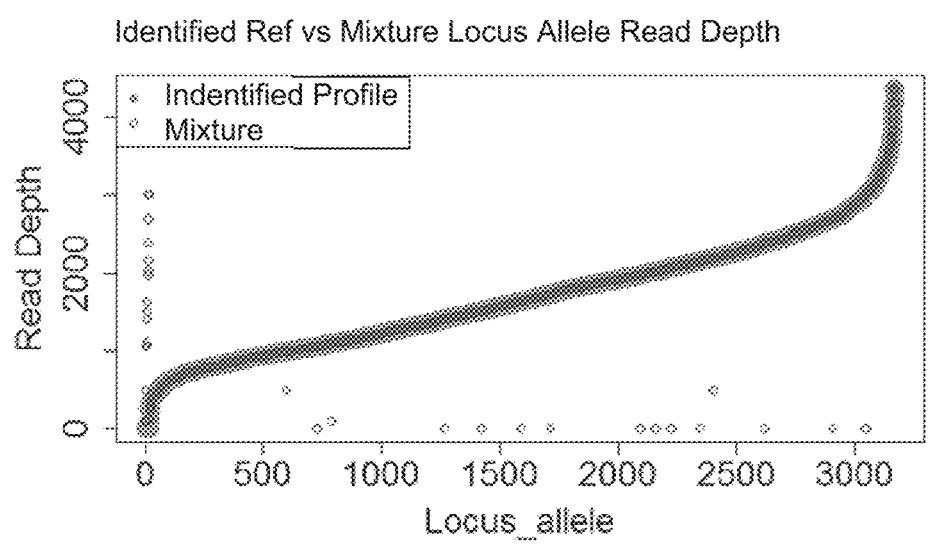
FIG. 48 shows an example mixture profile with known reference and partial profile for an unknown contributor.
Figure 49:
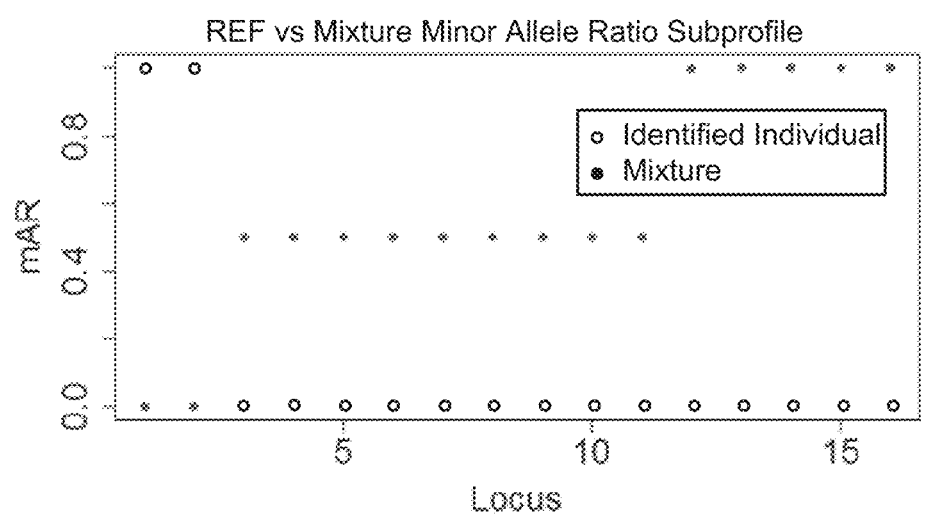
FIG. 49 shows example mixture alleles for Unknown Contributor shown with Known Contributor. The allele signature for the unknown contributor shown with the corresponding alleles from the known contributor from the mixture profile in FIG. 48.

A sample profile can contain 0, 1, or more individual contributors. For samples with 2 or more contributors, the DNA amplifies in proportion to the ratio of the DNA in the original sample. For SNP profiles, the ratio of major:major, major:minor, and minor:minor alleles is directly affected by the number of contributors. SNP panels will have different minor allele frequencies for different loci, but the general rule of allele frequencies with q representing the minor allele frequency for a loci, then the SNP frequencies for a loci are represented by $p*p+2*p*q+q*q=1$ with $p=1-q$ and p representing the major allele frequency. For unrelated individuals, the sharing of minor:minor alleles for both individuals will be a rare event by chance alone with frequencies approximating $q\wedge 4*N$ where N is the number of SNPs for a two person mixture and $q\wedge 6*N$ for a three person mixture, etc. In an opposite pattern, the number of major:minor allele positions increases with the number of contributors to mixtures with major:minor positions $=2*p*q+2*p*q-4*p\wedge 2*q\wedge 2$ (the addition of the two major:minor positions for each individual minus the chance overlap of shared major:minor positions for the two individuals). Thus, the observed major:major, major:minor, and minor:minor alleles observed for a sample are a reflection of the number of contributors to the sample. Samples consistent with having single contributors are candidate profiles for unknown individuals. FIGS. 46 and 47 are example profiles for individual profiles for SNP panels of 2,655 and 14,933 SNPs.

Locus Allele Method

The Locus Allele method can be used to isolate sub profiles of contributors to a mixed DNA sample after one or more contributor(s) have already been identified. The Locus Allele method identifies alleles present in the mixture sample that cannot have been contributed by any of the identified contributors (FIG. 3). These alleles are collected into a sub-profile of alleles from unknown contributors (FIG. 4). Sub-profile signatures consistent from being from a single contributor are candidate profiles for individual unknown contributors to the mixture. The general population frequencies of these alleles determine the resolution power for identifying this individual (i.e., random man not excluded P(RMNE), Likelihood Ratio (LR), etc.).

Figure 50:
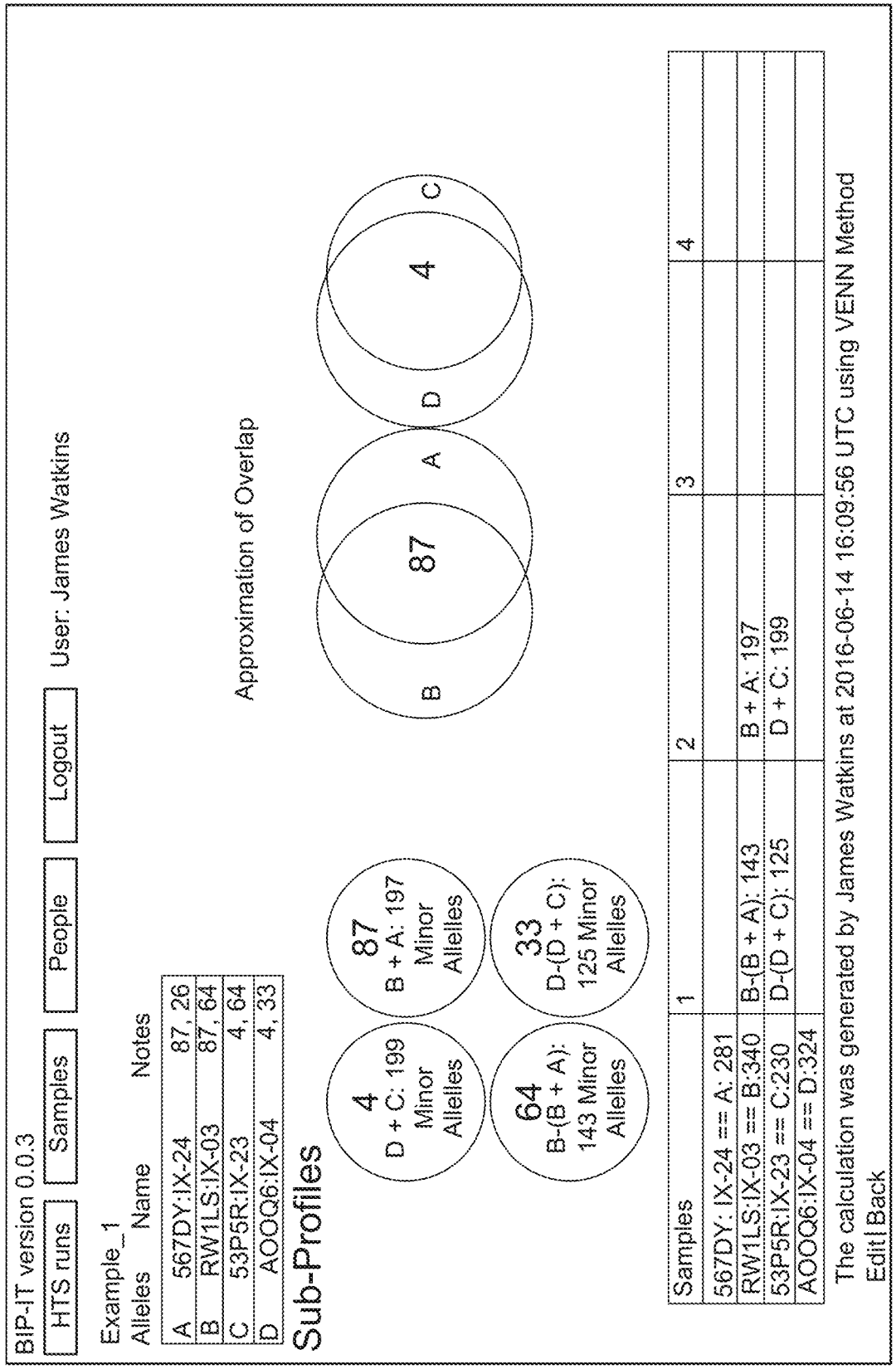
FIG. 50 shows an example Venn method for mixture deconvolution.
Figure 51:
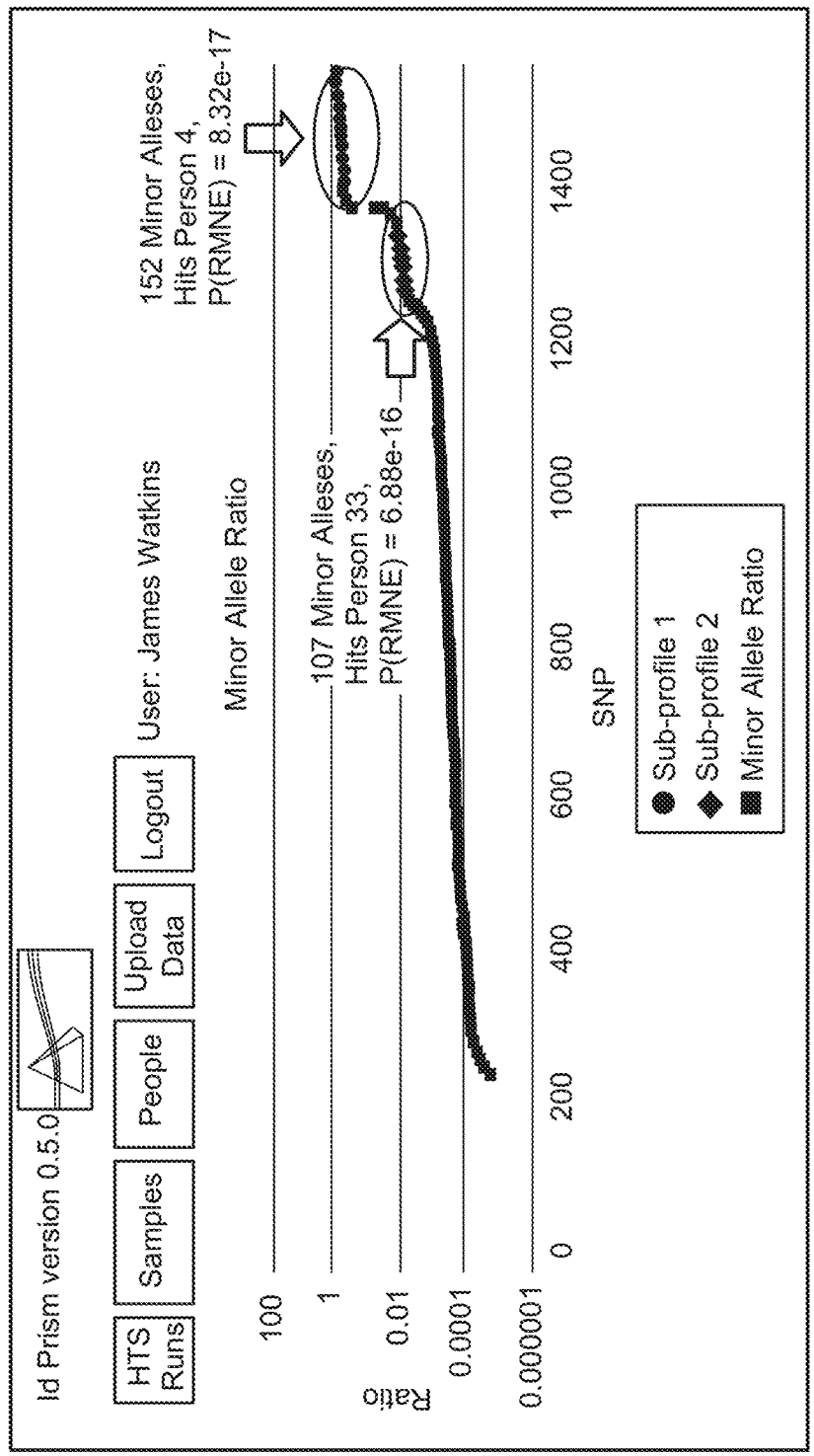
FIG. 51 shows an example Plateau method for mixture deconvolution.
Figure 52:
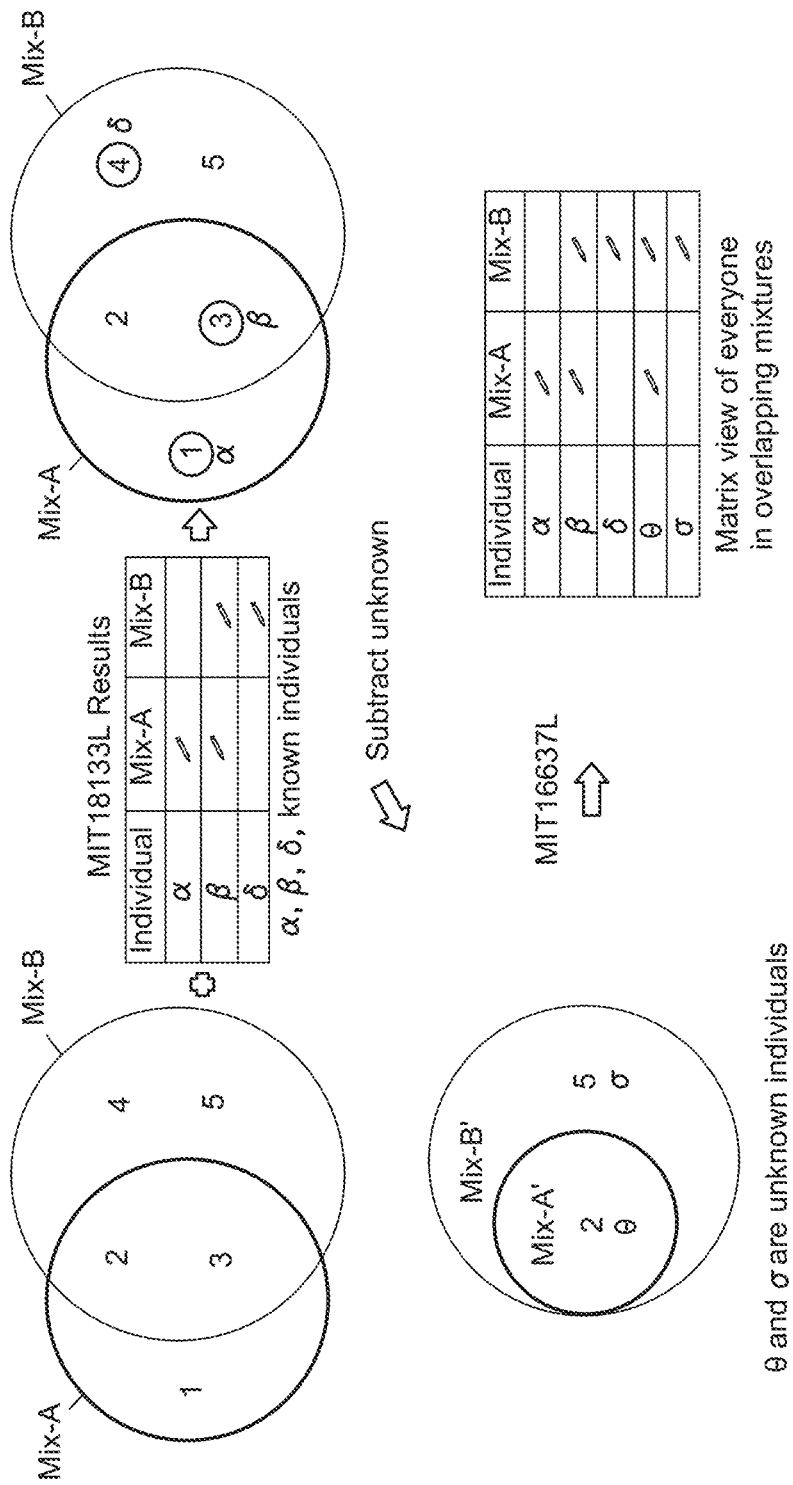
FIG. 52 shows an example Venn Matrix Method for identification of unknowns.

The Venn method shown in FIG. 50 can deconvolve a set of mixtures and references to identify unknown individuals. The Plateau method shown in FIG. 51 can deconvolve mixtures into sub-profiles of known and/or unknown individuals. The Venn Matrix method shown in FIG. 52 can deconvolve a set of mixtures and references to identify unknown individuals.

Estimating Individual Contributions to DNA Mixtures

DNA mixtures contain contributions from two or more individuals. High throughput sequencing (HTS) technologies now enable mixture analysis and deconvolution of DNA mixtures into individual profiles. Forensics sequencing panels have been created for short tandem repeats (STRs) and single nucleotide polymorphisms (SNPs). This example implementation provides a new method for estimating the proportion of DNA contributed by individuals for HTS sequenced SNP mixtures. For each individual, the average of the minor allele ratios (maR) is computed for loci where the individual has one minor allele and one major allele (heterozygous). The ratio of this average to the sum of the computed individual averages represents an estimate of the percentage that each individual contributed to the mixture. The most common allele at a SNP locus is referred to as the major allele (M). The less common allele is referred to as the minor allele (m). For each locus, an individual will have two major alleles (MM), one major allele and one minor allele (mM), or two minor alleles (mm). The minor allele ratio (maR) at a locus is defined as the number of minor allele reads observed divided by the total reads observed. After individual profiles have been identified for a mixture by FastId, Plateau Method, Venn Method, Venn Matrix method, or other means, the average of the maR for the mM alleles for each individual is determined. An individual's proportion to the mixture is estimated by the average of the mixture maR divided by the sum of the averages for all identified profiles.

Note that the median can be used as an alternative to the average in these calculations.

Example 1—Dilution Mixture Series

Figure 53:
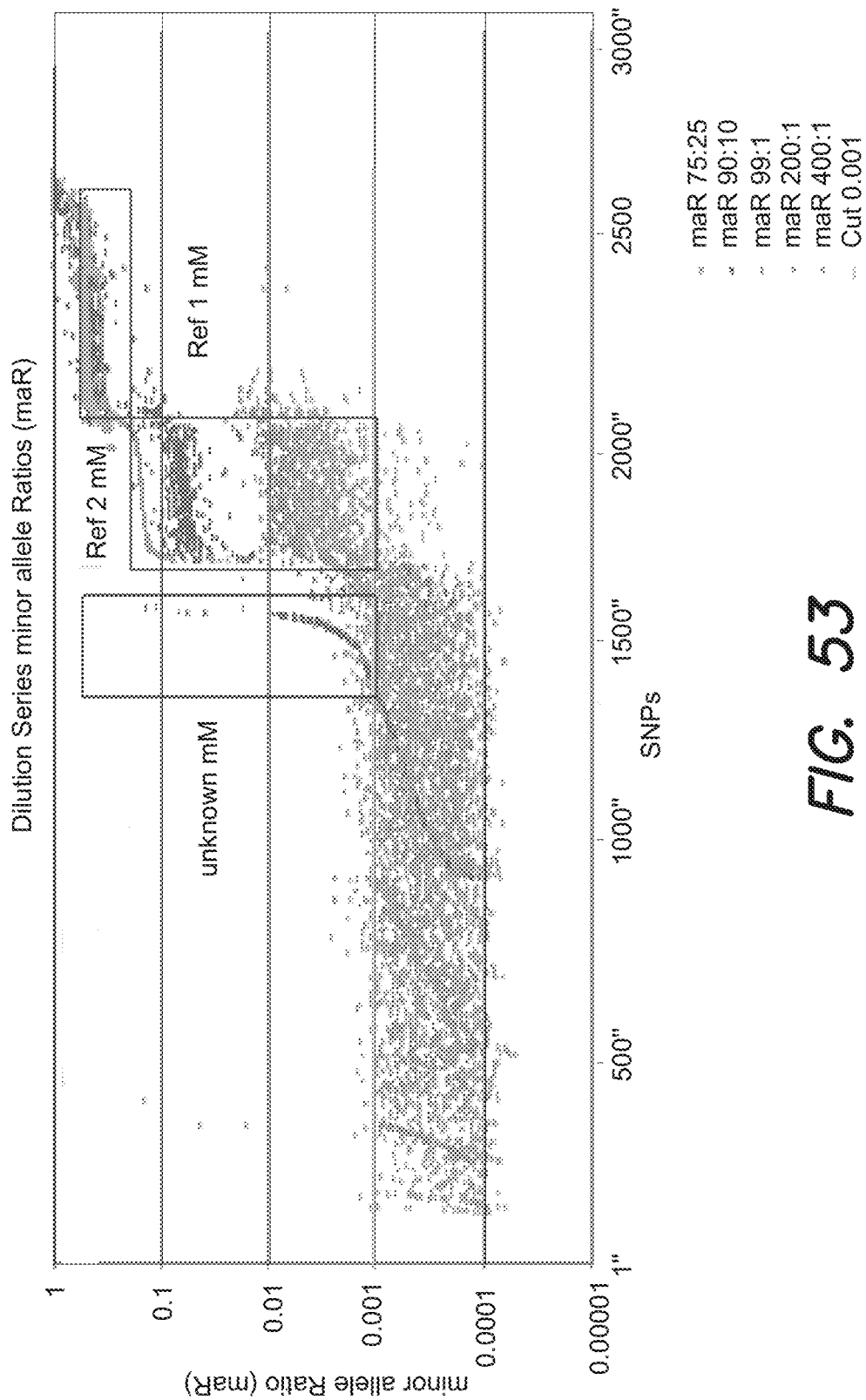
FIG. 53. shows an example two person dilution series for DNA ratios 75:25, 90:10, 99:1, 200:1, and 400:1 plus the detection of unknown trace profile in 90:10 dilution mixture.
Figure 54:
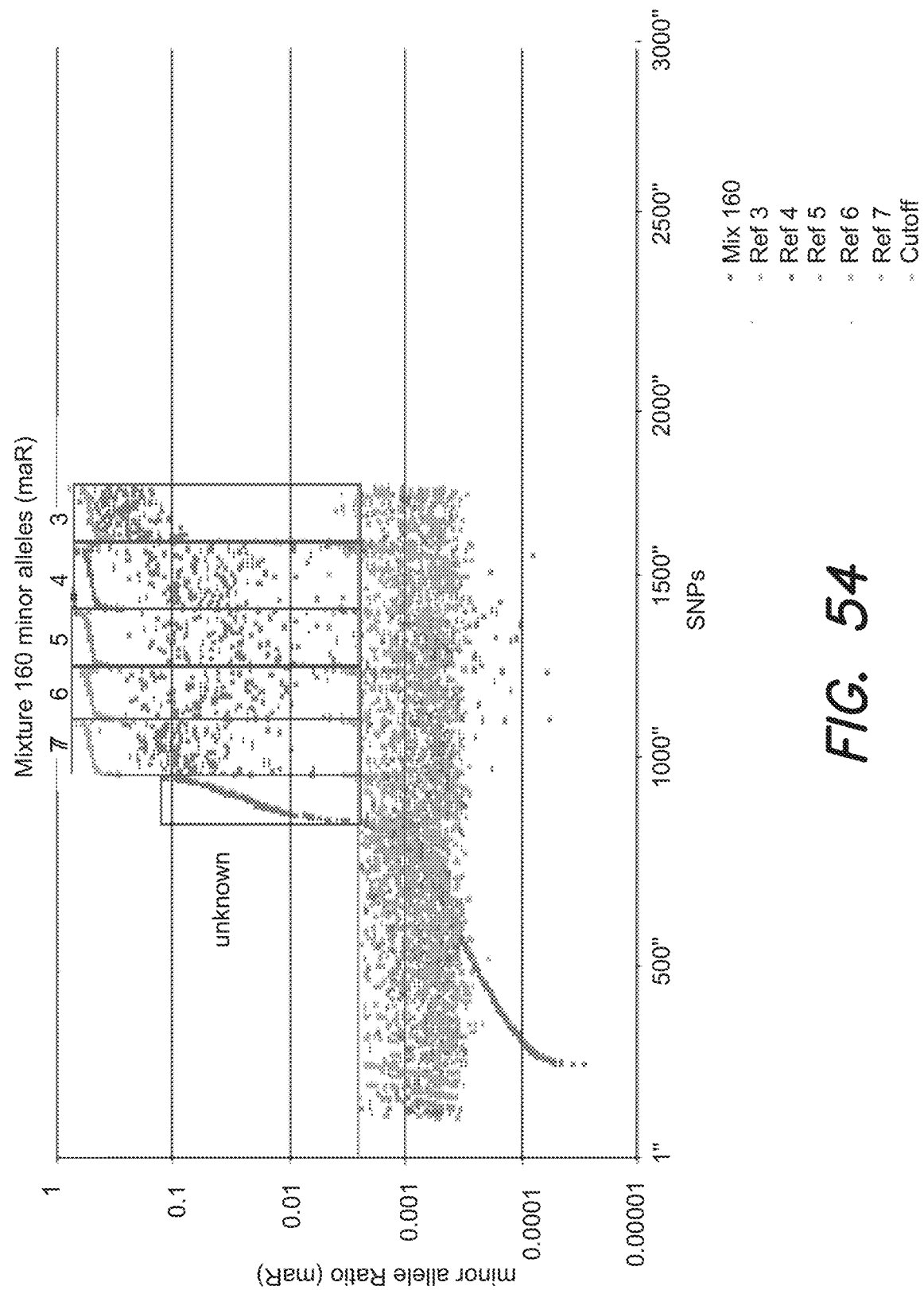
FIG. 54 shows an example touch mixture with six DNA contributors with touch order by individuals: 7, 7, 7, 8, 5, 7, 3, 7, 3, 7, 7, 3, and 4.

A dilution series of seven mixtures of two individuals is illustrated in FIG. 53 and Table 28 for DNA contributor ratios of 50:50, 60:40, 75:25, 90:10, 99:1, 200:1, and 400:1. Table 28 calculates the estimated contributions for each individual identified in the mixture. The mixture 90:10 contains an additional trace contribution for an unknown individual representing an estimated 3.8% of the total DNA contributed to the mixture (FIG. 53 and Table 28). Table 29 compares the estimated concentrations with the planned concentrations. Note that variability in pipetting DNA and PCR amplification for the experiments may contribute to differences between the planned concentration and the actual concentration. Estimates differed from planned concentrations by 0.2% to 2.3% with the addition of the unknown trace signature reducing the estimate for reference 1 in the 90:10 mixture from 90%; note that 90%-3.8% is 86.2% compared to the estimated 84.5% which differs by 1.7% of the modified expected value.

TABLE 28

Calculation of contributions for individuals for Dilution Series

| Planned | Ref 1 ave | Est. 1% | Ref 2 ave. | Est. 2% | Unknown | Est. % | Sum |
|---|---|---|---|---|---|---|---|
| 50:50 | 0.314 | 52.3% | 0.287 | 47.7% | | | 0.601 |
| 60:40 | 0.349 | 60.1% | 0.232 | 39.9% | | | 0.581 |
| 75:25 | 0.402 | 73.0% | 0.149 | 27.0% | | | 0.551 |
| 90:10 | 0.462 | 84.5% | 0.064 | 11.6% | 0.021 | 3.8% | 0.546 |
| 99:1 | 0.493 | 98.6% | 0.007 | 1.4% | | | 0.500 |
| 200:1 | 0.495 | 99.3% | 0.004 | 0.7% | | | 0.498 |
| 400:1 | 0.497 | 99.6% | 0.002 | 0.4% | | | 0.499 |

TABLE 29

Comparison of Planned concentrations with observed concentrations for Dilution Series

| | 1 Expected | 1 Observed | 1 Delta | 2 Expected | 2 Observed | 2 Delta |
|---|---|---|---|---|---|---|
| 50:50 | 50% | 52.3% | 2.3% | 50% | 47.7% | −2.3% |
| 60:40 | 60% | 60.1% | 0.1% | 40% | 39.9% | −0.1% |
| 75:25 | 75% | 73.0% | −2.0% | 25% | 27.0% | 2.0% |
| 90:10 | 90% | 84.5% | −5.5% | 10% | 11.6% | 1.6% |
| | (86.5%) | | (−2.0%) | (9.6%) | | (2.0%) |
| 99:1 | 99% | 98.6% | −0.4% | 1% | 1.4% | 0.4% |
| 200:1 | 99.5% | 99.3% | −0.2% | 0.5% | 0.7% | 0.2% |
| 400:1 | 99.75% | 99.6% | −0.15% | 0.25% | 0.4% | 0.15% |

Example 2—Touch Mixture

In the second example, a mixture was created from individuals touching an object, FIG. 2. The touch order for the individuals was recorded. Note that there is no truth information that can be compared to in this example. Individual 8 was not detected in the mixture, but may be represented by the signature marked "unknown". Individual 6 was also detected but was not recorded as touching the object. Table 3 estimates the relative contributions to the mixture by the individuals with both the average and median estimation calculations.

TABLE 30

Contributor concentrations estimates for touch mixture

| | Ref 3 | Ref 4 | Ref 5 | Ref 6 | Ref 7 | Unknown | Sum |
|---|---|---|---|---|---|---|---|
| mM Count | 144 | 165 | 156 | 134 | 144 | 130 | |
| Median | 0.254 | 0.047 | 0.020 | 0.036 | 0.085 | 0.022 | 0.464 |
| Average | 0.273 | 0.065 | 0.036 | 0.056 | 0.090 | 0.031 | 0.551 |
| Median Estimate | 54.7% | 10.1% | 4.3% | 7.8% | 18.3% | 4.8% | |
| Average Estimate | 49.6% | 11.8% | 6.5% | 10.2% | 16.4% | 5.6% | |

Slope Intercept Method

After individual profiles have been identified for a mixture by FastId, Plateau Method, Venn Method, Venn Matrix method, or other means, a line of best fit is created for each individual's unique maR profile. The slope intercept of each maR profile is summed. Each individual slope intercept is divided by the sum of slope intercepts to determine individual DNA concentrations.

Example 1—Dilution Mixture Series

Table 31 compares the estimated concentrations with the planned concentrations. Note that variability in pipetting DNA and PCR amplification for the experiments may contribute to differences between the planned concentration and the actual concentration. The mixture 90:10 contains an additional trace contribution for an unknown individual representing an estimated 2.3% of the total DNA contributed to the mixture using this method.

TABLE 31

Comparison of Planned concentrations with observed concentrations for Dilution Series

| | 1 Expected | 1 Observed | 1 Delta | 2 Expected | 2 Observed | 2 Delta |
|---|---|---|---|---|---|---|
| 50:50 | 50% | 62.30% | 12.30% | 50% | 37.70% | −13.30% |
| 60:40 | 60% | 48.60% | −11.40% | 40% | 51.40% | 11.40% |
| 75:25 | 75% | 65.30% | −4.70% | 25% | 34.70% | 9.70% |
| 90:10 | 90% | 90.60% | 0.60% | 10% | 9.40% | −0.60% |
| | | 87.70% | 2.9% | | | |
| 99:01 | 99% | 98.70% | 0.30% | 1% | 1.30% | 0.30% |
| 200:01 | 99.50% | 99.30% | −0.20% | 0.50% | 0.69% | 0.19% |
| 400:01 | 99.75% | 99.60% | −0.15% | 0.25% | 0.38% | 0.12% |

Extremely Fast Probability of Random Man not Excluded P(RMNE) Calculations

In some embodiments, it is appreciated that High throughput sequencing (HTS) of DNA single nucleotide polymorphism (SNP) panels have significant advantages for analysis of DNA mixtures and trace DNA profiles. One method of calculating the significance of a match between a DNA mixture and a reference profile is the random man not excluded P(RMNE) calculation. Performance and precision issues are being observed with current implementations of the P(RMNE) calculations. Some embodiments are provided herein for performing an extremely fast P(RMNE) calculation method that also has higher precision than current methods.

Figure 55:
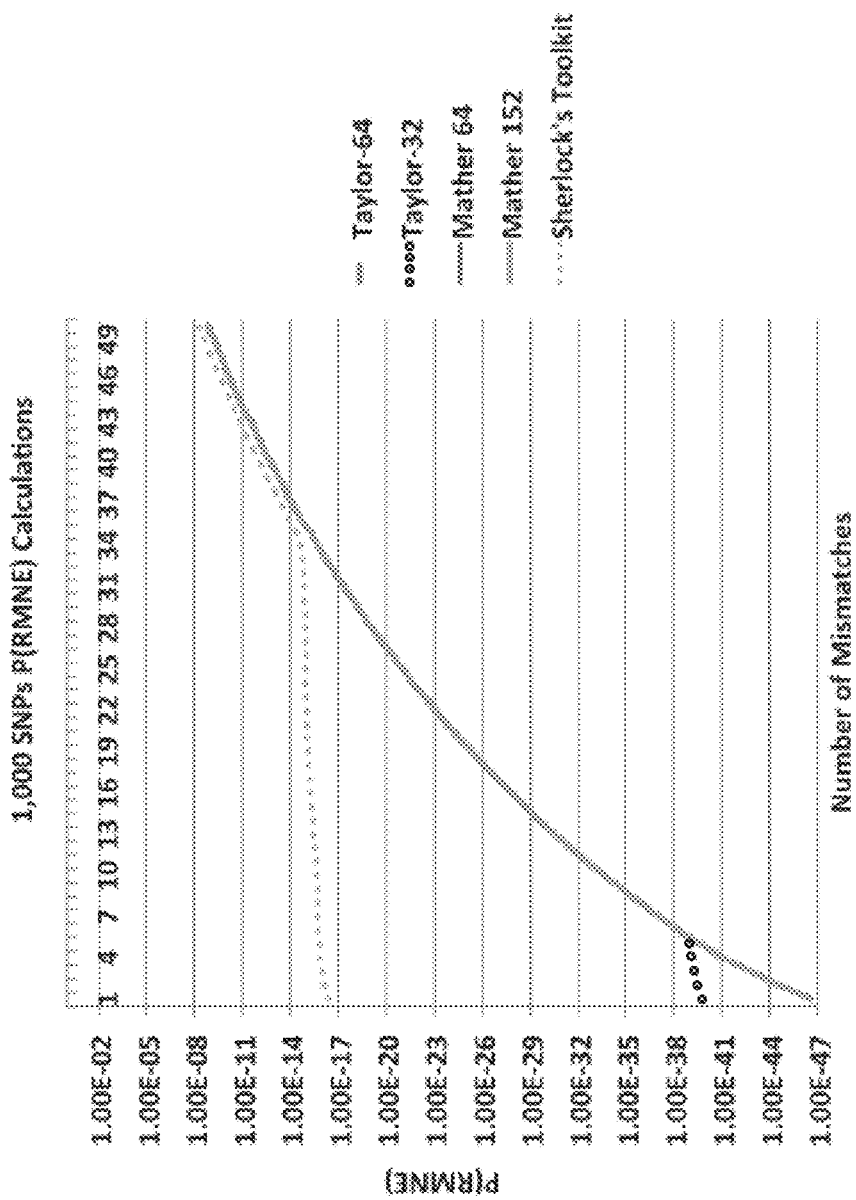
FIG. 55 shows example P(RMNE) calculation methods for 1,000 SNPs.

Most SNPs have just two alleles. The most common SNP allele is named the major allele. The least common SNP allele is named the minor allele. In a mixture profile, the minor allele ratio is calculated as the ratio of minor allele reads divided by the total number of reads. Methods for calculating P(RMNE) have been presented that focus on the SNP loci with no called minor alleles in a mixture profile (e.g., SNPs with minor allele ratios <=0.001 threshold). The P(RMNE) method described by Isaacson et al. was implemented in Sherlock's Toolkit. For larger DNA mixtures, an issue with precision was observed with the Sherlock's Toolkit implementation, see FIG. 55. Higher precision libraries were implemented in an effort to eliminate this precision issue (FIG. 55).

A mixture will have N loci with no called minor alleles. Let p be the average minor allele ratio at these mixture loci. Let q be defined as 1−p such that p+q=1. For an individual with two alleles at a SNP loci the probability for these alleles can be represented as $(p+q)^2 = p^2 + 2pq + q^2 = 1$. A perfect reference match to a mixture has major:major (MM) alleles at every locus with no called minor alleles in the mixture profile. Mismatches are defined as reference loci with major:minor (mM) or minor:minor (mm) at these mixture loci with no called minor alleles. The number of mismatches is defined as L between a reference and a mixture. Let K be $(1-q^2)/q^2$ represent the ratio of transition from MM to non-MM (i.e., mM' or mm). Let Combination represent that standard statistics combination operation for representing possible SNP loci that mismatch between a reference and a mixture.

$$\text{Combination}(n, i) = \binom{n}{i} = \frac{n!}{i!(n-i)!} = \frac{n(n-1)\ldots(n-i+1)}{i!}$$

P(RMNE) can be estimated by the term for no mutations, $q^{2N}$, times the possible combinations of L mismatches, $$\binom{N}{L},$$

times the transition term $K^L$.

$$P_{RMNE}(L) = q^{2N} * \text{Combination}(N,L) * K^L$$

To calculate individual P(RMNE) values:

$$P_{RMNE}(0) = q^{2N} * \text{Combination}(N,0) * K^{L0} = q^{2N}$$

Note that this is the same equation as proposed by Voskoboinik & Darvasi[1] for SNP mixtures with no mismatches.

$$P_{RMNE}(1) = q^{2N} * \text{Combination}(N, 1) * K^1 = q^{2N} * N * K$$

$$P_{RMNE}(L) =$$

$$q^{2N} * \text{Combination}(N, L) * K^L = q^{2N} * \frac{n(n-1)\ldots(n-L+1)}{L!} * K^L$$

Next, a series of P(RMNE) values for the mixture can be optimized for each value of L using the previous $P_{RMNE}(L-1)$ calculation:

$$P_{RMNE}(L+1) =$$

$$q^{2N} * \text{Combination}(N, L+1) * K^{L+1} = P_{RMNE}(L) * \frac{(n-L)}{L+1} * K$$

This optimization has the additional benefit of multiplying a large value, $$\frac{(N-L)}{L+1},$$

with a small value, K, where calculating $$\frac{N!}{L!(N-L)!}$$

by itself can stress the precision capability of an implementation for large values for N and L.

Figure 56:
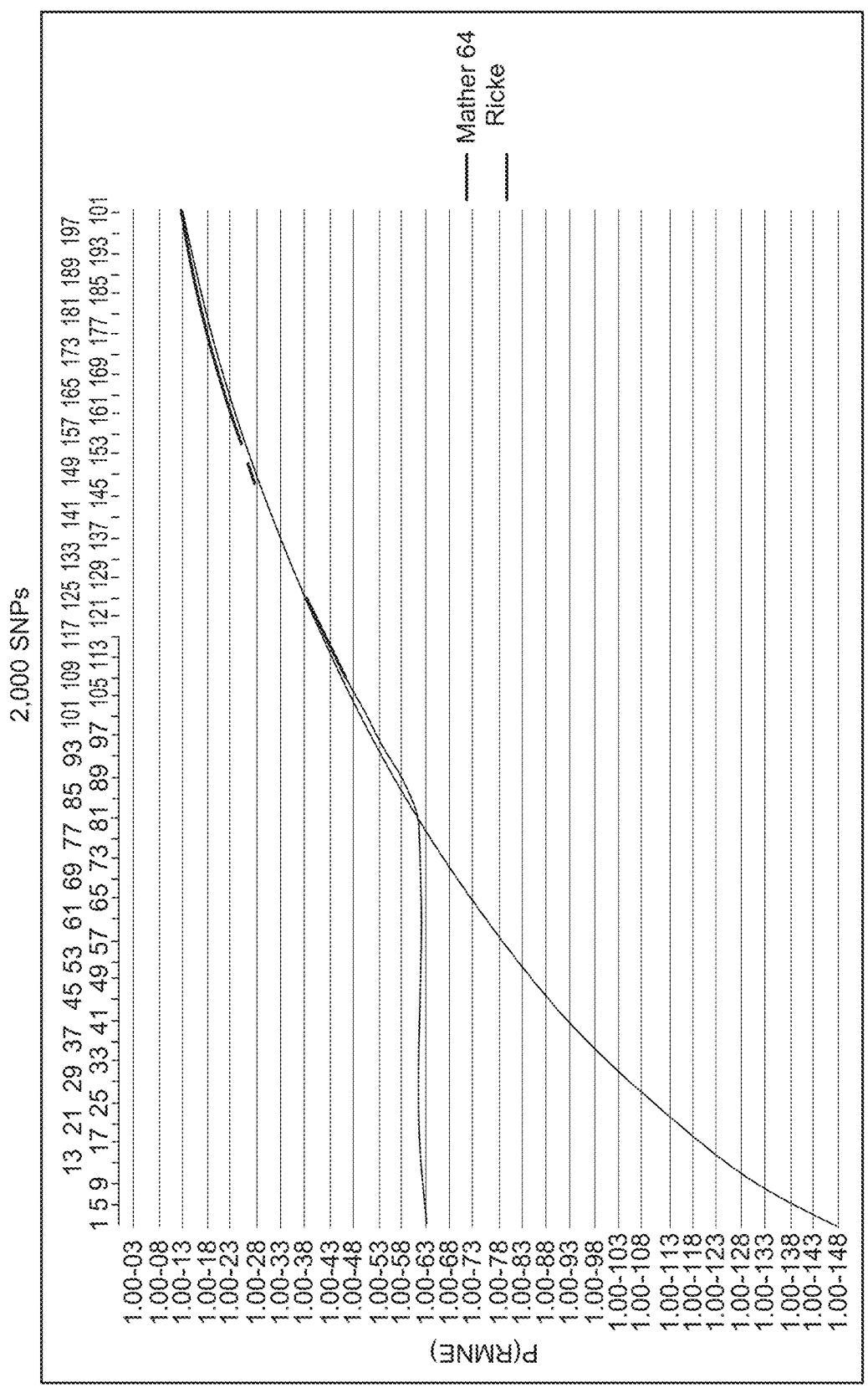
FIG. 56 shows example P(RMNE) calculations for 2,000 SNPs.
Figure 57:
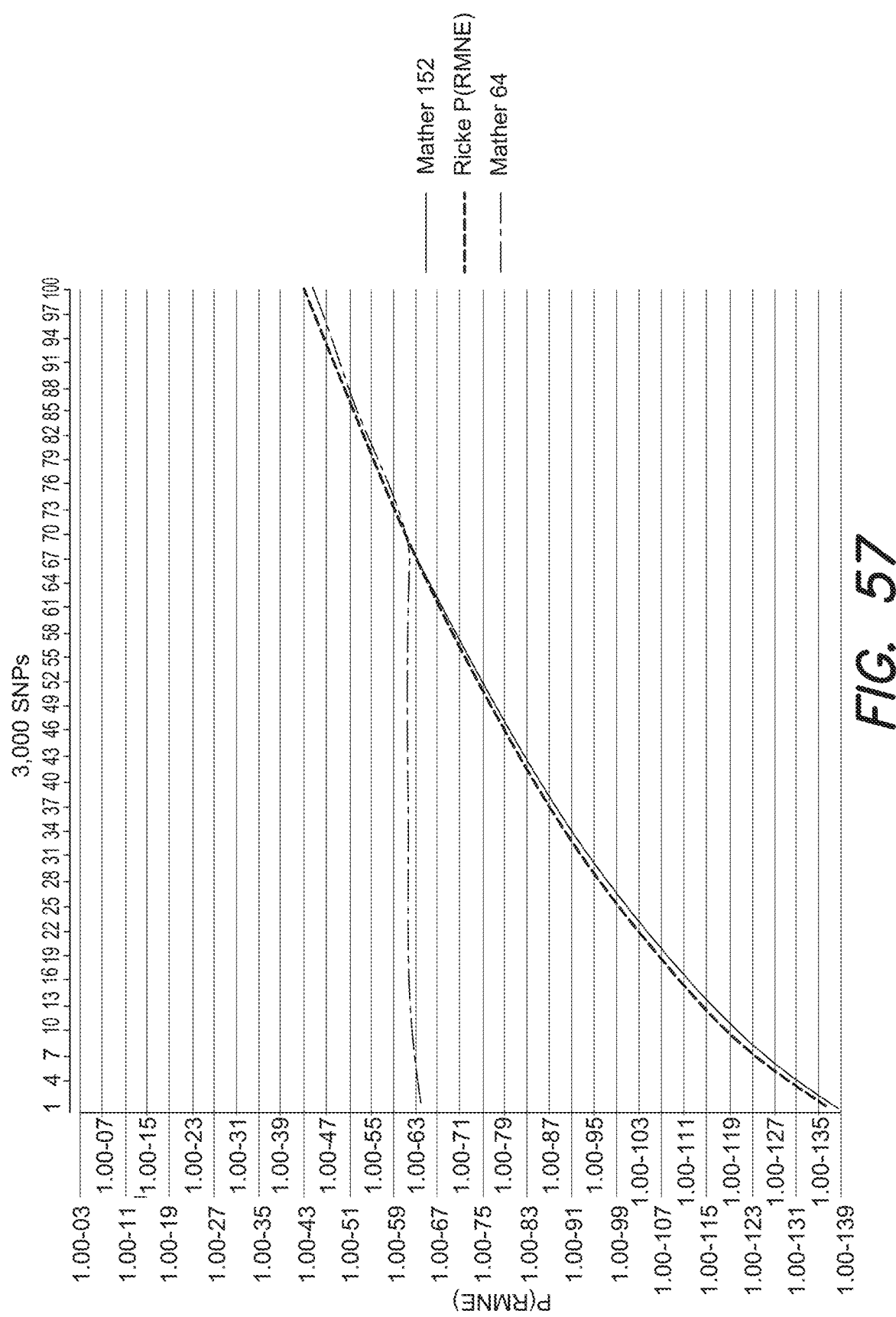
FIG. 57 shows example P(RMNE) calculations for 3,000 SNPs.
Figure 58:
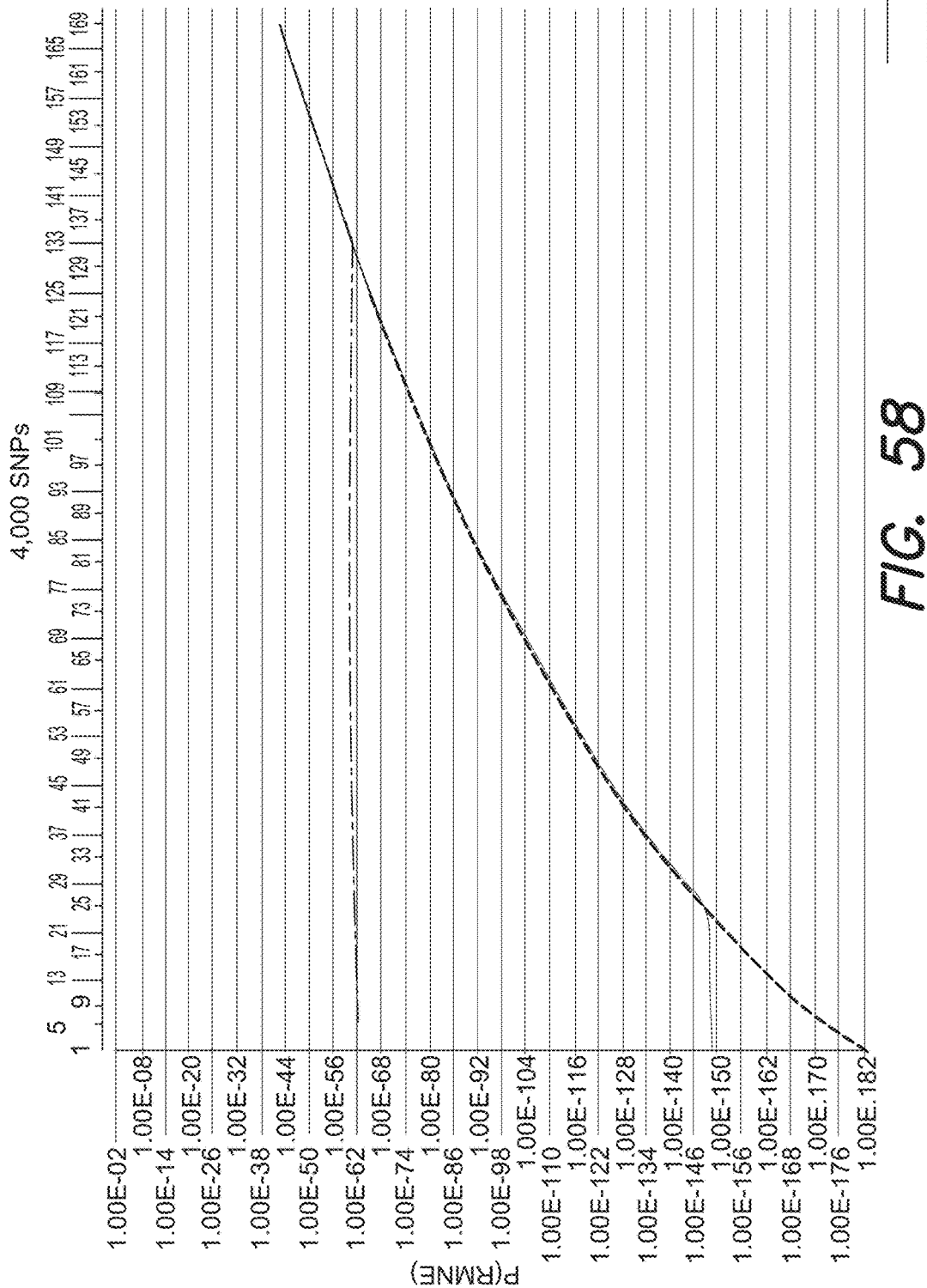
FIG. 58 shows example P(RMNE) calculations for 4,000 SNPs.
Figure 59:
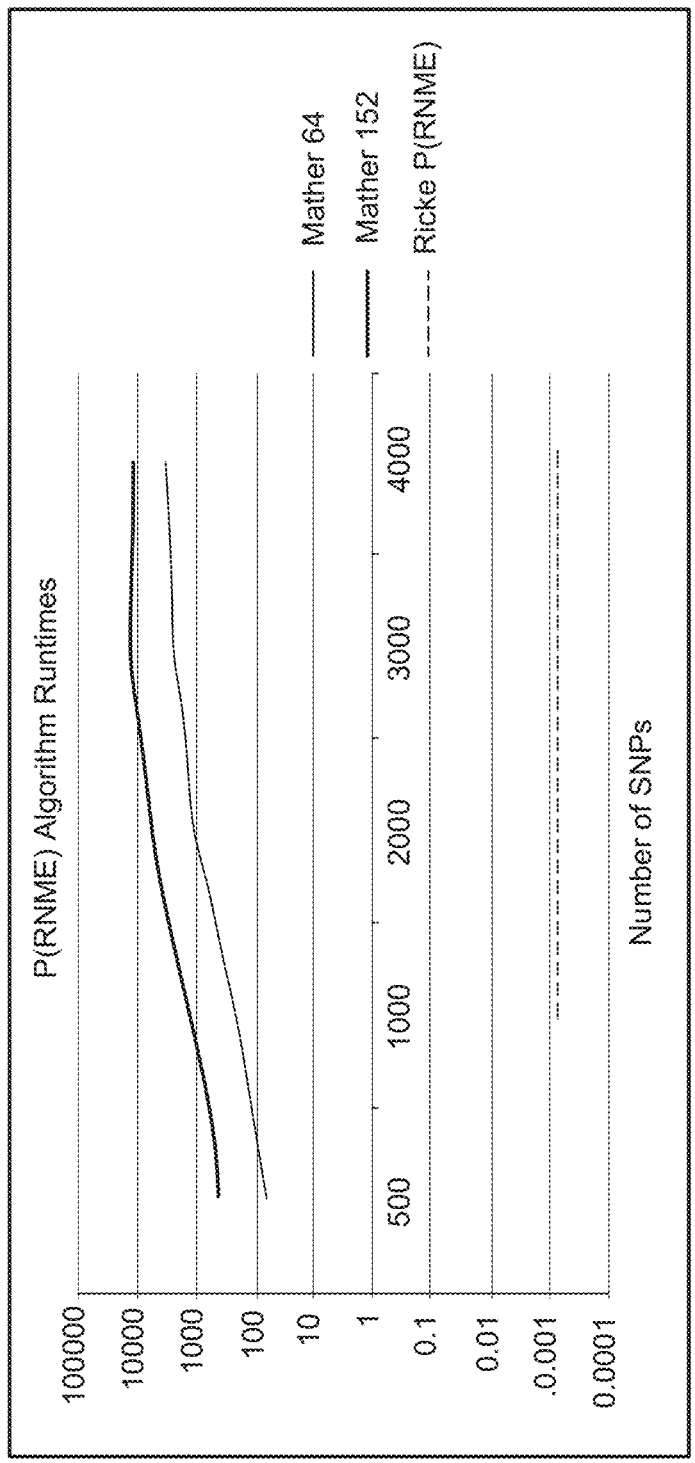
FIG. 59 shows example runtimes for P(RMNE) methods.

The P(RMNE) calculations for 2K, 3K, and 4K SNP panels are illustrated in FIGS. 56, 57, AND 58. The Taylor and Sherlock's Toolkit methods do not scale well and are not included. Note for the 2K SNP panel, the higher precision Mather 152 method fails completely after running for 98 minutes (FIG. 59). Note that precision issues are observed for the Mather 64 method on the 2K, 3K, and 4K SNP panels (FIGS. 56, 57, and 58). The Mather 152 method also has precision issues for the 4K SNP panel (FIG. 58). The method for calculating P(RMNE) in this disclosure is considerably faster than other methods, has high precision, and does not have stability issues related to SNP panels being evaluated.

High Performance Kinship Comparisons of DNA SNP Profiles

Individuals inherit DNA from each of their parents. For autosomal chromosomes, this results in two DNA alleles for single nucleotide polymorphisms (SNPs). Polymorphic loci are compared between two individuals to determine if they are related or unrelated. Four comparisons are needed to compare the possible alleles at each locus. For N loci, this is 4N comparisons. The alleles for one locus for an individual can be mapped onto binary hits labeled [ACGT][ACGT] with the first set of bits being used only when two of the same allele are present (e.g., TT encodes as hex 11, GG as 22, CC as 44, AA as 88, GT as 03, CT as 05, CG as 06, etc. A logical bit AND of the encoded alleles between two individuals will result in 0, 1, or 2 bits set in the result depending upon the number of shared alleles at the locus. The hardware population count instruction can count the number of bits set in a single computer instruction on most modern computer systems. Multiple alleles can be mapped onto computer register with 4 alleles for 32-bits, 8 alleles for 64-bits, and 32 alleles for 256-bit systems. With this encoding the alleles for two individuals can be compared in N/4, N/8, and N/32 AND instructions depending on computer system register size. This data encoding and comparison strategy enables high performance kinship comparisons between large numbers of individuals on current computer systems. Even higher performance (roughly 100-times faster) can be achieved by leveraging parallel cores on current graphics processing units (GPUs).

For a SNP locus with two possible alleles, an individual may have AA, AG, GA, or GG. Four comparisons are need to compare the alleles of two individuals Individual1($a_1a_2$) and Individual2($a_3a_4$) at a locus: $a_1 \times a_3$, $a_1 \times a_4$, $a_2 \times a_3$, and $a_2 \times a_4$. It might be possible to reduce the number of comparisons by using sorting order of alleles, but loci with alleles like AG and GT force extra comparisons. The number of comparisons can be reduced by mapping alleles to binary bit encodings. A one bit is set for the first allele in the lower set of binary bits [ACGT][ACGT] with one bit position for each possible DNA base. If the second allele is the same as the first allele, it is encoded in the left-most (upper) set of four bits. If the two alleles are different, then then each of the corresponding bits are set in the right-most (lower) bit set. This creates an 8-bit encoding for both alleles for an individual for a SNP locus. Table 32 illustrates hexadecimal bit encodings in binary. Shared alleles between two individuals can be compared with the logical AND operation (Table 33). If one allele is shared between two individuals, there will be a corresponding 1 bit in the right-most set of bits. If two alleles are shared, then there will be two 1 bits set in the 8-bit encoding. The hardware population count (popcount) instruction can count the number of bits set in the result in a single operation. Multiple loci can be mapped onto hardware registers with 8-bits required per locus. A 64-bit register can compare 8 alleles in one AND operation and a 256-bit register can compare 32 alleles in one AND operation. This data encoding and hardware instruction encoding will outperform traditional allele comparison algorithms. This method can be even further parallelized on graphics processing units (GPUs) like the NVidia K40 and K80 Tesla cards with likely greater than a 100× performance improvement over computer cores with parallelization with thousands of GPU cores.

TABLE 32

Hex Bit Representations

| Base 10 | Base 16 - Hex | Base 2 - Binary |
|---------|---------------|-----------------|
| 0  | 0 | 0000 |
| 1  | 1 | 0001 |
| 2  | 2 | 0010 |
| 3  | 3 | 0011 |
| 4  | 4 | 0100 |
| 5  | 5 | 0101 |
| 6  | 6 | 0110 |
| 7  | 7 | 0111 |
| 8  | 8 | 1000 |
| 9  | 9 | 1001 |
| 10 | A | 1010 |
| 11 | B | 1011 |
| 12 | C | 1100 |
| 13 | D | 1101 |
| 14 | E | 1110 |
| 15 | F | 1111 |

TABLE 33

Logic AND Operator

| Bit 1 | Bit 2 | Operator | Result |
|-------|-------|----------|--------|
| 0 | 0 | AND | 0 |
| 0 | 1 | AND | 0 |
| 1 | 0 | AND | 0 |
| 1 | 1 | AND | 1 |

Kinship Relationships

A parent and child share a common allele are all autosomal loci identity by descent (IBD). In a perfect set of data, all of the compared SNP loci will be at least 1 for this relationship. In contrast, siblings by chance alone may have no shared alleles at 25% of loci, 1 shared at 50%, and 2 shared at 25% by IBD. This makes it easy to distinguish between parent-child and sibling first degree relatives. Half-siblings should share roughly 50% of their autosomal SNP alleles by IBD as they randomly share or not the same chromosome segment from their shared parent. Grandparents and grandchildren, aunts/uncles and nieces/nephews have 25% IBD plus random allele matches. Alleles not inherited from a common ancestor may be identical by chance—identity by state (IBS).

High Throughput Sequencing Trace Profile Detection

Trace profiles are DNA profiles that exist in a DNA mixture at quantities that are too low to be detected by standard DNA mixture analysis techniques[1,2]. The minor alleles of trace profiles in DNA mixtures are often not detected because portions of these profiles are missing or hidden in the sequencing noise produced by High Throughput Sequencing (FITS). Three novel methods are introduced that enable the detection of trace profiles. The first method, mAR Zipper, enables better trace detection by creating new trace reference profiles that subset loci that are the most likely to have minor allele ratio (mAR) values above sequencing noise. This method creates special profiles of the strongest 50% of the SNP loci for references as the most likely to be above noise threshold in mixtures with trace profiles. The second and third methods (Experiment Read Count Minor allele cut-off, Experiment Read Count Optimization), enables the detection of trace profiles by reducing the amount of sequencing noise which makes it possible to distinguish some trace profiles from noise.

mAR Zipper Method

The most common allele at a SNP locus is referred to as the major allele (M). The less common allele is referred to as the minor allele (m). For each locus, an individual will have two major alleles (MM), two minor alleles (mm), or one major allele and one minor allele (mM). The minor allele ratio (mAR) at a locus is defined as the number of minor allele reads observed divided by the total number of reads observed. In traditional DNA mixture analysis, the SNP panel loci are characterized for reference and mixture profiles. To characterize a reference profile, loci that have one minor allele (mM) will have a mAR value between 0.1 and 0.9 with a majority having a mAR value near 0.5. Factors such as copy number variants, novel SNPs, and primer efficiency are likely sources to this large mAR range. Loci that have two minor alleles (mm) will have mAR values between 0.9 and 1. Loci without a minor allele (MM) will have mAR values less than 0.1.

Loci with high reference mAR values will have higher trace mixture mAR values. The loci colored blue in FIG. 1 represent loci with mAR values greater than 0.5 in a reference profile. This reference profile represents the low contributor in the 1:400 two person mixture in FIG. 2. In FIG. 2, loci colored blue represent loci with mAR values greater than 0.5 in the reference profile of the minor contributor. A higher percentage of these blue loci are above the 0.001 cut-off used in DNA mixture analysis to determine if a minor allele is present at a specific locus in a mixture. To leverage this difference the reference trace profile loci are selected as a subset that only include loci with mAR values less than 0.1 (MM) and greater than 0.5 (strongest mM and mm loci). The reference trace profiles are compared against DNA mixtures using standard DNA mixture techniques.

Figure 60:
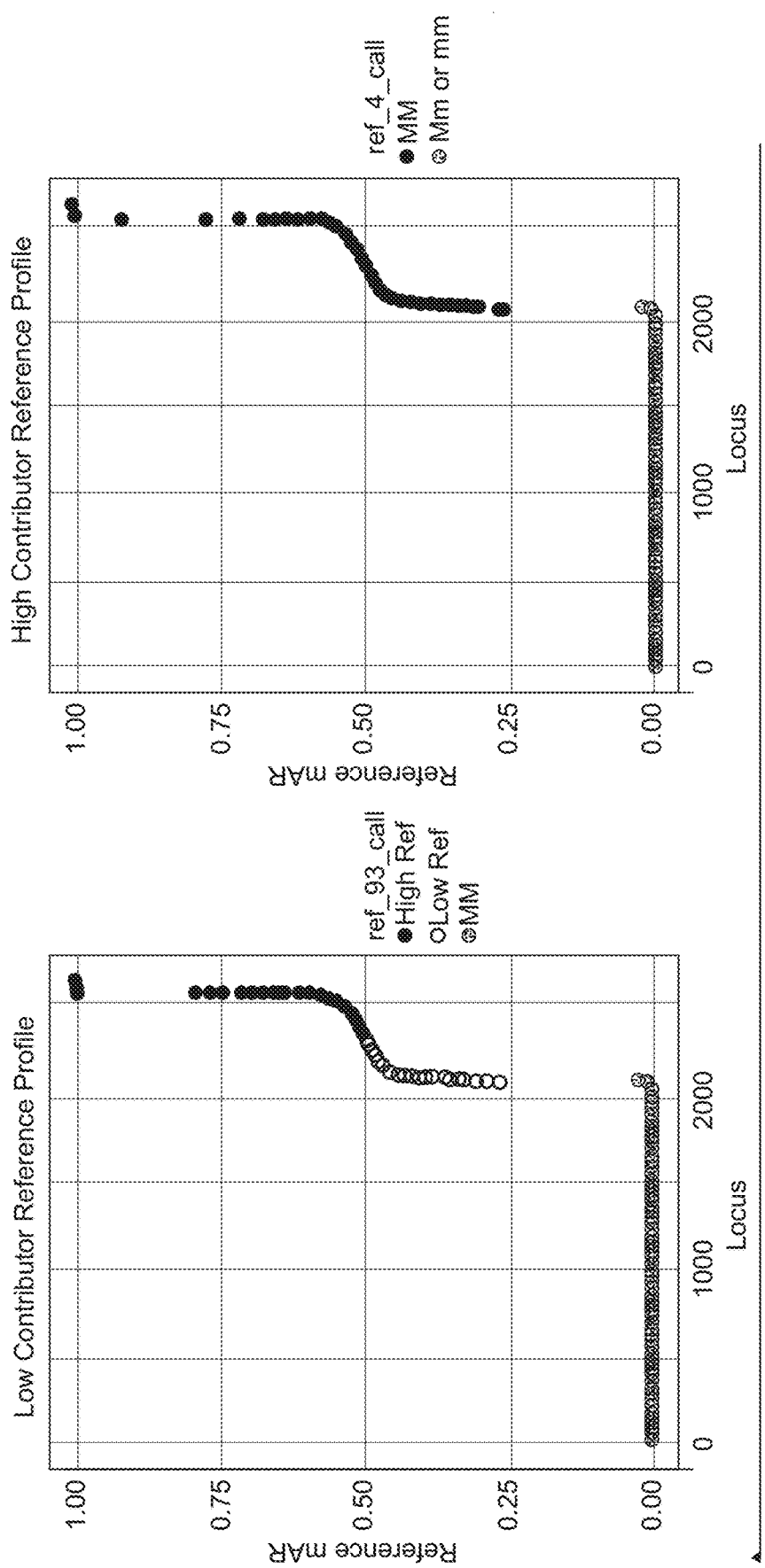
FIG. 60 shows reference mAR profiles of high and low contributors in the 1:400 defined mixture.

FIG. 60 shows reference mAR profiles of high and low contributors in the 1:400 defined mixture. Loci with mAR values greater than 0.1 are characterized as having at least one minor allele. Loci with mAR values greater than 0.5 are colored blue for the low contributor. Loci with mAR values less than 0.5 and greater than 0.1 are colored red for the low contributor. For the high contributor all loci with at least one minor allele are colored green. For both reference profiles loci without a minor allele (MM) are colored gray.

Figure 61:
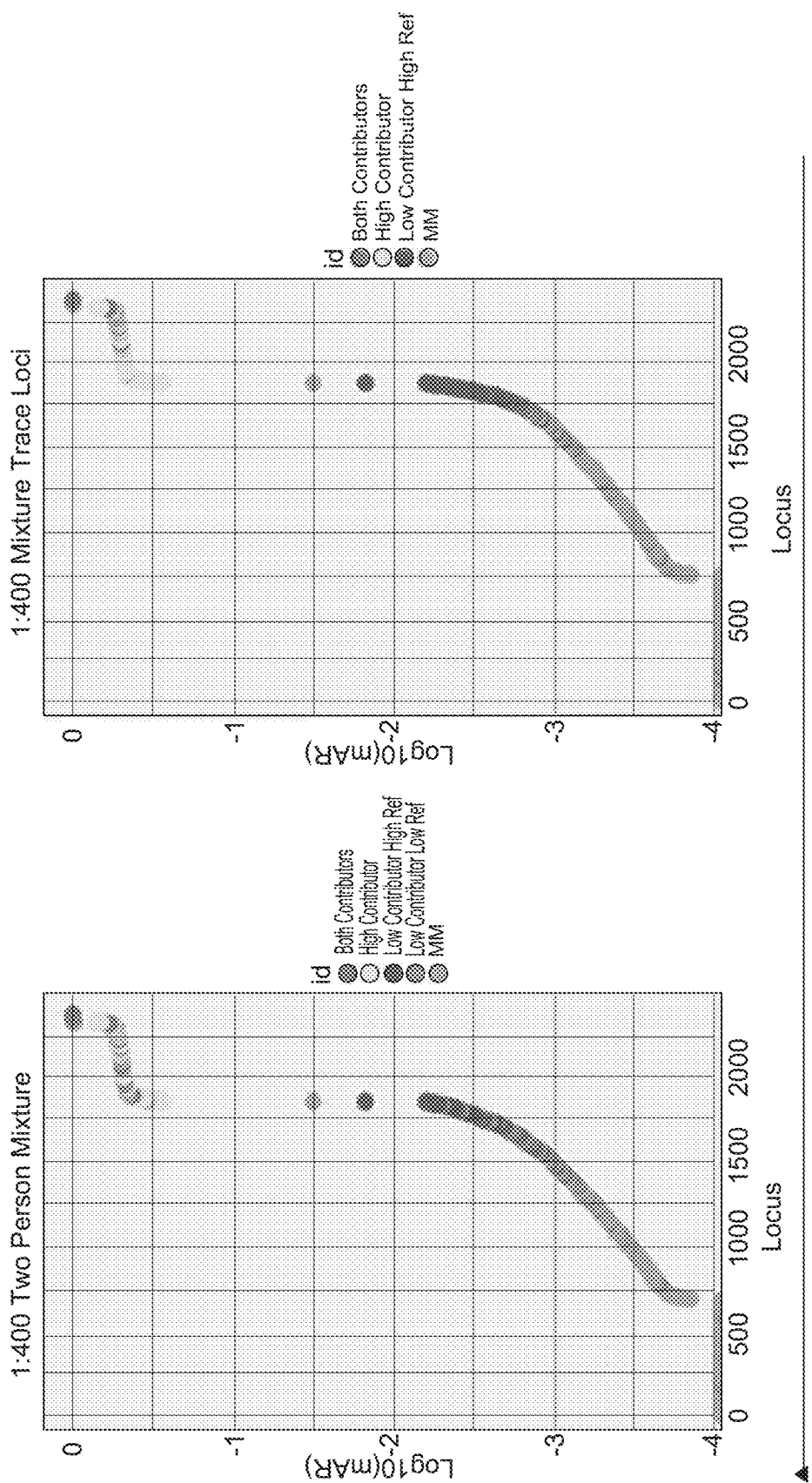
FIG. 61 shows a mAR plot of the 1:400 Defined Mixture experiment without any modifications on the left.

FIG. 61 shows a mAR plot of the 1:400 Defined Mixture experiment without any modifications on the left. Note the high number of red Low Ref loci below the Log(0.001) cut-off. On the right, the same 1:400 Mixture with only the MM and High Ref loci plotted from the low contributor. Note how fewer used loci fall below the 0.001 cut-off.

This method was tested on a 1:400 Defined DNA mixture and a DNA sample taken from a plastic object that had been touched by five separate individuals. The zipper method enabled the detection of the low contributor in the 1:400 Defined DNA mixture. Standard DNA mixture analysis was able to detect three of the five individuals that touched the plastic object. The mAR Mixture Zipper Method was able to detect four of the five individuals.

The cut-off values used to create the mAR zipper reference can be modified to reflect use-case. Using a higher mAR cut-off enables better detection of trace profiles but decreases mixture analysis capabilities due to fewer SNP comparisons. Using a lower cut-off value will decrease trace detection but increase mixture analysis.

Experiment Read Count Minor Allele Cut-Off Method

The Experiment Read Count Minor Allele Cut-Off method enables the detection of trace profiles by reducing the amount of sequencing noise which makes it possible to distinguish some trace profiles from noise. The mAR is calculated by dividing the number of minor alleles by the total number of reads at a locus. The mAR is used to determine if a minor allele exists at a locus. For DNA mixture analysis, if the mAR is greater than 0.001, then that locus is characterized as having at least one minor allele[1]. Loci that do not sequence well will have low total read counts. High throughput sequencing has a ~1% error rate which results in inaccurate reads[3]. As sequencing depth increases the total number of erroneous reads also increases. When sequencing error occurs at the minor alleles of poorly performing loci there is a risk that these loci will be improperly characterized. To prevent improper characterization a minimum minor allele count is required for the mAR to be calculated. This minimum minor allele count is dependent on the total number of reads in the experiment. If the number of minor allele reads does not meet the minimum, that locus is characterized as not having a minor allele. Table 34 shows the effect of filtering based on Read Count Optimization on mAR. With a read count filter of 10 reads, some loci where a minor allele was previously counted (mM) are now counted as having two major alleles (MM). These filtered minor alleles are likely the result of sequencing noise.

TABLE 34

Four loci and with mAR values before for and after apply the Experiment Read Count Optimization method.in a mixture. Note that with a Read Count Optimization filter of 10, two of these loci (1 and 2) are counted as having a minor allele. If this filter were not used locus 3 would not be characterized as having a. minor allele despite having the same number of minor alleles as locus 4. Reducing the amount of sequencing noise in a mixture improves mixture analysis.

| Locus | Minor Allele Reads | Total Reads | Unfiltered mAR | Filtered mAR |
|---|---|---|---|---|
| 1 | 11 | 100 | 0.11 | 0.11 |
| 2 | 11 | 10000 | 0.0011 | 0.0011 |
| 3 | 5 | 10000 | 0.0005 | 0 |
| 4 | 5 | 100 | 0.05 | 0 |

Experiment Read Count Optimization Method

An Experiment Read Count Optimization method enables the detection of trace profiles by reducing the amount of sequencing noise which makes it possible to distinguish some trace profiles from noise. If a trace profile exists in a DNA sample, sequencing that sample at very high coverage will results in more noise mixed in with the trace profile. This occurs because higher coverage results in more sequencing error. By limiting the number or reads in a forensics sample noise is reduced, which increases the trace signal. This method also optimizes high throughput sequencing by enabling more barcodes to be run per sequencing event.

Figure 62:
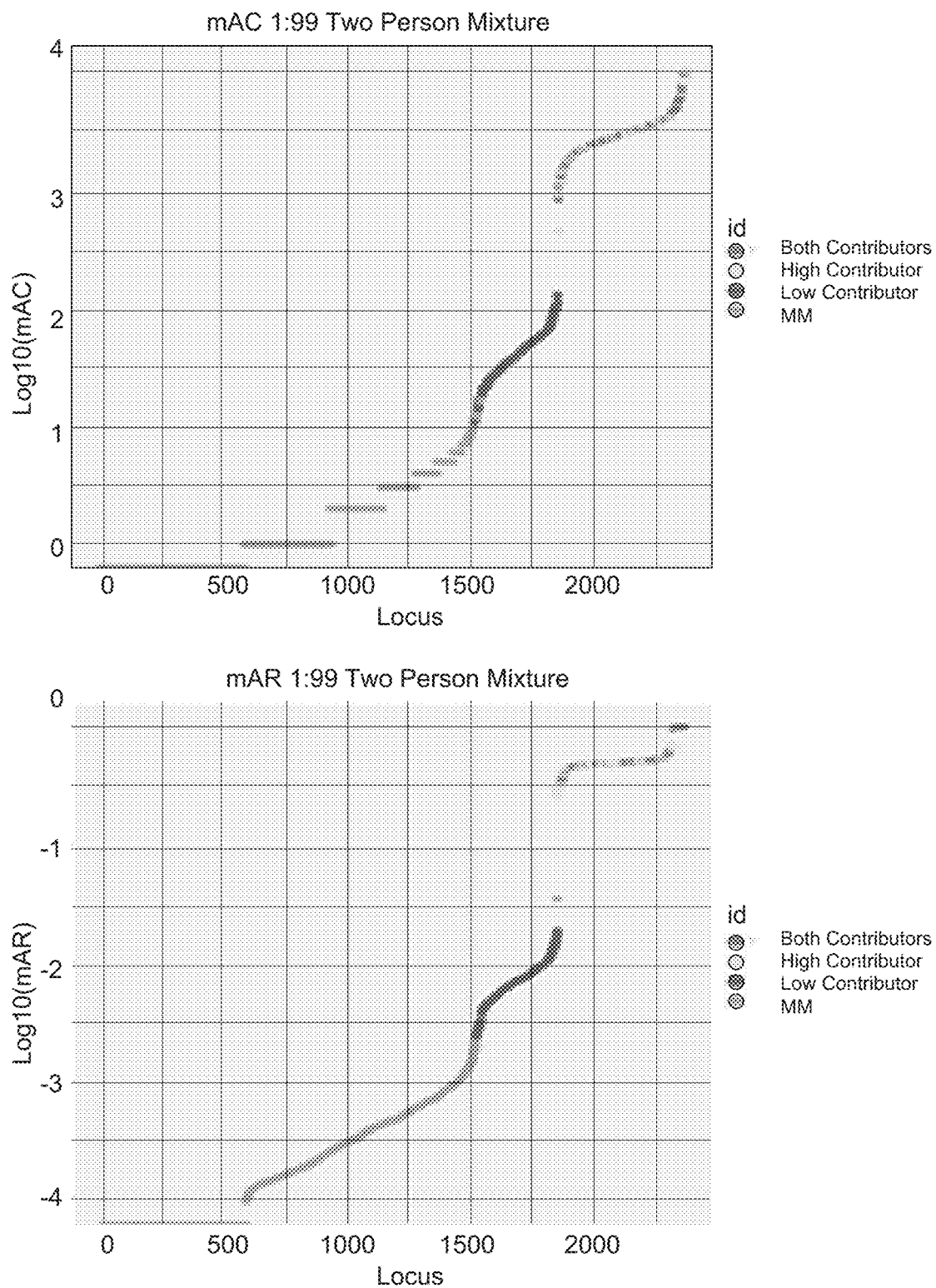
FIG. 62 shows an minor allele count (mAC) and minor allele ratio (mAR) plots of the 1:400 Defined Mixture experiment without any modifications on the left.

FIG. 62 shows an mAR plot of the 1:400 Defined Mixture experiment without any modifications on the left. Note the first ~400 loci in the plot where loci that should be MM do not have any minor allele counts. On the right the sequencing depth of this experiment was reduced in half to 10 million reads. This change results in ~700 loci that should be MM having no noise minor allele counts.

Minor Allele Count DNA Forensics Mixture Analysis

The minor allele ratio (mAR) may be used to determine if a minor allele is present at a specific locus in high throughout sequencing (HTS) data. The mAR is calculated as the number of minor alleles divided by the total number of reads at a locus. For DNA forensics applications, the minor allele count (mAC) at a specific locus can substitute for the mAR to determine if a minor allele is present at a specific locus. For mAC data, noise becomes easier to be identified and removed from sequencing experiments by using mAC frequency filters. The mAC approach appears to be an equivalent or possibly even superior approach for DNA mixture analysis.

The minor allele count (mAC) is defined as the number of minor allele reads observed at a SNP locus. For high concentration DNA contributors in mixtures the loci with a minor allele, strongly correlate with high mAC values. This correlation is proportional to contributor DNA concentration. Minor alleles for low DNA concentration contributors correlate with low mAC values unless they overlap with minor alleles of other individuals. If all subjects present in a mixture do not have a minor allele at a particular locus then the mAC for that locus should be equal to zero (i.e., major:major alleles for all individuals contributing to the mixture). Sequencing errors can result in low mAC values greater than zero at loci where no contributor has a minor allele. In DNA forensic mixture analysis there can be several people in the HTS data at varying quantities. By taking into account sequencing platform and sequencing depth, mAC value due to sequencing noise can be estimated. With this estimate, a mAC threshold is set just above estimated noise. Loci with mAC values above the noise threshold are correctly identified as having a minor allele.

Figure 63:
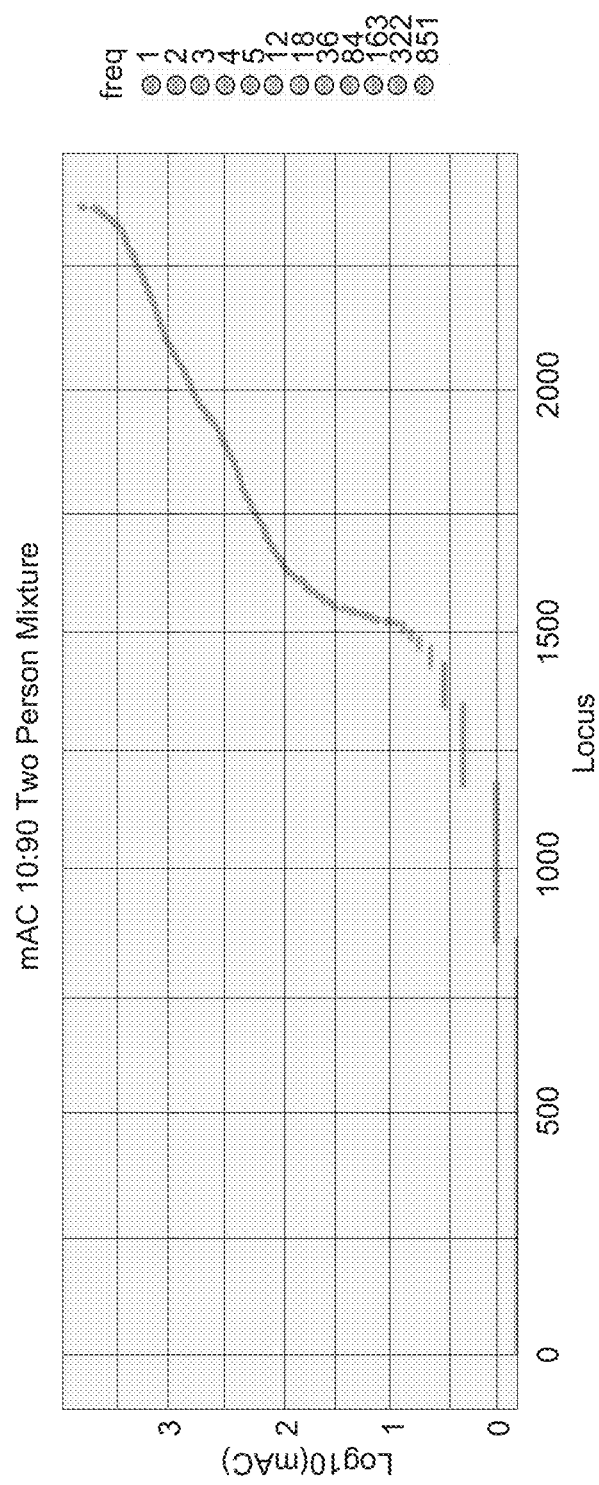
FIG. 63 shows plots of 1:99 two person defined mixture using the mAC on the left and mAR on the right.

FIG. 63 shows plots of 1:99 two person defined mixture using the mAC on the left and mAR on the right. Note the similarities between the two plots. Using the mAC method, a threshold of 10 would be used to determine if a minor allele is present in a mixture. This value is slightly higher than the number of reads that would be expected at a locus due to noise. Using the mAR method, a threshold of 0.001 would be used to determine if a minor allele is present in a mixture. This value was determined empirically. It is noted that the system may use mAC values instead of mAR values.

Minor Allele Count Frequency Filter

The Minor Allele Count Frequency Filter method enables the detection of added profiles by reducing the amount of sequencing noise which results in fewer mismatches and better detection of trace profiles. Sequencing noise occurs at a constant rate[1] while sequencing signal varies due to DNA concentration, and primer performance. This results in high mAC variability in sequencing signal and low mAC variability in sequencing noise. This difference in mAC variability can be used to filter out the sequencing noise. By converting loci with high mAC frequencies to 0 (i.e., major: major allele call), noise is filtered from the mixtures.

FIG. 63 shows plots of 10:90 two person defined mixture rank-ordered by mAC. Loci are colored by the mAC frequency. Eight-hundred and fifty-one loci did not have a minor allele. Three-hundred and twenty-two loci that should not have a minor allele have a mAC equal to 1. Twelve loci have a mAC equal to 7 that should not have a minor allele. Five loci have a mAC equal to 55. These loci have minor alleles that belong to the low contributor.

Figure 64:
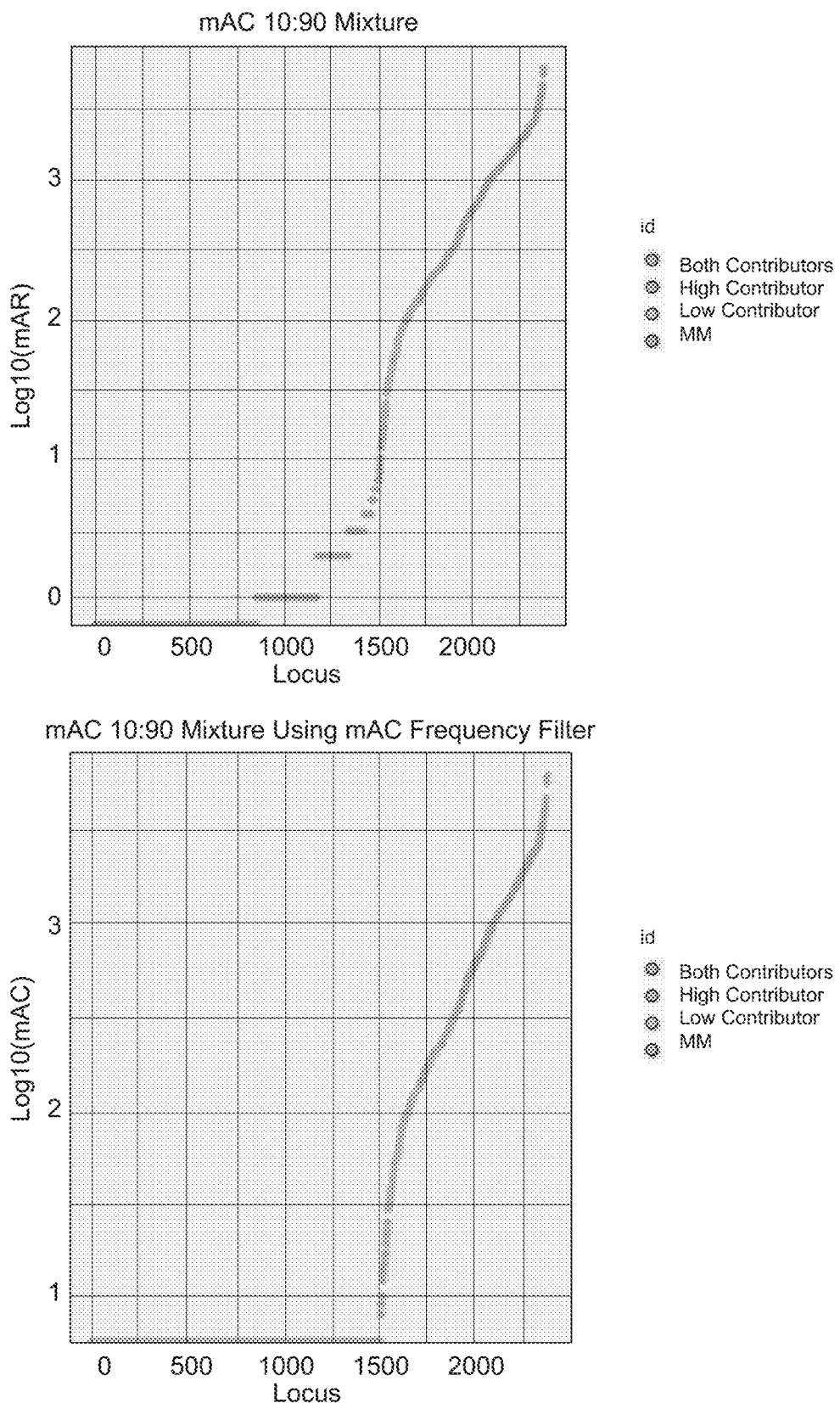
FIG. 64 shows plots of 10:90 two person defined mixture using the mAC on the left and mAC Frequency Filter on the right.
Figure 65:
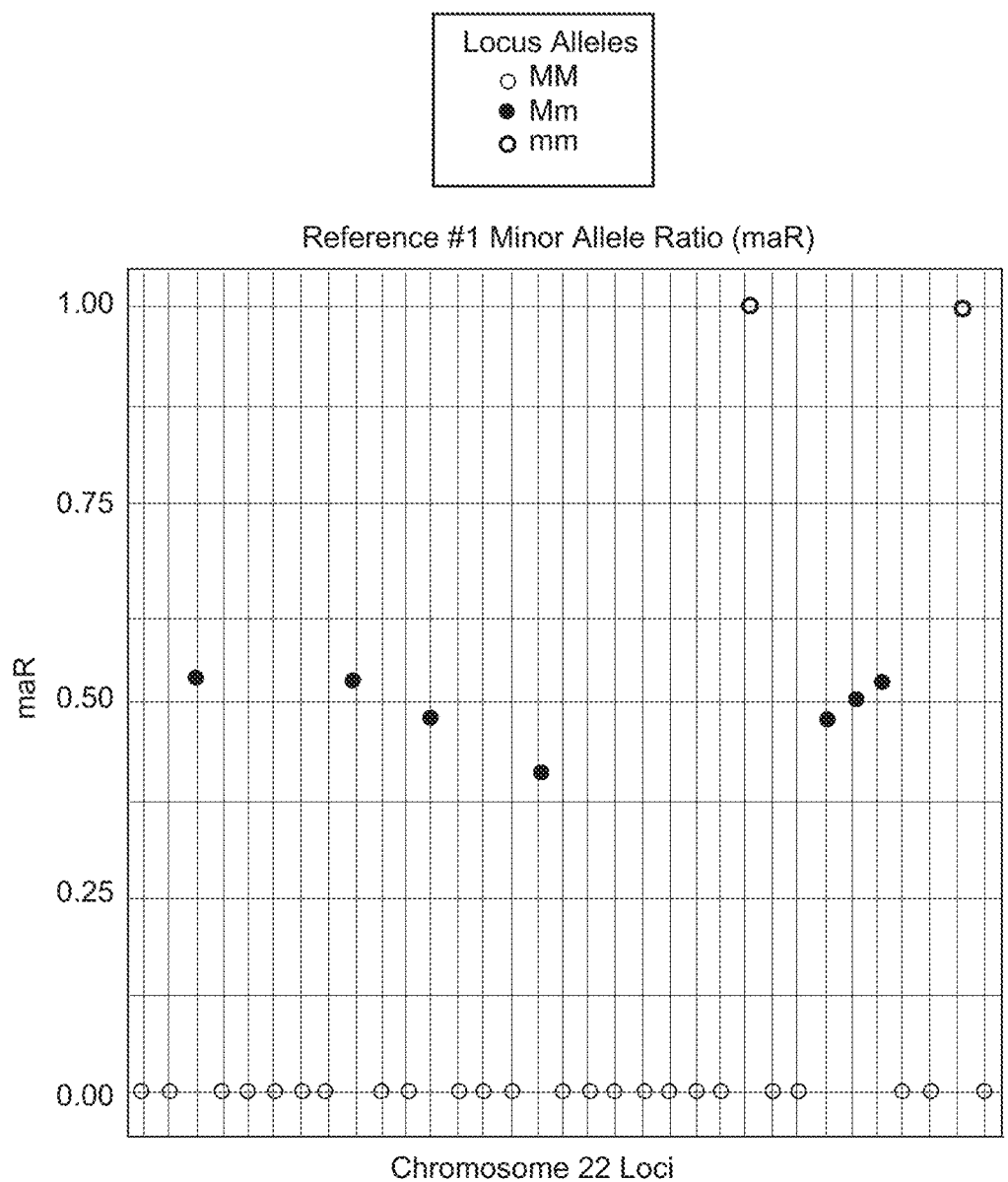
FIG. 65 shows an example reference 1 chromosome 22 loci minor allele ratios.
Figure 66:
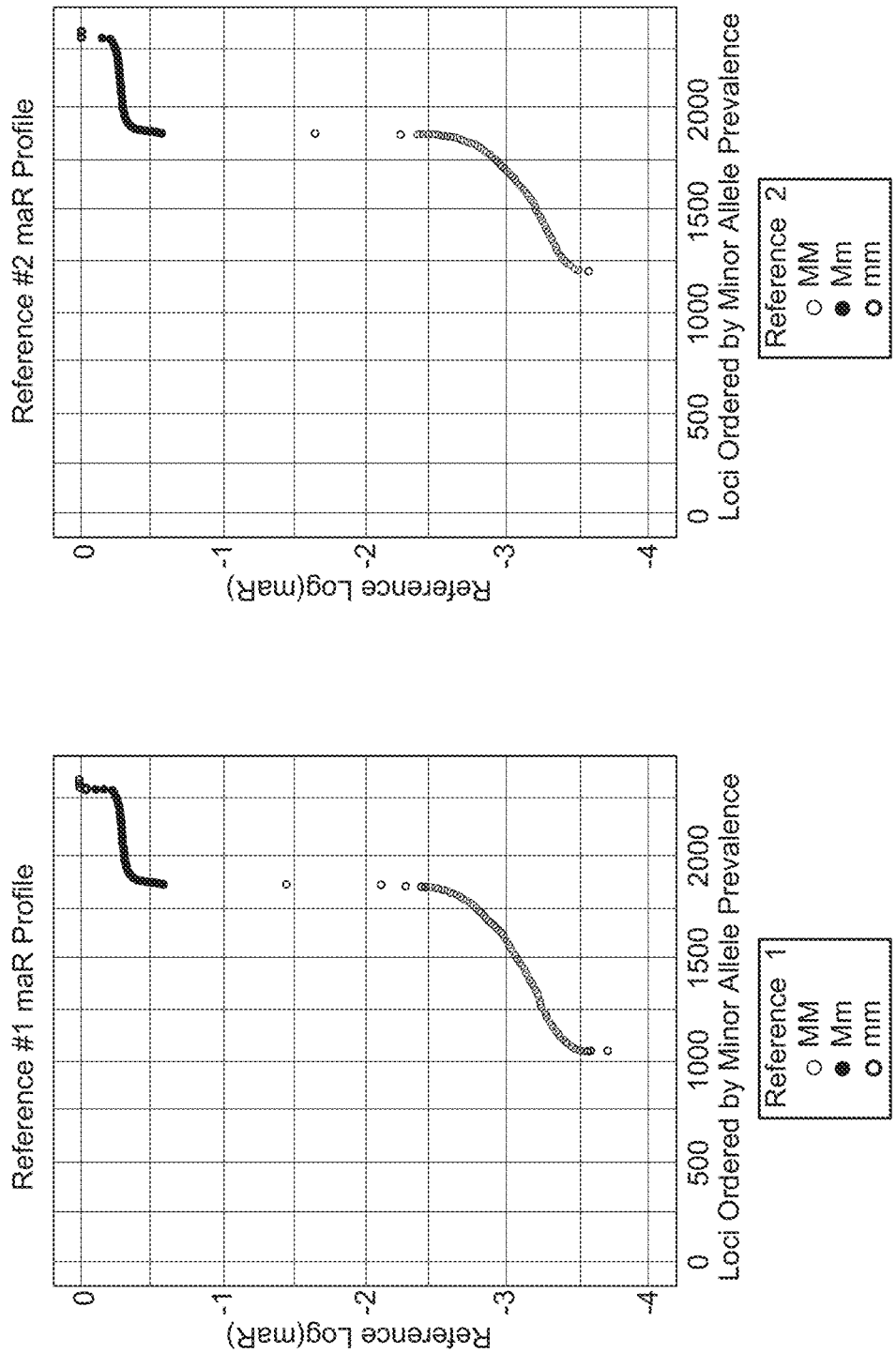
FIG. 66 shows example sorted minor allele ratios for references 1 and 2.
Figure 67A:
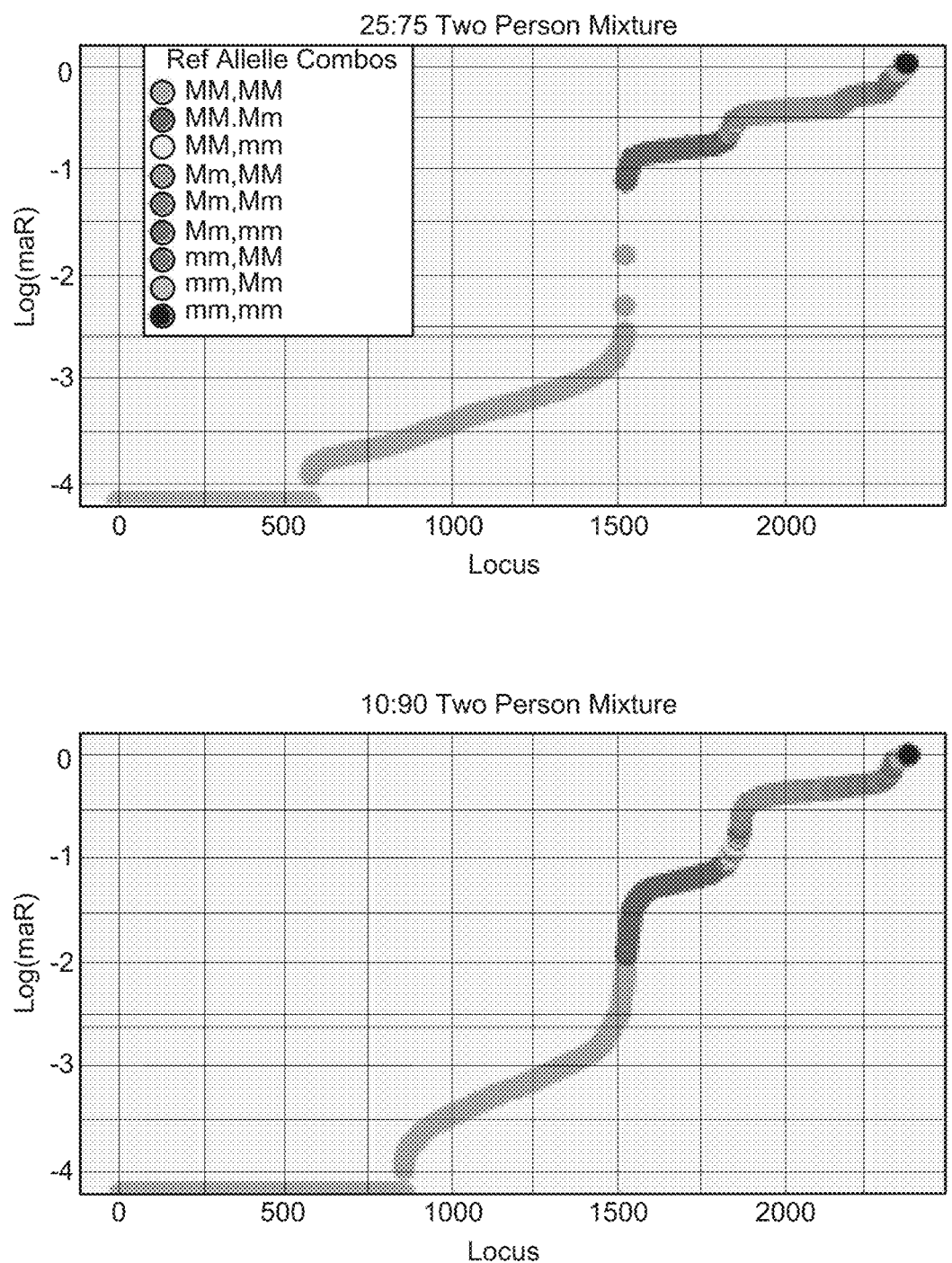
FIG. 67 shows example two-person Dilution Series with DNA ratios of 25:75, 10:90, 1:99, and 1:200.
Figure 67B:
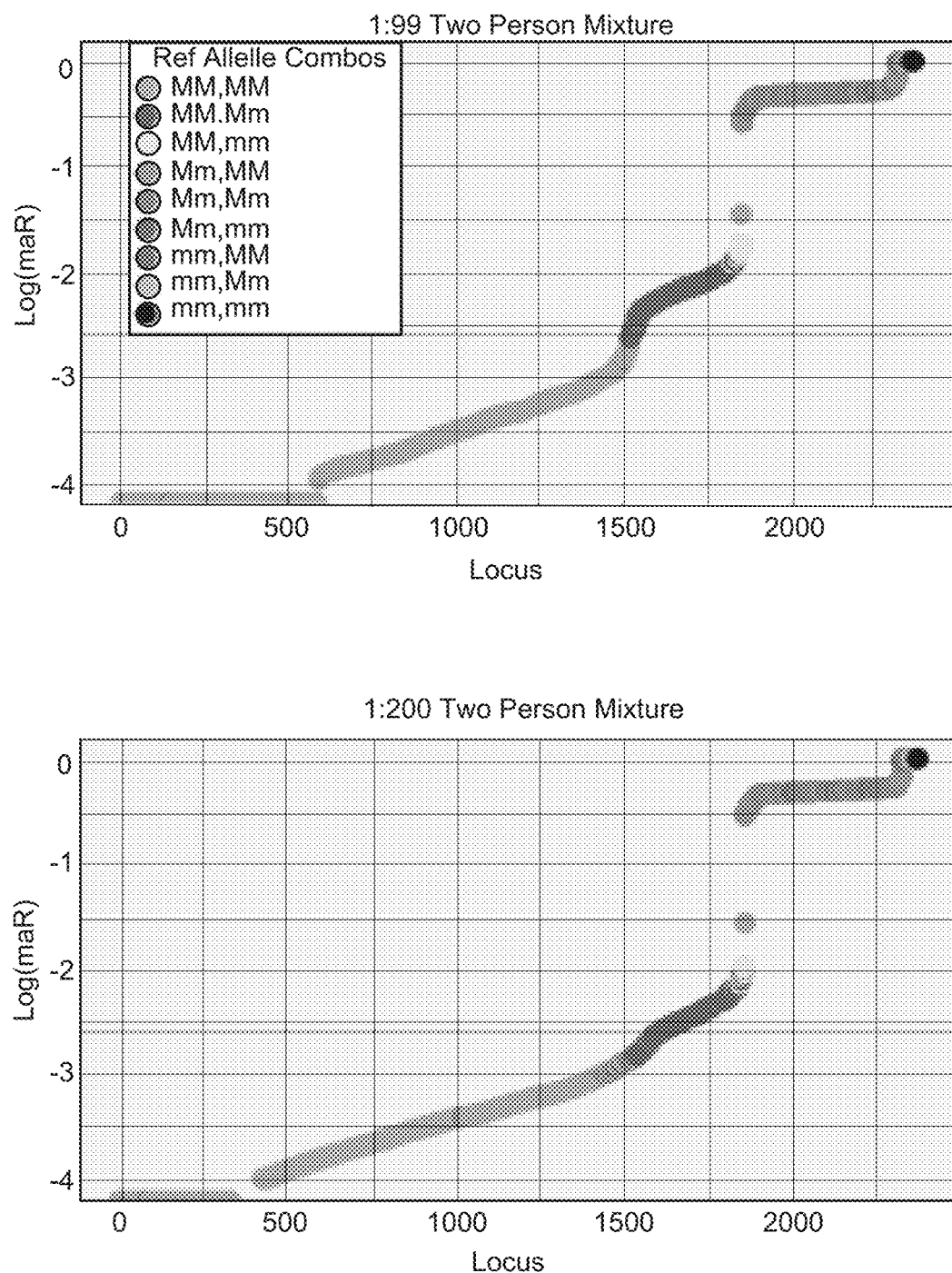
Figure 68:
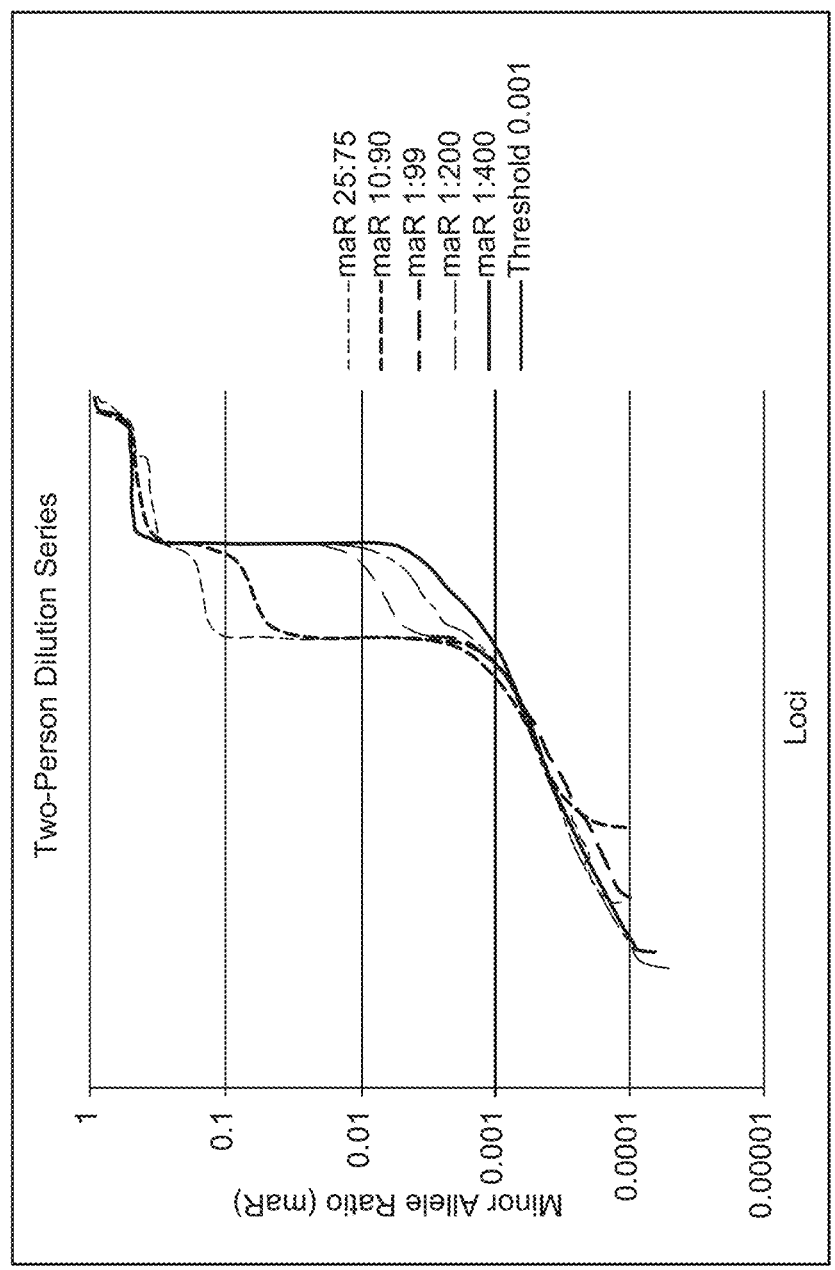
FIG. 68 shows example sorted two-person dilution series.
Figure 69:
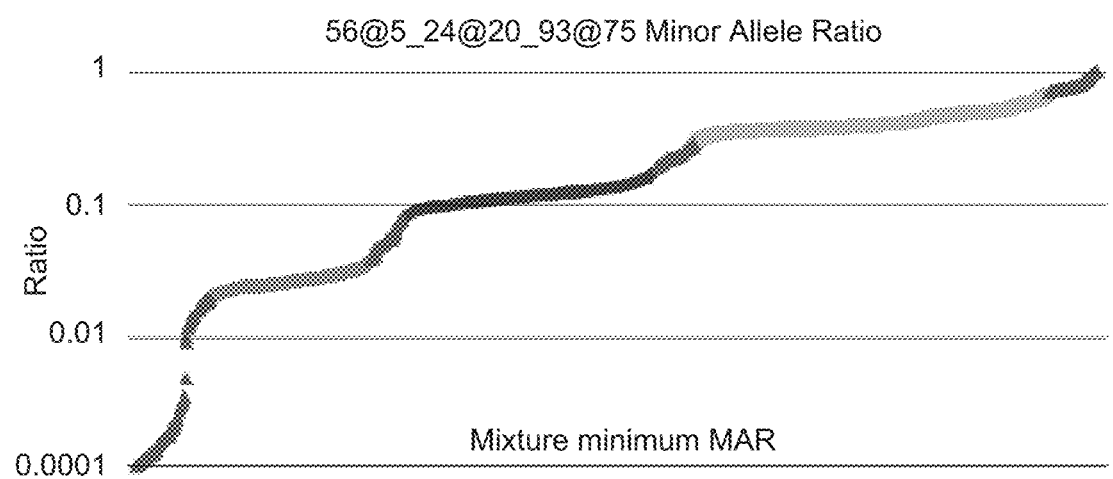
FIG. 69 shows an example of Plateau mixture deconvolution for three-person mixture with DNA concentrations 5%:20%:75%.
Figure 70:
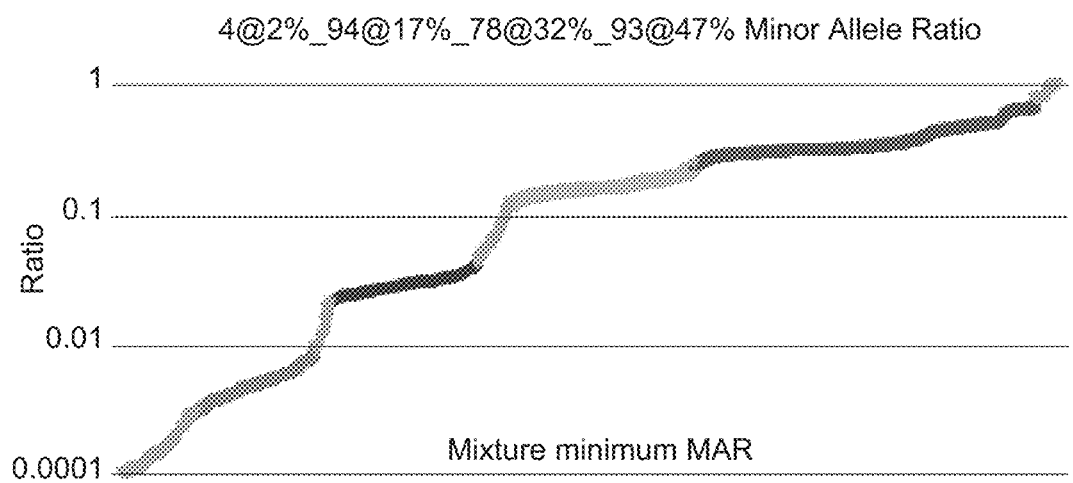
FIG. 70 shows an example of Plateau mixture deconvolution for four-person mixture with DNA concentrations 2%:17%:32%:47%.
Figure 72:
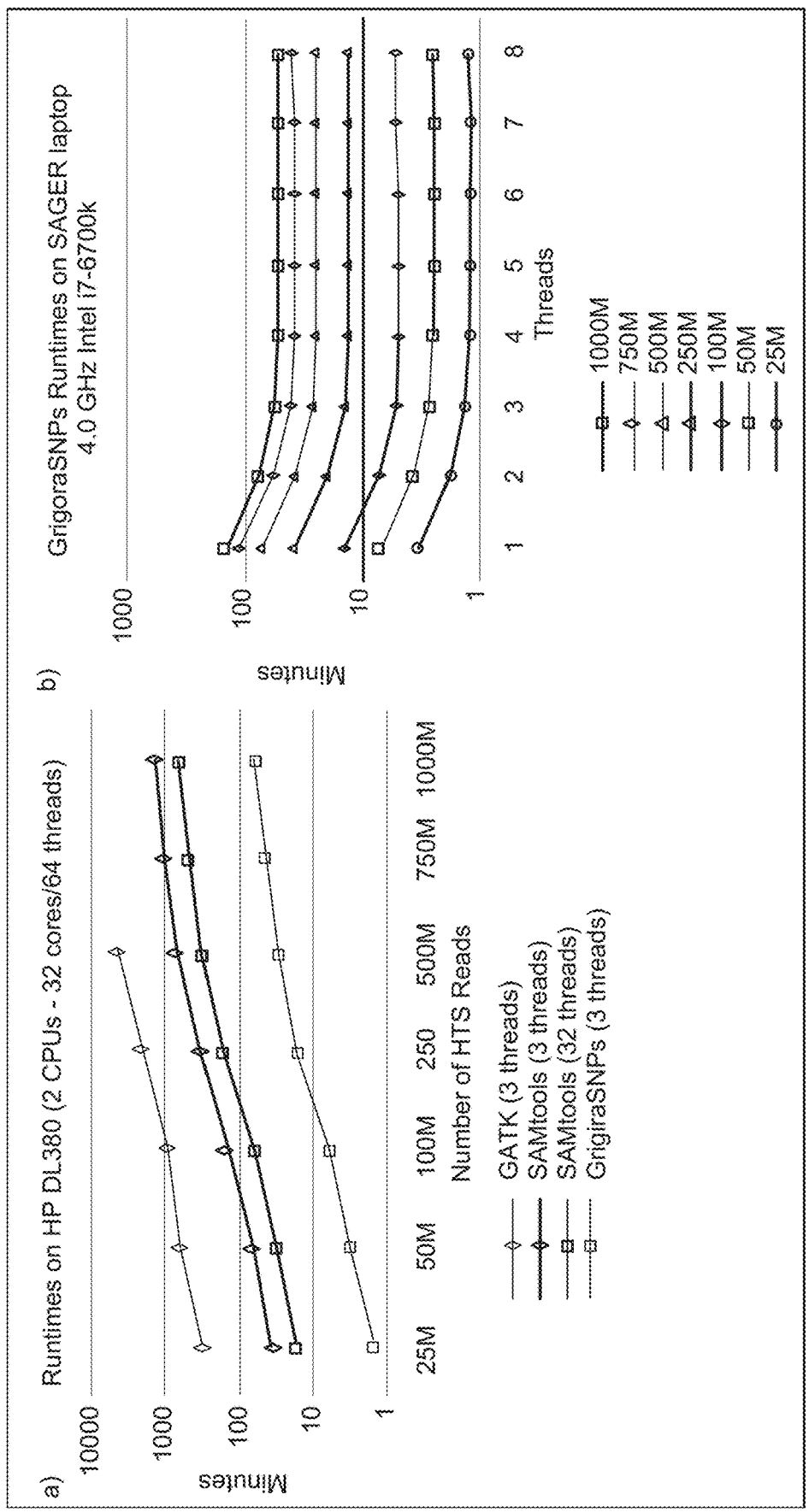
FIG. 72 shows example GrigoraSNPs runtimes.

FIG. 64 shows plots of 10:90 two person defined mixture using the mAC on the left and mAC Frequency Filter on the right. Any loci that had a mAC that occurred 12 or more time in this mixture was set to 0. This method correctly identified and removed the majority of sequencing noise from the mixture.

When individuals are present in trace quantities it can be challenging to separate sequencing noise from sequencing signal using mAR values. The use of mAR values to characterize SNPs enables noise to be incorrectly characterized on low performing primers and the loss of trace signal for very low concentration DNA contributors (e.g., less than 1/200). A poorly performing primer will have low total counts. When sequencing noise causes minor allele read counts at these loci those reads are magnified by using mAR values. If a mAR value greater than 0.0025 was used to positively identify a minor allele at a locus poorly performing loci with less than 400 total reads would only need one minor allele to put them over the mAR threshold. In this case, the locus would be incorrectly characterized as possessing the minor allele. When large differences in contribution concentrations exists the denominator (total counts) of the mAR can be so high that even moderate minor allele counts can be ignored using mAR values. For example, if 19 minor allele reads were detected at a locus but the total number of reads was 8,000 those minor alleles would be lost using mAR thresholds. In this case, the locus would be incorrectly characterized as lacking the minor allele.

Plateau Method for Forensic DNA SNP Mixture Deconvolution

Identification of individuals in forensic DNA mixtures remains a challenge for forensic analysts. Recent advances in high throughput sequencing (HTS) are enabling analysis of DNA mixture samples with expanded panels of Short Tandem Repeats (STRs) and/or Single Nucleotide Polymorphisms (SNPs). No methods are currently known for direct deconvolution of DNA SNP mixtures into individual profiles. We present the plateau method for direct SNP DNA mixture deconvolution into sub-profiles based on differences in contributor's DNA concentrations in the mixture samples without reference profiles. The plateau method can detect profiles for individuals down to roughly 1:400 concentration ratios in HTS mixtures.

DNA forensics is a common tool used within law enforcement and US intelligence agencies to identify unknown suspects and to accurately link crime scene evidence to criminal perpetrators. Crime scene evidence often contains DNA from multiple people, confounding current DNA analysis techniques. Currently, the forensics community uniquely identifies individual DNA samples through extraction of short tandem repeats (STRs). Capillary electrophoresis is used to quantify STR allele lengths. This methodology has been proven accurate for individual profile identification. However, if a given reference DNA profile is contained within a DNA mixture, identifying an individual profile is difficult and usually impossible using this methodology. Thus, the ability to build individual profiles from a mixture and the direct deconvolution of a mixture into candidate and/or individual component DNA signatures are unmet needs.

STR analysis of DNA mixtures works for samples with two contributors where the ratio of DNA concentrations does not exceed 1:10. Special techniques are applied to rape samples to isolate the perpetrator's profile. Current methods are limited to the resolution of capillary electrophoresis (CE) sizing of polymerase chain reaction (PCR) amplified STR allele peaks. PCR amplification introduces stutter peak artifacts that limit the discrimination of contributor STR alleles from these stutter artifacts. Progressing from sizing of alleles to sequencing alleles with high throughput sequencing (HTS) enables massively parallel sequencing (MPS) of forensic and reference samples. HTS also enables the expansion of forensic panels from the current FBI CODIS panel 20 STR loci up to 24,000 SNP loci with the Thermal Fisher Scientific Ion AmpliSeq panels. Selecting SNPs with low fixation index ($F_{ST}$) coupled with targeted minor allele ratios facilitate designing SNP panels for mixture analysis[5,6].

No methods currently exist for DNA mixture deconvolution. We introduce herein the Plateau method for direct deconvolution of some DNA mixtures with modest numbers of contributors and imbalances in DNA concentrations.

Mixture Analysis HTS SNP Panel Design

Optimal mixture analysis SNP panels need to work across all ethnicities. These panels can also be designed to minimize saturation on multiple contributor forensic samples. MIT Lincoln Laboratory has designed and tested HTS SNP panels using both the Fluidigm DNA amplification platform and the Thermal Fischer AmpliSeq platform. The following recommended guidelines can be applied to SNP selections for designing mixture analysis SNP panels:

Select loci with low fixation index ($F_{ST}$) (e.g., <0.6)
  Poor correlation between ancestry and genotype on ALFRED database,
Select loci with low average heterozygosity (e.g., 0.05 to 0.15),
Select loci with low minor allele frequency (mAF) (e.g., 0.03 to 0.07),
Avoid loci that tend to produce ambiguous results in reference samples,
Avoid loci that produce impossible results in parent-child pairs,
Avoid loci with consistently low read counts,
Avoid loci that tend to generate data from only one strand of DNA,
Avoid/resolve duplicate SNPs,
Avoid ambiguously mapped SNPs, and
Select loci with minimum distance between loci (e.g., 100,000 bases).

Other considerations include:
  Inclusion/exclusion of SNPs related to health

Ion Torrent HTS Sequencing

Buccal swabs (Bode cat #P13D04) were used to collect buccal cells from the inside cheeks of volunteers, rubbing up and down for at least 10 seconds, with pressure similar to that used while brushing teeth. DNA was isolated from swabs using the QIAamp DNA Investigator Kit (Qiagen cat #56504), using the "Isolation of Total DNA from Surface and Buccal Swabs" protocol, and eluted in 100 uL of low TE (carrier RNA not used; low TE has 0.1 mM of EDTA). Quantitation was done using Quantifilier HP kit (ThermoFisher cat #4482911) according to manufacturer. The standard run across all samples that quantities were calculated from was human genomic DNA from Aviva Systems Biology (cat #AVAHG0001). Target specific primers, consisting of 2,655 amplicons, were designed using the Ion AmpliSeq Designer online tool. The extracted DNA from volunteers, was pooled into mixtures, and the percent contribution of each volunteer is listed in Table 1. The AmpliSeq 2.0 library kit protocol was followed according to the manufacturer with this primer panel, with the exception that 19 cycles were done with no secondary amplification and the final elution was in 25 uL low TE instead of 50 uL. Each mixture was given a separate barcode. Library quantitation was done with the Ion Library Quantitation Kit (Thermofisher cat #4468802), according to the manufacturer.

Samples were pooled and diluted to 50 pmol, using 150 base pairs per amplicon average for the calculation based on primer panel. Template preparation and sequencing were performed using manufacturer protocols (Thermofisher Ion Chef and Proton cat #A27198 and Proton chips cat #A26771).

HTS SNP Data Analysis

The GrigoraSNPs program was used to call SNP alleles from multiplexed HTS FASTQ sequences. The called SNPs were loaded into the MIT Lincoln Laboratory IdPrism HTS DNA Forensics system.

Plateau Method

The minor allele ratio (mAR) is calculated for each locus for mixture samples. The loci are sorted by mAR where loci with minor alleles with differences in contributor DNA concentrations will form plateaus with different mAR ratios. Sub-profiles plateaus are identified by a sliding window approach that identifies clusters of SNPS with very similar minor allele ratios. Observed instrument sequencing errors create random base sequence errors with very low minor allele ratios. SNPs below a minimum mAR threshold are classified as two major alleles. Random HTS sequencing errors can generate mAR values as high as 0.0025 for loci with two major alleles in reference samples on Thermal Fischer Proton and S5 platforms. All SNP alleles identified as major:major are shared by all identified sub-profiles. For each sub-profile, the SNPs to the left of each plateau can be classified as major:major for that sub-profile when loci are sorted by increasing mAR values. The minor:minor alleles observed are assigned to the right-most sub-profile identified.

A reference profile consists of MM, mM, and mm SNP alleles. FIG. 1 illustrates chromosome 22 minor allele ratios (mAR) for reference 1. For reference samples, the mAR values at or near 0 represent MM alleles, near 0.5 —mM alleles, and 1.0—mm alleles. The sorted mAR profiles for two reference profiles are illustrated in FIG. 2. A mixture profile is composed of one or more individual contributors with mAR values ranging from 0 to 1. A dilution series of two person mixtures is shown in FIG. 3 for the dilutions 25:75, 10:90, 1:99, and 1:200. The individual alleles are colored by contributing individual. FIG. 4 illustrates the assigned alleles predicted by the Plateau method implemented in the MIT Lincoln Laboratory IdPrism DNA forensics system. The Plateau method can frequently separate individuals with DNA concentration differences of 15% or higher. Individual profiles can be resolved with DNA ratios as low as 1:400. FIGS. 5 and 6 illustrates the Plateau method with defined mixtures of three and four individuals. FIG. 77 illustrates the characterization of the identified individual sub-profiles compared to truth data for the individuals and mixtures in the two-person dilution series.

The sorted mAR plateaus in some DNA mixtures enable the direct deconvolution for the mixture into sub-profiles based on differences in individual mARs within the mixture. High confidence identifications can be made when references are known for some or all of the contributors. When no reference profiles exist for DNA contributors, the sub-profiles can be matched to other forensic samples and reference profiles obtained in the future. The Plateau method cannot resolve two or more individuals when the DNA concentrations are close to each other (e.g., roughly 10% of less on the Ion Torrent platform). Also, multi-contributor mixtures with more than five contributors may not be decomposable by this method. The detection range for this method appears to span from between 10 to 15% concentration difference down to approximately 1:400 for two contributor mixtures. To address forensic mixture deconvolution unmet needs, the Plateau method provides a method to confirm the co-occurrence of individual DNA profiles to build individual DNA profiles for unknown individuals from analysis of one or more DNA mixtures.

The Plateau method may be used for medical diagnosis and/or prognosis. In the field of cancer, biopsy samples often contain many cell types, of which a small proportion may form any part of a tumor. Consequently, DNA obtained from tumor biopsies is another form of complex DNA mixture. This method would resolve a question as to whether the tumors arose independently, or, on the other hand, if these tumors are related.

The Plateau method can identify individual(s) in DNA mixtures when the DNA SNP profile of any of the individual contributors is not known a-priori. This is the first SNP mixture deconvolution method to be described. Mixture direct deconvolution compliments DNA mixture analysis methods that match known references to DNA mixtures.

TABLE 35

DNA sample dilutions for defined mixtures

| 93 | 4 |
|---|---|
| 53.5 | 46.5 |
| 43.4 | 56.6 |
| 27.7 | 72.3 |
| 11.3 | 88.7 |
| 1.2 | 98.9 |
| 0.6 | 99.4 |
| 0.3 | 99.7 |

TABLE 36

Analysis of Plateau sub-profiles versus Reference Samples.

| Mixture | Number of Contributors | Reference | Number of Minor Alleles (Truth) | mm | Sub-Profile | P(RMNE) |
|---|---|---|---|---|---|---|
| 25:75 | 2 | 1 (4) | | | | 6.10E−106 |
| 10:90 | 2 | 1 | | | | |
| 1:99 | 2 | 1 | | | | |
| 1:200 | 2 | 1 | | | | |
| 1:400 | 2 | 1 | | | | |
| 25:75 | 2 | 2 (93) | 502 | 73 | 573 | 3.31E−64 |
| 10:90 | 2 | 2 | | | | 2.19E−110 |
| 1:99 | 2 | 2 | | | | |
| 1:200 | 2 | 2 | | | | |
| 1:400 | 2 | 2 | | | | |
| 5:20:75 | 3 | 2 | | | | |
| 5:20:75 | 3 | 3 (56) | | | | |
| 5:20:75 | 3 | 4 (24) | | | | |
| 2:17:32:47 | 4 | 1 | 504 mM | 80 mm | 573 | 2.64E−60 |
| 2:17:32:47 | 4 | 2 | | | | |
| 2:17:32:47 | 4 | 5 (94) | | | | |
| 2:17:32:47 | 4 | 6 (78) | 450 mM | 80 mm | 309 | 2.65E−60 |

Extremely Fast Forensics FITS DNA SNP and STR Sequence Analysis

Algorithm for extremely fast sequence analysis of High-Throughput Sequencing (FITS) forensics DNA samples that scales linearly in compute time with the number of DNA sequences being analyzed. DNA loci are identified by a lookup table with the start of the HTS sequence tag (extracted after the barcode sequence tag). SNP or STR loci are identified by locking in the flanking sequences immediately flanking the target SNP or STR. Standard analysis of HTS DNA sequences is of the complexity of Order(N×M×L) where N is the number of sequences, M is the number of loci, and L is the length of the HTS sequence. Using the flanking sequences for the SNP or STR reduces the computational complexity to identification of short (10 base pair) substrings on each side of the target SNP or STR; resulting in reduction of computational complexity to O(N×M). Each DNA sequence is compared against all possible loci to identify the correct loci for the sequence. Implementing a sequence tag lookup table reduces the complexity of the sequence analysis down to O(N) that scales linearly in compute time for the number of sequences to analyze, independently of sequence length and number of loci in the amplification panel. Observed computational runtimes on HTS experiments are reduced from roughly 300 (Intel) to 600 (AMD) minutes on 32 core SMP computers down to 12 minutes for 100 million sequences.

DNA forensics will shift in the near future from sizing of Short Tandem Repeats (STRs) to high-throughput sequencing of forensics DNA samples for both STRs and Single Nucleotide Polymorphisms (SNPs). Current DNA forensics techniques rely upon allele sizing of short tandem repeats by capillary electrophoresis. High throughput DNA sequencing enables characterizations of trace DNA samples for large numbers of DNA loci. DNA Sequence barcode tagging of samples for multiplexing of samples is used for increased throughput and decreased cost per sample. Advanced variant analysis algorithms enable improved kinship identification, biogeographic ancestry prediction, analysis of complex DNA mixtures, prediction of externally visible traits, and more. The slowest computational component of the DNA forensics analysis methods is the characterization of raw sequences to variant calls. The elapsed time from sample to results is critical in many forensic scenarios.

SNP panels are designed with multiple pairs of oligonucleotide primers that each amplifies target location(s) in the genome for characterization of SNP alleles. Each HTS sequence should contain the following components: multiplexing barcodes on the 5' and sometimes 3' end of each sequence, 5' and 3' primers, and the SNP surrounded by flanking DNA sequences (FIG. 1). HTS DNA datasets also contain other sequences arising from sequencing or polymerase chain reaction (PCR) amplification artifacts; these other sequences are ignored. For Ion Torrent Proton HTS SNP sequences, the 5' barcode starts at the first or second base pair position in ~94% of the valid SNP sequences.

The original Scala SNP caller was developed leveraging the Actors model for efficient parallel processing on symmetric multiprocessing (SMP) or remote actors on distributed systems. With a SNP dataset of N millions of sequences (length L) for a panel of M amplification loci is an order O(N×M×L) scale problem. Each sequence is compared against the specified set of barcodes used for the dataset. Reference sequences for each locus from dbSNP (http://www.ncbi.nlm.nih.gov/SNP/) are used as comparison references. For efficient processing, each sequence is compared against the 10 base pairs immediately flanking each reference SNP to identify target loci and SNP position, O(N×M). A minimum of 19 of the 20 flanking bases are required to be identical for correct positioning of called SNP (or STR).

In some embodiments, an enhanced Scala SNP caller was developed to implement various embodiments. A hash lookup table was added that uses a 12 base pair (k-mer) lookup tag using the sequences starting 4 bases after the end of the barcode and skipping over the linker bases (GAT) that follow immediately after the 5' barcode. A lookup table of tags to loci is added as an input file that is loci panel specific. When a 5' barcode is identified, the lookup tag can reduce the complexity of the analysis of the sequence from O(M) to O(1) speeding up the data analysis.

Results

Timing results on the AMD Operon 64 and Intel 64 (32 cores with hyperthreads) (Table 37) is shown for panels of 1,598 loci (Table 38), 5,396 loci (Table 39), and 14,942 loci (Table 40). For the Scala SNP caller, the timing results scale with the SpecInt of the two platforms with the Intel 64 having roughly 2X performance over the older AMD 64 SMP system. Performance on both of these platforms is scaling in time by both the number of sequences (N) and the panel size (M) for runtime complexity of O(N×M). The timing of the enhanced Scala SNP caller with the sequence tag lookup for loci identification scales linearly with number of sequences O(N) with no impact of panel size.

TABLE 37

SMP computers used for timing benchmarks

| Server | CPU/GPU Cores | Storage | Memory |
| --- | --- | --- | --- |
| AMD 64 | AMD Opteron 6282 (64-cores: 32-cores x 2 CPUs) | 7200 RPM HDs | 512 GB |
| I64 | Intel Xeon 2698 v3 (32-cores/64 threads) (16-cores/32-threads x 2 CPUs) | 10 K RPM HDs (718162-B21) | 512 GB |

TABLE 38

Timing results for DNA panel of 1,598 loci

| Sequences | Scala SNP caller AMD 64 | Scala SNP caller Intel 64 | Implementation version Intel 64 |
| --- | --- | --- | --- |
| 25 million | 20 min | 9 min | 2 min |
| 50 million | 34 min | 18 min | 4 min |
| 100 million | 65 min | 35 min | 9 min |
| 250 million | 153 min | 86 min | 26 min |
| 500 million | 303 min | 172 min | 65 min |

TABLE 39

Timing results for DNA panel of 5,396 loci

| Sequences | Scala SNP caller AMD 64 | Scala SNP caller Intel 64 | Implementation version Intel 64 |
| --- | --- | --- | --- |
| 25 million | 55 min | 27 min | 2 min |
| 50 million | 107 min | 53 min | 5 min |
| 100 million | 216 min | 103 min | 9 min |
| 250 million | 505 min | 271 min | 23 min |
| 500 million | 1098 min | 532 min | 65 min |

TABLE 40

Timing results for DNA panel of 14,942 loci

| Sequences | Scala SNP caller Intel 64 | Implementation version Intel 64 | Implementation on WL Intel 64 + WL |
| --- | --- | --- | --- |
| 25 million | 79 min | 2 min | 0.7 min |
| 50 million | 137 min | 5 min | 1.3 min |
| 100 million | 274 min | 11 min | 2.6 min |

Performance engineering of HTS SNP calling indicates that the problem remains compute bound on SMP computers. Increasing the number of cores or moving towards processors with higher SpecInt scores will reduce runtimes. The GrigoraSNPs out performs the original version substantially with linear runtime with respect to the number of FITS sequences. This method applies equally for both SNPs and STRs for HTS DNA sequence analysis. Runtimes are reduced by ~75% with faster reads on HP workload accelerator.

HTS sequencing enables characterization of forensics trace DNA samples. In DNA forensics, being able to go from sample to profile is fundamental. In some scenarios, being able to quickly characterize samples is essential for generating leads in a case.

Genetic Chain Rule for Probabilistic Kinship Estimation

Kinship prediction for DNA forensic samples has been limited to first degree relatives. High throughput sequencing will revolutionize DNA forensics with advanced mixture analysis capabilities and push the state of the art in kinship identification for forensic samples. Beyond predicting first degree relatives, current kinship identification models rely on statistics that do not adequately model the biology, or rely on machine learning algorithms that are prone to over optimization while requiring highly similar and extensive training data to ensure generalizability. This work presents an alternative approach using Bayesian statistics to model inheritance of single nucleotide polymorphism (SNPs) based on a given relationship between persons. The impact of panel size on predictions is visualized in terms of distribution of allelic differences between individuals. Confidence of predictions is made using the log likelihood. With a panel of 39108 SNPs evaluated on an in silico dataset, this method can resolve parents from siblings and distinguish 1st, 2nd, 3rd, and 4th degree relatives from each other and unrelated individuals, providing greater potential performance than current state of the art algorithms. First degree relatives can also be partially resolved but results overlap both 4th degree relatives and unrelated individuals.

High throughput sequencing (FITS) is revolutionizing capabilities in the fields of forensics, biology, and medicine. DNA forensics is evolving from sizing short tandem repeats (STRs) to sequencing STRs and single nucleotide polymorphisms (SNPs). Currently, DNA forensics currently uses STRs sized by capillary electrophoresis to per-form both identity and familial searching. Familial searching is a method in which STR matching requirements are relaxed to obtain a more expansive list of potentially related suspects. These additional matches are then filtered using statistical method such as identity by state (IBS) and/or kinship index (KI). Lineage testing is then per-formed using mitochondrial DNA or Y chromosome STRs to confirm paternal relationships. Familial searches are limited to First degree relatives due to the small number of STRs used (20 loci for US Combined DNA Index System—CODIS), and the large number of STR matches when matching parameters are set too low[4]. Familial searching and other kinship prediction methods rely on IBD/identity by state (IBS), and KI calculations. Ancestry prediction companies use DNA SNP microarrays and the aforementioned methods to predict close and distant relatives. These DNA SNP microarrays require a lot more DNA than is typically available for forensic samples. Machine learning and forensic HTS SNP panels have been used to predict familial relationships across a set of three families. This work trained a support vector ma-chine based on features including the KING coefficient, IBS, and IBD. While machine learning models have the potential for accurate performance, they are highly dependent on the consistency of the training data, and are prone to over-optimization.

Enhanced kinship prediction capabilities can be obtained by incorporating Bayes' Theorem with high throughput sequencing (FITS). This discussion formalizes the expected relationship between any two individuals using Bayesian statistics with applications to FITS forensic SNP panels. As discussed, a Genetic Chain Rule for Probabilistic Kinship Estimation provides a mathematical model that can predict likely relationship between two individuals. This model does not require training data, thereby increasing generalizability. Furthermore, this work reflects the biological underpinnings of inheritance allowing for further extensions based on improved understanding of the biology.

Methods

Input Data

All results were tested on an in silico dataset that simulated millions Of individuals across four ethnic groups. The minor allele frequencies for 39,108 SNPs were taken the Allele Frequency Database (ALFRED) for SNPs well characterized across African Americans, Estonians, Koreans, and Palestinians. The data were simulated across 9 generations with an intermarriage and marriage rate set to reflect public census data. Four generations of data were used to simulate individuals with relationships spanning first through fifth degree and strangers.

Data Representation

All data are represented as a series of SNPs, with each locus having a minor allele, coupled with a minor allele frequency (mAF). The probability of the major allele occurring across a population is represented as p, while the probability of the minor allele occurring across a population is represented as q. As the SNPs analyzed have one major, and one minor allele, p, and q are set such that:

$$p+q=1 \quad (1)$$

This follows Hardy-Weinberg equilibrium and leads to the number of people with a homozygous major genotype to occur with a frequency of p2, the number of individuals with a heterozygous genotype to occur with a frequency of 2pq, and the number of homozygous recessive genotypes to occur with a frequency of q2. By satisfying Eq. 1, it is ensured that $$p2+2pq+q2=1 \quad (2)$$

Using this information, we set out to derive the conditional probability of any genotype occurring, given another individual of a known relationship having a certain genotype.

Parent Child Relationships

Child Given Known Parent

The first relationship calculated is the probability of a child having a particular genotype Gc, given that their parent has a genotype Gp. Given that you know one parent's genotype, you know the possible alleles that they could pass on to their child. For instance, if a parent is homozygous major (AA), then you know that they will inevitably pass a major allele on to their children.

Thus, the probability that any individual child will be homozygous major, is the probability that the other parent passes on a major allele, which is p, and the child will be heterozygous with probability q.

Parent Given Known Child

Leveraging the information presented in Table 41, it is possible to calculate the probability of a parent having a particular genotype Gp, given that the child has a known genotype Ge. This is formulated through an application of Bayes' rule.

$$Pr(G_p \mid G_c) = \frac{Pr(G_c \mid G_p) * Pr(G_p)}{\sum_{G_i} Pr(G_c \mid G_p = G_i) Pr(G_p = G_i)} \quad (3)$$

In the above and subsequent equations, Gi, is used to represent all possible allelic combinations. As a result, Gi can be expressed as $$Gi \in (AA, Aa, aa) \quad (4)$$

Where A is a major allele, and a is a minor allele.

Sibling Relationships

It is possible to use this information to further compute the probability that a child will have a genotype Gc1 given that a sibling of theirs has an observed genotype Gc2. In order to properly compute the probability of genotype Ge1 occurring, it is essential to factor in genotypes of the two parents Gp1, and Gp2. Using this information, the desired sibling-sibling conditional probability is computed as the probability of Child 1 having a genotype Ge1 given the possible genotypes that their parents could have, multiplied by the probability of the two parents having genotypes Gp1 and Gp2 given the known genotype of Child 2.

$$Pr(G_{c1} \mid G_{c2}) = \quad (5)$$
$$\sum_{G_{i1}} \sum_{G_{i2}} Pr(G_{c1} \mid G_{p1} = G_{i1}, G_{p2} = G_{i2}) * Pr(G_{p1} = G_{i1}, G_{p2} = G_{i2} \mid G_{c2})$$

Bayesian Chain Rule of Kinship

Figure 73:
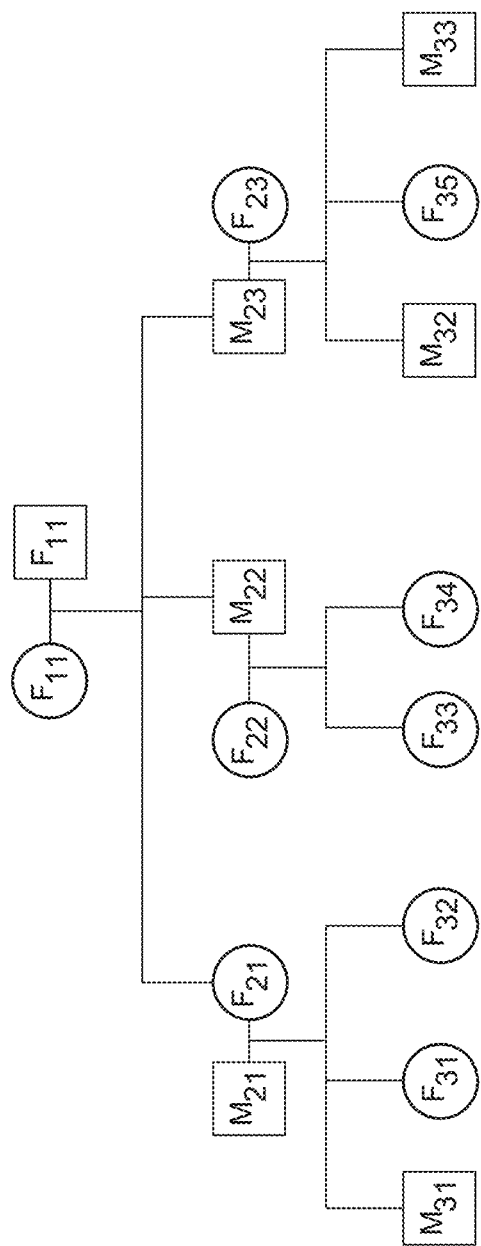
FIG. 73 shows a reference family tree.

The above framework can be generalized to compute the probability of a particular genotype given any relationship between two people. We define this formulation as the Bayesian Chain Rule of Kinship. The Bayesian Chain Rule of Kinship expresses any relationship between individuals as the product of a series of relationships. For instance, if we wished to compute the cousin relationship between M31 and F33 as shown in FIG. 73, we would represent this as the relationship between child and parent, parent and sibling, and the parent's sibling and their child. As can be noted, all components of the chain rule take the form of child given parent to move up the tree, sibling given sibling to move across the tree, and parent given child to move down the tree. These operations allow for complete navigation between any two individuals. Expressed another way:

$$Pr(G_{c1} \mid G_{c2}) = \quad (5)$$
$$\sum_{G_{i1}} \sum_{G_{i2}} Pr(G_{c1} \mid G_{p1} = G_{i1}, G_{p2} = G_{i2}) * Pr(G_{p1} = G_{i1}, G_{p2} = G_{i2} \mid G_{c2}).$$

TABLE 41

Probability of the event (e) an individual with a given genotype (Ind$_e$), conditioned (c) on another individual (Ind$_c$) having a given genotype.

| Ind$_e$ | Ind$_c$ | Pr(Ind$_e$ = Child\|Ind$_e$ = Parent$_1$) Parent$_1$: p$_1$, q$_1$ Parent$_2$: p$_2$, q$_2$ | Pr(Ind$_e$ = Parent$_1$\|Ind$_e$ = Child) Parent$_1$: p$_1$, q$_1$ Parent$_2$: p$_2$, q$_2$ | Pr(Ind$_e$ = Grandchild\|Ind$_e$ = Grandparent$_1$) Parent$_1$: p$_1$, q$_1$, Parent$_2$: p$_2$, q$_2$, Grandparent$_1$: p$_3$, q$_3$, Grandparent$_2$: p$_4$, q$_4$ |
|---|---|---|---|---|
| AA | AA | $p_2$ | $\frac{p_2 * p_1^2}{p_2 * p_1^2 + 0.5 p_2 * 2 p_1 q_1} = p_1$ | $p_2 p_4 + 0.5 p_2 q_4$ |
| AA | Aa | $q_2$ | $\frac{0.5 p_2 * 2 p_1 q_1}{p_2 * p_1^2 + 0.5 p_2 * 2 p_1 q_1} = q_1$ | $q_2 p_4 + 0.5 q_4$ |
| AA | aa | 0 | 0 | $0.5 q_2 q_4$ |
| Aa | AA | $0.5 p_2$ | $\frac{q_2 * q_1^2}{0.5 q_2 * 2 p_1 q_1 + q_2 * q_1^2} = q_1$ | $0.5 p_2 p_4 + 0.25 p_2$ |
| Aa | Aa | $0.5 p_2 + 0.5 q_2 = 0.5$ | $\frac{q_2 * p_1^2}{q_2 * p_1^2 + (0.5 p_2 + 0.5 q_2) * 2 p_1 q_1 + p_2 * q_1^2}$ | $0.5 p_2 q_4 + 0.25 + 0.5 q_2 p_4$ |
| Aa | aa | $0.5 q_2$ | $\frac{(0.5 p_2 + 0.5 q_2) * 2 p_1 q_1}{q_2 * p_1^2 + (0.5 p_2 + 0.5 q_2) * 2 p_1 q_1 + p_2 * q_1^2}$ | $0.25 q_2 + 0.5 q_2 q_4$ |
| aa | AA | 0 | 0 | $0.5 p_2 p_4$ |
| aa | Aa | $p_2$ | $\frac{p_2 * q_1^2}{q_2 * p_1^2 + (0.5 p_2 + 0.5 q_2) * 2 p_1 q_1 + p_2 * q_1^2}$ | $0.5 p_4 + p_2 q_4$ |
| aa | aa | $q_2$ | $\frac{0.5 q_2 * 2 p_1 q_1}{0.5 q_2 * 2 p_1 q_1 + q_2 * q_1^2} = p_1$ | $0.5 p_2 q_4 + q_2 q_4$ |

The genotype letter (A) represents the major allele with population frequency pi for individual i, while genotype letter (a) represents the minor allele with population frequency qi; this allows individuals to have different ethnicities.

This takes the product of all people between two individuals, and uses the Bayesian Chain Rule of Kinship to compute a probability of a genotype given a particular relationship.

Extended Relationships

Extended relationships can be computed using the previously defined Bayesian Chain Rule of Kinship.

FIG. 1 shows a family tree where each individual is identified as male (M) or female (F), and with two indices identifying their generation, along with a unique identifier for that individual within the generation. For instance F23 represents the third unique woman appearing in the second generation.

Grandchild Given Grandparent

The probability of a child (M31) having a given genotype Gc, given their grandparent (M11) has a known genotype Gg can easily be computed using the Markov and chain rule assumptions to model the child (M31) as dependent on their parent (F21), and the parent (F21) to be dependent on the grandparent (M11).

$$Pr(G_c \mid G_g) = \sum_{G_i} Pr(G_c \mid G_p = G_i) * Pr(G_p = G_i \mid G_g) \quad (7)$$

As the child is assumed to inherit grandparental DNA from only one parent, the probability equation decomposes into the child being directly dependent on their parent, and the parent being directly dependent on the grandparent. It is unnecessary to condition the child's genotype on the grandparent's genotype, as that is already factored into the parent's genotype. Given that the parent has an unknown genotype, Gi is used to marginalize over all possible genotypes for that parent.

Child Given Aunt/Uncle

The same principles apply to identify the likelihood that a child will have a genotype given that their aunt/uncle have a known genotype Gau. In this case, the probability of the child's genotype is decomposed into the relationship between child and parent, and parent and sibling.

$$Pr(G_c \mid G_{au}) = \sum_{G_{i1}} \sum_{G_{i2}} Pr(G_{c1} \mid G_{p1} = G_{i1}, G_{p2} = G_{i2}) * \quad (8)$$
$$Pr(G_{p1} = G_{i1} \mid G_{c2}) * Pr(G_{p2} = G_{i2} \mid G_{c2})$$

Log Likelihood Calculation

All of the above formulation can be further used to calculate the log likelihood of two individuals having a particular relationship given the observed data. The log likelihood is defined as the probability of data (D) given a hypothesis (H).

$$L = \log(Pr(D \mid H)) \quad (9)$$

In the case of familial identification, this is computed by taking the product of all conditional probabilities across SNPs. This allows for the computation of the likelihood of any relationship given the observed genotypes of two individuals.

Current Limitations

The current calculations rely on the independence of inheritance of all alleles. This simplifies the calculation; however, it does not account for haploblocks, or sex chromosomes. As a result of this, it is not possible to distinguish between different relationships that are two or more generations apart, or the directionality of the relationship (e.g. Parent given child, versus child given parent). However, this framework is generalizable, and fully capable of incorporating this information.

Results

The previously defined mathematical relationships are validated using an in silico database of ten million individuals that are separated across nine generations. The data are further subdivided into four different ethnic groups which have separate mAF values across the 39,108 sampled SNPs.

Data Relationship Separability

The relationship separability was examined as a function of the number of differences across SNPs. A difference was defined as the number of discordant alleles at each locus with a value between zero and two. The number of discrepancies was summed across all SNPs for a single pairwise relationship. This was then done for one thousand examples of each relationship. A kernel density estimate was fitted to this distribution and then shown in the figure below.

Figure 74:
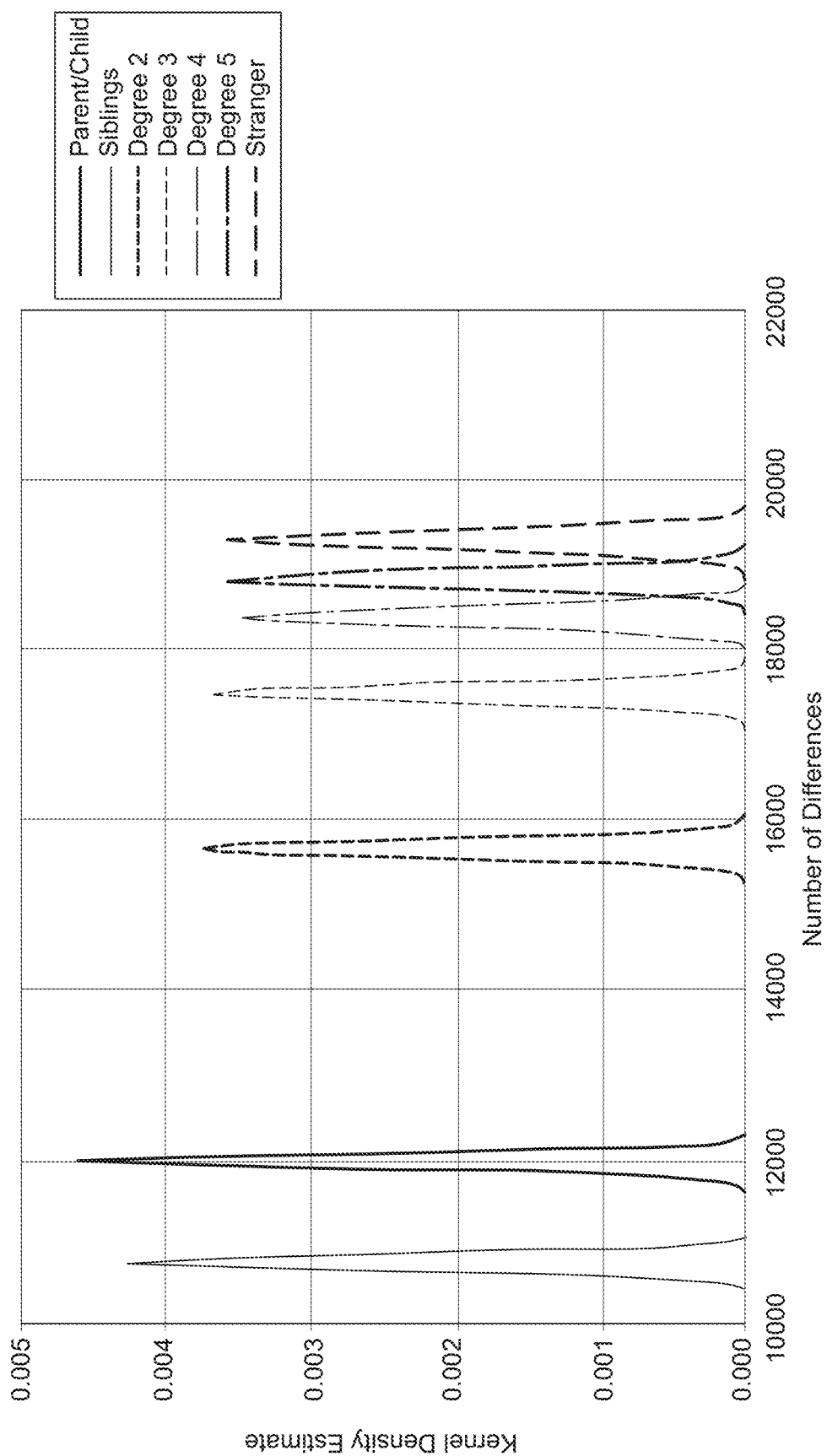
FIG. 74 shows differences separated by degree of relationship for 39k SNP panel.
Figure 75:
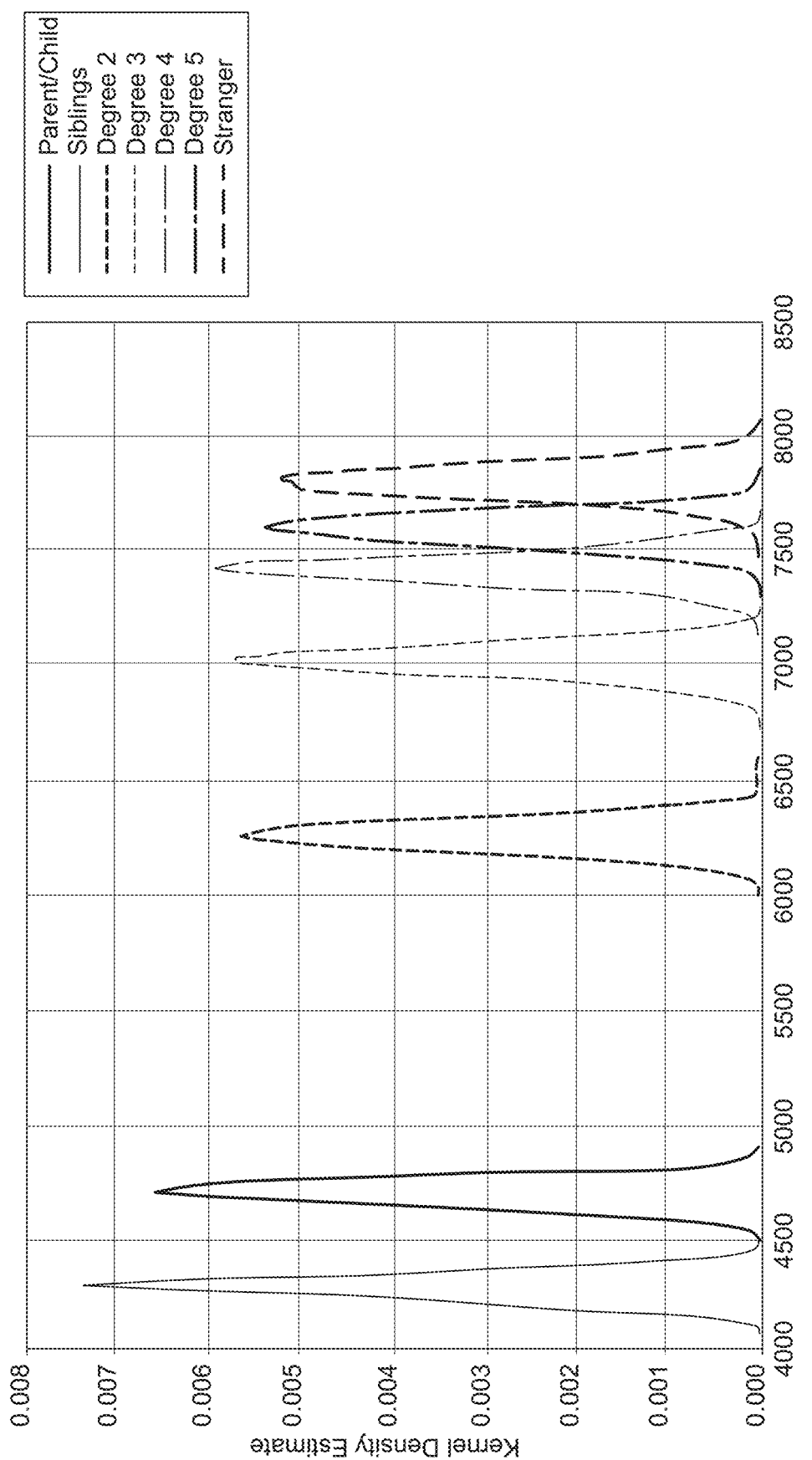
FIG. 75 shows differences separated by degree of relationship for 20k SNP panel.
Figure 76:
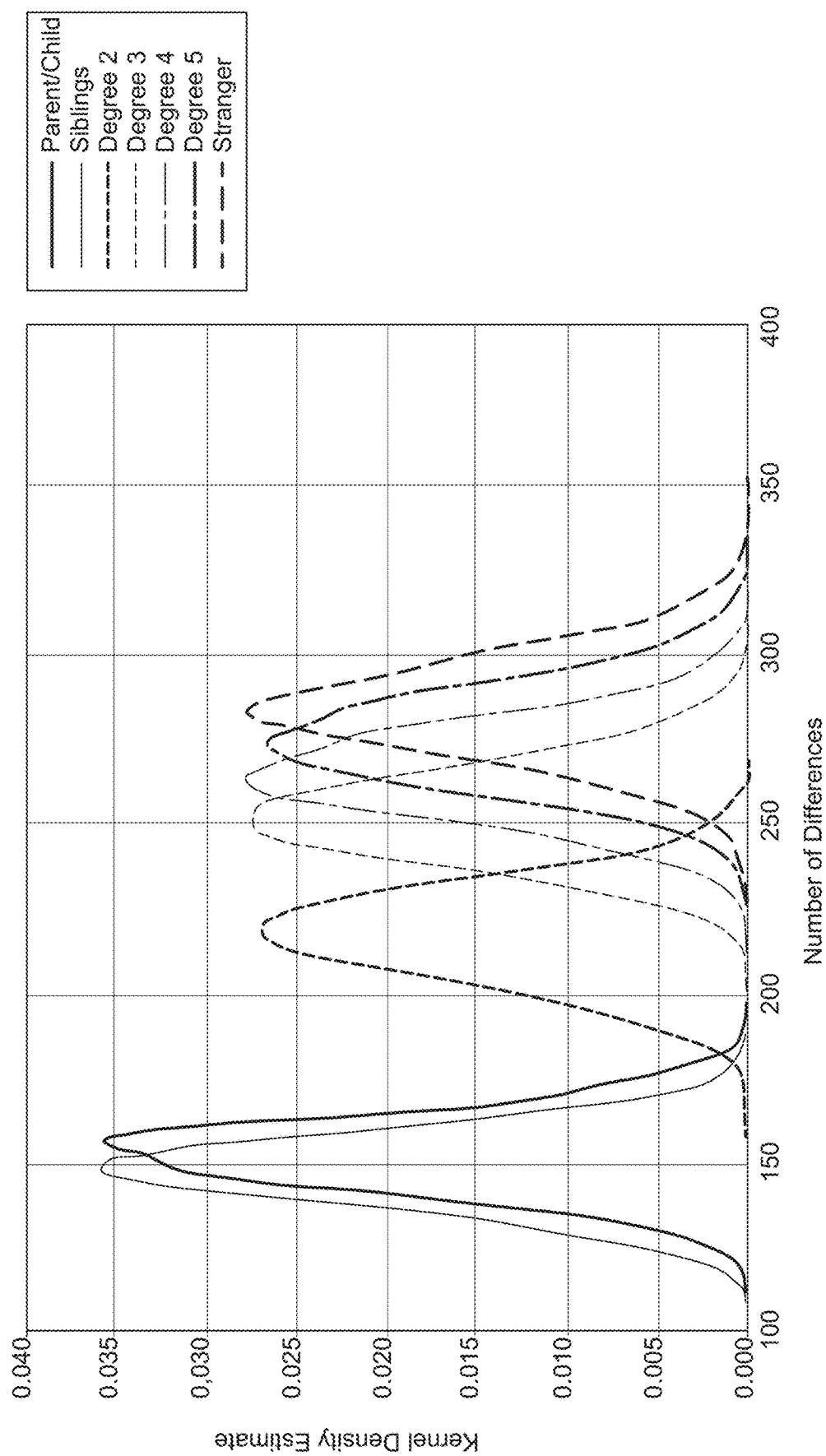
FIG. 76 shows differences separated by degree of relationship for 2k SNP panel.

The number of differences across degree was plotted while varying the number of SNPs used in the comparison. FIG. 74 plots differences across distributions using the full panel of 39k SNP loci. The level of separation is then plotted for half this panel, utilizing 20k SNPs as shown in FIG. 75, and finally the number of differences is examined with the panel reduced to only 2k SNPs, as shown in FIG. 76.

TABLE 42

Confusion matrix for degree prediction

| | Parent-Child | Sibling | Degree 2 | Degree 3 | Degree 4 | Degree 5 | Un-related |
|---|---|---|---|---|---|---|---|
| Parent-Child | 2000 | 0 | 0 | 0 | 0 | 0 | 0 |
| Sibling | 0 | 1000 | 0 | 0 | 0 | 0 | 0 |
| Degree 2 | 0 | 0 | 4000 | 0 | 0 | 0 | 0 |
| Degree 3 | 0 | 0 | 0 | 4997 | 3 | 0 | 0 |
| Degree 4 | 0 | 0 | 0 | 1 | 949 | 50 | 0 |
| Degree 5 | 0 | 0 | 0 | 0 | 53 | 903 | 44 |
| Stranger | 0 | 0 | 0 | 0 | 0 | 46 | 954 |

Log Likelihood Prediction

After examining differences between individuals, the log likelihood was then used to predict the degree of relation across pairs of individuals. At each pair, the algorithm identifies if it is a parent-child relationship, a sibling-sibling relationship, 2nd to 5th degree relationship, or two unrelated individuals. The performance for this assessment is shown in the Table 42.

As discussed, in silico data may be used to identify the degree of relatedness between individuals spanning four generations. FIG. 2 demonstrated a clear separability between parent-child relationships and siblings, as well as between individuals with second, third, and unrelated levels of relationship. This was reflected through the log likelihood being able to fully and correctly identify the difference between individuals of these different degrees. As the degree increases, the curves become closer together. The upper tail of the 4th degree relatives is near the lower tail of unrelated individuals. For the 39k SNP panel, the distribution for 5th degree relatives overlap the distributions for 4th degree relatives and unrelated individuals. Larger SNP panels are required to separate 5th degree relatives from 4th degree relatives and unrelated individuals. The confusion matrix shown in Table 42 for this method illustrates the high accuracy on these in silico pedigrees. The impact of reducing the SNP panel size is illustrated in FIG. 75 for 20k SNPs and FIG. 76 for 2k SNPs. For the 2k SNPs panel, the different relationships become much less separable. The curves also become wider as a function of racial heterogeneity/admixture. As the amount of mixed ancestry increased the standard deviation of the distributions also increases. This also increases the difficulty of distinguishing levels of relationship in less related individuals.

In conclusion, a Bayesian framework may be used for identifying the level of relation between different individuals. This framework builds on the biology of inheritance, along with Bayesian statistics to predict degree of relation with-out requiring a training database or parameter optimization. This allows for further improvement by incorporating more biological properties into the model.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

Based on the foregoing disclosure, it should be apparent to one of ordinary skill in the art that the embodiments disclosed herein are not limited to a particular computer system platform, processor, operating system, network, or communication protocol. Also, it should be apparent that the embodiments disclosed herein are not limited to a specific architecture or programming language.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Use of at least one of and a list of elements (e.g., A, B, C) is intended to cover one selection from A, B, C (e.g., A), two selections from A, B, C (e.g., A and B), three selections (e.g., A, B, C), and multiples of each selection.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A DNA analysis system, the system comprising:
   at least one processor operatively connected to a memory;
   a comparison component configured to generate a first error profile for a first DNA locus by comparing read data for the first DNA locus to known reference sequences for the first DNA locus;
   a receiver component configured to receive DNA analysis information including locus and allele read information generated from PCR amplification of DNA in a DNA sample;
   an analysis component, executed by the at least one processor, configured to:
evaluate the locus and allele read information against the first error profile to determine an adjusted read threshold;
confirm presence of the first locus and allele in the DNA sample;

responsive to the confirmed presence of the first locus and allele information adjust error analysis of at least a second allele or at least a second locus to account for amplification error reads of the confirmed first locus and allele in the DNA sample; and determine for each respective locus and allele associated with read data obtained from the DNA sample whether a total number of reads from the DNA sample exceeds an error profile adjusted threshold, and for each confirmation or exclusion of read data adjust the threshold based on the confirmation or exclusion.

2. The system of claim 1, wherein the analysis component is further configured to generate, by the least one processor, an identification profile for at least one individual within the DNA sample comprising each confirmed locus and allele for the at least one individual.

3. The system of claim 1, wherein the receiver component further comprises a physical DNA sample receiver and PCR analysis element for generating read information for respective loci and alleles.

4. The system of claim 1, wherein the error profile for the first locus and allele includes calculations of different threshold adjustments according to PCR amplification cycles executed on the sample.

5. The system of claim 4, wherein the error profile includes calculations for a number of reads associated with at least −1 stutter allele, a +1 stutter allele, and a −2 stutter allele, wherein the calculations are adjusted by the analysis component to a number of PCR amplification cycles.

6. The system of claim 1, wherein the analysis component is further configured to determine whether the total number of reads from the sample exceeds the error profile adjusted threshold based on a combined error read count derived from stutter alleles from at least a first and second allele.

7. The system of claim 1, wherein the analysis component is further configured to determine the total number of reads from the sample exceeds the error profile adjusted threshold based on a combined error read count derived from stutter alleles from at least a first, second, and third allele.

8. The system of claim 1, wherein the analysis component is further configured to identify PCR products from the sample for sequencing.

9. The system of claim 8, wherein the analysis component is further configured to evaluate confirmed alleles to determine information on a respective dominant −1 stutter allele and identify PCR products from the sample from sequencing based on the properties of the respective dominant −1 stutter allele.

10. The system of claim 9, wherein the analysis component is further configured to update confirmed allele information responsive to reducing reads counts for each dominant −1 stutter allele identified based on sequencing.

11. A method for analyzing DNA comprising:
generating a first error profile for a first DNA locus by comparing read data for the first DNA locus to known reference sequences for the first DNA locus;
receiving DNA analysis information including locus and allele read information generated from PCR amplification of DNA in a DNA sample;
evaluating the locus and allele read information against the first error profile to determine an adjusted read threshold;
confirming presence of the first locus and allele in the DNA sample;
responsive to the confirmed presence of the first locus and allele information, adjusting error analysis of at least a second allele or at least a second locus to account for amplification error reads of the confirmed first locus and allele in the DNA sample; and
determining for each respective locus and allele associated with read data obtained from the DNA sample whether a total number of reads from the DNA sample exceeds an error profile adjusted threshold, and for each confirmation or exclusion of read data adjust the threshold based on the confirmation or exclusion.

12. The method of claim 11, further comprising generating an identification profile for at least one individual within the DNA sample comprising each confirmed locus and allele for the at least one individual.

13. The method of claim 11, wherein the act of receiving further comprises controlling a physical DNA sample receiver and PCR analysis element for generating read information for respective loci and alleles.

14. The method of claim 11, wherein the error profile for the first locus and allele includes calculations of different threshold adjustments according to PCR amplification cycles executed on the sample.

15. The method of claim 14, wherein the error profile includes calculations for a number of reads associated with at least −1 stutter allele, a +1 stutter allele, and a −2 stutter allele, wherein the method comprises adjusting the calculations by the analysis component to a number of PCR amplification cycles.

16. The method of claim 11, further comprising determining whether the total number of reads from the sample exceeds the error profile adjusted threshold based on a combined error read count derived from stutter alleles from at least a first and second allele.

17. The method of claim 11, further comprising determining the total number of reads from the sample exceeds the error profile adjusted threshold based on a combined error read count derived from stutter alleles from at least a first, second, and third allele.

18. The method of claim 11, further comprising identifying PCR products from the sample for sequencing.

19. The method of claim 18, further comprising evaluating confirmed alleles to determine information on a respective dominant −1 stutter allele and identify PCR products from the sample from sequencing based on the properties of the respective dominant −1 stutter allele.

20. The method of claim 19, further comprising updating confirmed allele information responsive to reducing reads counts for each dominant −1 stutter allele identified based on sequencing.

* * * * *